(12) United States Patent
Lowery et al.

(10) Patent No.: US 6,632,621 B1
(45) Date of Patent: Oct. 14, 2003

(54) G PROTEIN-COUPLED RECEPTOR-LIKE RECEPTORS AND MODULATORS THEREOF

(75) Inventors: David E. Lowery, Portage, MI (US); Timothy G. Geary, Kalamazoo, MI (US); Teresa M. Kubiak, Richland, MI (US); Martha J. Larsen, Kalamazoo, MI (US)

(73) Assignee: Pharmacia & Upjohn Company, Kalamazoo, MI (US)

(*) Notice: Subject to any disclaimer, the term of this patent is extended or adjusted under 35 U.S.C. 154(b) by 96 days.

(21) Appl. No.: 09/721,870

(22) Filed: Nov. 24, 2000

Related U.S. Application Data
(60) Provisional application No. 60/167,523, filed on Nov. 24, 1999.

(51) Int. Cl.$^7$ ............... G01N 33/569; G01N 33/566; C07H 21/04; C07K 14/44

(52) U.S. Cl. ............... 435/7.22; 435/7.2; 435/7.21; 536/23.7; 530/350; 530/388.6; 930/210

(58) Field of Search ................... 435/7.2, 7.21, 435/7.22, 6, 7.72, 7.91, 7.8; 536/23.7; 530/350, 388.6; 930/210

(56) References Cited

U.S. PATENT DOCUMENTS

| | | | |
|---|---|---|---|
| 5,585,277 A | 12/1996 | Bowie et al. | 436/418 |
| 5,859,188 A | 1/1999 | Geary et al. | 530/329 |

FOREIGN PATENT DOCUMENTS

| | | |
|---|---|---|
| WO | WO 97/09433 | 3/1997 |
| WO | WO 97/48976 | 12/1997 |

OTHER PUBLICATIONS

Science. Genome sequence of he nematode C. elegans: a platform for investigating biology. (Dec. 1998) vol. 282, pp. 2012–2018.*
Gardner, A. NCBI accession No. T19340. Oct. 15, 1999.*
Murphy, et al., "From DNA to Drugs: The Orphan G–protein Coupled Receptors," *Cur. Opin. in Drug Disc. Dev.* 1:192–199 (1998).
Probst, et al., "Sequence Alignment of the G–Protein Coupled Receptors Superfamily," *DNA Cell Biol.* 11:1–20 (1992).
Altschul, et al., "Gapped BLAST and PSI–BLAST: A New Generation of Protein Database Search Programs," *Nucl. Acids Res.* 25:3389–3402 (1997).
Aujame, et al., "High–Affinity Human Antibodies by Phage Display," *Human Antibodies* 8:155–168 (1997).
Baindur, et al., "Selective Fluorescent Ligands for Pharmacological Receptors," *Drug Dev. Res.* 33:373–398 (1994).
Bargmann, C., "Neurobiology of the *Caenorhabditis elegans* Genome," *Science* 282:2028–2032 (1998).
Birgul, et al., "Reverse physiology in *Drosophila*: Identification of a Novel Allatostatin–like Neuropeptide and its Cognate Receptor Structurally Related to the Mammalian Somatostatin/galanin/opioid Receptor Family," *EMBO Journal* 18:5892–5900 (1999).
Bohm, et al., "Regulatory Mechanisms That Modulate Signalling by G–protein–coupled Receptors," *Biochemistry Journal* 322:1–18 (1997).
Bosse, et al., "Development of Nonseparation Binding and Functional Assays for G Protein–Coupled Receptors for High Throughput Screening: Pharmacological Characterization of the Immobilized CCR5 Receptor on FlashPlate®," *J. Biomol. Screening* 3:285–292 (1998).
Boulton, et al., "ERKs: A Family of Protein–Serine/Threonine Kinases That Are Activated and Tyrosine Phosphorylated in Response to Insulin and NGF," *Cell* 65:663–675 (1991).
Bruggemann, et al., "Production of Human Antibody Repertoires in Transgenic Mice," *Current Opinions in Biotechnology* 8:455–458 (1997).
Bruggemann, et al., "Strategies for Expressing Human Antibody Repertoires in Transgenic Mice," *Immunol. Today* 17:391–397 (1996).
Cane, et al., "Harnessing the Biosynthetic Code Combinations, Permutations, and Mutations," *Science* 282:63–68 (1998).
Cobbold, et al., "*Aequorin Measurements of Cytoplasmic Free Calcium*," in Cellular Calcium: A Practical Approach, (McCormack, et al., eds. Oxford, IRL Press 1991).
Cox, et al., "Cloning Characterization, and Expression of a G–Protein–Coupled Receptor from *Lymnaea stagnalis* and Identification of a Leucokinin–Like Peptide, PSFHSWSamide, as Its Endogenous Ligand," *J. Neurosci.* 17:1197–1205 (1997).
Day, et al., "Parasitic Peptides! The Structure and Function of Neuropeptides in Parasitic Worms," *Peptides* 20:999–1019 (1999).
de Bono, et al., "Natural Variation in a Neuropeptide Y Receptor Homolog Modifies Social Behavior and Food Response in *C. elegans,*" *Cell* 94:679–689 (1998).
Dooley, et al., Binding and In Vitro Activities of Peptides with High Affinity for the Nociceptin/Orphanin FQ Receptor, ORL1, *J. Pharm. & Exp. Therap.* 283:735–741 (1997).

(List continued on next page.)

Primary Examiner—Marjorie Moran
(74) Attorney, Agent, or Firm—Pharmacia & Upjohn Company; Edward F. Rehberg

(57) ABSTRACT

The invention provides neuropeptide ligands, G protein-coupled receptors and methods of screening for modulators of receptor activity. Identified modulators, including neuropeptide ligand mimetics, are useful as biostatic and biocidal agents of varying scope, ranging from lethal activity restricted to particular invertebrate parasites to broad spectrum invertebrate parasiticides active on a wide range of invertebrates, including helminths and insects.

21 Claims, 1 Drawing Sheet

OTHER PUBLICATIONS

Figure 1:
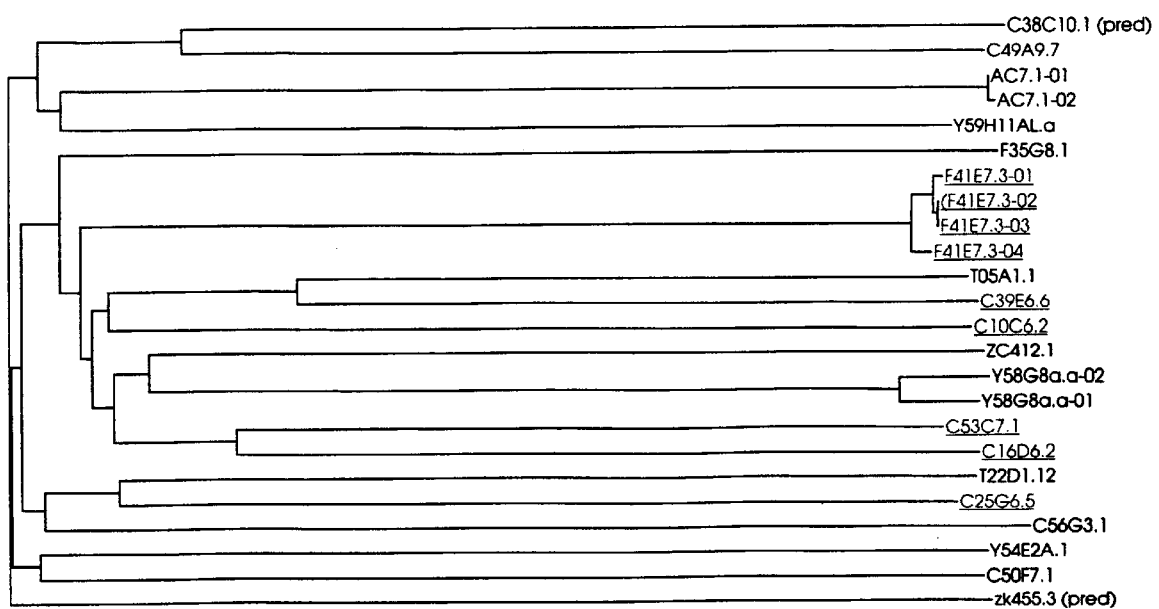

Dunlop, et al., Characterization of 5–HT$_{1A}$ Receptor Functional Coupling in Cells Expressing the Human 5–HT$_{1A}$ Receptor as Assessed with the Cytosensor Microphysiometer, *J. of Pharmacol. and Toxicol. Methods* 40:47–55 (1998).

Fields, et al., "A Novel Genetic System to Detect Protein–protein Interactions," *Nature* 340:245–246 (1989).

Fields, et al., "The Two–hybrid System: an Assay for Protein–protein Interactions," *Trends in Genetics* 10:286–292 (1994).

Frandsen, et al., "A Simple Ultrasensitive Method for the Assay of Cyclic AMP and Cyclic GMP in Tissues," *Life Sciences* 18:529–541 (1976).

Geary, et al., "Pharmacology of FMRFamide–Related Peptides in Helminths," *Annals N. Y. Acad. Sci.* 897:212–227 (1999).

Geary, et al., "The Pharmacology of FMRFamide–related Neuropeptides in Nematodes: New Opportunities for Rational Anthelmintic Discovery?," *International Journal of Parasitology* 25:1273–1280 (1995).

George, et al., "Evaluation of a CRE–Directed Luciferase Reporter Gene Assay as an Alternative to Measuring cAMP Accumulation," *J. Biomol. Screening* 2:235–240 (1997).

Gerhardt, et al., "Functional Characteristics of Heterologously Expressed 5–HT Receptors," *Eur. J. Pharmacol.* 334:1–23 (1997).

Guerrero, "Cloning of a cDNA from Stable Fly which Encodes a Protein with Homology to a Drosophila Receptor for Tachykinin–like Peptides," F.D., *Annals N.Y. Acad. Sci.* 814:310–311 (1997).

Hill, "Trends in Development of High–throughput Screening Technologies for Rapid Discovery of Novel Drugs," *Curr. Opin. In Drug Disc. & Dev.* 1:92–97 (1998).

Hodgson, "Receptor Screening and the Search for New Pharmaceuticals," *Bio/Technology* 10:973–980 (1992).

Holmes, et al., "Cloning and Transcriptional Expression of a Leucokinin–like Peptide Receptor from the Southern Cattle Tick, *Boophilus microplus* ( Acari: Ixodidae)," *Insect Mol. Biol.* (2000 in press).

Hoogenboom, "Designing and Optimizing Library Selection Strategies for Generating High–affinity Antibodies," *TIBTECH* 15:62–70 (1997).

Jaquette, et al., "Temperature Sensitivity of Some Mutants of Lutropin/Choriogonadotropin Receptor," *Endocrinology* 138:85–91 (1997).

Jayawickreme, et al., "Gene Expression Systems in the Development of High–throughput Screens," *Current Opinion in Biotechnology* 8:629–634 (1997).

Kanterman, et al., "Transfected D$_2$ Dopamine Receptors Mediate the Potentiation of Arachidonic Acid Release in Chinese Hamster Ovary Cells," *Molecular Pharmacology* 39:364–369 (1991).

Kowal, et al., "A [$^{35}$S]GTPγS Binding Assessment of Metabotropic Glutamate Receptor Standards in Chinese Hamster Ovary Cell Lines Expressing the Human Metabotropic Receptor Subtypes 2 and 4," *Neuropharmacology* 37:179–187 (1998).

Kozak, et al., "An Analysis of 5'–noncoding Sequences from 699 Vertebrate Messenger RNAs, " *Nucl. Acids Res.* 15:8125–8148 (1987).

Kuntzweiler, et al., "Rapid Assessment of Ligand Actions with Nicotinic Acetylcholine Receptors Using Calcium Dynamics and FLIPR," *Drug Development Research* 44:14–20 (1998).

Lajiness, et al., "D2 Dopamine Receptor Stimulation of Mitogenesis in Transfected Chinese Hamster Ovary Cells: Relationship to Dopamine Stimulation of Tyrosine Phosphorylations," *Journal of Pharmacology and Experimental Therapeutics* 267:1573–1581 (1993).

Lenz, et al., "Molecular Cloning and Genomic Organization of a Novel Receptor from *Drosophila melanogaster* Structurally Related to Mammalian Galanin Receptors," *Biochem. Biophys. Res. Comm.* 269:91–96 (2000).

Li, et al., "Neuropeptide Gene Families in the Nematode *Caenorhabditis elegans,*" *Annals N. Y. Acad. Sci.* 897:239–252 (1999).

Li, et al., "Cloning, Functional Expression, and Developmental Regulation of a Neuropeptide Y Receptor from *Drosophila melanogaster,*" *J. Biol. Chem.* 267:9–12 (1992).

Myers, P.L., "Will Combinatorial Chemistry Deliver Real Medicines?," *Current Opinion in Biotechnology* 8:701–707 (1997).

Nakayama, et al., "Microplate Assays for High–Throughput Screening," *Drug Disc. & Dev.* 1:85–91 (1998).

Pausch, M.H., "G–protein–coupled Receptors in *Saccharomyces cerevisiae*: High–throughput Screening Assays for Drug Discovery," *Trends in Biotech.* 15:487–494 (1997).

Radar, et al., "Phage Display of Combinatorial Antibody Libraries," *Current Opinions in Biotechnology* 8:503–508 (1997).

Rogers, "Light on High–throughput Screening: Fluorescence–based Assay Technologies," *Drug Disc. Today* 2:156–160 (1997).

Schroeder, et al., "FLIPR: A New Instrument for Accurate, High Throughput Optical Screening," *J. Biomol. Screening* 1:75–80 (1996).

Seifert, et al., "Reconstitution of β$_2$–adrenoceptor–GTP–binding–protein Interaction in Sf9 Cells High Coupling Efficiency in a B$_2$–adrenoceptor–G$_{sa}$ Fusion Protein," *Eur. J. Biochem.* 255:369–382 (1998).

Stables, et al., "A Bioluminescent Assay for Agonist Activity at Potentially Any G–Protein–Coupled Receptor," *Analytical Biochemistry* 252:115–126 (1997).

Stratowa, et al., "Use of a Luciferase Reporter System for Characterizing G–protein–linked Receptors," *Current Opinion in Biotechnology* 6:574–581 (1995).

Strosberg, et al., "Functional Expression of Receptors in Microorganisms," *Trends in Pharm. Science* 13:95–98 (1992).

Strosberg, "Structure/function Relationship of Proteins Belonging to the Family of Receptors Coupled to GTP–binding Proteins," *Eur. Journal of Biochemistry* 196:1–10 (1991).

Sutherlands, et al., "Some Aspects of the Biological Role of Adenosine 3',5'–monophosphate, (Cyclic AMP)," *Circulation* 37:279 (1968).

Sweetnam, et al., "The Role of Receptor Binding in Drug D," *J. Nat. Prod.* 56:441–455 (1993).

Tensen, et al., "The Lymnaea Cardioexcitatory Peptide (LyCEP) Receptor: A G–Protein–Coupled Receptor for a Novel Member of the RFamide Neuropeptide Family," *J. Neurosci.* 18:9812–9821 (1998).

Thompson, et al., "CLUSTAL W: Improving the Sensitivity of Progressive Multiple Sequence Alignment Through Sequence Weighting, Position–specific Gap Penalties and Weight Matrix Choice," *Nucl. Acids Res.* 22:4673–4680 (1994).

Thompson, et al., "Prospects for Rational Approaches to Anthelmintic Discovery," Parasitology 113:S217–S238 (1996).

Vanden Broeck, "G–Protein–Coupled Receptors in Insect Cells," *Intl. Rev. Cytol.* 164:189–268 (1996).

Wieboldt, et al., "Immunoaffinity Ultrafiltration with Ion Spray HPLC/MS for Screening Small–Molecule Libraries," *Anal. Chem.* 69:1683–1691 (1997).

Williams, "Receptor Binding in the Drug Discovery Process," *Med. Res. Review* 11:147–184 (1991).

Wilson, et al., "Orphan G–protein–coupled Receptors: The Next Generation of Drug Targets?," *Brit. Journal Pharmacol.* 125:1387–1392 (1998).

PCT/US/00/32225, International Search Report Dated Aug. 28, 2001.

Lee, et al., "Cloning and Expression of a G Protein–Linked Acetylcholine Receptor from *Caenorhabditis elegans,*" *J. Neurochem.* 72:58–65 (1999).

* cited by examiner-

G PROTEIN-COUPLED RECEPTOR-LIKE RECEPTORS AND MODULATORS THEREOF

This application claims benefit of U.S. Provisional Application No. 60/167,523, filed Nov. 24, 1999.

FIELD OF THE INVENTION

The present invention relates generally to G-protein, seven-transmembrane-receptor-like polynucleotides and polypeptides, as well as modulators of the interaction between the polypeptides and their ligand(s) that are useful for inhibiting the neurological activity of organisms, e.g., invertebrates.

BACKGROUND

It has been estimated that as many as one in three humans is infected by one or more species of parasitic helminth (flatworms and roundworms). Helminths also represent a chronic and continuing threat to the health of livestock and companion animals; their abundance and resistance to anthelmintic drugs effectively prevents animal agriculture in certain environments. Despite the prevalence of helminth-caused disease, little is known of helminth physiology. This ignorance, in turn, hampers efforts to identify agents capable of controlling these pathogens.

Flatworms (platyhelminths) are evolutionarily quite distinct from the roundworms (nematodes) and differ markedly in neuromuscular anatomy and physiology. Only a subset of one class of drugs (some of the benzimidazoles) shows activity against both flatworms and roundworms. The diversity among the animal species that threaten the health of man, livestock, crops, and sensitive environmental niches, presents a challenge to efforts to mount broad-based attacks on the pest organisms.

G protein-coupled receptors (i.e., GPCRs) form a vast superfamily of cell surface receptors which are present in virtually all animal cells and are characterized by an amino-terminal extracellular domain, a carboxy-terminal intracellular domain, and a serpentine structure that passes through the cell membrane seven times. Hence, such receptors are sometimes also referred to as seven transmembrane (7TM) receptors. These seven transmembrane domains define three extracellular loops and three intracellular loops, in addition to the amino- and carboxy-terminal domains. The extracellular portions of the receptor have a role in recognizing and binding one or more extracellular binding partners (e.g., ligands), whereas the intracellular portions have a role in recognizing and communicating with downstream effector molecules.

The G protein-coupled receptors bind a variety of ligands including calcium ions, hormones, chemokines, neuropeptides, neurotransmitters, nucleotides, lipids, odorants, and even photons. Not surprisingly, the GPCRs are important in the normal (and sometimes the aberrant) function of many cell types. [See generally Strosberg, Eur. J. Biochem., 196: 1–10 (1991) and Bohm et al., Biochem J., 322: 1–18 (1997).] When a specific ligand binds to its corresponding receptor, the ligand typically stimulates the receptor to activate a specific heterotrimeric guanine nucleotide-binding regulatory protein (G protein) that is coupled to the intracellular portion or region of the receptor. The G protein, in turn, transmits a signal to an effector molecule within the cell by either stimulating or inhibiting the activity of that effector molecule. These effector molecules include adenylate cyclase, phospholipases and ion channels. Adenylate cyclase and phospholipases are enzymes that are involved in the production of the second messenger molecules cAMP, inositol triphosphate and diacyglycerol. It is through this sequence of events that an extracellular ligand stimulus exerts intracellular changes through a G protein-coupled receptor. Each such receptor has its own characteristic primary structure, expression pattern, ligand binding profile, and intracellular effector system.

Because of the vital role of G protein-coupled receptors in the communication between cells and their environment, such receptors are attractive targets for therapeutic intervention, and drugs that activate or antagonize the activation of such receptors are known. For receptors having a known ligand, the identification of agonists or antagonists may be sought specifically for mimicking, enhancing or inhibiting the action of the ligand. Thus, GPCRs show promise as potential targets of methods for treating infestations and/or infections caused by a variety of invertebrate pests, including both ecto- and endo-parasites. However, such methods must be able to discriminate the GPCRs of the invertebrate pest organisms from the GPCRs found in those species of plants and vertebrate animals upon whom the pests prey.

A large family of peptides (typically 4–15 amino acids in length) that is largely, if not exclusively, found in invertebrate animals such as helminths is a class of neuropeptides known as FMRFamide related peptides (i.e., FaRPs). The prototypical FMRFamide peptides are so named because of the "FMRF" amino acid sequence, including the consensus "RF" sequence, at their C-termini. As neuropeptides, these molecules are involved in vital biological processes requiring controlled neuromuscular activity. Although some neurotransmitters and neuromodulators (including neuropeptides) have been shown to function as ligands for receptors, to date there has been no identification of a FaRP neuropeptide as a ligand of a GPCR.

Because of the toxic potential of broad-spectrum chemical parasiticides, there exists a need in the art for targeted biologicals capable of selectively interfering with the life cycle of harmful invertebrates such as helminths and insects without harming host plant and animal species, as well as the environment.

SUMMARY OF THE INVENTION

The present invention generally relates to materials and methods for the targeted interference with vital biological processes of pest invertebrates. By providing materials and methods for modulating the activity of invertebrate GPCRs involved in neuromuscular activity, the invention provides a biological approach to invertebrate pest control that can minimize the deleterious consequences to non-pest species of animals, including man, as well as plants and the environment in general.

One aspect of the invention is a screening method for identifying candidate anti-invertebrate modulators that affect one or more activities of an invertebrate GPCR-like receptor involved in neuromuscular functioning including, e.g., binding of a GPCR-like receptor to a ligand, typically a peptide ligand, and signal transduction. The method comprises the steps of: (a) contacting a test compound with a composition, wherein the composition contains a GPCR-like receptor encoded by a polynucleotide having a sequence selected from the group consisting of SEQ ID NOS: 1, 3, 5, 7, 9, 11, 13, 15, 17, 19, 21, 23, 25, 27, 29, 31, 33, 35, 37, 39, 41, 43, 45, 104, 106, 108, 110, 112, 114, 116, 176 and 178, or a polynucleotide hybridizing to the GPCR-like receptor under stringent conditions of hybridizing at 42° C. in a solution comprising 50% formamide, 1% SDS, 1 M NaCl, 10% dextran sulfate, and washing twice for 30 minutes at 60° C. in a wash solution comprising 0.1×SSC and 1% SDS; and (b) measuring the activity of the GPCR-like receptor in the presence and absence of the test compound. In preferred embodiments, the screening method includes a receptor, or fragment, variant or derivative thereof, having a sequence set forth in SEQ ID NOS: 7, 21, 25, 35, 43, 45, 105, 107, 109, 111, 113, 115, 117, 177 and 179.

As one of ordinary skill in the art would recognize, the above-described method can be practiced with a variety of GPCR-like receptors. For example, the GPCR-like receptor used in the screening method may be encoded by a polynucleotide having a sequence set forth in any one of SEQ ID NOS:43, 21, 45, 35, 7, 106, and 104. As noted above, such GPCR-like receptors may be used in screening assays designed to measure a GPCR-like receptor activity, including binding activity. Expressly contemplated are embodiments of the screening method comprising a GPCR-like receptor encoded by a polynucleotide comprising a sequence set forth in SEQ ID NO:43 and a peptide comprising a sequence selected from the group consisting of SEQ ID NOS:85, 86, 88, 89, and 118, wherein the peptide binds to the GPCR-like receptor. encoded by a polynucleotide having the sequence set forth in SEQ ID NO:43 is provided. In an alternative embodiment, the GPCR-like receptor comprises a sequence set forth in SEQ ID NO:21 and the peptide comprises a sequence selected from the group consisting of SEQ ID NOS:78, 79, 80, 84, 87, 92, 98, 100, 120, 171, 143, 122, 123, 97, 85, 83, 101, 102, 93, 88, 91, 94, 93, 90, 152, 153, 154, 155, 156, 157, 80, 158, 119, 159, 160, 161, 162, 163 and 164. Another embodiment involves a GPCR-like receptor comprising a sequence set forth in SEQ ID NO:45 and a peptide comprising a sequence selected from the group consisting of SEQ ID NOS:86, 118, 125, 88, 126, 127, 128, 129, 102, 131, 100, 133, 92, 135, 136, 137, 87, 139, 91, 141 and 83. In yet another embodiment, the GPCR-like receptor comprises a sequence set forth in SEQ ID NO:35 and a peptide comprising a sequence selected from the group consisting of SEQ ID NOS:99, 97, 96, 77, 82, 81, 87, 100, 92, 80, 98, 120, 121, 79 and 84. In still another embodiment, the GPCR-like receptor comprises a sequence set forth in SEQ ID NO:7 and a peptide comprising a sequence selected from the group consisting of SEQ ID NOS:94, 103, 95, 101, 85, 79, 84, 87, 86, 80, 92, 100, and 180. Yet another embodiment involves a GPCR-like receptor comprising a sequence selected from the group consisting of SEQ ID NO:106 and a peptide comprising a sequence selected from the group consisting of SEQ ID NOS:80, 92, 98, 100, 120, 121, 79, 84, 136, 87 and 86. Still another one of the many embodiments of this aspect of the invention involves a GPCR-like receptor comprising a sequence set forth in SEQ ID NO:104 and a peptide comprising a sequence selected from the group consisting of SEQ ID NOS:80, 92, 98, 100, 120, 121, 79, 84, 136, 87, 86, 150, 151, 133, 165, 91, 166, 131 and 167.

Another aspect of the invention is a method of identifying an anti-invertebrate modulator of an activity of an invertebrate GPCR-like receptor comprising the following steps: (a) contacting a test compound and a composition, wherein the composition contains a GPCR-like receptor selected from the group consisting of polypeptides encoded by a polynucleotide having a sequence selected from the group consisting of SEQ ID NOS: 1, 3, 5, 7, 9, 11, 13, 15, 17, 19, 21, 23, 25, 27, 29, 31, 33, 35, 37, 39, 41, 43, 45, 104, 106, 108, 110, 112, 114, 116, 176 and 178, or a polynucleotide hybridizing to the GPCR-like receptor under stringent conditions of hybridizing at 42° C. in a solution comprising 50% formamide, 1% SDS, 1 M NaCl, 10% Dextran sulfate, and washing twice for 30 minutes at 60° C. in a wash solution comprising 0.1×SSC and 1% SDS, optionally in the presence of a peptide or other ligand of the receptor; and (b) measuring the activity of the GPCR-like receptor in the presence and absence of the test compound. Modulators are identified as test compounds that alter (i.e., increase or decrease) a GPCR-like receptor function, such as a binding property of a receptor or an activity such as G protein-mediated signal transduction or membrane localization. The composition may contain an isolated GPCR-like receptor; alternatively, the composition may contain a GPCR-like receptor in association with, e.g., an intact cell or cell portion, such as a membrane. Presently preferred embodiments of the method use a GPCR-like receptor having an amino acid sequence set forth in SEQ ID NOS: 8, 22, 26, 36, 44, 105, 107, 109, 111, 113, 115, 117, 177 or 179. Preferred peptides are neuropeptides derived from invertebrates and include the FaRP family of neuropeptides. Particularly preferred are invertebrate neuropeptides having an amino acid sequence selected from the group consisting of SEQ ID NOS: 77–103 and 118–151. The methods of the invention embrace neuropeptides that are attached to a label, such as a radiolabel (e.g., $^{125}I$, $^{35}S$, $^{32}P$, $^{33}P$, $^{3}H$), a fluorescence label, a chemiluminescence label, an enzymic label and an immunogenic label.

In various embodiments of the method, the assay may take the form of an ion flux assay, a yeast growth assay, a non-hydrolyzable GTP assay such as a [$^{35}S$]-GTPγS assay, a cAMP assay, an inositol triphosphate assay, a diacylglycerol assay, an Aequorin assay, a Luciferase assay, a FLIPR assay for intracellular $Ca^{2+}$ concentration, a mitogenesis assay, a MAP Kinase activity assay, an arachidonic acid release assay (e.g., using [$^{3}H$]-arachidonic acid), and an assay for extracellular acidification rates, as well as other binding or function-based assays of GPCR activity that are generally known in the art. In several of these embodiments, the invention comprehends the inclusion of any of the G proteins known in the art, such as $G_{\alpha 16}$, $G_{\alpha 15}$, or chimeric $G_{qi5}$, $G_{qs5}$, $G_{qo5}$, or $G_{qz5}$.

In another aspect of the invention, a method of identifying a candidate anti-invertebrate modulator is provided. The method comprises the steps of: (a) contacting a test compound and a composition, wherein the composition contains a GPCR-like receptor encoded by a polynucleotide selected from the group consisting of receptor polyucleotides having a sequence set forth in SEQ ID NOS: 1, 3, 5, 7, 9, 11, 13, 15, 17, 19, 21, 23, 25, 27, 29, 31, 33, 35, 37, 39, 41, 43, 45, 104, 106, 108, 110, 112, 114, 116, 176 and 178, and polynucleotides hybridizing to the receptor polynucleotides under stringent conditions of hybridizing at 42° C. in a solution comprising 50% formamide, 1% SDS, 1 M NaCl, 10% dextran sulfate, and washing twice for 30 minutes at 60° C. in a wash solution comprising 0.1×SSC and 1% SDS; and (b) identifying a test compound that binds to or interacts with the composition as a candidate anti-invertebrate modulator. In a preferred embodiment, the polynucleotide encoding the GPCR-like receptor comprises a sequence selected from the group consisting of SEQ ID NOS: 7, 21, 25, 35, 43, 45, 105, 107, 109, 111, 113, 115, 117, 177 and 179.

Another aspect of the invention is a method of identifying an anti-invertebrate agent comprising the following steps: (a) identifying a modulator using the method described above; (b) contacting the modulator and an invertebrate tissue; and (c) measuring the response of the invertebrate tissue, e.g. neural signaling or neuromuscular activity, thereby identifying the modulator as an anti-invertebrate agent. Although any invertebrate tissue may be used in the method, presently preferred tissue sources are helminths and insects. An exemplary type of suitable invertebrate tissue is neuromuscular tissue, e.g. in isolated form or remaining in association with part, or all, of an invertebrate organism. The anti-invertebrate agents, and compositions comprising one of those agents, identified by this method constitute yet another aspect of the invention.

In a related aspect, the invention provides a method for treating an invertebrate comprising the step of contacting the invertebrate with a biologically effective amount of a modulator identified by the methods described herein. A biologically effective amount of a modulator is an amount that is sufficient to induce a desired response in the treated invertebrate. Thus, a biologically effective amount of a modulator may be the amount that interferes with physiological activity of the treated invertebrate in a non-lethal manner (i.e., a biostatic effect) or in a lethal manner (i.e., a biocidal effect). A preferred modulator for use in the treatment methods is an inhibitor of GPCR-like receptor activity. The invention is not limited to particular means for delivering the modulator to an invertebrate, nor is the invention limited as to the compositions comprising the modulator which may be delivered.

Another aspect of the invention is drawn to methods of producing an invertebrate GPCR-like receptor comprising the following steps:(a) incubating a source cell at a temperature of at least about 35° C.; (b) lowering the temperature to at most about 26° C.; and (c) detecting the GPCR-like receptor. In various embodiments, the temperatures may be varied to optimize production using no more than routine experimentation. For example, the cells may be incubated at temperatures higher than about 35° C., e.g., a temperature of at least about 37° C.; the temperature also may be lowered beyond 30° C., for example to at most 29° C., at most 28° C., at most 27° C., at most 26° C., at most 25° C. or at most 24° C. In some embodiments, both the incubation temperature may be raised above 35° C. and the temperature lowering may extend beyond 30° C. The method of producing an invertebrate GPCR-like receptor may further comprise recovering the GPCR-like receptor, which may be native or recombinant in origin. The receptor may be recovered in intact cells, cell portions (e.g., membranes) obtained as a result of cell lysis, or in isolated form. Any of a wide variety of cells may be used as source cells, such as cells derived from mammals, amphibians, arthropods (e.g., insects), mollusks, helminths, and others. It is anticipated that this method of producing a GPCR-like receptor is particularly suited to the recombinant production of GPCR-like receptors using non-invertebrate cells, such as mammalian cells.

The invention also comprehends compositions of matter, such as a modulator of an activity of the GPCR-like receptors identified by the methods described herein. The modulators of the invention exhibit a variety of chemical structures, which can be generally grouped into non-peptide mimetics of natural GPCR-like receptor ligands, peptide and non-peptide allosteric effectors of GPCR-like receptors, and peptides and non-peptide compounds that function as activators or inhibitors (competitive, uncompetitive and non-competitive) (e.g., antibody products) of an ultimate GPCR-like receptor activity. For example, such modulators may be compounds or compositions that are agonists or antagonists of ligand binding to a GPCR-like receptor, allosteric effectors thereof, or compounds (or compositions) that affect the ultimate activity of GPCR-like receptors through direct action on the receptor or an effect introduced downstream of the receptor in, e.g., a signal cascade. In addition, modulators according to the invention may be compounds or compositions that interfere with the expression of a GPCR-like receptor, either through inhibiting transcription of the DNA or translation of the corresponding mRNA. Expression of the GPCR-like receptor can be monitored by any methods known in the art, including Western blot analysis using polyclonal or monoclonal antibodies to the GPCR-like receptor or Northern blot analysis or quantitative polymerase chain reaction (PCR) using suitable probes or primers based on the sequence of the GPCR-like receptor gene. In particular, modulators that interfere with the expression of gene products include anti-sense polynucleotides and ribozymes that are complementary to the gene sequences. The invention further embraces modulators that affect the transcription of gene products of the invention through the formation of oligonucleotide-directed triplet helix formation. The invention does not restrict the sources for suitable modulators, which may be obtained from natural sources such as plant, animal or mineral extracts, or non-natural sources such as small molecule libraries, including the products of combinatorial chemical approaches to library construction, and peptide libraries. Preferred peptide receptors have an amino acid sequence selected from the group consisting of SEQ ID NOS: 8, 22, 26, 36, 44, 105, 107, 109, 111, 113, 115, 117, 177 or 179.

Another aspect of the invention is drawn to an isolated GPCR-like receptor comprising a sequence selected from the group consisting of SEQ ID NOS: 2, 4, 6, 8, 10, 12, 14, 16, 18, 20, 22, 24, 26, 28, 30, 32, 34, 36, 38, 40, 42, 44, 46, 105, 107, 109, 111, 113, 115, 117, 177, and 179, and variants and fragments thereof. Preferred receptors have sequences set forth in SEQ ID NOS: 8, 22, 26, 36, 44, 105, 107, 109, 111, 113, 115, 117, 177 and 179. Variants and fragments of GPCR-like receptors retain at least one biological or immunological property of the cognate GPCR-like receptor, and are at least 10, at least 15, at least 20, at least 25, at least 30, at least 40, at least 50, at least 60, at least 70, at least 225, 80, at least 90, at least 100, at least 125, at least 150, at least 175, at least 200, at least 225, at least 250, at least 275, at least 300, at least 325, at least 350, at least 375, at least 400, at least 425, or at least 450 amino acids in length. Fragments specifically include GPCR domains of the receptors. Biological activities of GPCR-like receptors according to the invention include, but are not limited to, the binding of a natural or an unnatural ligand, as well as any one of the functional activities of GPCRs known in the art. Other non-limiting examples of GPCR activities include transmembrane signaling of various forms, which may involve G protein association and/or the exertion of an influence over G protein binding of various guanidylate nucleotides; transmembrane localization; or binding of accessory proteins or polypeptides unrelated to known G proteins.

The invention also provides an isolated polynucleotide encoding a GPCR-like receptor. Such polynucleotides may be selected from the group consisting of: (a) a polynucleotide comprising a nucleotide sequence encoding any one of the amino acid sequences set forth in SEQ ID NOS: 2, 4, 6, 8, 10, 12, 14, 16, 18, 20, 22, 24, 26, 28, 30, 32, 34, 36, 38, 40, 42, 44, 46, 105, 107, 109, 111, 113, 115 117, 177, and 179 (including the nucleotide sequences set forth in SEQ ID NOS: 1, 3, 5, 7, 9, 11, 13, 15, 17, 19, 21, 23, 25, 27, 29, 31, 33, 35, 37, 39, 41, 43, 45, 104, 106, 108, 110, 112, 114, 116, 176, and 178); and (b) a polynucleotide which hybridizes under conditions of high stringency to the complement of the polynucleotide of (a). Exemplary conditions of high stringency are provided below. Such polynucleotides also include polynucleotides that exhibit at least 90%, at least 95%, at least 98%, at least 99% or at least 99.9% sequence identity to either a polynucleotide sequence disclosed in the sequence listing (i.e., SEQ ID NOS: 1, 3, 5, 7, 9, 11, 11, 13, 15, 17, 19, 21, 23, 25, 27, 29, 31, 33, 35, 37, 39, 41, 43, 45, 104, 106, 108, 110, 112, 114, 116, 176 and 178) or to a polynucleotide encoding a GPCR-like receptor comprising one of the sequences disclosed in the sequence listing (i.e., SEQ ID NOS: 2, 4, 6, 8, 10, 12, 14, 16, 18, 20, 22, 24, 26, 28, 30, 32, 34, 36, 38, 40, 42, 44, 46, 105, 107, 109, 111, 113, 115, 117, 177, and 179). Any one of the publicly available algorithms (e.g., the BLAST1 program of GCG) for comparing sequences may be used in determining the degree of sequence similarity (including appropriate penalties for gap introductions). A preferred algorithm is the BLAST algorithm implemented at the GenBank website under the auspices of the National Center for Biotechnology Information A on the World Wide Web at ncbi.nlm.nih.gov/BLAST/ using default parameters. A polynucleotide of the invention may be partially or wholly chemically synthesized and embraces an anti-sense polynucleotide which specifically hybridizes to the complement of one or more of the above-described polynucleotides. In related aspects, the invention comprehends vectors comprising these polynucleotides preferably operably linked to expression control sequences, including expression vectors, as well as non-native host cells transformed or transfected with a polynucleotide in accordance with the invention or a host cell transformed or transfected with a vector of the invention. All suitable native and non-native host cells are embraced by the invention, including mammalian cells (e.g., COS cells, CHO cells, HEK293 cells), insect cells (e.g., *Drosophila melanogaster* S2 cells, *Spodoptera frugiperda* Sf9 cells, High-5 cells), yeast cells, bacterial cells (e.g., *E. coli*) and helminthic cells. The suitability of a particular cell for use as a host cell in accordance with the invention will depend on the ability to introduce a polynucleotide of the invention into the cell by any known means of transformation or transfection. Preferred host cells will also be capable of stably maintaining the introduced polynucleotide and will present a minimum of obstacles to propagation.

Another aspect of the invention is directed to a genetically modified invertebrate comprising a polynucleotide encoding a heterologous GPCR-like receptor (e.g., transgene) as described above or comprising a modification in a native gene encoding a GPCR-like receptor (e.g., an insertional disruption or deletion of the gene). The GPCR-like receptor encoding gene may be expressed at normal levels for that gene or may be overexpressed or underexpressed. A preferred invertebrate for generation of genetically modified organisms is a member of the helminths.

Yet another aspect of the invention is drawn to diagnostic methods for determining neurological abnormalities associated with aberrant GPCR-like receptor activity. Such methods specifically measure the presence, and optionally quantity, of a GPCR-like receptor polynucleotide according to the invention or the presence, and optionally quantity or activity, of a GPCR-like receptor. Any method known in the art may be used to measure the specific polynucleotides or polypeptides of the invention, and measurements may be performed on intact organisms, isolated tissues, or cell cultures. In a related aspect, the invention contemplates methods for diagnosing invertebrate infestation of an organism (e.g., mammals such as humans, mammalian livestock, other vertebrates such as fish, and non-pest invertebrates such as molluscs) or an environment using a specific measurement of a polynucleotide or polypeptide according to the invention.

Another aspect of the invention is directed to treatment methods. The invention contemplates methods of killing or inhibiting the viability of invertebrates using the modulators described above or identified as described above, including antibodies and antisense polynucleotides. Such methods include methods for treating infestations and/or infections caused by a variety of invertebrate pests, including both ecto- and endo-parasites. A variety of human and other animal ailments, particularly those ailments relating to aberrant neurological functioning, are treated by administering a biologically effective amount of a modulator, GPCR-like receptor polynucleotide or GPCR-like receptor to a cell, tissue, organism, or environment using techniques known in the art.

Use of such modulators in the preparation of a medicament for treating parasitic infection is also contemplated. A variety of administration regimens known in the art are available to deliver a therapeutically effective (i.e., a level of activity capable of deleteriously affecting at least one biological process of a parasite, or more generally, of a pest organism) activity level of a modulator, directly or indirectly, to a parasite or pest, or to an environment associated with the parasite or pest.

Numerous additional aspects and advantages of the invention will become apparent to those skilled in the art upon consideration of the following detailed description of the preferred embodiments of the invention.

DETAILED DESCRIPTION OF THE PREFERRED EMBODIMENTS

The present invention has several aspects, one of which is modulating the activity of invertebrate G protein-coupled receptors, which is useful in controlling a wide variety of pest organisms that affect the health of humans and other animals such as domestic pets and livestock, as well as plants. The G protein-coupled receptors typically transduce signals involved in the neurophysiological functioning of the target invertebrates and interference with that functioning frequently proves fatal to the target organism. Moreover, these receptors are found only in invertebrates, so that specific modulators are safe for use around humans, as well as their pets, livestock, and crops.

A "GPCR-like receptor" is a polypeptide receptor exhibiting the structural characteristics of G protein-coupled receptors (GPCRs), i.e., an N-terminal extracellular region, comprising several loop-like domains (typically three), a transmembrane region comprising seven transmembrane domains arranged in a typical serpentine disposition, and an intracellular region comprising several loop-like domains (typically three).

Invertebrate neuropeptides show profound neuromuscular effects and FaRPs represent the largest family of such neuropeptides known to date. A "FaRP" is a "FMRFamide-related peptide." A "FMRFamide," in turn, is a relatively small peptide, typically having 4–15 amino acids, that matches at least three of the four listed amino acids (FMRF) at its C-terminus. Generally, FaRPs exhibit neurophysiological effects and are therefore properly grouped in a class of neuropeptides that frequently function as ligands of GPCR-like receptors. A "modulator" is an effector of a GPCR-like receptor function, which include the binding of one or more ligands, localization to a membrane, and signal transduction. Signal transduction may involve a change in the relative affinities of a GPCR-associated G protein for various guanidylate nucleotides. With respect to polynucleotides and polypeptides of the invention, "synthesized," as used herein and understood in the art, refers to polynucleotides or polypeptides produced by purely chemical, as opposed to enzymatic, methods. "Wholly" synthesized sequences are therefore produced entirely by chemical means, and "partially" synthesized sequences embrace those wherein only portions of the resulting polynucleotide or polypeptide were produced by chemical means.

The present invention provides purified and isolated polynucleotides (e.g., DNA sequences and RNA transcripts, both sense and complementary antisense strands, including splice variants thereof) encoding invertebrate G protein-coupled receptors. DNA polynucleotides of the invention include genomic DNA, cDNA, and DNA that has been chemically synthesized in whole or in part.

Genomic DNA of the invention comprises the protein coding region for a polypeptide of the invention and includes allelic variants thereof. It is widely understood that, for many genes, genomic DNA is transcribed into RNA transcripts that undergo one or more splicing events wherein intron (i.e., non-coding regions) of the transcripts are removed, or "spliced out." RNA transcripts that can be spliced by alternative mechanisms, and therefore be subject to removal of different RNA sequences but still encode the same polypeptide, are referred to in the art as splice variants. Splice variants therefore are encoded by the same original genomic DNA sequences but arise from distinct mRNA transcripts found in at least one cell. By way of non-limiting example, several embodiments of the invention are characterized by one of the particular splice variants identified in Table 1, below.

TABLE 1

| SEQ ID NO | Name | Wormpep sequence | Difference(s) |
|---|---|---|---|
| 1 | CEGPCR1a[1] | AC7.1 | 94 bp deletion between nucleotides 594–595 of SEQ ID NO:1 |
| 3 | CEGPCR1f | AC7.1 | 94 bp deletion between nucleotides 594–595 of SEQ ID NO:3; addition of nucleotides 868–912 of SEQ ID NO:3 |
| 5 | CEGPCR12c | F41E7.3 | 90 bp addition at 5' end of SEQ ID NO:5; deletion of 52 bp between nucleotides 173–174 of SEQ ID NO:5; deletion of 6 bp between nucleotides 1115–1116 of SEQ ID NO:5 |
| 7 | CEGPCR12h | F41E7.3 | 90 bp addition at 5' end of SEQ ID NO:7; deletion of 52 bp between nucleotides 173–174 of SEQ ID NO:7; deletion of 12 bp between nucleotides 1115–1116 of SEQ ID NO:7 |
| 9 | CEGPCR12u | F41E7.3 | 90 bp addition at 5' end of SEQ ID NO:9; deletion of 52 bp between nucleotides 173–174 of SEQ ID NO:9 |
| 11 | CEGPCR12v | F41E7.3 | 90 bp addition at 5' end of SEQ ID NO:11; deletion of 52 bp between nucleotides 173–174 of SEQ ID NO:11; addition of 97 bp between nucleotides 1115–1212 of SEQ ID NO:11 |

[1]The "CEGPCR" labeling system used herein corresponds to the "PNU" labeling system used in related USSN 60/162,523 (e.g., CEGPCR1a corresponds to PNU1a).

| SEQ ID NO | Name | Wormpep sequence | Difference(s) |
|---|---|---|---|
| 17 | CEGPCR18a | Y54E2A.1 | deletion of 58 bp between nucleotides 1089–1090 of SEQ ID NO: 17; deletion of 32 bp between nucleotides 1331–1332 of SEQ ID NO:17 |
| 106 | CEGPCR19.1 | Y58G8a.1 | |
| 104 | CEGPCR19.2 | Y58G8a.2 | |
| 114 | CECPCR24a | Y59H11A1.a-01 | |
| 116 | CEGPCR24b | Y59H11A1.a-02 | |

Allelic variants are modified forms of a wild-type gene sequence, the modification resulting from recombination during chromosomal segregation or exposure to conditions which give rise to genetic mutation. Allelic variants, like wild type genes, are naturally occurring sequences (as opposed to non-naturally occurring variants which arise from in vitro manipulation), and are also comprehended by the invention.

The invention also comprehends cDNA that is obtained through reverse transcription of an RNA polynucleotide encoding invertebrate GPCR-like receptors (conventionally followed by second strand synthesis of a complementary strand to provide a double-stranded DNA). In addition to cDNA forms of the polynucleotides identified in Table 1 as splice variants, preferred cDNAs according to the invention include those polynucleotides having sequences selected from the group consisting of SEQ ID NOS: 13, 15 and 21. These sequences differ from sequences in the Wormpep database that exhibit some similarity thereto, as shown in Table 2.

TABLE 2

| SEQ ID NO | Name | Wormpep sequence | Difference(s) |
|---|---|---|---|
| | CEGPCR1a cegpcr1(a,f), cegpcr4, cegpcr5, cegpcr11, cegpcr12(c,h,u,v), cegpcr13, cegpcr14, cegpcr18, cegpcr19(L,S), cegpcr22, cegpcr24(a,b) | | |
| 21 | CEGPCR4 | C16D6.2 | deletion of 55 bp between nucleotides 1070–1071 of SEQ ID NO:21 |
| | CEGPCR5 CEGPCR11 CEGPCR12c CEGPCR12h CEGPCR12u CEGPCR12v | | |
| 13 | CEGPCR13 | T05A1.1 | deletion of 85 bp between nucleotides 753–754 of SEQ ID NO:13; addition of 226 bp between nucleotides 926–1152 of SEQ ID NO:13 |
| 15 | CEGPCR14 | ZC412.1 | deletion of 92 bp between nucleotides 1277–1278 of SEQ ID NO:15 |
| 17 | CEGPCR18a | Y54E2A.1a | |
| 106 | CEGPCR19.1 | Y58G8a.1 | |
| 104 | CEGPCR19.2 | Y58C8a.2 | |
| 110 | CEGPCR22 | C06G4.5 | |
| 114 | CEGPCR24a | Y59H11A L.a | |
| 116 | CEGPCR24b | Y59H11A L.b | |

Preferred DNA sequences encoding invertebrate GPCR-like receptor polypeptides are set out in SEQ ID NOs: 1, 3, 5, 7, 9, 11, 13, 15, 17, 19, 21, 23, 25, 27, 29, 31, 33, 35, 37, 39, 41, 43, 45, 104, 106, 108, 110, 112, 114, 116, 176 and 178. A preferred DNA of the invention comprises a double stranded molecule (for example, the molecule having one of the sequences set forth in the above-referenced SEQ ID NOs, along with the complementary molecule (the "non-coding strand" or "complement") having a sequence unambiguously deducible from one of those sequences, according to Watson-Crick base-pairing rules for DNA). Also preferred are other polynucleotides encoding one of the invertebrate GPCR-like receptor polypeptides of SEQ ID NOs: 2, 4, 6, 8, 10, 12, 14, 16, 18, 20, 22, 24, 26, 28, 30, 32, 34, 36, 38, 40, 42, 44, 46, 105, 107, 109, 111, 113, 115, 117, 177, and 179 which may differ in sequence from the corresponding polynucleotides of SEQ ID NOs: 1, 3, 5, 7, 9, 11, 13, 15, 17, 19, 21, 23, 25, 27, 29, 31, 33, 35, 37, 39, 41, 43, 45, 104, 106, 108, 110, 112, 114, 116, 176 and 178 by virtue of the well-known degeneracy of the universal genetic code.

The invention further embraces invertebrate species (preferably helminth and insect) homologs of the disclosed GPCR-like DNAs. Species homologs, sometimes referred to as "orthologs," in general share at least 35%, at least 40%, at least 45%, at least 50%, at least 60%, at least 65%, at least 70%, at least 75%, at least 80%, at least 85%, at least 90%, at least 95%, at least 98%, or at least 99% similarity with the DNA sequences disclosed herein. Percent sequence "similarity" with respect to polynucleotides of the invention is defined herein as the percentage of nucleotide bases in the candidate sequence that are identical to nucleotides in the relevant sequences set forth in the sequence listing below, after aligning the sequences and introducing gaps, if necessary, to achieve the maximum percent sequence identity. Preferred for comparative sequence analyses is the BLAST program available from GCG, implemented with default parameters. Also preferred is the Blastall program available from NCBI.

The polynucleotide sequence information provided by the invention makes possible large scale expression of an encoded polypeptide by techniques well known and routinely practiced in the art. Polynucleotides of the invention also permit identification and isolation of polynucleotides encoding related GPCR-like polypeptides, such as the aforementioned allelic variants and species homologs, by well known techniques including Southern and/or Northern hybridization, and by polymerase chain reaction (PCR). Examples of related polynucleotides include polynucleotides encoding polypeptides homologous to the invertebrate GPCRs and structurally related polypeptides sharing one or more biological, immunological, and/or physical properties of those GPCRs. Invertebrate genes encoding proteins homologous to the disclosed GPCRs can also be identified by Southern and/or PCR analysis and are useful in methods of the invention described below. Knowledge of the sequence of the disclosed GPCR-encoding DNAs also makes possible, through use of Southern hybridization, polymerase chain reaction (PCR), and other known techniques, the identification of genomic DNA sequences encoding GPCR expression control regulatory sequences such as promoters, operators, enhancers, repressors, and other regulatory sequences known in the art. Polynucleotides of the invention are also useful in hybridization assays to detect the capacity of cells to express an invertebrate GPCR.

The disclosure herein of a full-length polynucleotide encoding invertebrate GPCR-like polypeptides makes readily available to the worker of ordinary skill in the art every possible fragment of the full-length polynucleotides. The invention therefore provides fragments of invertebrate GPCR-encoding polynucleotides comprising at least 14–15, and preferably at least 18, 20, 25, 50, or 75 consecutive nucleotides of a polynucleotide encoding an invertebrate GPCR.

Fragment polynucleotides contemplated by the invention encode immunologically active peptides capable of interacting with specific anti-GPCR antibodies, as well as domains of GPCRs. The GPCR domains (i.e., the N-terminal extracellular domain, one or more of the three extracellular loop domains, one or more of the seven transmembrane domains, one or more of the three intracellular loop domains, or the C-terminal intracellular domain) of invertebrate GPCRs disclosed herein are characterized in Example 2 and Table 6, below. Full length or fragment polynulcleotides can be linked to polynucleotides encoding heterologous polypeptides, e.g., for producing variants that are fusion proteins.

Preferably, fragment polynucleotides of the invention comprise sequences unique to one of the disclosed GPCR-encoding sequences, and therefore hybridize under highly stringent or moderately stringent conditions only (i.e., "specifically") to polynucleotides encoding a disclosed invertebrate GPCR (or fragments thereof) and not to polynucleotides encoding other GPCRs. Polynucleotide fragments of genomic sequences of the invention comprise not only sequences unique to the coding region, but also fragments of the full-length sequence derived from introns, regulatory regions, and/or other non-translated sequences. Sequences unique to polynucleotides of the invention are recognizable through sequence comparison to other known polynucleotides, and can be identified through use of alignment programs routinely utilized in the art, e.g., those made available in public sequence databases. Such sequences also are recognizable from Southern hybridization analyses to determine the number of fragments of genomic DNA to which a polynucleotide will hybridize. Polynucleotides of the invention can be labeled in a manner that permits their detection, including radioactive, fluorescent, and enzymatic labeling.

Fragment polynucleotides are particularly useful as probes for detection of full-length invertebrate GPCR-like polynucleotides, or other polynucleotide fragments thereof. One or more fragment polynucleotides can be included in kits that are used to detect the presence of a polynucleotide encoding an invertebrate GPCR-like receptor polypeptide, or used to detect variations in a polynucleotide sequence encoding such a polypeptide.

The invention also embraces DNAs encoding invertebrate GPCR-like polypeptides that hybridize under conditions of moderate or high stringency to the non-coding strand, or complement, of a polynucleotide comprising one of the sequences set forth in SEQ ID NOs: 1, 3, 5, 7, 9, 11, 13, 15, 17, 19 21, 23, 25, 27, 29, 31, 33, 35, 37, 39, 41, 43, 45, 104, 106, 108, 110, 112, 114, 116, 176 and 178.

Exemplary conditions of high stringency are as follows: hybridization at 42° C. in a solution (i.e., a hybridization solution) comprising 50% formamide, 1% SDS, 1 M NaCl, 10% Dextran sulfate, and washing twice for 30 minutes at 60° C. in a wash solution comprising 0.1×SSC and 1% SDS. It is understood in the art that conditions of equivalent stringency can be achieved through variation of temperature and buffer, or salt concentration, as described in Ausubel, et al. (Eds.), *Protocols in Molecular Biology*, John Wiley & Sons (1994), pp.6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), *Molecular Cloning: A Laboratory Manual*, Cold Spring Harbor Laboratory Press: Cold Spring Harbor, N.Y. (1989), pp. 9.47 to 9.51.

The invention also provides a purified and isolated invertebrate GPCR-like polypeptide encoded by a polynucleotide of the invention. Presently preferred is a polypeptide comprising one of the amino acid sequences set out in SEQ ID NOs: 2, 4, 6, 8, 10, 12, 14, 16, 18, 20, 22, 24, 26, 28, 30, 32, 34, 36, 38, 40, 42, 44, 46, 105, 107, 109, 111, 113, 115, 117, 177, and 179, and species homologs thereof. The invention also embraces a GPCR-like polypeptide encoded by a DNA selected from the group consisting of: (a) the DNA sequence set out in any one of SEQ ID NOs: 1, 3, 5, 7, 9, 11, 13, 15, 17, 19, 21, 23, 25, 27, 29, 31, 33, 35, 37, 39, 41, 43, 45, 104, 106, 108, 110, 112, 114, 116, 176 and 178 and species homologs thereof, and (b) a DNA molecule encoding a GPCR-like gene product that hybridizes under conditions of moderate or high stringency to the DNA of (a). The invention further embraces polypeptides that have at least about 99%, at least about 95%, at least about 90%, at least about 85%, at least about 80%, at least about 75%, at least about 70%, at least about 65%, at least about 60%, at least about 55%, and at least about 50% identity and/or homology to the preferred polypeptides of the invention. Percent amino acid sequence "identity" with respect to the preferred polypeptides of the invention is defined herein as the percentage of amino acid residues in the candidate sequence that are identical with the residues in the GPCR-like gene product sequence after aligning both sequences and introducing gaps, if necessary, to achieve the maximum percent sequence identity, and not considering any conservative substitutions as part of the sequence identity. Percent sequence "homology" with respect to the preferred polypeptides of the invention is defined herein as the percentage of amino acid residues in the candidate sequence that are identical with the residues in one of the GPCR-like receptor polypeptide sequences after aligning the sequences and introducing gaps, if necessary, to achieve the maximum percent sequence identity, and also considering any conservative substitutions as part of the sequence identity. Conservative substitutions are defined as set out in Tables 3 and 4.

GPCR polypeptides of the invention may be isolated from natural invertebrate cell sources or may be chemically synthesized, but are preferably produced by recombinant procedures involving host cells of the invention. GPCR-like gene products of the invention may be full-length polypeptides, biologically active fragments, or variants thereof which retain specific biological or immunological activity. Variants may comprise GPCR-like polypeptide analogs wherein one or more of the specified (i.e., naturally encoded) amino acids is deleted or replaced or wherein one or more non-specified amino acids are added: (1) without loss of one or more of the biological activities or immunological characteristics specific for the GPCR-like receptor; or (2) with specific disablement of a particular biological activity of the GPCR-like polypeptide. Contemplated deletion variants also include fragments lacking portions of a GPCR-like polypeptide not essential for biological activity, and insertion variants include fusion polypeptides in which the wild-type GPCR-like polypeptide or fragment thereof has been fused to another polypeptide.

TABLE 3

Conservative Substitutions I

| SIDE CHAIN CHARACTERISTIC | | AMINO ACID | | | | | |
|---|---|---|---|---|---|---|---|
| Aliphatic | Non-polar | G | A | P | I | L | V |
| | Polar-uncharged | C | S | T | M | N | Q |
| | Polar-charged | D | E | K | R | | |
| Aromatic | | H | F | W | Y | | |
| Other | | N | Q | D | E | | |

TABLE 4

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W Y |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

Variant GPCR-like polypeptides include those wherein conservative substitutions have been introduced by modification of polynucleotides encoding polypeptides of the invention. Conservative substitutions are recognized in the art to classify amino acids according to their related physical properties and can be defined as set out in Table 3. (See, WO 97/09433, page 10, published Mar. 13, 1997 (PCT/GB96/02197, filed Sep. 6, 1996).) Alternatively, conservative amino acids can be grouped as defined in Lehninger, [*Biochemistry*, Second Edition; Worth Publishers, Inc. NY:NY (1975), pp.71–77] as set out in Table 4.

Variant GPCR-like polypeptides of the invention include mature GPCR-like gene products, i.e., wherein leader or signal sequences are removed, having additional amino terminal residues. GPCR-like gene products having an additional methionine residue at position-1 are contemplated, as are GPCR-like receptors having additional methionine and lysine residues at positions-2 and -1. Variants of these types are particularly useful for recombinant protein production in bacterial cell types. Variants of the invention also include gene products wherein amino terminal sequences derived from other proteins have been introduced, as well as variants comprising amino terminal sequences that are not found in naturally occurring proteins.

Another component useful in some methods for identifying modulators of GPCR-like receptor activity, described below, is a class of neuropeptides that includes FaRPs. The FaRPs comprise a large family of peptides that typically function as neurotransmitters in the invertebrate nervous system. The FaRPs that are associated with these neurophysiological functions generally are about four to about nine amino acid residues in length and include a C-terminal amino acid sequence motif of (aromatic)-X-R-Famide, where X is typically M, L, I or V. Day et al., Peptides 20:999–1019 (1999), which is incorporated by reference in its entirety. However, peptides that are exceptions to this rule are also contemplated by the invention, particularly those that are co-encoded on FaRP precursor genes or those that share the characteristics of conforming peptides. Also contemplated by the invention are neuropeptide variants, including FaRP variants, peptides exhibiting an RYamide motif, and other peptides such as retro-inverso neuropeptides (e.g., FaRPs comprising the D stereoisomers of amino acids in a sequence that is reversed from a reference FaRP). For example a retro-inverso variant of $A_L$-$F_L$-$M_L$-$R_L$-$F_L$ would be $F_D$-$R_D$-$M_D$-$F_D$-$A_D$.

Neuropeptides such as FaRPs have been found in a wide variety of invertebrates, including arthropods such as insects (e.g., locusts and flies such as Drosophila) and lobsters, mollusks such as the snail *Lymnaea stagnalis*, and helminths such as nematodes (e.g., *C. elegans, A. suum, Haemonchus contortus*), trematodes (e.g., *Schistosoma mansoni*) and cestodes, among others, including Manduca. Information relating to the structure, function, and structure-function relationships of these neuropeptides is known in the art [Day et al. (1999)]. Table 5 below provides a classification of several known *C. elegans* FaRPs, which are examples of the class of neuropeptides useful in practicing the invention.

TABLE 5

*C. elegans* FMRFamide-related peptides (FaRPs) and encoding genes

| GENE AND CHROMOSOME NUMBER | STRUCTURALLY CHARACTERIZED FaRPs | PEPTIDES PREDICTED FROM GENE |
|---|---|---|
| FLP-1 | SDPNFLRFa | KPNFMRYa |
| | SADPNFLRFa | AGSDPNFLRFa |
| | | SQPNFLRFa |
| | SQPNFLRFa | ASGDPNFLRFa |
| | ASGDPNFLRFa | SDPNFLRFa |
| | AAADPNFLRFa | AAADPNFLRFa |
| | | SADPNFLRFa |
| | | KPNFLRFa |
| FLP-2 | | LRGEPIRFa |
| | | SPREPIRFa |
| FLP-3 | | SPLGTMRFa |
| | | TPLGTMRFa |
| | | SAEPFGTMRFa |
| | | NPENDTPFGTMRFa |
| | | ASEDALFGTMRFa |
| | | EDGNAPFGTMRFa |
| | | EAEEPLGTMRFa |
| | | SADDSAPFGTMRFa |
| | | NPLGTMRFa |
| FLP-4 | | PTFIRFa |
| | | ASPSFIRFa |
| FLP-5 | | APKPKFIRFa |
| | | AGAKFRFa |
| | | GAKFIRFa |
| FLP-6 | KSAYMRFa | (6 copies) KSAYMRFa |
| FLP-7 | | (2 copies) |
| | | TPMQRSSMVRFa |
| | | (3 copies) |
| | | SPMQRSSMVRFa |
| | | SPMERSAMVRFa |
| | | SPMDRSKMVRFa |
| FLP-8 | | (3 copies) KNEFIRFa |
| FLP-9 | KPSFVRFa | (2 copies) KPSFVRFa |
| FLP-10 | | QPKARSGYIRFa |
| FLP-11 | | AMRNALVRFa |
| | | ASGGMRNALVRFa |
| | | NGAPQPFVRFa |
| FLP-12 | | RNKFEFTRFa |

TABLE 5-continued

C. elegans FMRFamide-related peptides (FaRPs) and encoding genes

| GENE AND CHROMOSOME NUMBER | STRUCTURALLY CHARACTERIZED FaRPs | PEPTIDES PREDICTED FROM GENE |
|---|---|---|
| FLP-13 | | SDRPTRAMDSPLIRFa (2 copies) |
| | | AADGAPLIRFa (2 copies) |
| | | APEASPFIRFa |
| | | ASPSAPLIRFa |
| | | SPSAVPLIRFa |
| | | SAAAPLIRFa |
| | | ASSAPLIRFa |
| FLP-14 | | (4 copies) KHEYLRFa |
| FLP-15 | | GGPQGPLRFa |
| | | GPSGPLRFa |
| FLP-16 | | AQTFVRFa |
| | | GQTFVRFa |
| FLP-17 | | (2 copies) KSAFVRFa |
| | | KSQYIRFa |
| FLP-18 | | DFDGAMPGVLRFa |
| | | DMPGVLRFa |
| | | KSVPGVLRFa |
| | | SVPGVLRFa |
| | | EIPGVLRFa |
| | | SEVPGVLRFa |
| | | DVPGVLRFa |
| | | SVPGVLRFa |
| OTHER PUTATIVE FLP GENES | | TKFQDFLRFa |
| | | AMRNSLVRFa |
| | | DYDFVRFa |
| | | DGFVRFa |
| | | AFFKNVLRFa |

"a" means amide.

Further characterization of the structure-function relationships of neuropeptides, such as FaRPs, that are embraced by the invention may be readily accomplished by one of ordinary skill in the art. For example, amino acid-scan modifications (e.g., alanine-scan), in which each residue is sequentially replaced with another amino acid such as alanine are available. Additionally, given the knowledge in the art (see generally, Geary et al., 1999), such modifications to known neuropeptides (e.g., FaRPs) as the internal or terminal deletion of one or more amino acids, as well as the internal or terminal addition of residues, involves no more than routine experimentation. Such "variants" of FaRPs and related neuropeptides are among the neuropeptides contemplated for use in the methods of the invention.

The GPCR-like receptor polypeptides and neuropeptides produced by the methods described above are useful in assays for modulators of GPCR-like receptor activities, including binding partner (e.g., ligand) binding. Assays contemplated by the invention include both binding assays and activity assays; these assays may be performed in conventional or high throughput formats. GPCR-like receptor activity is defined as including the binding of any binding partner, such as a ligand, as well as the propagation of any transmembrane signal (e.g., stimulation of a G protein or influence on the flux of an ion across a membrane). Modulator screens are designed to identify stimulatory and/or inhibitory agents. The sources for potential agents to be screened include natural sources, such as a cell extract (e.g., invertebrate cells including, but not limited to, bacterial, fungal, algal, and plant cells) and synthetic sources, such as chemical compound libraries. For proteins with known activity, function assays are established based on the activity, and a large number of potential agents are screened for the ability to either stimulate or inhibit the activity.

Binding assays are used to detect GPCR-like receptor binding activity to neuropeptide or non-peptide ligands. Both functional and binding assays of GPCR-like receptor activity are readily adapted to screens for modulators such as inhibitory compounds.

The invention contemplates a multitude of assays to screen and identify inhibitors of ligand binding to GPCR-like receptors. In one example, the GPCR-like receptor is immobilized and interaction with a binding partner is assessed in the presence and absence of a candidate modulator such as an inhibitor compound. In another example, interaction between the GPCR-like receptor and its binding partner is assessed in a solution assay, both in the presence and absence of a candidate inhibitor compound. In either assay, an inhibitor is identified as a compound that decreases binding between the GPCR-like receptor and its binding partner. Another contemplated assay involves a variation of the di-hybrid assay wherein an inhibitor of protein/protein interactions is identified by detection of a positive signal in a transformed or transfected host cell.

Candidate modulators contemplated by the invention include any chemical compounds, including libraries of chemical compounds. There are a number of different libraries used for the identification of small molecule modulators, including: (1) chemical libraries, (2) natural product libraries, and (3) combinatorial libraries comprised of random peptides, oligonucleotides or organic molecules. Chemical libraries consist of random chemical structures, or analogs of known compounds, or analogs of compounds that have been identified as "hits" or "leads" in prior drug discovery screens, some of which may be derived from natural products or from non-directed synthetic organic chemistry. Natural product libraries are collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. For a review, see Science 282:63–68 (1998). Combinatorial libraries are composed of large numbers of peptides, oligonucleotides, or organic compounds as a mixture. These libraries are relatively easy to prepare by traditional automated synthesis methods, PCR, cloning, or synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Biotechnol. 8:701–707 (1997). Identification of modulators through use of the various libraries described herein permits modification of the candidate "hit" (or "lead") to optimize the capacity of the "hit" to modulate activity.

Candidate modulators contemplated by the invention can be designed and include soluble forms of binding partners, as well as chimeric, or fusion, proteins thereof. A "binding partner" as used herein broadly encompasses non-peptide modulators, peptide modulators (e.g., neuropeptide variants), antibodies (including monoclonal and polyclonal antibodies, single chain antibodies, chimeric antibodies, bifunctional/bispecific antibodies, humlianized antibodies, human antibodies, and complementary determining region (CDR)-grafted antibodies, including compounds which include CDR and/or antigen-binding sequences, which specifically recognize a polypeptide of the invention), antibody fragments, and modified compounds comprising antibody domains that are immunospecific for the expression product of the identified GPCR-like gene.

A number of assays are known in the art that can identify chemical compounds that bind to or interact with a GPCR-like receptor. Such assays are useful, for example, in methods of identifying candidate modulators described herein, or in methods for identifying specific neuropeptide ligands of a GPCR-like receptor. Assays that measure binding or interaction of compounds with target proteins include assays that identify compounds that inhibit unfolding or denaturation of a target protein, assays that separate compounds that bind to target proteins through affinity ultrafiltration followed by ion spray mass spectroscopy/HPLC methods or other physical and analytical methods, capillary electrophoresis assays and two-hybrid assays.

One such screening method to identify direct binding of test ligands to a target protein is described in U.S. Pat. No. 5,585,277, incorporated herein by reference. This method relies on the principle that proteins generally exist as a mixture of folded and unfolded states, and continually alternate between the two states. When a test ligand binds to the folded form of a target protein (i.e., when the test ligand is a ligand of the target protein), the target protein molecule bound by the ligand remains in its folded state. Thus, the folded target protein is present to a greater extent in the presence of a test ligand which binds the target protein, than in the absence of a ligand. Binding of the ligand to the target protein can be determined by any method which distinguishes between the folded and unfolded states of the target protein. The function of the target protein need not be known in order for this assay to be performed. Virtually any agent can be assessed by this method as a test ligand, including, but not limited to, metals, polypeptides, proteins, lipids, polysaccharides, polynucleotides and small organic molecules.

Another method for identifying ligands of a target protein is described in Wieboldt et al., Anal. Chem., 69:1683–1691 (1997), incorporated herein by reference. This technique screens combinatorial libraries of 20–30 agents at a time in solution phase for binding, to the target protein. Agents that bind to the target protein are separated from other library components by simple membrane washing. The specifically selected molecules that are retained on the filter are subsequently liberated from the target protein and analyzed by HPLC and pneumatically assisted electrospray (ion spray) ionization mass spectroscopy. This procedure selects library components with the greatest affinity for the target protein, and is particularly useful for small molecule libraries.

Alternatively, such binding interactions are evaluated indirectly using the yeast two-hybrid system described in Fields et al., Nature, 340:245–246 (1989), and Fields et al., Trends in Genetics, 10:286–292 (1994), both of which are incorporated herein by reference. The two-hybrid system is a genetic assay for detecting interactions between two proteins or polypeptides. It can be used to identify proteins that bind to a known protein of interest, or to delineate domains or residues critical for an interaction. Variations on this methodology have been developed to clone genes that encode DNA binding proteins, to identify peptides that bind to a protein, and to screen for drugs. The two-hybrid system exploits the ability of a pair of interacting proteins to bring a transcription activation domain into close proximity with a DNA binding domain that binds to an upstream activation sequence (UAS) of a reporter gene, and is generally performed in yeast. The assay requires the construction of two hybrid genes encoding (1) a DNA-binding domain that is fused to a first protein and (2) an activation domain fused to a second protein. The DNA-binding domain targets the first hybrid protein to the UAS of the reporter gene; however, because most proteins lack an activation domain, this DNA-binding hybrid protein does not activate transcription of the reporter gene. The second hybrid protein, which contains the activation domain, cannot by itself activate expression of the reporter gene because it does not bind the UAS. However, when both hybrid proteins are present, the noncovalent interaction of the first and second proteins tethers the activation domain to the UAS, activating transcription of the reporter gene.

When the function of the GPCR-like receptor is unknown and no ligands are known to bind the gene product, the yeast two-hybrid assay can be used to identify proteins that bind to the receptor. In an assay to identify proteins that bind to a GPCR-like receptor, or fragment thereof, a fusion polynucleotide encoding both a GPCR-like receptor or fragment (i.e., a first protein) and a UAS binding domain may be used. In addition, a large number of hybrid genes each encoding a different second protein fused to an activation domain are produced and screened in the assay. Typically, the second protein is encoded by one or more members of a total cDNA or genomic DNA fusion library, with each second protein coding region being fused to the activation domain. This system is applicable to a wide variety of proteins, and it is not even necessary to know the identity or function of the second binding protein. The system is highly sensitive and can detect interactions not revealed by other methods; even transient interactions may trigger transcription to produce a stable mRNA that can be repeatedly translated to yield the reporter protein.

In addition, when the GPCR-like receptor or fragment thereof is known to interact with another protein or nucleic acid, the two-hybrid assay can be used to detect agents that interfere with the binding interaction. Expression of the reporter gene is monitored as different test agents are added to the system. The presence of an inhibitory agent, for example, results in lack of or reduction in a reporter signal.

The candidate modulators identified by the initial screens are evaluated for their effect on neuromuscular function using in vivo or ex vivo systems. A preferred evaluation method exposes the candidate modulators to A. suum neuromuscular strips and records neuromuscular activity relative to control strips exposed to compounds other than the candidate modulator under investigation. Other methods of screening for modulators are described in the following examples, and still other screening methods are well known in the art. Other aspects and advantages of the present invention will be understood upon consideration of the following illustrative examples. Example 1 describes the cloning of GPCR-like receptors; Example 2 provides an analysis of the polynucleotide sequences encoding those receptors in the context of their structural features such as regions and domains; Example 3 discloses GPCR-like receptor expression studies; Example 4 describes antibodies to GPCR-like receptors; Example 5 provides a variety of assays to identify modulators of GPCR-like receptor activity; and Example 6 describes approaches to the identification of candidate GPCR-like receptors, as well as the cloning and characterization of such receptors.

EXAMPLE 1

Cloning of GPCR-Like Receptors

A. Database Search

The Wormpep database, containing all of the predicted protein sequences encoded by the C. elegans genome, used in these studies, was obtained through the Sanger Centre Web site at sanger.ac.ukJProjects/C_elegans on the world wide web. Wormpep versions 13 (Feb. 13, 1998) through 23 (released Sep. 4, 2000). This database contains 19,430 protein sequences, including 388 splice variants. C. elegans genomic DNA sequences were accessed through ACEDB (Release WS3 4-25). The databases were searched and manipulated using programs from the Wisconsin Package GCG programs.

B. Subcloning of the Coding Region via PCR

Standard molecular biology techniques were performed as described in Ausubel, et al. (Eds.), *Protocols in Molecular Biology*, John Wiley & Sons (1994). Based on the database analyses described above, 22 candidate GPCR-like receptor genes were chosen for PCR amplification. The sequences of primers used for PCR amplification are provided in SEQ ID NOS: 47–76. PCR primers were designed to incorporate an optimized translation initiation sequence (Kozak et al., Nucl. Acids Res. 15(20):8125–8148 (1987)) around the initiator methionine codon and to incorporate a unique restriction site at the 3' end for subsequent linearization of the PCR-amplified fragments. The Expand™ High Fidelity PCR System (Boehringer-Mannheim Corp., Indianapolis, Ind.), including a mixture of Taq and Pwo DNA polymerases, was used for the PCR experiments. Reaction volumes of 100 µl contained 2.6 Units of enzyme mix ("Units" defined by the supplier), 200 µM of each standard dNTP, 1×Expand™ HF buffer with 15 mM $MgCl_2$, 300 nM of each primer, and 2 µl (approximately 10 ng) of a DNA template preparation, described below. DNA template preparations were the products of a first-strand cDNA synthesis reaction (heat-inactivated after completion) catalyzed by SuperScript reverse transcriptase (GIBCO-BRL, Gaithersburg, Md.) with random hexamers to prime the synthesis using a preparation of total C. elegans RNA as template. PCR amplifications were performed in a Perkin-Elmer 9600 thermocycler using the following conditions: 2 minutes at 94° C.; 30 cycles of 15 seconds at 94° C., 30 seconds at 50° C., 2 minutes at 70° C.; and a final incubation at 70° C. for 7 minutes. PCR products were electrophoresed through 0.8% agarose/TAE gels and visualized using ethidium bromide.

Amplified PCR products were cloned using the pCR2.1 TA-tailed vectors (Stratagene, La Jolla, Calif.). PCR products were excised from the agafose gels and purified using QIAquick columns (Qiagen, Valencia, Calif.). Ligation reactions were performed in accordance with the recommendations of the supplier (Stratagene); Ligation reactions were transformed into *E. coli* DH5α competent cells and plated on LB plates containing 5-bromo-4-chloro-3-indolyl-β-D-galactopyranoside (X-gal). White colonies were picked and examined for the presence of the appropriate size insert by a commercial mini-prep DNA isolation procedure (Qiagen). To facilitate subsequent expression studies, all cloned receptors were subcloned into the mammalian expression vector, pCR3.1 (Stratagene). Two microgram aliquots of vector and each GPCR-like receptor clone were digested using either BstXI (clones CEGPCR1a, CEGPCR1f; each showing some sequence similarity to Wormpep AC7.1) or EcoRI (clones CEGPCR3 (Wormpep C10C6.2), CEGPCR7 (Wormpep C39E6.6), CEGPCR8 (Wormpep C50F7.1), CEGPCR9 (Wormpep C56G3.1), CEGPCR12h and CEGPCR12u (each having some sequence similarity to Wormpep F41E7.3), CEGPCR13 (having some sequence similarity to Wormpep T05A1.1), and CEGPCR15 (Wormpep C49A9.7)). Restriction endonucleases were purchased from New England Biolabs (Beverly, Mass.) and were used according to the manufacturer's instructions. Following digestion, the linear vector and the GPCR-like receptor sequences were isolated from 1% TAE agarose gels and purified using a QIAquick gel extraction kit (Qiagen). Ligation reactions were performed at 14° C. for 16 hours and contained 100 ng vector DNA, 100 ng GPCR-like insert DNA and 1 Unit T4 DNA ligase (Boehringer Mannheim). Plasmids were propagated in *E. coli* strain DH5α, then isolated and purified using, a Qiagen column. Subclones were identified and insert orientation determined by restriction endonuclease analysis as follows: CEGPCR1a and CEGPCR15 (SEQ ID NOS: 1 and 33), HindIII; CEGPCR3 and CEGPCR8, (SEQ ID NOS: 43 and 27) AvaI; CEGPCR7, (SEQ ID NO:25) BamHI; CEGPCR13, (SEQ ID NO:13) HincII/HindIII; CEGPCR1f, (SEQ ID NO:3) BamHI/BglII; and CEGPCR9, CEGPCR12h and CEGPCR12u, (SEQ ID NOS: 29, 7 and 9) XbaI.

EXAMPLE 2

Analysis of the GPCR-Like Receptor Sequences

DNA from pCR2.1 recombinant plasmids containing the expected insert size were sequenced using BigDye dye terminator chemistry (PE Applied Biosystems, Foster City, Calif.) on an ABI 377 automated DNA sequencer. Complete sequences were assembled using Sequencher software (GeneCodes, Ann Arbor, Mich.) and compared against the expected sequence as predicted from Wormpep. Each of the 22 putative GPCR-like receptor clones appeared to contain a full-length coding region, although some of the encoded GPCR-like receptor sequences could not be confirmed as having a sequence reported in the Wormpep database. In particular, clones CEGPCR1a, CEGPCR1f, CEGPCR4, CEGPCR12c, CEGPCR12h, CEGPCR12u, CEGPCR12v, CEGPCR13, CEGPCR14, and CEGPCR18a are known to differ from sequences found in the Wormpep database (see Tables 1 and 2, above), while clones CEGPCR5, CEGPCR6, CEGPCR10, CEGPCR11, CEGPCR19 and CEGPCR20 are not known to have sequences found in the Wormpep database.

All 22 of the cloned GPCR-like receptor sequences exhibited the structural characteristics of GPCRs. Each coding region encoded seven hydrophobic stretches of amino acids consistent with transmembrane domains, the characteristic N-terminal extracellular domain, C-terminal cytoplasmic domain and both extracellular and intracellular loops. Table 6 lists the endpoints of all seven transmembrane domains in each of the 22 GPCR-like receptors. In identifying the transmembrane domains, moreover, the N-terminal extracellular domains are effectively identified (the start of the amino acid sequence to the start of the first transmembrane domain), the three extracellular loop domains (the end of 2TM to the start of 3TM, the end of 4TM to the start of 5TM, and the end of 6TM to the start of 7TM, respectively, in Table 6), the three intracellular loop domains (the end of 1TM to the start of 2TM, the end of 3TM to the start of 4TM, and the end of 5TM to the start of 6TM, respectively, in Table 6), and the C-terminal intracellular domain (the end of 7TM to the end of the amino acid sequence).

TABLE 6

| SIN | TM1 start | TM1 end | TM2 start | TM2 end | TM3 start | TM3 end | TM4 start | TM4 end | TM5 start | TM5 end | TM6 start | TM6 end | TM7 start | TM7 end |
|---|---|---|---|---|---|---|---|---|---|---|---|---|---|---|
| CEGPCR1a | 47 | 71 | 83 | 109 | 121 | 142 | 161 | 181 | 213 | 233 | 262 | 282 | 298 | 321 |
| CEGPCR1f | 47 | 71 | 83 | 109 | 121 | 142 | 161 | 181 | 213 | 233 | 277 | 297 | 313 | 336 |
| CEGPCR2 | 42 | 66 | 78 | 104 | 116 | 137 | 158 | 178 | 204 | 224 | 320 | 340 | 351 | 374 |
| CEGPCR3 | 26 | 50 | 62 | 88 | 100 | 121 | 140 | 160 | 196 | 216 | 252 | 272 | 285 | 308 |
| CEGPCR4 | 28 | 52 | 64 | 90 | 102 | 123 | 142 | 162 | 192 | 212 | 256 | 276 | 293 | 316 |
| CEGPCR5 | 40 | 64 | 76 | 102 | 114 | 135 | 154 | 174 | 212 | 232 | 222 | 292 | 305 | 328 |
| CEGPCR6 | 12 | 36 | 48 | 74 | 85 | 106 | 126 | 146 | 178 | 198 | 229 | 249 | 263 | 286 |
| CEGPCR7 | 27 | 51 | 63 | 89 | 101 | 122 | 141 | 161 | 192 | 212 | 278 | 298 | 322 | 345 |
| CEGPCR8 | 30 | 54 | 66 | 92 | 104 | 125 | 146 | 166 | 194 | 214 | 244 | 264 | 283 | 306 |
| CEGPCR9 | 51 | 75 | 87 | 113 | 125 | 146 | 167 | 187 | 239 | 259 | 330 | 350 | 368 | 391 |
| CEGPCR11 | 25 | 49 | 61 | 87 | 99 | 120 | 139 | 159 | 189 | 209 | 246 | 266 | 286 | 309 |
| CEGPCR12c | 38 | 62 | 74 | 100 | 112 | 133 | 157 | 177 | 207 | 227 | 255 | 275 | 291 | 314 |
| CEGPCR12h | 38 | 62 | 74 | 100 | 112 | 133 | 157 | 177 | 207 | 227 | 255 | 275 | 291 | 314 |
| CEGPCR12u | 38 | 62 | 74 | 100 | 112 | 133 | 157 | 177 | 207 | 227 | 255 | 275 | 291 | 314 |
| CEGPCR12v | 38 | 62 | 74 | 100 | 112 | 133 | 157 | 177 | 207 | 227 | 255 | 275 | 291 | 314 |
| CEGPCR13 | 27 | 51 | 63 | 89 | 101 | 122 | 141 | 161 | 190 | 210 | 276 | 296 | 320 | 343 |
| CEGPCR14 | 30 | 54 | 65 | 91 | 103 | 124 | 143 | 163 | 198 | 218 | 254 | 274 | 299 | 322 |
| CEGPCR15 | 62 | 86 | 98 | 124 | 136 | 157 | 176 | 196 | 235 | 255 | 285 | 305 | 321 | 344 |
| CEGPCR16 | 29 | 53 | 65 | 91 | 103 | 124 | 143 | 163 | 193 | 213 | 250 | 270 | 287 | 310 |
| CEGPCR17 | 36 | 60 | 72 | 98 | 110 | 131 | 150 | 170 | 220 | 246 | 274 | 294 | 306 | 329 |
| CEGPCR18a | 10 | 34 | 46 | 72 | 84 | 105 | 126 | 146 | 185 | 205 | 282 | 302 | 320 | 343 |
| CEGPCR19.1 | 56 | 80 | 92 | 118 | 130 | 151 | 170 | 190 | 228 | 248 | 287 | 307 | 324 | 347 |
| CEGPCR19.2 | 56 | 80 | 92 | 118 | 130 | 151 | 170 | 190 | 228 | 248 | 287 | 307 | 324 | 347 |
| CEGPCR20 | 44 | 68 | 79 | 105 | 117 | 138 | 159 | 179 | 215 | 235 | 283 | 303 | 323 | 346 |
| CEGPCR21 | 76 | 100 | 112 | 138 | 151 | 172 | 193 | 213 | 249 | 269 | 336 | 356 | 373 | 396 |
| CEGPCR22 | 55 | 79 | 95 | 121 | 132 | 153 | 173 | 193 | 233 | 253 | 279 | 299 | 319 | 342 |
| CEGPCR23 | 21 | 45 | 64 | 90 | 101 | 122 | 142 | 162 | 203 | 223 | 249 | 269 | 287 | 310 |
| CEGPCR24a | 51 | 75 | 87 | 113 | 128 | 149 | 170 | 189 | 223 | 243 | 279 | 299 | 316 | 339 |
| CEGPCR24b | 51 | 75 | 87 | 113 | 128 | 149 | 170 | 189 | 223 | 243 | 279 | 299 | 316 | 339 |

Where "SIN" refers to SEQ ID NOS.

EXAMPLE 3

Recombinant Expression of GPCR-Like Receptors

Recombinant pCR3.1 clones encoding invertebrate GPCR-like receptors were transformed into wild-type CHO-K1 cells and functional expression was achieved using a temperature-shift incubation protocol. The CHO-K1 cells were cultured at 37° C. in a humidified atmosphere of 5% $CO_2$ in air in DMEM medium supplemented with 10% heat-inactivated fetal bovine serum (i.e., FBS), 10 μg/ml gentamicin, and 0.1 mM nonessential amino acids to give complete DMEM medium. Additionally, for incubations at temperatures lower than 37° C., the medium was fortified with 10 mM HEPES (pH 7.4). Cells were transfected with recombinant pCR3.1 clones containing GPCR-like receptor DNAs, using LipofectAMINE PLUS™, essentially according to the manufacturer's instructions. Briefly, CHO-K1 cells were plated on 10 cm sterile tissue culture dishes (Corning Glass Works, Corning, N.Y.) and were incubated until the plates showed about 50–60% confluent growth. In separate plastic tubes, PLUS (20 μl/plate; Life Technologies) was added to 0.75 ml/plate of recombinant plasmid DNA in OptiMEM (5 μg/plate; Gibco/BRL—Life Technologies), mixed and incubated at room temperature for 15 minutes. Separately, LipofectAMINE (30 μl/plate) was mixed with 0.75 ml OptiMEM and added to the pre-complexed DNA/PLUS mixture and incubated at room temperature for 15 minutes. The culture medium was then replaced with serum-free transfection medium (DMEM, 5 ml/plate). The DNA-PLUS-LipofectAMINE complex was then added to the plates (1.5 ml/plate) and mixed gently into the medium, followed by a 3 hour incubation at 37° C. in 5% $CO_2$. At this time, the medium was supplemented with complete DMEM medium containing 20% FBS (6.5 ml/plate) and incubation was continued at 37° C. in 5% $CO_2$. After a total of 24 hours at 37° C. in 5% $CO_2$, the medium was replaced with complete DMEM medium fortified with 10 mM HEPES (10 ml/plate) and the cells were moved to an incubator maintained at 28–30° C. in a humidified atmosphere of 5% $CO_2$ in air. The incubation continued for an additional 24 hours, typically at the lower temperature indicated above. A plasmid encoding Green Fluorescent Protein (i.e., GFP, 4 μg/plate) was used for transient GFP expression in CHO-K1 cells to estimate the transfection yields under the same conditions as used for GPCR-like receptor polynucleotides.

To assess expression, membranes were prepared from transfected CHO-K1 cells. Transfected cells were washed once with ice-cold Dulbecco's phosphate-buffered saline (i.e., PBS), 5 ml per 10 cm plate, and the cells were scraped into 5 ml of the same buffer. Cell suspensions from multiple plates were combined and centrifuged at 500×g for 10 minutes at 4° C. The cell pellet was reconstituted in ice-cold TEE (25 mM Tris, pH 7.4, 5 mM EGTA, 5 mM EDTA). Convenient aliquots were snap-frozen in liquid nitrogen and stored at −70° C. After thawing, the cells were homogenized and centrifuged at 500×g for 5 minutes at 4° C. to pellet nuclei and unbroken cells. Tile supernatant was centrifuged at 47,000×g for 30 minutes at 4° C. The membrane pellet was washed once with TEE, resuspended in 20 mM HEPES, pH 7.4, 100 mM NaCl, 10 mM $MgCl_2$, 1 mM EDTA (assay buffer), distributed into aliquots of 0.5–1.0 ml, and frozen in liquid nitrogen. Membrane aliquots were stored at −70° C. Membrane protein concentration was determined using the BCA Protein Assay Reagent from Pierce (Rockford, Ill.), with bovine serum albumin (i.e., BSA) as a standard.

Expression of the recombinant GPCR-like receptors was assessed using a function-based [$^{35}$S]GTPγS assay, which is described in greater detail in Example 5F, below. In general, the post-transfection reduction in incubation temperature led to significant increases in detectable GPCR-like receptor activity. More specifically, a controlled study of three cloned GPCR-like receptors, CEGPCR3 (Wormpep C10C6.2), CEGPCR12c (exhibiting some sequence similarity to Wormpep F41E7.3), and CEGPCR7 (Wormpep C39E6.6), demonstrated that the temperature reduction resulted in significant increases in the expression levels of all three receptors. The GTPγS assay described in Example 5F was also used to screen for neuropeptide (including FaRP) ligands binding to invertebrate GPCR-like receptors. The results are presented in Tables 8–13, below, which identify GPCR-like receptors binding to one or more neuropeptide (e.g., FaRP) ligands, GPCR-like receptors binding to neuropeptide ligands having specified structures, the sources of those particular ligands, and $EC_{50}$ (nM) values. As shown in the tables, such ligands were identified for CEGPCR3, CEGPCR4, CEGPCR5, CEGPCR7, CEGPCR12c, CEGPCR12h, CEGPCR12u, CEGPCR12v, CEGPCR16, CEGPCR19.1, and CEGPCR19.2, and on that basis these receptors have been identified as neuropeptide (FaRP) receptors.

CEGPCR3, CEGPCR4, CEGPCR5, CEGPCR12c and CEGPCR16 were not detectably activated by their matched ligands, GNSFLRFamide (SEQ ID NO:88), PDVDHVFL-RFamide (SEQ ID NO:94), GLGPRPLRFamide (SEQ ID NO:86), PDVDHVFLRFamide (SEQ ID NO: 94), and ASEDALFGTMRFamide (SEQ ID NO: 77), respectively, when cell membranes were prepared from cells transfected and maintained at 37° C. In contrast, a temperature shift to 28° C. 24 hours after transfection resulted in significant stimulation of ligand-induced [$^{35}$S]GTPγS binding.

In the case of the CEGPCR7-AF9 system, cell transfections and constant temperature (37° C.) incubations were performed three times. No stimulation of the GLGPRPLR-Famide (AF9)-induced [$^{35}$S]GTPγS binding was detected in two of these experiments while in the third one, a 1.4 fold elevated [$^{35}$S]GTPγS binding was recorded. The extent of this stimulation was, however, considerably smaller than the stimulation in activity achieved by using the cooling (28° C.) protocol (2.6 fold elevation in activity). Thus, the temperature downshift was important for the functional expression of C. elegans GPCRs expressed in mammalian cells. In contrast, the responses of the human D2 receptor control to its ligand, dopamine, were the same regardless of the transfection protocol used. Moreover, no temperature-dependent receptor activity was detected when the hD2 receptor control was exposed to a number of neuropeptides, including FaRPs, indicating that the temperature-dependent GPCR-like receptor activity was specific to the cloned receptors.

All invertebrate GPCR-like receptors, including those receptors identified in Table 6, are screened against the invertebrate neuropeptides, including many FaRPs. It is expected that each one of the invertebrate GPCR-like receptors will be activated by one or more neuropeptides of the class including FaRPs, using an assay disclosed in Example 5, such as the GTPγS assay.

EXAMPLE 4

Antibodies to GPCR-Like Receptors

Standard techniques are employed to generate polyclonal or monoclonal antibodies to the GPCR-like receptors, and to generate useful antigen-binding fragments thereof or variants thereof. Such protocols can be found, for example, in Sambrook et al., *Molecular Cloning: a Laboratory Manual*. Second Edition, Cold Spring Harbor, N.Y.: Cold Spring Harbor Laboratory (1989); Harlow et al. (Eds), *Antibodies A Laboratory Manual*; Cold Spring Harbor Laboratory; Cold Spring Harbor, N.Y. (1988). In one embodiment, recombinant GPCR-like polypeptides (or cells or cell membranes containing such polypeptides) are used as antigens to generate the antibodies. In another embodiment, one or more peptides having amino acid sequences corresponding to an immunogenic portion of a GPCR-like receptor (e.g., 6, 7, 8, 9, 10, 11, 12, 13, 14, 15, 16, 17, 18, 19, 20, or more amino acids) are used as antigen. Peptides corresponding to extracellular portions of GPCR-like receptors, especially hydrophilic extracellular portions, are preferred. The antigen may be mixed with an adjuvant or linked to a hapten to increase antibody production. Polyclonal and monoclonal antibodies, chimeric (e.g., humanized) antibodies, fragments of antibodies, and all other forms of antibody molecules disclosed herein are referred to collectively as antibody products.

A. Polyclonal or Monoclonal Antibodies

As one exemplary protocol, a recombinant GPCR-like polypeptide or a synthetic fragment thereof is used to immunize a mouse for generation of monoclonal antibodies (or larger mammal, such as a rabbit, for polyclonal antibodies). To increase antigenicity, peptides are conjugated to Keyhole Lympet Hemocyanin (Pierce), according to the manufacturer's recommendations. For an initial injection, the antigen is emulsified with Freund's Complete Adjuvant and injected subcutaneously. At intervals of two to three weeks, additional aliquots of GPCR-like receptor antigen are emulsified with Freund's Incomplete Adjuvant and injected subcutaneously. Prior to the final booster injection, a serum sample is taken from the immunized mice and assayed by Western blot to confirm the presence of antibodies that immunoreact with a GPCR-like polypeptide. Serum from the immunized animals may be used as a polyclonal antisera or used to isolate polyclonal antibodies that recognize a GPCR-like receptor. Alternatively, the mice are sacrificed and their spleens are removed for generation of monoclonal antibodies.

To generate monoclonal antibodies, the spleens are placed in 10 ml serum-free RPMI 1640, and single-cell suspensions are formed by grinding the spleens in serum-free RPMI 1640, supplemented with 2 mM L-glutamine, 1 mM sodium pyruvate, 100 Units/ml penicillin, and 100 μg/ml streptomycin (RPMI) (Gibco, Canada). The cell suspensions are filtered and washed by centrifugation and resuspended in serum-free RPMI. Thymocytes taken from three naive Balb/c mice are prepared in a similar manner and used as a Feeder Layer. NS-1 myeloma cells, kept in log phase in RPMI with 10% (FBS (Hyclone Laboratories, Inc., Logan, Utah) for three days prior to fusion, are centrifuged and washed as well.

To produce hybridoma fusions, spleen cells from the immunized mice are combined with NS-1 cells and centrifuged, and the supernatant is aspirated. The cell pellet is dislodged by tapping the tube, and 2 ml of 37° C. PEG 1500 (50% in 75 mM HEPES, pH 8.0) (Boehringer-Mannheim) is stirred into the pellet, followed by the addition of serum-free RPMI. Thereafter, the cells are centrifuged and resuspended in RPMI containing 15% FBS, 100 μM sodium hypoxanthine, 0.4 μM aminopterin, 16 μM thynidine (HAT) (Gibco), 25 Units/ml IL-6 (Boehringer-Mannheim) and 1.5×10$^6$ thymocytes/ml and plated into 10 Coming flat-bottom 96-well tissue culture plates (Coming, Coming N.Y.).

On days 2, 4, and 6 after the fusion, 100 μl of medium is removed from the wells of the fusion plates and replaced with fresh medium. On day 8, the fusions are screened by ELISA, testing for the presence of mouse IgG that binds to a GPCR-like receptor polypeptide. Selected fusions are further cloned by dilution until monoclonal cultures producing anti-GPCR-like receptor antibodies are obtained.

B. GPCR-like Receptor-Neutralizing Antibodies from Phage Display

GPCR-like receptor-neutralizing antibodies are generated by phage display techniques such as those described in Aujame et al., *Human Antibodies*, 8(4):155–168 (1997); Hoogenboom, *TIBTECH*, 15:62–70 (1997); and Rader et al., *Curr. Opin. Biotechnol.*, 8:503–508 (1997), all of which are incorporated by reference. For example, antibody variable regions in the form of Fab fragments or linked single chain Fv fragments are fused to the amino terminus of filaments phage minor coat protein pIII. Expression of the fusion protein and incorporation thereof into the mature phage coat results in phage particles that present an antibody on their surface and contain the genetic material encoding the antibody. A phage library comprising such constructs is expressed in bacteria, and the library is screened for GPCR-like receptor-specific phage-antibodies using labeled or immobilized GPCR-like receptor as antigen-probe.

C. GPCR-like Receptor-Neutralizing Antibodies from Transgenic Animals

GPCR-like receptor-neutralizing antibodies are generated in transgenic animals, such as mice, essentially as described in Bruggemann et al., *Immunol. Today* 17(8):391–97 (1996) and Bruggemann et al., *Curr. Opin. Biotechnol.* 8:455–58 (1997). Transgenic mice carrying V-genie segments in germline configuration, and expressing the transgenes in their lymphoid tissue, are immunized with a GPCR-like polypeptide composition using conventional immunization protocols. Hybridomas are generated from B cells of the immunized mice using conventional protocols and screened to identify hybridomas secreting anti-GPCR-like receptor antibodies (e.g., as described above).

EXAMPLE 5

Assays to Identify Modulators of GPCR-Like Receptor Activity

Two general approaches exist for the discovery of novel compounds that are binding partners for receptors, especially GPCRs. Each of the general approaches is compatible with high throughput screening (i.e., HTS) formats, which are preferred formats for identifying ligands and other binding partners of GPCR-like receptor polypeptides, such as modulators of receptor activity. The first approach involves measuring the binding of a known ligand, preferably labeled with a radiolabel, to a preparation that contains the receptor, either found in native tissue or based on expression of the gene encoding the receptor, typically in a heterologous system. The recombinant system involves the expression of a recombinant GPCR, and is the presently preferred system for binding assays. The second approach to the identification of GPCR-like receptor binding partners involves the measurement of the activity of the receptor, which may be influenced by either the binding of ligands that are agonists, and elevate receptor activity, or by the binding of antagonists, which interfere with agonist binding, thereby reducing the level of receptor activity. As for binding assays, recombinant systems are the presently preferred forms for function-based assays.

Receptor Binding Assays (RBA) as HTS Systems for Drug Discovery

The literature is replete with examples of the use of radiolabeled ligands in FITS binding assays for drug discovery (see Williams, Med. Res. Rev. 11:147–184 (1991); Sweetnam et al., J. Nat. Prod. 56:441–455 (1993) for review). It is also possible to screen for novel anthielmintic compounds with radiolabeled ligands in HTS binding screens (Geary et al., 1999). However, native nematode tissue, particularly tissue from parasitic nematodes, is difficult to acquire and native nematode tissue binding assays are not well-suited for HTS because the density of receptor sites in these preparations is typically much lower than found in mammalian tissues (Thompson, et al., Parasitology 113:S217–S238 (1996)). Other reasons that recombinant receptors are preferred for HTS binding assays include better specificity (higher relative purity) and ability to generate large amounts of receptor material (see Hodgson, Bio/Technology 10:973–980 (1992)).

A variety of heterologous systems are available for expression of recombinant receptors and are well known to those skilled in the art. Such systems include bacteria (Strosberg et al., Trends in Pharm. Sci. 13:95–98 (1992)), yeast (Pausch, Trends in Biotech. 15:487–494 (1997)), several kinds of insect cells (Vanden Broeck, Intl. Rev. Cytol. 164:189–268 (1996)), amphibian cells (Jayawickreme et al., Curr. Opin. Biotechnol. 8:629–634 (1997)) and several mammalian cell lines (CHO, HEK293, COS, etc.; see Gerhardt et al., Eur. J. Pharmacol. 334:1–23 (1997); Wilson et al., Brit. J. Pharmacol. 125:1387–1392 (1998)). These examples do not preclude the use of other possible cell expression systems, including cell lines obtained from nematodes (WO 98/37177).

A *C. elegans* orphan GPCR expressed in one of the described recombinant systems can be used for HTS binding assays in conjunction with its defined ligand, in this case the corresponding neuropeptide (e.g., FaRP) that activates it. The identified peptide is labeled with a suitable radioisotope, including, but not limited to, $^{125}$I (preferred; see Geary et al., 1999), $^3$H, $^{35}$S or $^{32}$P, by methods that are well known to those skilled in the art. Alternatively, the peptides may be labeled by well-known methods with a suitable fluorescent derivative (Baindur et al., Drug Dev. Res. 33:373–398 (1994); Rogers, Drug Disc. Today 2:156–160 (1997)). Radioactive ligand specifically bound to the receptor in membrane preparations made from the cell line expressing the recombinant protein can be detected in HTS assays in one of several standard ways, including filtration of the receptor-ligand complex to separate bound ligand from unbound ligand (Williams, 1991; Sweetnam et al., 1993). Alternative methods include a scintillation proximity assay (SPA) or a FlashPlate format in which such separation is unnecessary (Nakayama et al., Drug Disc. & Dev. 1:85–91 (1998); Boss et al., J. Biomol. Screening 3:285–292 (1998)). Binding of fluorescent ligands can be detected in various ways, including fluorescence energy transfer (FRET), direct spectrophotofluorometric analysis of bound ligand, or fluorescence polarization (see Rogers, 1997; Hill, Curr. Opin. in Drug Disc. & Dev. 1:92–97 (1998)).

A binding assay that has proven useful is a Flp18 binding assay or screen.

A peptide ligand screening assay that measures ligand binding to a suitable GPCR-like receptor according to the invention is exemplified using a modified *C. elegans* Flp18 peptide ligand. The modified *C. elegans* Flp18 peptide, YDVPGVLRFamide (SEQ ID NO:147), is extended by an N-terminal tyrosine residue. Iodination of the peptide is accomplished using a standard chloramine T procedure. Added to a 2 ml glass vial are 10 μl of a 1 mM water solution of the Flp18 peptide, 10 μl of 0.1M (pH 7.99) sodium phosphate buffer, 1.0 mCi [$^{125}$I] sodium iodide and 5 μl of a 2 mg/ml chloramine T solution (in the phosphate buffer). The mixture is vortexed for 60 seconds and the reaction is stopped by the addition of 25 μl of a 5 mg/ml solution of sodium metabisulfite in phosphate buffer. The mixture is then subjected to HPLC gradient fractionation by injecting it onto a Vydac C18 (0.45×15 cm) column. The gradient used is 70% A and 30% B at time zero to 20% A and 80% B at time 25 minutes (A=0.1M $NH_4$ acetate in water; B=0.1M NH4 acetate in water 40%: $CH_3CN$ 60%, v/v). The flow rate is 1.0 ml/minute. Samples are collected into 0.25 ml capture buffer (0.1M sodium phosphate buffer with 0.5% bovine serum albumin, 0.1% Triton X100 and 0.05% Tween 20) at 30 second intervals from t=8 to t=20 minutes. Monoiodo YDVPGVLRFamide (SEQ ID NO:119) typically elutes at t=11 minutes and the yield is approximately 100 μCi in 0.75 ml.

Membranes for use in the assay are derived from cells stably transfected with a GPCR-like receptor expression construct. The transfected cells are grown in 10 cm dishes to subconfluence, rinsed once with 5 ml of ice-cold $Ca^{2+}$/$Mg^{2+}$—free PBS, and scraped into 5 ml of the same buffer. Cells are pelleted by centrifugation (500×g, 5 minutes), resuspended in 25 mM Tris, pH 7.5, 5 mM EDTA, 5 mM EDTA, pH 7.5 (TEE), and frozen in liquid nitrogen. After thawing, the cells are homogenized using a Dounce homogenizer (one ml TEE per plate of cells), and centrifuged at 1,000×g for 5 minutes to remove nuclei and unbroken cells.

The homogenate supernatant is centrifuged at 20,000×g for 20 minutes to isolate the membrane fraction, and the membrane pellet is washed once with TEE and resuspended in binding buffer (20 mM HEPES, pH 7.5, 150 mM NaCl, 10 mM $MgCl_2$, 1 mM EDTA). The resuspended membranes are optionally frozen in liquid nitrogen and stored at −70° C. until use.

Aliquots of cell membranes prepared as described above and stored at −70° C. are thawed, homogenized, and diluted into assay buffer as described below.

The peptide ligand screening assay is facilitated by use of 96-well plates Millipore Multiscreen® filtration plates (FB opaque 1.0 μM glass fiber type B, catalog number MAFBNOB50). Protein reaction products are collected using a Millipore Multiscreen® solvent resistant manifold (catalog number MAVMO960R). Each replicate of the assay is contained in a single well and has a volume of 100 ul containing 5 ug protein (preparation described above). Each test group contains two replicates. For each test compound, one group is run with [$^{125}$I]YDVPGVLRFamide (SEQ ID NO:119) only to determine total binding, and one group is run with 1 μM (or as designated) concentration of the test compound and [$^{125}$I]YDVPGVLRFamide (SEQ ID NO:119; for non-specific binding). The order of adding reagents for each replicate is as follows: assay buffer (20 mM HEPES, 10 mM $MgCl_2$, 1% bovine serum albumin, pH 7.4) test compound (made up in assay buffer), [$^{125}$I] YDVPGVLRFamide (SEQ ID NO:119; in assay buffer) and membrane suspension (in assay buffer). The addition of the membrane suspension initiates the binding reaction which is run for 30 minutes at room temperature (22° C.). Following the 30 minute incubation each plate is placed on the filtration manifold and vacuum is applied, pulling the liquid through the filter (the liquid is discarded) and catching the protein on the filters in each well. For washing, the vacuum is released and 200 μl assay buffer is added to each well followed by reapplication of the vacuum. This washing is repeated twice more (total of 3 washes for each replicate). Following washing, the plastic covering on the underside of each plate is removed and the plate is placed in a bottom-sealed Microbeta® scintillation counting cassette (catalog number 1450-105). Twenty five μl of scintillant is added to each well and the plate is placed on a rotary shaker at 80 rpm for one hour and then allowed to sit overnight. The following day, the plate is counted in a Microbeta® scintillation counter. The mean non-specific binding is subtracted from the mean total binding to yield specific binding for both the standard (YDVPGVLRFamide, SEQ ID NO:147) and the unknowns.

Response-based GPCR HTS Systems

It is well known that activation of heterologous receptors expressed in recombinant systems results in a variety of biological responses, which are typically mediated by G proteins expressed in the host cells. Agonist binding to a GPCR results in exchange of bound GDP for GTP at a binding site on the G subunit; one can use a radioactive, non-hydrolyzable derivative of GTP, such as [$^{35}$S]GTPγS, to measure binding of an agonist to the receptor. (Seifert et al., Eur. J. Biochem. 255:369–382 (1998).) One can also use this binding to measure the ability of antagonists to bind to the receptor by decreasing binding of GTP[$^{35}$S] in the presence of a known agonist.

The G proteins required for functional expression of heterologous GPCRs can be native constituents of the host cell or can be introduced through well-known recombinant technology. The G proteins can be intact or chimeric. Often, a nearly universally competent G protein (e.g., $G_{\alpha 16}$) is used to couple any given receptor to a detectable response pathway. G protein activation results in the stimulation or inhibition of other native proteins, events that can be linked to a measurable response.

Examples of such biological responses include, but are not limited to, the following responses: the ability to survive in the absence of a limiting nutrient in specifically engineered yeast cells (Pausch, 1997); changes in intracellular $Ca^{2+}$ concentration as measured by fluorescent dyes (Murphy et al., Curr. Opin. in Drug Disc. & Dev. 1:192–199 (1998)). Fluorescence changes can also be used to monitor ligand-induced changes in membrane potential or intracellular pH; an automated system suitable for HTS has been described for these purposes (Schroeder et al., J. Biomol. Screening 1:75–80 (1996)). Melanophores prepared from *Xenopus laevis* show a ligand-dependent change in pigment organization in response to heterologotis GPCR activation; this response is adaptable to HTS formats (Jayawickreme et al., 1997). Assays are also available for the measurement of common second messengers, including cAMP, phosphoinositides and arachidonic acid. Set forth in the following subsections are exemplary function-based assays for identifying modulators (agonists and antagonists) of GPCR-like receptor activity. Among the modulators that can be identified by these assays are natural ligand compounds of the receptor; synthetic analogs and derivatives of natural ligands; antibodies, antibody fragments, and/or antibody-like compounds derived from natural antibodies or from antibody-like combinatorial libraries; and/or synthetic compounds identified by high throughput screening of libraries; and other libraries known in the art. All modulators that bind GPCR-like receptors are useful for identifying GPCR-like polypeptides in tissue samples (e.g., for diagnostic purposes, pathological purposes, and other purposes known in the art). Agonist and antagonist modulators are useful for up-regulating and down-regulating GPCR-like receptor activity, respectively, to treat invertebrate infestations and/or infections of man, other animals, plants or the environment. GPCR-like receptor binding partners also may be used to deliver a therapeutic compound or a label to cells that express a GPCR-like receptor (e.g., by attaching the compound or label to the binding partner). The assays may be performed using single putative modulators; they may also be performed using a known agonist in combination with candidate antagonists (or visa versa).

A. cAMP Assays

In one type of assay, levels of cyclic adenosine monophosphate (cAMP) are measured in GPCR-like receptor-transfected cells that have been exposed to candidate modulator compounds. Protocols for cAMP assays have been described in the literature. [See, e.g., Sutherland et al., Circulation, 37:279 (1968); Frandsen, et al., Life Sciences, 18:529–541 (1976); Dooley et al., J. Pharm. & Exp. Therap., 283(2):735–41 (1997); and George et al., J. Biomol. Screening, 2(4):235–40 (1997).] An exemplary protocol for such an assay, using an Adenylyl Cyclase Activation Flash-Plate® Assay from NEN™ Life Science Products, is set forth below.

Briefly, the GPCR-like receptor coding sequence (e.g., a cDNA or intronless genomic DNA) is subcloned into a commercial expression vector, such as pzeoSV2 (Invitrogen, San Diego, Calif.), and transiently transfected into Chinese Hamster Ovary (CHO) cells using known methods, such as the transfection reagent FuGENE 6 (Boehringer-Mannheim) and the transfection protocol provided in the product insert. The transfected CHO cells are seeded into the 96-well microplates of the FlashPlate® assay kit, which are coated with solid scintillant to which antisera to cAMP has been bound. For a control, some wells are seeded with wild type (untransfected) CHO cells. Other wells on the plate receive various amounts of cAMP standard solution for use in creating a standard curve.

One or more test compounds are added to the cells in each well, with water and/or compound-free medium/diluent serving as a control. After treatment, cAMP is allowed to accumulate in the cells for exactly 15 minutes at room temperature. The assay is terminated by the addition of lysis buffer containing $[^{125}I]$-labeled cAMP, and the plate is counted using a Packard Topcount™ 96-well microplate scintillation counter. Unlabeled cAMP from the lysed cells (or from standards) competes with the fixed amounts of $[^{125}I]$-cAMP for antibody bound to the plate. A standard curve is constructed, and cAMP values for the unknowns are obtained by interpolation. Changes in intracellular cAMP level of the cells in response to exposure to a test compound are indicative of GPCR-like receptor modulating activity. Modulators that act as agonists at receptors which couple to the $G_s$ subtype of G proteins will stimulate production of cAMP, leading to a measurable 3–10 fold increase. Agonists OF receptors which couple to the $G_{i/o}$ subtype of G proteins will inhibit forskolin-stimulated cAMP production, leading to a measurable decrease of 50–100%. Modulators that act as inverse agonists will reverse these effects at receptors that are either constitutively active or activated by known agonists.

B. Aequorin Assays

In another function based assay, cells (e.g., CHO cells) are transiently co-transfected with both a GPCR-like receptor expression construct and a construct that encodes the photoprotein apoaquorin. In the presence of the cofactor coelenterazine, apoacquorin will emit a measurable luminescence that is proportional to the amount of intracellular (cytoplasmic) free calcium. [See generally Cobbold P. H. and Lee, J. A. C. "Aequorin measurements of cytoplasmic free calcium. In: McCormack J. G. and Cobbold P. H., eds., *Cellular Calcium: A Practical Approach*. Oxford:IRL Press (1991); Stables et al., *Analytical Biochemistry*, 252: 115–26 (1997); and Haugland, R. P. *Handbook of Fluorescetit Probes and Research Chemicals*. Sixth edition. Eugene Oreg.: Molecular Probes (1996).]

In one exemplary assay, a GPCR-like receptor is subcloned into the commercial expression vector pzeoSV2 (Invitrogen, San Diego, Calif.) and transiently co-transfected along with a construct that encodes the photoprotein apoaequorin (Molecular Probes, Eugene, Oreg.) into CHO cells using the transfection reagent FuGENE 6 (Boehringer-Mannheim) and the transfection protocol provided in the product insert. Alternatively, the GPCR-like receptor may be subcloned into pCR3.1 and transfected into CHO cells using LipofectAMINE PLUS™, as described above.

The cells are cultured for 24 hours at 37° C. in DMEM (Gibco/BRL, Gaithersburg, Md.) supplemented with 10% fetal bovine serum, 2 mM glutamine, 10 Units/ml penicillin and 10 µg/ml streptomycin, at which time the medium is changed to serum-free DMEM containing 5 µM coelenterazine (Molecular Probes, Eugene, Oreg.), and the cells are cultured for two additional hours at 37° C. Cells are then detached from the plate using VERSEN (Gibco/BRL), washed, and resuspended at 200,000 cells/ml in serum-free DMEM.

Dilutions of candidate GPCR-like receptor modulator drugs are prepared in serum-free DMEM and dispensed into wells of an opaque 96-well assay plate, 50 µl/well. Plates are loaded onto an MLX microtiter plate luminometer (Dynex Technologies, Inc., Chantilly, Va.). The instrument is programmed to dispense a 50 µl cell suspension into each well, one well at a time, and immediately read luminescence for 15 seconds. Dose-response curves for the modulator candidates are constructed using the area under the curve for each light signal peak. Data are analyzed with SlideWrite, using the equation for 1-site ligand, and $EC_{50}$ values are obtained. Changes in luminescence caused by the drugs are considered indicative of modulatory activity. Modulators that act as agonists at receptors which couple to the $G_q$ subtype of G proteins give an increase in luminescence of up to 100 fold. Modulators that act as inverse agonists will reverse this effect at receptors that are either constitutively active or activated by known agonists.

C. Luciferase Reporter Gene Assay

The photoprotein luciferase provides another useful tool for assaying for modulators of GPCR-like receptor activity. Cells (e.g., CHO cells or COS 7 cells) are transiently co-transfected with both a GPCR-like receptor expression construct (e.g., a GPCR-like receptor in pzeoSV2 (Invitrogen, San Diego, Calif.)) and a reporter construct which includes a luciferase coding region downstream from a transcription factor, either the cAMP-response element (CRE), AP-1, or NF-κB. Agonist binding to receptors coupled to the $G_s$ subtype of G proteins leads to increases in cAMP, activating the CRE transcription factor and resulting in expression of the luciferase gene. Agonist binding to receptors coupled to the $G_q$ subtype of G proteins leads to production of diacylglycerol that activates protein kinase C, which activates the AP-1 or NF-κB transcription factors resulting in expression of the luciferase gene. Expression levels of luciferase reflect the activation status of the signaling events. [See generally George et al., *Journal of Biomolecular Screening*, 2(4): 235–40 (1997); and Stratowa et al., *Current Opinion in Biotechnology*, 6: 574–81 (1995).] Luciferase activity may be quantitatively measured using, e.g., luciferase assay reagents that are commercially available from Promega (Madison, Wis.).

In one exemplary assay, CHO cells are plated in 24-well culture dishes at a density of 100,000 cells/well one day prior to transfection and cultured at 37° C. in DMEM (Gibco/BRL, Gaithersburg, Md.) supplemented with 10% fetal bovine serum, 2 mM glutamine, 10 Units/ml penicillin and 10 µg/ml streptomycin. Cells are transiently co-transfected with both a GPCR-like receptor expression construct and a reporter construct containing the luciferase gene. The reporter plasmids CRE-luciferase, AP-1-luciferase and NF-κB-luciferase may be purchased from Stratagene (LaJolla, Calif.). Transfections are performed using FuGENE 6 transfection reagent (Boehringer-Mannheim), following the protocol provided in the product insert. Cells transfected with the reporter construct alone are used as a control. Twenty-four hours after transfection, cells are washed once with phosphate buffered saline (PBS) pre-warmed to 37° C. Serum-free DMEM is then added to the cells either alone (control) or with one or more candidate modulators and the cells are incubated at 37° C. for five hours. Thereafter, cells are washed once with ice-cold PBS and lysed by the addition of 100 µl of lysis buffer/well (from the luciferase assay kit, Promega, Madison, Wis.). After incubation for 15 minutes at room temperature, 15 µl of the lysate is mixed with 50 µl substrate Solution (Promega) in an opaque white 96-well plate, and the luminescence is read immediately on a Wallace model 1450 MicroBeta scintillation and luminescence counter (Wallace Instruments, Gaithersburg, Md.).

Differences in luminescence in the presence versus the absence of a candidate modulator compound are indicative of modulating activity. Receptors that are either constitutively active or activated by agonists typically give a 3–20 fold stimulation of luminescence compared to cells transfected with the reporter gene alone. Modulators that act as inverse agonists will reverse this effect.

D. Intracellular Calcium Measurement Using FLIPR

Changes in intracellular calcium levels are another recognized indicator of G protein-coupled receptor activity, and such assays can be employed to assay for modulators of GPCR-like receptor activity. For example, CHO cells stably transfected with a GPCR-like receptor expression construct are plated at a density of $4\times10^4$ cells/well in Packard black-walled 96-well plates specially designed to isolate fluorescent signals to individual wells. The cells are incubated for 60 minutes at 37° C. in modified Dulbecco's PBS (D-PBS), containing 36 mg/L pyruvate and 1 g/L glucose with the addition of 2.5 mM probenecid (Sigma Chemical Co.) and one of four calcium indicator dyes (Fluo3™ AM, Fluo4™ AM, Calcium Green™-1 AM, or Oregon Green™ 488 BAPTA-1 AM) at a concentration of 4 µM. Plates are washed once with modified D-PBS without 1% fetal bovine serum and incubated for 10 minutes at 37° C. to remove residual dye from the cellular membrane. In addition, a series of washes with modified D-PBS is performed immediately prior to activation of the calcium response.

Calcium response is initiated by the addition of one or more candidate receptor agonist compounds, or a positive control such as a calcium ionophore A23187 (10 µM), or ATP (4 µM). Fluorescence is measured by Molecular Device's FLIPR with an argon laser, excitation at 488 nm. [See, e.g., Kuntzweiler et al., *Drug Development Research*, 44(1): 14–20 (1998).] The F-stop for the detector camera was set at 2.5 and the length of exposure was 0.4 msec. Basal fluorescence of cells was measured for 20 seconds prior to addition of agonist, ATP, or A23187, and was subtracted from the response signal. The calcium signal is measured for approximately 200 seconds, taking readings every two seconds. The calcium ionophore and ATP increase the calcium signal 200% above baseline levels. In general, activated GPCRs increase the calcium signal approximately 10–15% above baseline signal.

E. Mitogenesis Assay

In mitogenesis assays, the ability of candidate modulators to induce or inhibit GPCR-like receptor-mediated cell growth is determined. [See, e.g., Lajiness et al., *Journal of Pharmacology and Experimental Therapeutics*, 267(3): 1573–81 (1993).] For example, CHO cells stably expressing a GPCR-like receptor are seeded into 96-well plates at a density of 5000 cells/well and grown at 37° C. in DMEM with 10% fetal calf serum for 48 hours, at which time the cells are rinsed twice with serum-free DMEM. After rinsing, 80 µl of fresh DMEM, or DMEM containing a known mitogen, is added along with 20 µl DMEM containing varying concentrations of one or more test compounds diluted in serum-free medium. As controls, some wells on each plate receive serum-free medium alone, and some receive medium containing 10% fetal bovine serum. Untransfected cells or cells transfected with the vector alone also may serve as controls.

After culture for 16–18 hours, 1 µCi/well of [³H]-thymidine is added to the wells and cells are incubated for an additional 2 hours at 37° C. The cells are trypsinized and harvested onto filter mats with a cell harvester (Tomtec) and the filters are counted in a Betaplate counter. The incorporation of [³H]-thymidine in serum-free test wells is compared to the results achieved in cells stimulated with serum. Use of multiple concentrations of test compounds permits creation and analysis of dose-response curves using the non-linear, least squares fit equation: $A=B\times[C/(D+C)]+G$ where A is the percent of serum stimulation; B is the maximal effect minus baseline; C is the $EC_{50}$; D is the concentration of the compound; and G is the maximal effect. Parameters B, C and G are determined by Simplex optimization.

Agonists that bind to the receptor are expected to increase [³H]-thymidine incorporation into cells, showing up to 80% of the response to serum. Antagonists that bind to the receptor will inhibit the stimulation seen with a known agonist by up to 100%.

F. [³⁵S]GTPγS Binding Assay

Because G protein-coupled receptors signal through intracellular G proteins whose activity involves GTP/GDP binding and hydrolysis, measurement of binding of the non-hydrolyzable GTP analog [³⁵S]GTPγS in the presence and absence of putative modulators provides another indicator of modulator activity. [See, e.g., Kowal, et al., *Neuropharmacology*, 37: 179–87 (1998).]

In one exemplary assay, cells stably transfected with a GPCR-like receptor expression construct are grown in 10 cm dishes to subconfluence, rinsed once with 5 ml of ice-cold $Ca^{2+}/Mg^{2+}$—free PBS, and scraped into 5 ml of the same buffer. Cells are pelleted by centrifugation (500×g, 5 minutes), resuspended in 25 mM Tris, pH 7.5, 5 mM EDTA, 5 mM EDTA, pH 7.5 (TEE), and frozen in liquid nitrogen. After thawing, the cells are homogenized using a Dounce homogenizer (one ml TEE per plate of cells), and centrifuged at 1,000×g for 5 minutes to remove nuclei and unbroken cells.

The homogenate supernatant is centrifuged at 20,000×g for 20 minutes to isolate the membrane fraction, and the membrane pellet is washed once with TEE and resuspended in binding buffer (20 mM HEPES, pH 7.5, 150 mM NaCl, 10 mM $MgCl_2$, 1 mM EDTA). The resuspended membranes can be frozen in liquid nitrogen and stored at −70° C. until use.

Aliquots of cell membranes prepared as described above and stored at −70° C. were thawed, homogenized, and diluted into buffer containing 20 mM HEPES, pH 7.4, 10 mM $MgCl_2$, 1 mM EDTA, and 100 mM NaCl at a concentration of 10–50 μg/ml. Reaction mixtures were prepared in 96-well polypropylene plate, Nunc. Twenty microliters of a 10× putative modulator compound (including but not limited to potential peptide ligands) solution or a water control (20 μl), 18.2 M GDP (0.11 ml, 10 μM final concentration), and a membrane preparation were mixed and placed on ice. The modulator/ligand-GDP-membrane mixtures were incubated for 20 minutes at room temperature on a shaking platform and then placed on ice. To each sample, 20 μl guanosine 5'-O-(3[$^{35}$S]thio) triphosphate (NEN, 600–1200 Ci/mmol; [$^{35}$S]-GTPγS), was added to approximately 40,000 cpm/0.2 ml, or a final concentration of 100 pM. Plates with the incubation mixtures (0.2 ml/well total) were incubated at room temperature for 45 minutes. Reaction mixture aliquots, 0.175 ml each, were then transferred into pretreated (100 μl/well wash buffer) 96-well FB MultiScreen filter plates (Millipore). Membranes were subsequently washed three times with 0.25 ml ice-cold wash buffer (10 mM HEPES, pH 7.4, 10 mM $MgCl_2$) per well each time and vacuum-filtered. After the last wash, Supermix Optiphase scintillation fluid (25 μl/well, Wallac) was added and the plates were sealed and counted in a Trilux 1450 Microbeta counter (Wallac) for one minute per well. As positive controls, membranes from CHO cells stably expressing a rat dopamine type 2 ($rD_2$) receptor, were treated with 1 mM dopamine in 0.025% ascorbic acid (100 μM dopamine final concentration). Non-specific binding was measured in the presence of 100 μM cold GTPγS and was subtracted from the total. Each treatment was typically carried out in triplicate.

Ligand-induced stimulation of [$^{35}$S]GTPγS binding was expressed as a multiple of the basal activity with no ligand added. Each treatment was run either in triplicate, or, on occasion in duplicate and bindings (cpm) were calculated as means +/– standard deviations. Dose-response curves for the receptor/ligand systems were analyzed using a non-linear least squares SAS model, with $y=B_{max} X/(K_d+X)$. Other dose-response curves were analyzed using Prism (GraphPad Software, Inc. San Diego, Calif.) and the following equation $y=Bottom+(Top-Bottom)/(1+10^{LogEc_{50}-X})$.

Originally, the GTPγS assay was chosen as a functional assay because agonist-driven stimulation revealed by the GTPγS assay reflects early events in the GPCR activation cascade, regardless of further activation pathways of various down-stream signaling events. This appears especially useful for the assessment of possible activation of orphan GPCRs (i.e., GPCRs having unknown functions and unknown signaling pathways). The GTPγS assay was carried out with membranes prepared from CHO cells transiently transfected with DNA encoding *C. elegans* GPCRs using a 96-well MultiScreen G/FB filter plates and a MultiScreen vacuum manifold (Millipore) for filtration. Because the GTPγS assay is known to poorly recognize GPCRs coupled to the Gq class of G-proteins, a $Ca^{+2}$ mobilization assay, based on a FLIPR readout, was used as well to evaluate putative Gq-coupled orphan GPCRs transiently transfected into CHO cells. It was essential to use a 37° C. to 28° C. temnperature downshift and to incubate the cells for an additional 24–48 hours for functional receptor expression. The temperature shift was implemented 24 hours after transfection. Without the temperature downshift, expression of functional receptor could not be detected.

"The CEGPCR3 receptor (SEQ ID NO:43) was found to be activated by several peptide ligands (Table 7), as determined in the GTPγS assay. Chinese hamster ovary cells were incubated for 24 hours at 37° C. after transfection, followed by an additional 24 hours incubation at 28° C. before cell harvesting for membrane preparation. CEGPCR3 was matched with two *C. elegans* peptides encoded by flp15, GGPQGPLRF-$NH_2$ (SEQ ID NO:85; $EC_{50}$ 152 nM) and GPSGPLRF-$NH_2$ (SEQ ID NO:89; $EC_{50}$ 422 nM). A Manduca peptide, GNSFLRF-$NH_2$ (SEQ ID NO:88; $EC_{50}$ 7900 nM), also activated the CEGPCR3 receptor, albeit with a potency about 19–52-fold lower than that determined for the two *C. elegans* flp15 peptides. Based on these data, we identified CEGPCR3 as the receptor for flp15 peptides.

TABLE 7

| Receptor | Peptide ligand | SEQ ID NO | Species of origin | $EC_{50}$ range |
|---|---|---|---|---|
| CEGPCR3 | GGPQGPLRF-$NH_2$ | 85 | *C. elegans*/flp15 | 150–400 nM |
| (SEQ ID | GPSGPLRF-$NH_2$ | 89 | *C. elegans*/flp15 | |
| NO:44) | GNSFLRF-$NH_2$ | 88 | Manduca | ~8 μM |
| CEGPCR7 | GLGPRPLRF-$NH_2$ | 86 | *A. suum* (AF9)/ | ~200–250 nM |
| (SEQ ID | | | *C. elegans* (flp21) | |
| NO:26) | [I]Y$^0$-GLGPRPLRF-$NH_2$ | 118 | Synthetic AF9 analog | |

In addition, peptide ligands were identified for the CEGPCR7 receptor (SEQ ID NO:25), as revealed in Table 7. One peptide bears the sequence GLGPRPLRF-$NH_2$ (SEQ ID NO:86; AF9) ($EC_{50}$ 207 nM). It is worth noting that [I]Y$^0$GLGPRPLRF-$NH_2$ (SEQ ID NO:118), representing an AF9 analog N-terminally extended with a 3-iodo-Tyr residue, was also active ($EC_{50}$ 237 nM). The functional activity of [I]Y$^0$AF9 indicates that this analog is an agonist and, in labeled (e.g., radioiodinated) form is useful as a probe for binding assays, including high-throughput screening (HTS) assays."

The CEGPCR4 receptor was activated by several peptide ligands, as determined using the GTPγS assay (Table 8). To perform the assays. Cl-10 cells were incubated as described above in the context of assaying CEGPCR3. The *C. elegans* peptides encoded on flp18 were the most potent ($EC_{50}$'s in the low nM range). Also very potent were several *A. suum* peptides, with high sequence homology to the *C. elegans* FLP18 peptides (all having the same sequence, PGVLRF-$NH_2$, at their C-termini). In addition to the FLP18 FaRPs, a battery of peptides from different invertebrate species (*Manduca, lobster, locust, Drosophila*), also activated this receptor. The latter were, however, significantly less potent ($EC_{50}$s in the high nanomolar to micromolar range). Based on the $EC_{50}$ values, we identified CEGPCR4 as the receptor for *C. elegans* flp18 peptides. As shown in Table 8, [IodoY] DVPGVLRF-$NH_2$, which is a N-terminally iodo-Tyr-extended flp18 analog (SEQ ID NO:119, $EC_{50}$=8), was essentially as potent as its parent peptide, DVPGVLRF-$NH_2$. This finding, as well as high affinity binding of [$^{125}$I-Y]DVPGVLRF-$NH_2$ (SEQ ID NO:80) to the CEGPCR4/CHO membranes (Kd in the subnanomolar range), showed that [$^{125}$I-Y]DVPGVLRF-NH$_2$ (SEQ ID NO:119) is an excellent probe, preferably radioiodinated, for a high throughput binding assay as a screen for modulators of the ligand-receptor interaction.

Shown in Table 8 are the synthetic peptides, various analogs of DVPGVLRF-NH$_2$ that acted as agonists of the CEGPCR4 receptor in CHO cells. Most of the synthetic peptides were very active (EC$_{50}$s in the nanomolar range in the GTPγS assay, and IC$_{50}$s in the low nanomolar range in the competition binding assay). The C-terminal tetrapeptide VLRF-NH2 was considerably less potent with an EC$_{50}$ of about 4 micromolar in the GTPγS assay, and an IC50 of about 400 nM in the competition binding assay. In general, iodo-Tyr-modified peptide analogs, particularly those disclosed herein (e.g., Table 8), represent good potential probes for binding assays and may be conveniently labeled with $^{125}$I.

Evaluation of CEGPCR5 expressed in CHO cells in the [$^{35}$S]GTPγS assay, as described above, yielded several active peptide ligands, as shown in Table 9. A peptide ligand designated AF9 (which also binds CEGPCR7, see above) bearing the sequence GLGPRPLRF-NH$_2$ (SEQ ID NO:86) was the most potent activator (EC$_{50}$ in the low nanomolar range) of CEGPCR5. An analog extending AF9 by an iodo-Tyr residue at its N-terminus, [iodoY]-GLGPRPLRF-NH$_2$ (SEQ ID NO:118), was about 200-fold less potent (EC$_{50}$ range of 176–273 nM), but was active enough to serve as a ligand in binding assays designed to identify modulators. Based on the GTPγS assay results, the *C. elegans* CEGPCR5 was identified as an AF9 or flp21 peptide receptor.

TABLE 8

| Receptor | Peptide ligand | SEQ ID NO | Species of origin | EC$_{50}$ range-GTPγS assay | IC$_{50}$ range-binding assay |
| --- | --- | --- | --- | --- | --- |
| CEGPCR4 (SEQ ID NO:22) | DVPGVLRF-NH$_2$ | 80 | *C. elegans*/flp18 | ~5–80 nM | 0.5–10 nM |
| | KSVPGVLRF-NH$_2$ | 92 | *C. elegans*/flp18 | | |
| | SEVPGVLRF-NH$_2$ | 98 | *C. elegans*/flp18 | | |
| | SVPGVLRF-NH$_2$ | 100 | *C. elegans*/flp18 | | |
| | DFDGAMPGVLRF-NH$_2$ | 120 | *C. elegans*/flp18 | | |
| | EIPGVLRF-NH$_2$ | 121 | *C. elegans*/flp18 | | |
| | AVPGVLRF-NH$_2$ (AF3) | 79 | *A. suum* | | |
| | GDVPGVLRF-NH$_2$ (AF4) | 84 | *A. suum* | | |
| | GMPGVLRF-NH$_2$ (AF20) | 87 | *A. suum* | | |
| | ASPSFIRF-NH$_2$ | 78 | *C. elegans*/flp4 | | |
| CEGPCR4 (SEQ ID NO:22) | GNSFLRF-NH$_2$ | 88 | Manduca | 0.4–9 μM | 60–900 μM |
| | KPNFLRF-NH$_2$ | 91 | *C. elegans*/flp1 | | |
| | PDVDHVFLRF-NH$_2$ (SchistoFLRFa) | 94 | Locust | | |
| | pQDVDHVFLRF-NH$_2$ (leucomyosuppressin)$^\#$ | 95 | Locust | | |
| | ILNleRF-NH$_2$ | 90 | synthetic | | |
| CEGPCR4 (SEQ ID NO:22) | SPLGTMRF-NH$_2$ | 143 | *C. elegans*/flp3 | 10 μM or higher | 50–500 μM |
| | SDNFMRF-NH$_2$ | 122 | Drosophila | | |
| | PDNFMRF-NH$_2$ | 123 | Drosophila | | |
| | SAEPFGTMRF-NH$_2$ | 97 | *C. elegans*/flp3 | | |
| | GGPQGPLRF-NH$_2$ | 85 | *C. elegans*/flp15 | | |
| | EIVFHQISPIFFRF-NH$_2$ | 83 | *C. elegans*/flp14 | | |
| | TDVDHVFLRF-NH$_2$ | 101 | Drosophila | | |
| | TNRNFLRF-NH$_2$ (Lobster peptide II) | 102 | Lobster | | |
| | NGAPQPFVRF-NH$_2$ | 93 | *C. elegans*/flp11 | | |
| CEGPCR4 (SEQ ID NO:22) | VLRF-NH$_2$ | 152 | synthetic | ~4 μM | ~0.4 μM |
| CEGPCR4 (SEQ ID NO:22) | GVLRF-NH$_2$ | 153 | Synthetic peptides | ~5–400 nM | ~1–60 nM |
| | Ac-GVLRF-NH$_2$ | 154 | | | |
| | PGVLRF-NH$_2$ | 155 | | | |
| | VPGVLRF-NH$_2$ | 156 | | | |
| | Ac-VPGVLRF-NH$_2$ | 157 | | | |
| | DVPGVLRF-NH$_2$ | 80 | | | |
| | Y-DVPGVLRF-NH$_2$ | 158 | | | |
| | 3-Iodo-Y-DVPGVLRF-NH$_2$ | 119 | | | |
| | Y-VPGVLRF-NH$_2$ | 159 | | | |
| | 3-Iodo-Y-VPGVLRF-NH$_2$ | 160 | | | |
| | Y-PGVLRF-NH$_2$ | 161 | | | |
| | 3-Iodo-Y-PGVLRF-NH$_2$ | 162 | | | |
| | Y-GVLRF-NH$_2$ | 163 | | | |
| | 3-Iodo-Y-GVLRF-NH$_2$ | 164 | | | |

TABLE 9

| Receptor | Peptide | SEQ ID NO | Species of origin | EC$_{50}$ range |
|---|---|---|---|---|
| CEGPCR5 (SEQ ID NO:46) | GLGPRPLRF-NH$_2$ (AF9) | 86 | C. elegans(flp21), A. suum | ~1–10 nM |
| CEGPCR5 (SEQ ID NO:46) | YGLGPRPLRF-NH$_2$ | 125 | [Y$^0$]AF9 analog | ~80–800 nM |
| | [iodo Y]GLGPRPLRF-NH$_2$ | 118 | [iodo Y$^0$ AF9 analog] | |
| | GNSFLRF-NH$_2$ | 88 | Manducca | |
| | YLRF-NH$_2$ | 126 | Leech | |
| | SDRNFLRF-NH$_2$ | 127 | Lobster | |
| | FLRF-NH$_2$ | 128 | Trematoda | |
| | FMRF-NH$_2$ | 129 | Mollusca | |
| | TNRNFLRF-NH$_2$ | 102 | Lobster | |
| | DPSFLRF-NH$_2$ | 131 | Manducca | |
| | SVPGVLRF-NH$_2$ | 100 | C. elegans (flp18) | |
| CEGPCR5 (SEQ ID NO:46) | AGPRFIRF-NH$_2$ | 133 | A. suum | ~1–8 μM |
| | KSVPGVLRF-NH$_2$ | 92 | C. elegans (flp18) | |
| | KPNFLRY-NH$_2$ | 135 | C. elegans (flp18) | |
| | ARGPQLRLRF-NH$_2$ | 136 | L. decemlineata | |
| | YIRF-NH$_2$ | 137 | Thematoda | |
| | GMPGVLRF-NH$_2$ | 87 | A. suum | |
| | AGAKFIRF-NH$_2$ | 139 | C. elegans (flp5) | |
| | KPNFLRF-NH$_2$ | 91 | C. elegans (flp1) | |
| | KHEYLRF-NH$_2$ | 141 | C. elegans (flp14) | |
| | EIVFHQISPIFFRF-NH$_2$ | 83 | C. elegans (flp14) | |

The CEGPCR16 receptor, expressed in CHO cells as described for CEGPRC3, was also used in a [$^{35}$S]GTPγS assay to screen for peptide ligands, which resulted in the identification of peptides encoded by the C. elegans flp3 gene. Of the peptides investigated, the Flp3 peptides were the most potent activators (Table 10), with EC$_{50}$ values of 100–330 nM. One noteworthy ligand is the Flp 18 peptide, SVPGVLRF-NH$_2$ (SEQ ID NO:100, EC$_{50}$=64 nM), which is comparable to, or more potent than, the Flp3 peptides in activating CEGPCR16; most of the other Flp18 peptides were either inactive or had an EC$_{50}$ in the high nanomolar to low micromolar range.

The CEGPCR12 h receptor, and the related splice variant isoforms CEGPCR12c, CEGPCR12u, and CEGPCR12v were expressed in CHO cells as described for CEGPRC3 and used in [$^{35}$S]GTPγS assays to screen for peptide ligands. The results presented in Table 11, specifically presented for CEGPCR12 h, apply to all CEGPCR12 isoforms. As shown therein, the most active peptide ligand was schistoFLRFa-mide and its N-terminally iodinated derivative, exhibiting EC$_{50}$ values of 330 nM and 478 nM, respectively. Candidate peptide ligands were tested at 5 μM.

TABLE 10

| Receptor | Sequence | SEQ ID NO | Species of origin | EC$_{50}$ range |
|---|---|---|---|---|
| CEGPCR16 (SEQ ID NO:36) | SPLGTMRF-NH$_2$ | 99 | C. elegans flp3 | ~60–300 nM |
| | SAFPFGTMRF-NH$_2$ | 97 | C. elegans flp3 | |
| | SADDSAPFGTMRF-NH$_2$ | 96 | C. elegans flp3 | |
| | ASEDALFGTMRF-NH$_2$ | 77 | C. elegans flp3 | |
| | EDGNAPFGTMRF-NH$_2$ | 82 | C. elegans flp3 | |
| | EAEEPLGTMRF-NH$_2$ | 81 | C. elegans flp3 | |
| | GMPGVLRF-NH$_2$ (AF20) | 87 | A. suum | |
| | SVPGVLRF-NH$_2$ | 100 | C. elegans flp18 | |
| CEGPCR16 (SEQ ID NO:36) | KSVPGVLRF-NH$_2$ | 92 | C. elegans flp18 | ~0.7–4.6 μM |
| | DVPGVLRF-NH$_2$ | 80 | C. elegans flp18 | |
| | SEVPGVLRF-NH$_2$ | 98 | C. elegans flp18 | |
| | DFDGAMPGVLRF-NH$_2$ | 120 | C. elegans flp18 | |
| | EIPGVLRF-NH$_2$ | 121 | C. elegans flp18 | |
| | AVPGVLRF-NH$_2$ (AF3) | 79 | A. suum | |
| | GDVPGVLRF-NH$_2$ (AF4) | 84 | A. suum | |

TABLE 11

| Receptor | Peptide sequence | SEQ ID NO | Species of origin | EC$_{50}$ range |
|---|---|---|---|---|
| CEGPCR12h (SEQ ID NO:8) | PDVDHVFLRF-NH$_2$ (SchistoFLRF-NH$_2$) | 94 | Locust | ~300–500 nM |
|  | [I]Y°PDVDHVFLRF-NH$_2$ | 103 | Locust (modified) |  |
|  | FDDYGHLRF-NH$_2$ | 180 | Drosophila |  |
| CEGPCR12h (SEQ ID NO:8) | pQDVDHVFLRF-NH$_2$ (leucomyosuppressin)[+] | 95 | Locust Drosophila | ~1.5–3.0 μM |
|  | TDVDHVFLRF-NH$_2$ (dromyosuppressin) | 101 | C. elegans |  |
|  | GGPQGPLRF-NH$_2$ | 85 |  |  |
| CEGPCR12h (SEQ ID NO:8) | AVPGVLRF-NH$_2$ (AF3) | 79 | A. suum | Peptides active at 5 μM |
|  | GDVPGVLRF-NH$_2$ (AF4) | 84 | A. suum |  |
|  | GMPGVLRF-NH$_2$ | 87 | A. suum |  |
|  | GLGPRPLRF-NH$_2$ (AF9) | 86 | C. elegans, A. suum |  |
|  | DVPGVLRF-NH$_2$ | 80 | C. elegans/flp18 |  |
|  | KSVPGVLRF-NH$_2$ | 92 | C. elegans/flp18 |  |
|  | SVPGVLRF-NH$_2$ | 100 | C. elegans/flp18 |  |

[+]pQ denotes pyroglutamic acid residue.

The CEGPCR19.1 and CEGPCR19.2 receptors, expressed in CHO cells, were subjected to screens for peptide ligands (present at 10 μM each) using a calcium mobilization assay (FLIPR). This calcium flux assay provides an alternative to the use of other screening assays disclosed herein. The assay, known in the art, was performed on transiently transfected CHO cells that had been incubated for 24 hours at 37° C. immediately following transfection, followed by a 48-hour period at 28° C. Cells were then loaded with 4 M Fluo-3 and 2.5 mM probenecid for calcium signaling (FLIPR) analysis. The results shown in Table 12 indicate that CEGPCR19.1 was activated by Flp18 peptides and some structurally similar A. suum peptides (identical C-terminal sequences of PGVLRF-NF$_2$). EC$_{50}$ values for CEGPCR19.1 binding of Flp18 peptides, and AF3 and AF4 peptides, ranged from 20–100 nM (similar EC$_{50}$ values were observed for CEGPCR19.2, described below). The results support the conclusion that CEGPCR19.1 is either an isoform of, or closely related to, the CEGPCR4 receptor because both CEGPCR19.1 and CEGPCR4 were activated by the same Flp18 peptides as well as by A. suum peptides sharing a high degree of similarity with those Flp18 peptides.

CEGPCR19.2, which is a splice variant of CEGPCR19.1, was activated (calcium assay) by the same peptides that activated CEGPCR19.1, as well as by several additional A. suum peptides not identified as activators of CEGPCR19.2 (SEQ ID NOS:91, 99, 131, 133, 150 and 151), as shown in Table 13.

TABLE 12

| Receptor | Peptide sequence | SEQ ID NO | Species of origin | EC$_{50}$ range |
|---|---|---|---|---|
| CEGPCR19.1 (SEQ ID NO:107) | DVPGVLRF-NH$_2$ | 80 | C. elegans/flp18 | ~30–100 nM |
|  | KSVPGVLRF-NH$_2$ | 92 | C. elegans/flp18 |  |
|  | SEVPGVLRF-NH$_2$ | 98 | C. elegans/flp18 |  |
|  | SVPGVLRF-NH$_2$ | 100 | C. elegans/flp18 |  |
|  | DFDGAMPGVLRF-NH$_2$ | 120 | C. elegans/flp18 |  |
|  | EIPGVLRF-NH$_2$ | 121 | C. elegans/flp18 |  |
|  | AVPGVLRF-NH$_2$ (AF3) | 79 | A. suum |  |
|  | GDVPGVLRF-NH$_2$ (AF4) | 84 | A. suum |  |
| CEGPCR19.1 (SEQ ID NO:107) | ARGPQLRLRF-NH$_2$ | 136 | L. decemlineata | ~200–1500 nM |
|  | GMPGVLRF-NH$_2$ | 87 | A. suum |  |
|  | GLGPRPLRF-NH$_2$ (AF9) | 86 | A. suum, C. elegans/flp21 |  |

TABLE 13

| Receptor | Peptide sequence | SEQ ID NO | Species of origin | EC$_{50}$ range |
|---|---|---|---|---|
| CEGPCR19.2 (SEQ ID NO:105) | DVPGVLRF-NH$_2$ | 80 | C. elegans/flp18 | ~20–70 μM |
|  | KSVPGVLRF-NH$_2$ | 92 | C. elegans/flp18 |  |
|  | SEVPGVLRF-NH$_2$ | 98 | C. elegans/flp18 |  |
|  | SVPGVLRF-NH$_2$ | 100 | C. elegans/flp18 |  |
|  | DFDGAMPGVLRF-NH$_2$ | 120 | C. elegans/flp18 |  |
|  | EIPGVLRF-NH$_2$ | 121 | C. elegans/flp18 |  |
|  | AVPGVLRF-NH$_2$ (AF3) | 79 | A. suum |  |
|  | GDVPGVLRF-NH$_2$ (AF4) | 84 | A. suum |  |
| CEGPCR19.2 | GLGPRPLRF-NH$_2$ (AF9) | 86 | A. suum, | ~0.6–5 μM |

TABLE 13-continued

| Receptor | Peptide sequence | SEQ ID NO | Species of origin | EC$_{50}$ range |
|---|---|---|---|---|
| (SEQ ID NO:105) | | | *C. elegans*/flp21 | |
| | AEGLSSPLIRF-NH$_2$ | 150 | *A. suum* | |
| | FDRDFMHF-NH$_2$ | 151 | *A. suum* | |
| | AGPRFIRF-NH$_2$ | 133 | *A. suum* | |
| | GMPGVLRF-NH$_2$ | 87 | *A. suum* | |
| | ARGPQLRLRF-NH$_2$ | 136 | *L. decemlineata* | |
| CEGPCR19.2 | KPNFIRF-NH$_2$ (PF4) | 165 | *P. redivivus* | peptides active |
| (SEQ ID NO:105) | KPNFLRF-NH$_2$ | 91 | *C. elegans*/flp1 | at 10 μM |
| | SQPNFLRF-NH$_2$ | 166 | *C. elegans*/flp1 | |
| | SPLGTMRF-NH$_2$ | 99 | *C. elegans*/flp3 | |
| | DPSFLRF-NH$_2$ | 131 | Manduca | |
| | LQPNFLRF-NH$_2$ | 167 | *H. contortus* | |

G. MAP Kinase Activity Assay

Evaluation of MAP Kinase activity in cells expressing a GPCR-like receptor provide another assay to identify modulators of GPCR-like polypeptide activity. [See, e.g., Lajiness et al., *Journal of Pharmacology and Experimental Therapeutics*, 267(3): 1573–81 (1993); and Boulton et al., *Cell*, 65: 663–75 (1991).]

In one embodiment, CHO cells stably transfected with a GPCR-like receptor are seeded into 6-well plates at a density of 70,000 cells/well 48 hours prior to the assay. During this time, the cells are cultured at 37° C. in DMEM medium supplemented with 10% fetal bovine serum, 2 mM glutamine, 10 Units/ml penicillin and 10 μg/ml streptomycin. The cells are starved for serum for 1–2 hours prior to the addition of stimulants.

For the assay, the cells are treated with medium alone or medium containing a putative agonist, or the positive control phorbol myristoyl acetate (i.e., PMA), and the cells are incubated at 37° C. for varying times. To stop the reaction, the plates are placed on ice, the medium is aspirated, and the cells are rinsed with 1 ml of ice-cold PBS containing 1 mM EDTA. Thereafter, 200 μl cell lysis buffer (12.5 mM MOPS, pH 7.3, 12.5 mM β-glycerophosphate, 7.5 mM MgCl$_2$, 0.5 mM EGTA, 0.5 mM sodium vanadate, 1 mM benzamidine, 1 mM dithiothreitol, 10 μg/ml leupeptin, 10 μg/ml aprotinin, 2 μg/ml pepstatin A, and 1 μM okadaic acid) is added to the cells. The cells are scraped from the plates and homogenized by 10 passages through a 23¾ needle. The cytosol fraction is then prepared by centrifugation at 53,000 rpm for 15 minutes.

Aliquots (5–10 μl containing 1–5 μg protein) of cytosols are mixed with 1 mM MAPK Substrate Peptide (APRTPGGRR, Upstate Biotechnology, Inc. N.Y.) and 50 μM [γ-$^{32}$P]ATP, (NEN, 3000 Ci/mmol) diluted to a final specific activity of ~2000 cpm/pmol in a total volume of 25 μl. The samples are incubated for 5 minutes at 30° C., and reactions are stopped by spotting 20 μl on 2 cm$^2$ of Whatman P81 phosphocellulose paper. The filter squares are washed in four changes of 1% H$_3$PO$_4$, and the squares are counted by liquid scintillation spectroscopy. Equivalent cytosolic extracts are incubated without MAPK substrate peptide, and the cpm from these samples are subtracted from the matched samples with the substrate peptide. The cytosolic extract from each well is used as a separate point. Protein concentrations are determined by a dye binding protein assay (Bio-Rad). Agonist activation of the receptor is expected to result in up to a five-fold increase in MAPK enzyme activity. This increase is blocked by antagonists.

H. [$^3$H]Arachidonic Acid Release

The activation of GPCRs has been observed to potentiate arachidonic acid release in cells, providing yet another useful assay for modulators of GPCR-like receptor activity. [See, e.g., Kanterman et al., *Molecular Pharmacology*, 39: 364–9 (1991).] For example, CHO cells that are stably transfected with a GPCR-like receptor expression construct are plated in 24-well plates at a density of 15,000 cells/well and grown in DMEM medium supplemented with 10% fetal bovine serum, 2 mM glutamine, 10 Units/ml penicillin and 10 μg/ml streptomycin for 48 hours at 37° C. before use. Cells of each well are labeled by incubation with [$^3$H]-arachidonic acid (Amersham Corp., 210 Ci/mmol) at 0.5 μCi/ml in 1 ml DMEM supplemented with 10 mM HEPES, pH 7.5, and 0.5% fatty-acid-free bovine serum albumin for 2 hours at 37° C. The cells are then washed twice with 1 ml of the same buffer.

Candidate modulator compounds are added in 1 ml of the same buffer, either alone or containing 10 μM ATP as a positive control and the cells are incubated at 37° C. for 30 minutes. Buffer alone and mock-transfected cells are used as controls. Samples (0.5 ml) from each well are counted by liquid scintillation spectroscopy. Agonists which activate the receptor will lead to potentiation of the ATP-stimulated release of [$^3$H-]-arachidonic acid. This potentiation is blocked by antagonists.

I. Extracellular Acidification Rate

In yet another assay, the effects of putative modulators of GPCR-like receptor activity are assayed by monitoring extracellular changes in pH induced by the putative modulators. [See, e.g., Dunlop et al., *Journal of Pharmacological and Toxicological Methods*, 40(I): 47–55 (1998).]

CHO cells transfected with a GPCR-like receptor expression construct are seeded into 12 mm capsule cups (Molecular Devices Corp.) at 4×10$^5$ cells/cup in DMEM supplemented with 10% fetal bovine serum, 2 mM L-glutamine, 10 Units/ml penicillin, and 10 μg/ml streptomycin. The cells are incubated in this medium at 37° C. in 5% CO$_2$ for 24 hours.

Extracellular acidification rates are measured using a Cytosensor microphysiometer (Molecular Devices Corp.). The capsule cups are loaded into the sensor chambers of the microphysiometer and the chambers are perfused with running buffer (bicarbonate free DMEM supplemented with 4 mM L-glutamine, 10 Units/ml penicillin, 10 μg/ml streptomycin, 26 mM NaCl) at a flow rate of 100 μl/minute. Agonists or other agents are diluted into the running buffer and perfused through a second fluid path. During each 60-second pump cycle, the pump is run for 38 seconds and is off for the remaining 22 seconds. The pH of the running buffer in the sensor chamber is recorded during the cycle from 43–58 seconds, and the pump is re-started at 60 seconds to start the next cycle. The rate of acidification of the running buffer during the recording time is calculated by the Cytosoft program. Changes in the rates of acidification are calculated by subtracting the baseline value (the average of four rate measurements immediately before addition of modulator candidates) from the highest rate measurement obtained after addition of a modulator candidate. The selected instrument detects 61 mV/pH unit. Modulators that act as agonists at the receptor result in an increase in the rate of extracellular acidification as compared to the rate in the absence of agonist. This response is blocked by modulators which act as antagonists at the receptor.

EXAMPLE 6

To avoid impediments imposed by potential artifacts of PCR-based cloning, alternative approaches to the cloning of neuropeptide (e.g., FaRP) receptors was developed. By increasing the versatility of the cloning approach, FaRP receptors having desired relationships (e.g., particular levels of primary, or structural, sequence similarity or identity, common activities, or related sources) could be targeted. For example, targeted neuropeptide (e.g., FaRP) receptors might exhibit 70%, 75%, 80%, 85%, 90%, 95%, 99%, 99.9%, or 99.99% similarity; also, the targeted receptors might be selected from invertebrates, from insects, from flat- and round-worms, from particular round-worm genera, or from particular round-worm species, sub-species or variants.

The identification of several authentic neuropeptide (FaRP) receptors also makes possible additional bioinformatics strategies. Comparison of confirmed receptors with the *C. elegans* database should aid in the identification of additional neuropeptide receptors, including FaRP receptors. Likewise, the identification of the *C. elegans* neuropeptide receptors make possible a similar approach using other databases, including Drosophila and human databases.

The sequences of a total of 20 cloned receptors are listed, including all of the receptors exhibiting high levels of similarity to the confirmed neuroepeptide (FaRP) receptors. Finally, the results of bioinformatic analyses using the current databases and biochemical information are presented.

Bioinformatic Selection of Receptors

Later releases of the Wormpep database were searched in a manner similar to that described above for the initial identification of candidate receptors. Wormpep releases through Wormpep 23 were downloaded from the Sanger Centre web site. The database was searched using BLAST 2.0, Altschul et al., Nucl. Acids Res. 25(17):3389–402 (1997), with known *C. elegans* neuropeptide (e.g., FaRP) receptors (CEGPCR3, CEGPCR4, CEGPCR5, CEGPCR7, CEGPCR12c, CEGPCR12h, CEGPCR12u, CEGPCR12v, and CEGPCR16). A composite BLAST score was assembled from these searches by calculating the product of the "e" values from all of the searches for a given receptor. Release 118 of GenPept was used for general searches against public sequences and as a source of sequences used for the phylogenetic analyses. Alignments and phylogenetic relationships were prepared using the AlignX (ClustalW, Thompson et al., Nucl. Acids Res. 22(22):4673–80 (1994)) alignment program (Vector NTI suite, Informax, N. Bethesda, Md.).

Cloning of Receptors

Receptors were cloned using PCR techniques. Initially, the predicted sequence was used to design PCR primers. The 5' PCR primer incorporated the *C. elegans* initiator ATG within an optimized 5' untranslated region (Kozak, M., Nucl. Acids Res. 15(20):8125–48 (1987). The 3' PCR primer usually contained a restriction enzyme site not contained within the receptor sequence to simplify later production of cRNA for injection studies.

If the initial approach using primers designed to the predicted sequence did not readily produce a PCR product, or if the predicted sequence was obviously in error (as judged by alignment with other GPCRs), then either an anchored PCR approach (used successfully for CEGPCR4 and CEGPCR22), or a rational primer design approach (see below) was followed to obtain an intact clone.

Typically, a PCR product was obtained using either XL rTth polymerase (Perkin-Elmer Applied Biosystems, Foster City, Calif.) or the Expand HF mix (Boehringer Mannheim, Indianapolis, Ind.). PCR primer sequences are presented in the sequence listing, with "f" and "r" suffixes added to a given GPCR clone designation to unambiguously refer to forward and reverse primer pairs. The DNA template for the reaction was either a first strand cDNA synthesis reaction (using random hexamers to prime synthesis from a preparation of total *C. elegans* RNA) or a *C. elegans* cDNA library in pBluescript, constructed by performing an in vivo excision reaction on a cDNA commercial library constructed in a Uni-ZAP XR lambda vector (Stratagene, La Jolla, Calif., catalog number 937006). PCR products were typically gel-purified using QIAquick columns (Qiagen, Valencia, Calif.) and either cloned directly into pCR3.1 (Invitrogen, Carlsbad, Calif.), or indirectly through an initial cloning step into pCR2.1. Plasmids containing the appropriate inserts were prepared by a mini-prep DNA isolation procedure (Qiagen) and were sequenced using BigDye dye terminator chemistry (PE Applied Biosystems, Foster City, Calif.) on an ABI 377 automated DNA sequencer, as described above. Complete sequences were assembled using Sequencher software (Version 3.0, GeneCodes, Ann Arbor, Mich.) and compared against the expected sequence predicted from the Wormpep database.

Cloning CEGPCR2

CEGPCR2 (SEQ ID NO:176) was cloned using PCR. The template for the reaction was a plasmid library of *C. elegans* cDNA isolated from an in vivo excision of a commercially available library (constructed in a Uni-ZAP XR vector; Stratagene, La Jolla, Calif.) according to the manufacturer's instructions. The PCR reaction was performed using the Expand HF kit (Boehringer Mannheim, Indianapolis, Ind.) and contained: 0.5 µM each primer, 150 nM dNTPs, 0.5 mM $MgCl_2$, and 1.4 units Expand High Fidelity enzyme mix. The PCR reaction was carried out in a Stratagene Robocycler, using the following conditions: 30 cycles at 95° C. for 30 seconds, 50° C. for 30 seconds, 72° C. for 2 minutes, followed by 72° C. for 5 minutes. A TA cloning kit (Invitrogen, Carlsbad, Calif.) was used to clone the gel-purified PCR product into pCR2.1. The ligation mixture was transformed into *E. coli* DH5α, and transformed cells were identified using a colony PCR method to screen transformants for the presence of the appropriate insert. Purified plasmid DNA was obtained using a mini-prep procedure (Qiagen Valencia, Calif.). Plasmids were sequenced using dye terminator chemistry (PE Applied Biosystems, Foster City, Calif.) and an automated sequencer (ABI 377). A clone with an intact open reading frame was obtained and subcloned into pcDNA3.1(+) using EcoRI. XhoI was used to determine the orientation of insert fragments.

Cloning CEGPCR21

CEGPCR21 was cloned as described above in the context of CEGPCR2, using the same template, PCR conditions, and cloning strategy. HindIII was used to determine the orientation of inserts.

Cloning CEGPCR23

The C. elegans receptor CEGPCR23 was cloned using the C. elegans cDNA plasmid library as template. The PCR reaction was set up using 0.5 μM each primer, 200 μM dNTPs, 1.15 mM Mg(OAc)$_2$, and 4 units rTth DNA polymerase, XL. The PCR reactions were performed in a Perkin-Elmer 9600 Thermal Cycler using the following program: 25 cycles at 94° C. for 30 seconds, 50° C. for 10 minutes, and 72° C. for 10 minutes. The resulting PCR product was gel-purified, cloned into pCR2.1, and propagated in E. coli DH5α. Plasmid DNA was isolated and verified by sequencing. An intact clone was selected and subcloned into pcDNA3.1(+) (Invitrogen) using BstXI. Subclones with inserts in the correct orientation were identified using BamHI/BglII.

Cloning CEGPCR22

An anchored PCR approach was used to obtain the correct ends for CEGPCR22. Internal primers were designed to the exon containing 7TM. PCR experiments using these internal primers with the initial flanking primers confirmed that the 3' PCR primer was nonfunctional. Using the internal primer (SCN162—5'-ACG TTT AAG AGC TCT CAA ATC CCA T-3'; SEQ ID NO:171) and T7/M13 reverse vector primers, along with the C. elegans cDNA plasmid library, a PCR product was successfully obtained that corresponded to the correct 3' end. Using that information, a new 3' PCR primer was designed and used in conjunction with the initial 5' PCR primer. CEGPCR22 was then cloned in a similar manner to CEGPCR23. Template and PCR conditions were identical to CEGPCR23, except that the PCR program included 30 cycles at 94° C. for 15 seconds, 55° C. for 5 minutes, and 72° C. for 10 minutes. The resulting PCR product was directly cloned into pCR3.1.

Cloning CEGPCR4

An anchored PCR approach was used to obtain the correct ends for CEGPCR4. Internal primers were synthesized. PCR experiments using these internal primers with the initial flanking primers confirmed that the 3' end of the cDNA was incorrectly predicted. Using an internal primer (SCN160—5'-CCAGAGCTCATCAAAACTCAAGAAT-3'; SEQ ID NO:172) and T7/M13 reverse vector primers, along with the C. elegans cDNA plasmid library, a PCR product was successfully obtained that corresponded to the correct 3' end, extending beyond the stop codon. Using that information, a new 3' PCR primer (SCN189, 5'-TTACAATTTAAAACTAGGTGCTTCT-3'; SEQ ID NO:174) was designed and used in conjunction with the initial 5' PCR primer. CEGPCR4 was then cloned using identical conditions to CEGPCR23, except that the template was derived from a first strand cDNA synthesis of C. elegans mRNA and the PCR program included 25 cycles at 94° C. for 15 seconds, 60° C. for 5 minutes, and 72° C. for 10 minutes. The PCR product was cloned initially in pCR2.1, and subcloned into pcDNA3.1(+) using EcoRI, and clones with the correct orientation were found using digestion with SacI.

Cloning CEGPCR5

CEGPCR5 was cloned using the same PCR reaction components as CEGPCR22 and first strand cDNA as template. PCR conditions were: 35 cycles at 94° C. for 30 seconds, 60° C. for 5 minutes, and 72° C. for 10 minutes. The reactions were carried out in a Perkin-Elmer 9600 thermal cycler. The resulting PCR product was cloned directly into pCR3.1 and transformed into E. coli DH5α. Clones were identified by colony PCR. Plasmids were isolated, purified, and sequenced as described above.

Cloning CEGPCR19.1

The short splice variant of clone CEGPCR19 was cloned using conditions identical to those described for CEGPCR5, with the exception of a 50° C. hybridization step for the PCR reaction.

Cloning CEGPCR19.2

The long splice variant of clone CEGPCR19 was cloned using conditions identical to those described for CEGPCR5, with the exception of a 55° C. hybridization step for the PCR reaction.

Cloning CEGPCR1a and CEGPCR1f

The cloning of the two splice isoforms of CEGPCR1 were described in the examples above. Those initial clones were based on the Wormpep 13-predicted sequence. Although the receptors were successfully amplified and cloned, alignment of the sequences suggested that other variant clones might also exist that contained an initiator ATG in a more conventional location than within the first transmembrane region. Subsequent releases of the database included a longer AC7.1 sequence corresponding to CEGPCR1 (but still not the splice variants). Using that new sequence from the Wormpep database, a new primer (SCN-199, 5'-GCCGCCATGAACTTTTCGGCCACCGATTCGA-3'; SEQ ID NO:175) was designed and additional clones were isolated (using the identical procedures and 3' PCR primer described in the preceding examples for CEGPCR1).

Cloning CEGPCR12c, CEGPCR12h, and CEGPCR12u

Similar to CEGPCR1, alignment of the initially amplified clones for CEGPCR12 suggested that additional variants might exist. In the case of CEGPCR12, it was anticipated that variants encoding polypeptides having additional N-terminal sequence would be identified. Using the rational primer design approach, PCR primers were designed for several potential exons. Primer DEL-1850 (5'-GCCGCCATGTCGAATGATCTCGTGCCTTCAG-3', SEQ ID NO:173) and the original 3' PCR primer (SEQ ID NO:70; using PCR conditions as described for the initial amplification of CEGPCR12) were then used to amplify the longer version. The PCR product was cloned directly into PCR3.1 as described above. Intact versions for CEGPCR12c, CEGPCR12h, and CEGPCR12u were obtained.

The C. elegans Wormpep 23 database was searched using BLAST 2.0 (Altschul, et al., Nucl. Acids Res. 25(17):3389–402 (1997)), with the six currently known C. elegans neuropeptide (e.g., FaRP) receptors (CEGPCR3, CEGPCR4, CEGPCR5, CEGPCR7, CEGPCR12c, CEGPCR12h, CEGPCR12u, CEGPCR12v, and CEGPCR16). Using the e-values from these searches, a composite BLAST score was calculated. Using this approach, a group of 11 receptors was discernable from the rest of the C. elegans GPCRs. These receptors include the above-six confirmed neuropeptide (FapP) receptors, and CEGPCR13, CEGPCR17, CEGPCR14, CEGPCR19 (both CEGPCR19.1 and CEGPCR19.2), and CEGPCR11. An additional group of receptors fell into a second tier. This group included CEGPCR20, CEGPCR1 (Both CEGPCR1a and CEGPCR1f), CEGPCR15, CEGPCR18a, CEGPCR25 (SEQ ID NO:178), and CEGPCR3. BLAST comparisons against the GenBank database showed that these receptors were also likely peptide receptors, although they have not yet been matched to ligands.

An alignment of the receptors using CLUSTALW shows that the receptors exhibit the classic characteristics of the seven transmembrane family of receptors, including higher degrees of similarity through the transmembrane regions and very few absolutely conserved residues (for a review see Probst et al., Cell Biol 11(1): 1–20 (1992)). The only unusual feature for the receptors is a few atypical amino acids in the conserved 'DRY' motif immediately following 3TM, e.g., 'HEF' in the CEGPCR1a and 1f sequences and 'DKF' for the CEGPCR18a and 18b sequences.

The *C. elegans* receptors can also be classified using a phylogenetic approach. FIG. 1 shows an alignment of the *C. elegans* GPCRs described above resulting from a typical phylogenetic analysis. This analysis showed that ten of the eleven members of the above-mentioned family of receptors, including the neuropeptide receptors identified to date, fall into two distinct groups. The only other receptors that fall into these groups are the 'GRL105' receptor from *Lymnaea stagnalis* (an invertebrate NPY receptor) and the DmGPCR1 and DmGPCR2 receptors from Drosophila. We have recently confirmed that the DmGPCR1 receptor has a neuropeptide (i.e., FaRP) ligand.

This analysis also showed that the second tier of *C. elegans* receptors from the BLAST analysis tends to fall into classes with other known neuropeptide receptors. CEGPCR1 and CEGPCR24 fall into an interesting group with the *L. stagnalis* lymnokinin receptor (Cox et al., J. Neurosci. 17(4):1197–205 (1997)), the *L. stagnalis* cardioexcitatory peptide (an RFamide ligand) receptor (Tensen et al., J. Neurosci. 18(23):9812–21 (1998)), the *Stomoxys calcitrans* (stable fly) 'tachykinin-like' receptor (Guerrero, F. D., Annals N.Y. Acad. Sci. 814:310–1 (1997)), a receptor for a leucokinin-like peptide from cattle tick (Holmes, et al., Insect Mol Biol (2000; in press)) and the DmGPCR6 receptor [Li, et al., J. Biol. Chem. 267(1):9–12 (1992). We have recently identified this last receptor as having a neuropeptide (i.e., FaRP) ligand. This group is separate, and contains only invertebrate receptors, but is most closely related to the vertebrate family of neurokinin (NK-1,2,3) receptors. The *C. elegans* receptors CEGPCR6 and CEGPCR15 are in a group distinct from, but related to, the vertebrate neurokinin receptors. A cluster containing a variety of cholecystokinin receptors contains the *C. elegans* receptor Y39A3B.5. The receptor CEGPCR20 falls into a group containing the Drosophila receptor for an allatostatin-related peptide (Birgul et al., EMBO Journal 18(21):5892–900 (1999)) and DmGPCR4, both of which recognize allatostatin peptide ligands. CEGPCR18 variants are included in a group containing several vertebrate orphan receptors, most closely related to the clusters containing bombesin receptors, galanin receptors, gastrin releasing peptide receptors and the above mentioned allatostatin receptors. CEGPCR8 (and CEGPCR21) cannot obviously be linked to any particular group of receptors, being most closely related to a broad cluster containing a variety of receptors, including some falling outside the domain of those receptors recognizing peptide ligands (e.g., serotonin receptors, opsins). The receptors CEGPCR9, CEGPCR23 and CEGPCR22 are all listed in a small group apart from a group containing a variety of receptors with peptide ligands, including somatostatin, galanin, and bombesin receptors. BLAST results are slightly in contrast with these results for CEGPCR9, listing the highest scoring hits for this receptor as NPY-type receptors. BLAST results indicate the five highest scoring matches to CEGPCR22 and CEGPCR23 are all other *C. elegans* receptors (Y116A8B.5, C43C3.2, T02D1.6), but immediately following those are a series of vertebrate somatostatin and kappa-opioid receptors.

The receptors were cloned using several strategies, all based on the use of PCR. The first strategy involved the simple design of PCR primers using the predicted cDNA sequence of the GPCR. In cases where a PCR product was not obtained using primers designed on the basis of the predicted sequence, an alternative approach was used to design new PCR primers. The failure in the initial PCR experiments was typically due to the inability of the gene prediction software to accurately predict the ends of the GPCR sequences. Alignment of the predicted amino acid sequences for the GPCRs often revealed the errors, e.g., one of the ends of the encoded protein sequences would be much longer that any of the other aligned sequences. In some cases the alignment showed that a product that did amplify by PCR had been inaccurately predicted, e.g., showing an initiator ATG that was within the predicted 1TM region. The incorrectly predicted end could usually be pinpointed by the use of internal PCR primers, located within a conserved and unspliced region, in conjunction with the original flanking PCR primers. Using this information, new PCR primers were designed. Taking into account the possible open reading frames, potential mRNA processing sites, and proximity to the presumed correct sequence, a series of alternative PCR primers were synthesized and tested. This rational primer design approach, although labor-intensive, was extremely successful, resulting in a high rate of successful PCR amplification.

Based on comparisons of cloned cDNAs to predicted sequences, 11 of 22 GPCR-like receptor sequences selected from Wormpep were incorrectly predicted. As would be expected, most of these errors have occurred in the prediction of the N- and C-termini of the encoded proteins. Although an anchored PCR approach has been successful in obtaining the ends of an incorrectly predicted GPCR-like receptor in a couple of cases, the rational primer design approach, although laborious, has had a much higher success rate.

Phylogenetic analyses can be used to speculate on possible functions for the receptors. It should be noted that there are numerous methods and variables that can be used to build phylogenetic relationships. Although the results described herein are based on one method Thompson et al., Nucl. Acids Res. 22(22):4673–80 (1994)), several methods and permutations of phylogenetic analyses were investigated, with all methods giving very similar results, especially with regards to the overall relationships observed for the confirmed neuropeptide (e.g., FaRP) receptors.

At this point in time, a total of six *C. elegans* receptors and two Drosophila receptors have been matched to neuropeptide (FaRP) ligands. Phylogenetic analyses of the *C. elegans* and Drosophila receptors, along with all of the peptidergic receptors in the public databases, show that all of the *C. elegans* FaRP receptors may be grouped together. This group contains an additional five *C. elegans* receptors (CEGPCR13, CEGPCR14, CEGPCR17, and CEGPCR19.1 and CEGPCR19.2) that are expected to have FaRP ligands. The only other receptors within this group are two Drosophila receptors, one of which has been confirmed to have a FaRP ligand (DmGPCR1), and a single receptor from *L.*

*stagnalis* (GRL105) (Tensen et al., J. Neurosci. 18(23):9812–21 (1998)). The GRL105 receptor has been linked to a *L. stagnalis* neuropeptide Y homologue (an RFamide). The phylogenetic analysis would predict that it may also have a FaRP ligand. The grouping of these invertebrate receptors in a category that contains no known vertebrate receptors is consistent with FaRP receptors providing a relatively invertebrate-specific target.

The other *C. elegans* receptor that received a high score in the BLAST analyses was CEGPCR11. This receptor falls into a group that is highly related to the group containing confirmed FaRP receptors, described above, and includes the dog and human orexin receptors. Slight alterations in the conditions used in the analysis would result in CEGPCR11 being grouped with the above receptors.

Another group of receptors that is of interest is derived from *C. elegans* neuropeptide receptors. This group includes the *C. elegans* receptors CEGPCR24a, CEGPCR24b, and CEGPCR1. The recent identification of a FaRP ligand for the Drosophila receptor DmGPCR6, also located within this group of receptors, increases the interest in these *C. elegans* receptors.

Two clones (CEGPCR6 and CEGPCR20) included in the table have yet to be amplified. These clones do not PCR-amplify using primers designed from the predicted sequences in Wormpep. It is very likely that one, or both, of the termini of these clones is incorrectly predicted. At the time of the receptor cloning, these receptors were not classified in the group of receptors that contained the first verified FapP receptors. CEGPCR20 groups with a family of receptors that include the vertebrate galanin receptors, the Drosophila allatostatin-like peptide receptor (Birgul et al., EMBO Journal 18(21):5892–900 (1999)), the Drosophila 'galanin' receptor Lenz et al., BBRC 269(1):91–96 (2000) (ligand assigned by homology, the Drosophila receptor DmGPCR4, which has recently been confirmed to be an additional Drosophila allatostatin receptor, and a series of four orphan *L. stagnalis* receptors. Based on this information, is expected that CEGPCR20 recognizes an allatostatin-like peptide ligand. CEGPCR6 falls into a grouping with CEGPCR1a, CEGPCR1f, CEGPCR15, and two Drosophila receptors. With the recent discovery that one of the Drosophila receptors recognizes a FaRP ligand, there is a renewed interest in this group of receptors.

Based on analyses to date, the invertebrate GPCR-like receptors do not appear to have highly similar sequences in other organisms, such as vertebrates and plants. However, receptors bearing lower levels of similarity, e.g., 55%, 60%, 65%, 70%, 75%, 80%, 85%, and preferably 90%, 95%, 98%, 99% and more preferably 99.5% similarity to a GPCR-like receptor amino acid sequence disclosed herein are also contemplated by the invention. Analogously, the invention comprehends receptor-encoding polynucleotides exhibiting 55%, 60%, 65%, 70%, 75%, 80%, 85%, 90%, and preferably 95%, 98%, 99and more preferably 99.5% similarity to a polynucleotide disclosed herein. Similarities can be determined using any of a variety of algorithms known in the art, with the BLAST algorithm implemented at the GenBank website (http://www.ncbi.nlm.nih.gov/BLAST/), using default parameters, being preferred. These receptor sequences are anticipated to be useful in a variety of contexts. For example, it is expected that vertebrate, and more particularly mammalian, receptor sequences showing some similarity to the invertebrate GPCR-like receptors will be useful in diagnosing, and treating, a variety of neurological ailments or conditions.

The following, clones (deposit numbers indicated parenthetically) were deposited with the ARS Patent Culture Collection, 1815 North University Street, Peoria, Ill. 61604 on Nov. 3, 2000: CEGPCR1a (UC20129 NRRL B-30361), CEGPCR1f (UC20130 NRRL B-30362), CEGPCR3 (UC20132 NRRL B-30364), CEGPCR4 (UC20133 NRRL B-30365), CEGPCR5 (UC20134 NRRL B-30366), CEGPCR7 (UC20135 NRRL B-30367), CEGPCR8 (UC20136 NRRL B-30368), CEGPCR9 (UC20137 NRRL B-30369), CEGPCR12c (UC20138 NRRL B-30370), CEGPCR12h (UC20139 NRRLB-30371), CEGPCR12u (UC20140 NRRL B-30372). On Nov. 10, 2000, the following clones were deposited with the ARS Patent Culture Collection: CEGPCR11 (UC20141 B-30381), CEGPCR13 (UC20142 B-30382), CEGPCR14 (UC20143 B-30383), CEGPCR15 (UC20144 B-30384), CEGPCR16 (UC20145 B-30385), CEGPCR17 (UC20146 B-30386), CEGPCR18a (UC20147 B-30387), CEGPCR19.2 (UC20148 B-30388), CEGPCR19.1 (UC20149 B-30389), CEGPCR21 (UC20150 B-30390), CEGPCR22 (UC20151 B-30391), and CEGPCR23 (UC20152 B-30392).

Numerous modifications and variations in the invention as set forth in the above illustrative examples are expected to occur to those skilled in the art. Consequently only such limitations as appear in the appended claims should be placed on the invention.

---

What is claimed is:

1. A method of identifying a modulator of an activity of a GPCR-like receptor comprising the following steps:
   (a) contacting a test compound with a composition, wherein said composition comprises an invertebrate GPCR-like receptor polypeptide encoded by a polynucleotide having a sequence that is at least 98% identical to the sequence of SEQ ID NO:21; and
   (b) measuring the activity of said GPCR-like receptor in the presence and absence of said test compound wherein if the test compound alters a GPCE-like receptor activity, the test compound is identified as a modulator.

2. The method according to claim 1 wherein the activity of said GPCR-like receptor is the binding of a ligand.

3. The method according to claim 1 wherein the activity of said GPCR-like receptor is the propagation of a transmembrane signal.

4. The method according to claim 1 wherein said method is selected from the group consisting of an ion flux assay, a yeast growth assay, a non-hydrolyzable GTP assay, a cAMP assay, an inositol triphosphate assay, and a diacylglycerol assay.

5. The method according to claim 1 wherein said modulator is an inhibitor of said GPCR-like receptor activity.

6. The method according to claim 1 wherein said composition further comprises a G-protein.

7. The method according to claim 6 wherein said G-protein is selected from the group consisting of $G_{\alpha 16}$, $G_{\alpha 15}$, $G_{qd5}$, $G_{qs5}$, $G_{qo5}$, and $G_{q25}$.

8. The method according to claim 1 wherein said composition further comprises a peptide that binds to said GPCR-like receptor.

9. The method according to claim 8 wherein said peptide is attached to a label.

10. The method according to claim 9 wherein said label is selected from the group consisting of a fluorescence label, a radioactive label, a chemiluminescence label, an enzymic label and an immunogenic label.

11. A method of identifying a candidate anti-invertebrate modulator comprising the steps of:

(a) contacting a test compound with a composition, wherein said composition comprises an invertebrate GPCR-like receptor polypeptide encoded by a polynucleotide having a sequence that is at least 98% identical to the sequence of SEQ ID NO:21; and (b) identifying a test compound that binds to or interacts with said composition as a candidate anti-invertebrate modulator.

12. The method according to claim 11 wherein the polynucleotide encoding said GPCR-like receptor comprises the sequence of SEQ ID NO:21.

13. An isolated GPCR-like receptor consisting of the amino acid sequences of SEQ ID NO:22.

14. An isolated polynucleotide encoding a GPCR-like receptor wherein the polynucleotide comprises a sequence that is at least 98% identical to SEQ ID NO:21.

15. The polynucleotide according to claim 14 wherein said polynucleotide comprises a sequence set forth in SEQ ID NO:21.

16. A non-native host cell transformed or transfected with the polynucleotide according to claim 14.

17. A vector comprising the polynucleotide according to claim 14.

18. The vector according to claim 17 wherein said vector is an expression vector and said polynucleotide is operably linked to a polynucleotide comprising an expression control sequence.

19. A host cell transformed or transfected with the expression vector according to claim 18.

20. The host cell according to claim 19 wherein said host cell is selected from the group consisting of mammalian cells, insect cells, yeast cells, helminthic cells, and bacterial cells.

21. The host cell according to claim 20 herein said host cell is selected from the group consisting of a COS cell, a CHO cell, an HEK293 cell, a Drosophila S2 cell, an insect Sf9 cell, an insect High-5 cell, and an *E. coli* cell.

* * * * *

UNITED STATES PATENT AND TRADEMARK OFFICE
CERTIFICATE OF CORRECTION

PATENT NO. : 6,632,621 B1
DATED : October 14, 2003
INVENTOR(S) : Lowery et al.

It is certified that error appears in the above-identified patent and that said Letters Patent is hereby corrected as shown below:

Column 259,
Line 62, please insert a -- , -- after compound.

Column 261,
Line 24, please delete "sequences" and insert -- sequence --.

Column 262,
Line 4, plaese insert a -- , -- after claim 14.
Line 20, please delete "herein" and insert -- wherein --.

Signed and Sealed this

Twenty-fourth Day of August, 2004

JON W. DUDAS
*Director of the United States Patent and Trademark Office*

SEQUENCE LISTING

<160> NUMBER OF SEQ ID NOS: 180

<210> SEQ ID NO 1
<211> LENGTH: 1157
<212> TYPE: DNA
<213> ORGANISM: Homo sapiens
<220> FEATURE:
<221> NAME/KEY: CDS
<222> LOCATION: (1)..(1155)
<220> FEATURE:
<223> OTHER INFORMATION: Clone identifier: CEGPCR1a

<400> SEQUENCE: 1

```
atg aac ttt tcg gcc acc gat tcg ata ttg gca tca acg ata aca acg      48
Met Asn Phe Ser Ala Thr Asp Ser Ile Leu Ala Ser Thr Ile Thr Thr
```

|  |  |  |  |  |  |  |  |  |  |  |  |  |  |  |  |
|---|---|---|---|---|---|---|---|---|---|---|---|---|---|---|---|
| 1 |  |  |  | 5 |  |  |  |  | 10 |  |  |  |  | 15 |  |

| gtg | att | ggt | gga | gct | gga | gtt | ttg | gca | gaa | gca | ggc | gaa | gct | gaa | cta | 96 |
|---|---|---|---|---|---|---|---|---|---|---|---|---|---|---|---|---|
| Val | Ile | Gly | Gly | Ala | Gly | Val | Leu | Ala | Glu | Ala | Gly | Glu | Ala | Glu | Leu | |
|  |  |  | 20 |  |  |  |  | 25 |  |  |  |  | 30 |  |  |  |

| tct | ggt | gat | gat | gat | ttt | tat | gag | ctg | act | cct | gta | gaa | ttg | ata | ata | 144 |
|---|---|---|---|---|---|---|---|---|---|---|---|---|---|---|---|---|
| Ser | Gly | Asp | Asp | Asp | Phe | Tyr | Glu | Leu | Thr | Pro | Val | Glu | Leu | Ile | Ile | |
|  |  | 35 |  |  |  |  | 40 |  |  |  |  | 45 |  |  |  |  |

| tgg | tgc | atg | ctg | tat | gca | att | ata | gcc | ttc | atg | gca | gtt | gtt | gga | aat | 192 |
|---|---|---|---|---|---|---|---|---|---|---|---|---|---|---|---|---|
| Trp | Cys | Met | Leu | Tyr | Ala | Ile | Ile | Ala | Phe | Met | Ala | Val | Val | Gly | Asn | |
|  | 50 |  |  |  |  | 55 |  |  |  |  | 60 |  |  |  |  |  |

| ctt | ctg | gtt | ctc | tac | ata | aca | ctg | ttc | aga | tta | aga | gtc | cgt | tcc | atc | 240 |
|---|---|---|---|---|---|---|---|---|---|---|---|---|---|---|---|---|
| Leu | Leu | Val | Leu | Tyr | Ile | Thr | Leu | Phe | Arg | Leu | Arg | Val | Arg | Ser | Ile | |
| 65 |  |  |  |  | 70 |  |  |  |  | 75 |  |  |  |  | 80 |  |

| aca | acc | tac | ttc | att | ctg | aac | ctc | gga | ttt | gct | gac | ctc | ttc | act | ggt | 288 |
|---|---|---|---|---|---|---|---|---|---|---|---|---|---|---|---|---|
| Thr | Thr | Tyr | Phe | Ile | Leu | Asn | Leu | Gly | Phe | Ala | Asp | Leu | Phe | Thr | Gly | |
|  |  |  |  | 85 |  |  |  |  | 90 |  |  |  |  | 95 |  |  |

| att | ttt | gcg | att | ccc | ttc | aag | ttt | cag | gct | gct | ctt | ttt | caa | gaa | tgg | 336 |
|---|---|---|---|---|---|---|---|---|---|---|---|---|---|---|---|---|
| Ile | Phe | Ala | Ile | Pro | Phe | Lys | Phe | Gln | Ala | Ala | Leu | Phe | Gln | Glu | Trp | |
|  |  |  | 100 |  |  |  |  | 105 |  |  |  |  | 110 |  |  |  |

| ttc | ctg | ccg | cga | tca | ctc | tgc | cgg | ata | gtt | cca | tac | gtg | gaa | aca | gtt | 384 |
|---|---|---|---|---|---|---|---|---|---|---|---|---|---|---|---|---|
| Phe | Leu | Pro | Arg | Ser | Leu | Cys | Arg | Ile | Val | Pro | Tyr | Val | Glu | Thr | Val | |
|  |  | 115 |  |  |  |  | 120 |  |  |  |  | 125 |  |  |  |  |

| gct | ctg | aca | gtt | tca | gtc | ttc | aca | ctt | gtg | acg | tca | gca | gtt | cat | gaa | 432 |
|---|---|---|---|---|---|---|---|---|---|---|---|---|---|---|---|---|
| Ala | Leu | Thr | Val | Ser | Val | Phe | Thr | Leu | Val | Thr | Ser | Ala | Val | His | Glu | |
|  | 130 |  |  |  |  | 135 |  |  |  |  | 140 |  |  |  |  |  |

| ttc | cgt | aca | atg | ttc | ttc | tcg | aaa | tgc | tca | caa | atg | agc | cca | aga | tct | 480 |
|---|---|---|---|---|---|---|---|---|---|---|---|---|---|---|---|---|
| Phe | Arg | Thr | Met | Phe | Phe | Ser | Lys | Cys | Ser | Gln | Met | Ser | Pro | Arg | Ser | |
| 145 |  |  |  |  | 150 |  |  |  |  | 155 |  |  |  |  | 160 |  |

| gca | aaa | cga | tgt | gta | ctt | ttg | ata | tgg | ata | atg | gcg | gtt | ctt | gtg | tct | 528 |
|---|---|---|---|---|---|---|---|---|---|---|---|---|---|---|---|---|
| Ala | Lys | Arg | Cys | Val | Leu | Leu | Ile | Trp | Ile | Met | Ala | Val | Leu | Val | Ser | |
|  |  |  |  | 165 |  |  |  |  | 170 |  |  |  |  | 175 |  |  |

| cta | cca | cat | gga | ttg | ttc | cat | aat | aca | tac | gaa | ttt | cca | gat | gac | aat | 576 |
|---|---|---|---|---|---|---|---|---|---|---|---|---|---|---|---|---|
| Leu | Pro | His | Gly | Leu | Phe | His | Asn | Thr | Tyr | Glu | Phe | Pro | Asp | Asp | Asn | |
|  |  |  | 180 |  |  |  |  | 185 |  |  |  |  | 190 |  |  |  |

| aat | act | tca | att | gta | cag | tgt | ctc | cca | gta | tat | cct | gat | gct | ggt | tgg | 624 |
|---|---|---|---|---|---|---|---|---|---|---|---|---|---|---|---|---|
| Asn | Thr | Ser | Ile | Val | Gln | Cys | Leu | Pro | Val | Tyr | Pro | Asp | Ala | Gly | Trp | |
|  |  | 195 |  |  |  |  | 200 |  |  |  |  | 205 |  |  |  |  |

| tgg | aaa | aca | tac | aat | gtc | tac | ctt | gtc | ata | atc | caa | tat | ttt | gtt | cca | 672 |
|---|---|---|---|---|---|---|---|---|---|---|---|---|---|---|---|---|
| Trp | Lys | Thr | Tyr | Asn | Val | Tyr | Leu | Val | Ile | Ile | Gln | Tyr | Phe | Val | Pro | |
|  | 210 |  |  |  |  | 215 |  |  |  |  | 220 |  |  |  |  |  |

| atg | att | att | ctt | gac | act | gcg | tac | aca | atg | att | gct | gtt | aaa | ata | tgg | 720 |
|---|---|---|---|---|---|---|---|---|---|---|---|---|---|---|---|---|
| Met | Ile | Ile | Leu | Asp | Thr | Ala | Tyr | Thr | Met | Ile | Ala | Val | Lys | Ile | Trp | |
| 225 |  |  |  |  | 230 |  |  |  |  | 235 |  |  |  |  | 240 |  |

| tca | ttg | agt | cag | tca | aga | gtt | gaa | ctt | gat | gaa | aca | aaa | atg | gca | acc | 768 |
|---|---|---|---|---|---|---|---|---|---|---|---|---|---|---|---|---|
| Ser | Leu | Ser | Gln | Ser | Arg | Val | Glu | Leu | Asp | Glu | Thr | Lys | Met | Ala | Thr | |
|  |  |  |  | 245 |  |  |  |  | 250 |  |  |  |  | 255 |  |  |

| cag | aag | ctt | atg | cgt | act | ctc | atc | att | gtc | gtt | gcc | tgt | ttc | tca | ttg | 816 |
|---|---|---|---|---|---|---|---|---|---|---|---|---|---|---|---|---|
| Gln | Lys | Leu | Met | Arg | Thr | Leu | Ile | Ile | Val | Val | Ala | Cys | Phe | Ser | Leu | |
|  |  |  | 260 |  |  |  |  | 265 |  |  |  |  | 270 |  |  |  |

| tgt | tgg | ttt | cca | ttg | gag | acg | tat | cta | ctt | ttg | aat | gaa | ttg | aaa | ccg | 864 |
|---|---|---|---|---|---|---|---|---|---|---|---|---|---|---|---|---|
| Cys | Trp | Phe | Pro | Leu | Glu | Thr | Tyr | Leu | Leu | Leu | Asn | Glu | Leu | Lys | Pro | |
|  |  | 275 |  |  |  |  | 280 |  |  |  |  | 285 |  |  |  |  |

| gaa | att | aat | gga | tgg | aaa | tac | atc | aat | ttg | gtg | ttc | ttc | ttt | tca | cat | 912 |
|---|---|---|---|---|---|---|---|---|---|---|---|---|---|---|---|---|
| Glu | Ile | Asn | Gly | Trp | Lys | Tyr | Ile | Asn | Leu | Val | Phe | Phe | Phe | Ser | His | |
|  | 290 |  |  |  |  | 295 |  |  |  |  | 300 |  |  |  |  |  |

| tgg | ctg | gcg | atg | agc | aat | tct | tgt | ctt | aat | cca | att | att | tat | gga | ctt | 960 |
|---|---|---|---|---|---|---|---|---|---|---|---|---|---|---|---|---|
| Trp | Leu | Ala | Met | Ser | Asn | Ser | Cys | Leu | Asn | Pro | Ile | Ile | Tyr | Gly | Leu | |
| 305 |  |  |  |  | 310 |  |  |  |  | 315 |  |  |  |  | 320 |  |

| tac | aat | aca | aaa | tac | aac | gag | gaa | tat | cgt | cgt | ttg | ttt | cgc | caa | att | 1008 |

-continued

```
                Tyr Asn Thr Lys Tyr Asn Glu Glu Tyr Arg Arg Leu Phe Arg Gln Ile
                            325                 330                 335 gga tgc att tgg caa cgg cag aaa agt ttg gac gat tcg atg aaa ccg        1056
Gly Cys Ile Trp Gln Arg Gln Lys Ser Leu Asp Asp Ser Met Lys Pro
            340                 345                 350 gag cgt cgt tgg aat tct tca aat gat tgt caa gat caa cag gaa att        1104
Glu Arg Arg Trp Asn Ser Ser Asn Asp Cys Gln Asp Gln Gln Glu Ile
355                 360                 365 gat caa att gtt gat att cca cca gtt att tct aca aat aat ctt tct        1152
Asp Gln Ile Val Asp Ile Pro Pro Val Ile Ser Thr Asn Asn Leu Ser
        370                 375                 380 ccc tg                                                                 1157
Pro
385

<210> SEQ ID NO 2
<211> LENGTH: 385
<212> TYPE: PRT
<213> ORGANISM: Homo sapiens

<400> SEQUENCE: 2

Met Asn Phe Ser Ala Thr Asp Ser Ile Leu Ala Ser Thr Ile Thr Thr
 1               5                  10                  15

Val Ile Gly Gly Ala Gly Val Leu Ala Glu Ala Gly Glu Ala Glu Leu
             20                  25                  30

Ser Gly Asp Asp Phe Tyr Glu Leu Thr Pro Val Glu Leu Ile Ile
         35                  40                  45

Trp Cys Met Leu Tyr Ala Ile Ile Ala Phe Met Ala Val Val Gly Asn
     50                  55                  60

Leu Leu Val Leu Tyr Ile Thr Leu Phe Arg Leu Arg Val Arg Ser Ile
65                  70                  75                  80

Thr Thr Tyr Phe Ile Leu Asn Leu Gly Phe Ala Asp Leu Phe Thr Gly
                 85                  90                  95

Ile Phe Ala Ile Pro Phe Lys Phe Gln Ala Ala Leu Phe Gln Glu Trp
            100                 105                 110

Phe Leu Pro Arg Ser Leu Cys Arg Ile Val Pro Tyr Val Glu Thr Val
        115                 120                 125

Ala Leu Thr Val Ser Val Phe Thr Leu Val Thr Ser Ala Val His Glu
    130                 135                 140

Phe Arg Thr Met Phe Phe Ser Lys Cys Ser Gln Met Ser Pro Arg Ser
145                 150                 155                 160

Ala Lys Arg Cys Val Leu Leu Ile Trp Ile Met Ala Val Leu Val Ser
                165                 170                 175

Leu Pro His Gly Leu Phe His Asn Thr Tyr Glu Phe Pro Asp Asp Asn
            180                 185                 190

Asn Thr Ser Ile Val Gln Cys Leu Pro Val Tyr Pro Asp Ala Gly Trp
        195                 200                 205

Trp Lys Thr Tyr Asn Val Tyr Leu Val Ile Ile Gln Tyr Phe Val Pro
    210                 215                 220

Met Ile Ile Leu Asp Thr Ala Tyr Thr Met Ile Ala Val Lys Ile Trp
225                 230                 235                 240

Ser Leu Ser Gln Ser Arg Val Glu Leu Asp Glu Thr Lys Met Ala Thr
                245                 250                 255

Gln Lys Leu Met Arg Thr Leu Ile Ile Val Val Ala Cys Phe Ser Leu
            260                 265                 270

Cys Trp Phe Pro Leu Glu Thr Tyr Leu Leu Leu Asn Glu Leu Lys Pro
```

```
                    275                 280                      285
Glu Ile Asn Gly Trp Lys Tyr Ile Asn Leu Val Phe Phe Ser His
                290                 295                 300

Trp Leu Ala Met Ser Asn Ser Cys Leu Asn Pro Ile Ile Tyr Gly Leu
305                 310                 315                 320

Tyr Asn Thr Lys Tyr Asn Glu Glu Tyr Arg Arg Leu Phe Arg Gln Ile
                325                 330                 335

Gly Cys Ile Trp Gln Arg Gln Lys Ser Leu Asp Asp Ser Met Lys Pro
                340                 345                 350

Glu Arg Arg Trp Asn Ser Ser Asn Asp Cys Gln Asp Gln Gln Glu Ile
                355                 360                 365

Asp Gln Ile Val Asp Ile Pro Pro Val Ile Ser Thr Asn Asn Leu Ser
370                 375                 380

Pro
385

<210> SEQ ID NO 3
<211> LENGTH: 1202
<212> TYPE: DNA
<213> ORGANISM: Homo sapiens
<220> FEATURE:
<221> NAME/KEY: CDS
<222> LOCATION: (1)..(1200)
<220> FEATURE:
<223> OTHER INFORMATION: Clone identifier:  CEGPCR1f

<400> SEQUENCE: 3 atg aac ttt tcg gcc acc gat tcg ata ttg gca tca acg ata aca acg      48
Met Asn Phe Ser Ala Thr Asp Ser Ile Leu Ala Ser Thr Ile Thr Thr
  1               5                  10                  15 gtg att ggt gga gct gga gtt ttg gca gaa gca ggc gaa gct gaa cta      96
Val Ile Gly Gly Ala Gly Val Leu Ala Glu Ala Gly Glu Ala Glu Leu
             20                  25                  30 tct ggt gat gat gat ttt tat gag ctg act cct gta gaa ttg ata ata     144
Ser Gly Asp Asp Asp Phe Tyr Glu Leu Thr Pro Val Glu Leu Ile Ile
         35                  40                  45 tgg tgc atg ctg tat gca att ata gcc ttc atg gca gtt gtt gga aat     192
Trp Cys Met Leu Tyr Ala Ile Ile Ala Phe Met Ala Val Val Gly Asn
     50                  55                  60 ctt ctg gtt ctc tac ata aca ctg ttc aga tta aga gtc cgt tcc atc     240
Leu Leu Val Leu Tyr Ile Thr Leu Phe Arg Leu Arg Val Arg Ser Ile
 65                  70                  75                  80 aca acc tac ttc att ctg aac ctc gga ttt gct gac ctc ttc act ggt     288
Thr Thr Tyr Phe Ile Leu Asn Leu Gly Phe Ala Asp Leu Phe Thr Gly
                 85                  90                  95 att ttt gcg att ccc ttc aag ttt cag gct gct ctt ttt caa gaa tgg     336
Ile Phe Ala Ile Pro Phe Lys Phe Gln Ala Ala Leu Phe Gln Glu Trp
            100                 105                 110 ttc ctg ccg cga tca ctc tgc cgg ata gtt cca tac gtg gaa aca gtt     384
Phe Leu Pro Arg Ser Leu Cys Arg Ile Val Pro Tyr Val Glu Thr Val
        115                 120                 125 gct ctg aca gtt tca gtc ttc aca ctt gtg acg tca gca gtt cat gaa     432
Ala Leu Thr Val Ser Val Phe Thr Leu Val Thr Ser Ala Val His Glu
    130                 135                 140 ttc cgt aca atg ttc ttc tcg aaa tgc tca caa atg agc cca aga tct     480
Phe Arg Thr Met Phe Phe Ser Lys Cys Ser Gln Met Ser Pro Arg Ser
145                 150                 155                 160 gca aaa cga tgt gta ctt ttg ata tgg ata atg gcg gtt ctt gtg tct     528
Ala Lys Arg Cys Val Leu Leu Ile Trp Ile Met Ala Val Leu Val Ser
                165                 170                 175
```

| | | | | | | | | | | | | | | | |
|---|---|---|---|---|---|---|---|---|---|---|---|---|---|---|---|
| cta | cca | cat | gga | ttg | ttc | cat | aat | aca | tac | gaa | ttt | cca | gat | gac | aat | 576 |
| Leu | Pro | His | Gly | Leu | Phe | His | Asn | Thr | Tyr | Glu | Phe | Pro | Asp | Asp | Asn | |
| | | | 180 | | | | | 185 | | | | | 190 | | | |
| aat | act | tca | att | gta | cag | tgt | ctc | cca | gta | tat | cct | gat | gct | ggt | tgg | 624 |
| Asn | Thr | Ser | Ile | Val | Gln | Cys | Leu | Pro | Val | Tyr | Pro | Asp | Ala | Gly | Trp | |
| | | 195 | | | | | 200 | | | | | 205 | | | | |
| tgg | aaa | aca | tac | aat | gtc | tac | ctt | gta | ata | atc | caa | tat | ttt | gtt | cca | 672 |
| Trp | Lys | Thr | Tyr | Asn | Val | Tyr | Leu | Val | Ile | Ile | Gln | Tyr | Phe | Val | Pro | |
| | 210 | | | | | 215 | | | | | 220 | | | | | |
| atg | att | att | ctt | gac | act | gcg | tac | aca | atg | att | gct | gtt | aaa | ata | tgg | 720 |
| Met | Ile | Ile | Leu | Asp | Thr | Ala | Tyr | Thr | Met | Ile | Ala | Val | Lys | Ile | Trp | |
| 225 | | | | | 230 | | | | | 235 | | | | | 240 | |
| tca | ttg | agt | cag | tca | aga | gtt | gaa | ctt | gat | gaa | aca | aaa | atg | gca | acc | 768 |
| Ser | Leu | Ser | Gln | Ser | Arg | Val | Glu | Leu | Asp | Glu | Thr | Lys | Met | Ala | Thr | |
| | | | | 245 | | | | | 250 | | | | | 255 | | |
| cag | aag | ata | tca | gtg | gta | tca | atg | gtt | tca | cca | aac | act | caa | tta | tcg | 816 |
| Gln | Lys | Ile | Ser | Val | Val | Ser | Met | Val | Ser | Pro | Asn | Thr | Gln | Leu | Ser | |
| | | | 260 | | | | | 265 | | | | | 270 | | | |
| cag | ctt | atg | cgt | act | ctc | atc | att | gtc | gtt | gcc | tgt | ttc | tca | ttg | tgt | 864 |
| Gln | Leu | Met | Arg | Thr | Leu | Ile | Ile | Val | Val | Ala | Cys | Phe | Ser | Leu | Cys | |
| | | 275 | | | | | 280 | | | | | 285 | | | | |
| tgg | ttt | cca | ttg | gag | acg | tat | cta | ctt | ttg | aat | gaa | ttg | aaa | ccg | gaa | 912 |
| Trp | Phe | Pro | Leu | Glu | Thr | Tyr | Leu | Leu | Leu | Asn | Glu | Leu | Lys | Pro | Glu | |
| | 290 | | | | | 295 | | | | | 300 | | | | | |
| att | aat | gga | tgg | aaa | tac | atc | aat | ttg | gtg | ttc | ttc | ttt | tca | cat | tgg | 960 |
| Ile | Asn | Gly | Trp | Lys | Tyr | Ile | Asn | Leu | Val | Phe | Phe | Phe | Ser | His | Trp | |
| 305 | | | | | 310 | | | | | 315 | | | | | 320 | |
| ctg | gcg | atg | agc | aat | tct | tgt | ctt | aat | cca | att | att | tat | gga | ctt | tac | 1008 |
| Leu | Ala | Met | Ser | Asn | Ser | Cys | Leu | Asn | Pro | Ile | Ile | Tyr | Gly | Leu | Tyr | |
| | | | | 325 | | | | | 330 | | | | | 335 | | |
| aat | aca | aaa | tac | aac | gag | gaa | tat | cgt | cgt | ttg | ttt | cgc | caa | att | gga | 1056 |
| Asn | Thr | Lys | Tyr | Asn | Glu | Glu | Tyr | Arg | Arg | Leu | Phe | Arg | Gln | Ile | Gly | |
| | | | 340 | | | | | 345 | | | | | 350 | | | |
| tgc | att | tgg | caa | cgg | cag | aaa | agt | ttg | gac | gat | tcg | atg | aaa | ccg | gag | 1104 |
| Cys | Ile | Trp | Gln | Arg | Gln | Lys | Ser | Leu | Asp | Asp | Ser | Met | Lys | Pro | Glu | |
| | | 355 | | | | | 360 | | | | | 365 | | | | |
| cgt | cgt | tgg | aat | tct | tca | aat | gat | tgt | caa | gat | caa | cag | gaa | att | gat | 1152 |
| Arg | Arg | Trp | Asn | Ser | Ser | Asn | Asp | Cys | Gln | Asp | Gln | Gln | Glu | Ile | Asp | |
| | 370 | | | | | 375 | | | | | 380 | | | | | |
| caa | att | gtt | gat | att | cca | cca | gtt | att | tct | aca | aat | aat | ctt | tct | ccc | 1200 |
| Gln | Ile | Val | Asp | Ile | Pro | Pro | Val | Ile | Ser | Thr | Asn | Asn | Leu | Ser | Pro | |
| 385 | | | | | 390 | | | | | 395 | | | | | 400 | |
| tg | | | | | | | | | | | | | | | | 1202 |

<210> SEQ ID NO 4
<211> LENGTH: 400
<212> TYPE: PRT
<213> ORGANISM: Homo sapiens

<400> SEQUENCE: 4

Met Asn Phe Ser Ala Thr Asp Ser Ile Leu Ala Ser Thr Ile Thr Thr
 1               5                  10                  15

Val Ile Gly Gly Ala Gly Val Leu Ala Glu Ala Gly Glu Ala Glu Leu
            20                  25                  30

Ser Gly Asp Asp Asp Phe Tyr Glu Leu Thr Pro Val Glu Leu Ile Ile
        35                  40                  45

Trp Cys Met Leu Tyr Ala Ile Ile Ala Phe Met Ala Val Val Gly Asn
    50                  55                  60

```
Leu Leu Val Leu Tyr Ile Thr Leu Phe Arg Leu Arg Val Arg Ser Ile
 65                  70                  75                  80

Thr Thr Tyr Phe Ile Leu Asn Leu Gly Phe Ala Asp Leu Phe Thr Gly
             85                  90                  95

Ile Phe Ala Ile Pro Phe Lys Phe Gln Ala Ala Leu Phe Gln Glu Trp
            100                 105                 110

Phe Leu Pro Arg Ser Leu Cys Arg Ile Val Pro Tyr Val Glu Thr Val
        115                 120                 125

Ala Leu Thr Val Ser Val Phe Thr Leu Val Thr Ser Ala Val His Glu
    130                 135                 140

Phe Arg Thr Met Phe Phe Ser Lys Cys Ser Gln Met Ser Pro Arg Ser
145                 150                 155                 160

Ala Lys Arg Cys Val Leu Leu Ile Trp Ile Met Ala Val Leu Val Ser
                165                 170                 175

Leu Pro His Gly Leu Phe His Asn Thr Tyr Glu Phe Pro Asp Asp Asn
            180                 185                 190

Asn Thr Ser Ile Val Gln Cys Leu Pro Val Tyr Pro Asp Ala Gly Trp
        195                 200                 205

Trp Lys Thr Tyr Asn Val Tyr Leu Val Ile Ile Gln Tyr Phe Val Pro
    210                 215                 220

Met Ile Ile Leu Asp Thr Ala Tyr Thr Met Ile Ala Val Lys Ile Trp
225                 230                 235                 240

Ser Leu Ser Gln Ser Arg Val Glu Leu Asp Glu Thr Lys Met Ala Thr
                245                 250                 255

Gln Lys Ile Ser Val Val Ser Met Val Ser Pro Asn Thr Gln Leu Ser
            260                 265                 270

Gln Leu Met Arg Thr Leu Ile Ile Val Val Ala Cys Phe Ser Leu Cys
        275                 280                 285

Trp Phe Pro Leu Glu Thr Tyr Leu Leu Leu Asn Glu Leu Lys Pro Glu
    290                 295                 300

Ile Asn Gly Trp Lys Tyr Ile Asn Leu Val Phe Phe Ser His Trp
305                 310                 315                 320

Leu Ala Met Ser Asn Ser Cys Leu Asn Pro Ile Ile Tyr Gly Leu Tyr
                325                 330                 335

Asn Thr Lys Tyr Asn Glu Glu Tyr Arg Arg Leu Phe Arg Gln Ile Gly
            340                 345                 350

Cys Ile Trp Gln Arg Gln Lys Ser Leu Asp Asp Ser Met Lys Pro Glu
        355                 360                 365

Arg Arg Trp Asn Ser Ser Asn Asp Cys Gln Asp Gln Gln Glu Ile Asp
    370                 375                 380

Gln Ile Val Asp Ile Pro Pro Val Ile Ser Thr Asn Asn Leu Ser Pro
385                 390                 395                 400

<210> SEQ ID NO 5
<211> LENGTH: 1214
<212> TYPE: DNA
<213> ORGANISM: Homo sapiens
<220> FEATURE:
<221> NAME/KEY: CDS
<222> LOCATION: (1)..(1212)
<220> FEATURE:
<223> OTHER INFORMATION: Clone identifier: CEGPCR12c

<400> SEQUENCE: 5 atg tcg aat gat ctc gtg cct tca gtg tct tct ata cta aat gaa aca     48
Met Ser Asn Asp Leu Val Pro Ser Val Ser Ser Ile Leu Asn Glu Thr
 1               5                  10                  15
```

| | | |
|---|---|---|
| aca cct tca tat caa agt aca tgt aaa atc aaa aac aac ccc atg gaa<br>Thr Pro Ser Tyr Gln Ser Thr Cys Lys Ile Lys Asn Asn Pro Met Glu<br>                20                  25                  30 | 96 |
| atg gaa tat ttc cgc cca ttc ttt att tct atg tat tgt gct gtt ttt<br>Met Glu Tyr Phe Arg Pro Phe Phe Ile Ser Met Tyr Cys Ala Val Phe<br>        35                      40                      45 | 144 |
| ttg gtt gct agt tcc ggt aat ttt ttg gtg gtg tac gtt gtg atg acg<br>Leu Val Ala Ser Ser Gly Asn Phe Leu Val Val Tyr Val Val Met Thr<br>  50                      55                  60 | 192 |
| aac aag cga atg cag acg atc acc aac att ttt att aca aat ctc gca<br>Asn Lys Arg Met Gln Thr Ile Thr Asn Ile Phe Ile Thr Asn Leu Ala<br> 65                  70                  75               80 | 240 |
| gtt tct gat ata atg gtt aac ttt aca tcg ttg tgg ctt aca cca aca<br>Val Ser Asp Ile Met Val Asn Phe Thr Ser Leu Trp Leu Thr Pro Thr<br>                  85                  90                  95 | 288 |
| tac acc tca ata gga cat tgg ata ttc gga ggt gga ttg tgt cat ggt<br>Tyr Thr Ser Ile Gly His Trp Ile Phe Gly Gly Gly Leu Cys His Gly<br>              100                  105               110 | 336 |
| tta ccc ctg ttc caa ggt aca agt atc ttc atc agt acg tgg aca ctt<br>Leu Pro Leu Phe Gln Gly Thr Ser Ile Phe Ile Ser Thr Trp Thr Leu<br>       115                  120               125 | 384 |
| acg gct ata gcc ata gat cga tac ata gtg atc gtg cac aac tca tca<br>Thr Ala Ile Ala Ile Asp Arg Tyr Ile Val Ile Val His Asn Ser Ser<br>130                  135                  140 | 432 |
| aat atc aat ata aat gat aga atg tcc atg aga tct tgc ctt tcg ttc<br>Asn Ile Asn Ile Asn Asp Arg Met Ser Met Arg Ser Cys Leu Ser Phe<br>145                  150                  155               160 | 480 |
| att gtc ctc att tgg cta tgc tca ttg ctt ctg gtc act ccg tat gcc<br>Ile Val Leu Ile Trp Leu Cys Ser Leu Leu Leu Val Thr Pro Tyr Ala<br>              165                  170               175 | 528 |
| atc aac atg aag ctc aac tac att cat gaa cca tgt gat ttt ctg ata<br>Ile Asn Met Lys Leu Asn Tyr Ile His Glu Pro Cys Asp Phe Leu Ile<br>       180                  185               190 | 576 |
| tgt agt gag gac tgg agc aat gcc gaa ttt cga tct att ttt gga att<br>Cys Ser Glu Asp Trp Ser Asn Ala Glu Phe Arg Ser Ile Phe Gly Ile<br>              195                  200               205 | 624 |
| gtg gtg atg att ctt caa ttc att ttg cca ttt gta ctc att gcc att<br>Val Val Met Ile Leu Gln Phe Ile Leu Pro Phe Val Leu Ile Ala Ile<br>210                  215                  220 | 672 |
| agt tac ata aaa ata tgg ttg ttc cta aat agc cgt caa agt atg acc<br>Ser Tyr Ile Lys Ile Trp Leu Phe Leu Asn Ser Arg Gln Ser Met Thr<br>225                  230                  235               240 | 720 |
| gag aga aaa tcc gat atc aag cgc aaa aag cgt tta cta cgg atg ttg<br>Glu Arg Lys Ser Asp Ile Lys Arg Lys Lys Arg Leu Leu Arg Met Leu<br>              245                  250               255 | 768 |
| att gtc atg gtg gtc atc ttc gca att tgc tgg ttc cca ttc aac ctc<br>Ile Val Met Val Val Ile Phe Ala Ile Cys Trp Phe Pro Phe Asn Leu<br>            260                  265               270 | 816 |
| tta aac tgt ctc cga gat ctc aag ttg gat aat ttc atg cgt ggc tac<br>Leu Asn Cys Leu Arg Asp Leu Lys Leu Asp Asn Phe Met Arg Gly Tyr<br>       275                  280               285 | 864 |
| ttc agt ttt gtt ttc ctt tcc gtg cat ttg atg agt atg aca gct acc<br>Phe Ser Phe Val Phe Leu Ser Val His Leu Met Ser Met Thr Ala Thr<br>       290                  295               300 | 912 |
| gcc tgg aat cca atc ctc tac gca ttc atg aat gag acc ttc cgt gag<br>Ala Trp Asn Pro Ile Leu Tyr Ala Phe Met Asn Glu Thr Phe Arg Glu<br>305                  310                  315               320 | 960 |
| gag ttc gca aaa gtt gtt ccc tgc ttg ttt gcg cgt cgt cct gga act<br>Glu Phe Ala Lys Val Val Pro Cys Leu Phe Ala Arg Arg Pro Gly Thr | 1008 |

```
              325                 330                 335
ggt cca att cgc gtc atc act gaa cgc acc gct atg ata act aac ccg     1056
Gly Pro Ile Arg Val Ile Thr Glu Arg Thr Ala Met Ile Thr Asn Pro
        340                 345                 350 ttt cga cgt gca aac cga aaa aaa aaa gtg gag gaa cag cct gtt acg     1104
Phe Arg Arg Ala Asn Arg Lys Lys Lys Val Glu Glu Gln Pro Val Thr
            355                 360                 365 gtg att tct gat tca gag agt cca ctt caa act gca gtg gag ccg cag     1152
Val Ile Ser Asp Ser Glu Ser Pro Leu Gln Thr Ala Val Glu Pro Gln
    370                 375                 380 cgc agt atc gtg tat ctc gat gag cct gag aac gga tca agt tgt cag     1200
Arg Ser Ile Val Tyr Leu Asp Glu Pro Glu Asn Gly Ser Ser Cys Gln
385                 390                 395                 400 acg ctt ctg ctt ta                                                   1214
Thr Leu Leu Leu
```

<210> SEQ ID NO 6
<211> LENGTH: 404
<212> TYPE: PRT
<213> ORGANISM: Homo sapiens

<400> SEQUENCE: 6

```
Met Ser Asn Asp Leu Val Pro Ser Val Ser Ile Leu Asn Glu Thr
 1               5                  10                  15

Thr Pro Ser Tyr Gln Ser Thr Cys Lys Ile Lys Asn Asn Pro Met Glu
            20                  25                  30

Met Glu Tyr Phe Arg Pro Phe Ile Ser Met Tyr Cys Ala Val Phe
        35                  40                  45

Leu Val Ala Ser Ser Gly Asn Phe Leu Val Val Tyr Val Val Met Thr
    50                  55                  60

Asn Lys Arg Met Gln Thr Ile Thr Asn Ile Phe Ile Thr Asn Leu Ala
65                  70                  75                  80

Val Ser Asp Ile Met Val Asn Phe Thr Ser Leu Trp Leu Thr Pro Thr
                85                  90                  95

Tyr Thr Ser Ile Gly His Trp Ile Phe Gly Gly Leu Cys His Gly
            100                 105                 110

Leu Pro Leu Phe Gln Gly Thr Ser Ile Phe Ile Ser Thr Trp Thr Leu
        115                 120                 125

Thr Ala Ile Ala Ile Asp Arg Tyr Ile Val Ile Val His Asn Ser Ser
    130                 135                 140

Asn Ile Asn Ile Asn Asp Arg Met Ser Met Arg Ser Cys Leu Ser Phe
145                 150                 155                 160

Ile Val Leu Ile Trp Leu Cys Ser Leu Leu Val Thr Pro Tyr Ala
                165                 170                 175

Ile Asn Met Lys Leu Asn Tyr Ile His Glu Pro Cys Asp Phe Leu Ile
            180                 185                 190

Cys Ser Glu Asp Trp Ser Asn Ala Glu Phe Arg Ser Ile Phe Gly Ile
        195                 200                 205

Val Val Met Ile Leu Gln Phe Ile Leu Pro Phe Val Leu Ile Ala Ile
    210                 215                 220

Ser Tyr Ile Lys Ile Trp Leu Phe Leu Asn Ser Arg Gln Ser Met Thr
225                 230                 235                 240

Glu Arg Lys Ser Asp Ile Lys Arg Lys Arg Leu Leu Arg Met Leu
                245                 250                 255

Ile Val Met Val Val Ile Phe Ala Ile Cys Trp Phe Pro Phe Asn Leu
            260                 265                 270
```

```
Leu Asn Cys Leu Arg Asp Leu Lys Leu Asp Asn Phe Met Arg Gly Tyr
            275                 280                 285

Phe Ser Phe Val Phe Leu Ser Val His Leu Met Ser Met Thr Ala Thr
        290                 295                 300

Ala Trp Asn Pro Ile Leu Tyr Ala Phe Met Asn Glu Thr Phe Arg Glu
305                 310                 315                 320

Glu Phe Ala Lys Val Val Pro Cys Leu Phe Ala Arg Arg Pro Gly Thr
                325                 330                 335

Gly Pro Ile Arg Val Ile Thr Glu Arg Thr Ala Met Ile Thr Asn Pro
            340                 345                 350

Phe Arg Arg Ala Asn Arg Lys Lys Lys Val Glu Glu Gln Pro Val Thr
        355                 360                 365

Val Ile Ser Asp Ser Glu Ser Pro Leu Gln Thr Ala Val Glu Pro Gln
370                 375                 380

Arg Ser Ile Val Tyr Leu Asp Glu Pro Glu Asn Gly Ser Ser Cys Gln
385                 390                 395                 400

Thr Leu Leu Leu
```

<210> SEQ ID NO 7
<211> LENGTH: 1208
<212> TYPE: DNA
<213> ORGANISM: Homo sapiens
<220> FEATURE:
<221> NAME/KEY: CDS
<222> LOCATION: (1)..(1206)
<220> FEATURE:
<223> OTHER INFORMATION: Clone identifier: CEGPCR12h

<400> SEQUENCE: 7

```
atg tcg aat gat ctc gtg cct tca gtg tct tct ata cta aat gaa aca        48
Met Ser Asn Asp Leu Val Pro Ser Val Ser Ser Ile Leu Asn Glu Thr
 1               5                  10                  15 aca cct tca tat caa agt aca tgt aaa atc aaa aac aac ccc atg gaa        96
Thr Pro Ser Tyr Gln Ser Thr Cys Lys Ile Lys Asn Asn Pro Met Glu
             20                  25                  30 atg gaa tat ttc cgc cca ttc ttt att tct atg tat tgt gct gtt ttt       144
Met Glu Tyr Phe Arg Pro Phe Phe Ile Ser Met Tyr Cys Ala Val Phe
         35                  40                  45 ttg gtt gct agt tcc ggt aat ttt ttg gtg gtg tac gtt gtg atg acg       192
Leu Val Ala Ser Ser Gly Asn Phe Leu Val Val Tyr Val Val Met Thr
     50                  55                  60 aac aag cga atg cag acg atc acc aac att ttt att aca aat ctc gca       240
Asn Lys Arg Met Gln Thr Ile Thr Asn Ile Phe Ile Thr Asn Leu Ala
 65                  70                  75                  80 gtt tct gat ata atg gtt aac ttt aca tcg ttg tgg ctt aca cca aca       288
Val Ser Asp Ile Met Val Asn Phe Thr Ser Leu Trp Leu Thr Pro Thr
                 85                  90                  95 tac acc tca ata gga cat tgg ata ttc gga ggt gga ttg tgt cat ggt       336
Tyr Thr Ser Ile Gly His Trp Ile Phe Gly Gly Gly Leu Cys His Gly
            100                 105                 110 tta ccc ctg ttc caa ggt aca agt atc ttc atc agt acg tgg aca ctt       384
Leu Pro Leu Phe Gln Gly Thr Ser Ile Phe Ile Ser Thr Trp Thr Leu
        115                 120                 125 acg gct ata gcc ata gat cga tac ata gtg atc gtg cac aac tca tca       432
Thr Ala Ile Ala Ile Asp Arg Tyr Ile Val Ile Val His Asn Ser Ser
    130                 135                 140 aat atc aat ata aat gat aga atg tcc atg aga tct tgc ctt tcg ttc       480
Asn Ile Asn Ile Asn Asp Arg Met Ser Met Arg Ser Cys Leu Ser Phe
145                 150                 155                 160
```

-continued

| | | | | | | | | | | | | | | | |
|---|---|---|---|---|---|---|---|---|---|---|---|---|---|---|---|
| att | gtc | ctc | att | tgg | cta | tgc | tca | ttg | ctt | ctg | gtc | act | ccg | tat | gcc | 528 |
| Ile | Val | Leu | Ile | Trp | Leu | Cys | Ser | Leu | Leu | Leu | Val | Thr | Pro | Tyr | Ala |
| | | | | 165 | | | | 170 | | | | | 175 | | |
| atc | aac | atg | aag | ctc | aac | tac | att | cat | gaa | cca | tgt | gat | ttt | ctg | ata | 576 |
| Ile | Asn | Met | Lys | Leu | Asn | Tyr | Ile | His | Glu | Pro | Cys | Asp | Phe | Leu | Ile |
| | | | 180 | | | | | 185 | | | | | 190 | | |
| tgt | agt | gag | gac | tgg | agc | aat | gcc | gaa | ttt | cga | tct | att | ttt | gga | att | 624 |
| Cys | Ser | Glu | Asp | Trp | Ser | Asn | Ala | Glu | Phe | Arg | Ser | Ile | Phe | Gly | Ile |
| | | 195 | | | | | 200 | | | | | 205 | | | |
| gtg | gtg | atg | att | ctt | caa | ttc | att | ttg | cca | ttt | gta | ctc | att | gcc | att | 672 |
| Val | Val | Met | Ile | Leu | Gln | Phe | Ile | Leu | Pro | Phe | Val | Leu | Ile | Ala | Ile |
| | 210 | | | | | 215 | | | | | 220 | | | | |
| agt | tac | ata | aaa | ata | tgg | ttg | ttc | cta | aat | agc | cgt | caa | agt | atg | acc | 720 |
| Ser | Tyr | Ile | Lys | Ile | Trp | Leu | Phe | Leu | Asn | Ser | Arg | Gln | Ser | Met | Thr |
| 225 | | | | | 230 | | | | | 235 | | | | | 240 |
| gag | aga | aaa | tcc | gat | atc | aag | cgc | aaa | aag | cgt | tta | cta | cgg | atg | ttg | 768 |
| Glu | Arg | Lys | Ser | Asp | Ile | Lys | Arg | Lys | Lys | Arg | Leu | Leu | Arg | Met | Leu |
| | | | | 245 | | | | 250 | | | | | 255 | | |
| att | gtc | atg | gtg | gtc | atc | ttc | gca | att | tgc | tgg | ttc | cca | ttc | aac | ctc | 816 |
| Ile | Val | Met | Val | Val | Ile | Phe | Ala | Ile | Cys | Trp | Phe | Pro | Phe | Asn | Leu |
| | | | 260 | | | | | 265 | | | | | 270 | | |
| tta | aac | tgt | ctc | cga | gat | ctc | aag | ttg | gat | aat | ttc | atg | cgt | ggc | tac | 864 |
| Leu | Asn | Cys | Leu | Arg | Asp | Leu | Lys | Leu | Asp | Asn | Phe | Met | Arg | Gly | Tyr |
| | | 275 | | | | | 280 | | | | | 285 | | | |
| ttc | agt | ttt | gtt | ttc | ctt | tcc | gtg | cat | ttg | atg | agt | atg | aca | gct | acc | 912 |
| Phe | Ser | Phe | Val | Phe | Leu | Ser | Val | His | Leu | Met | Ser | Met | Thr | Ala | Thr |
| | 290 | | | | | 295 | | | | | 300 | | | | |
| gcc | tgg | aat | cca | atc | ctc | tac | gca | ttc | atg | aat | gag | acc | ttc | cgt | gag | 960 |
| Ala | Trp | Asn | Pro | Ile | Leu | Tyr | Ala | Phe | Met | Asn | Glu | Thr | Phe | Arg | Glu |
| 305 | | | | | 310 | | | | | 315 | | | | | 320 |
| gag | ttc | gca | aaa | gtt | gtt | ccc | tgc | ttg | ttt | gcg | cgt | cgt | cct | gga | act | 1008 |
| Glu | Phe | Ala | Lys | Val | Val | Pro | Cys | Leu | Phe | Ala | Arg | Arg | Pro | Gly | Thr |
| | | | | 325 | | | | | 330 | | | | | 335 | |
| ggt | cca | att | cgc | gtc | atc | act | gaa | cgc | acc | gct | atg | ata | act | aac | ccg | 1056 |
| Gly | Pro | Ile | Arg | Val | Ile | Thr | Glu | Arg | Thr | Ala | Met | Ile | Thr | Asn | Pro |
| | | | 340 | | | | | 345 | | | | | 350 | | |
| ttt | cga | cgt | gca | aac | cga | aaa | aaa | aaa | gtg | gag | gaa | cag | cct | gtt | acg | 1104 |
| Phe | Arg | Arg | Ala | Asn | Arg | Lys | Lys | Lys | Val | Glu | Glu | Gln | Pro | Val | Thr |
| | | 355 | | | | | 360 | | | | | 365 | | | |
| gtg | att | tct | gag | agt | cca | ctt | caa | act | gca | gtg | gag | ccg | cag | cgc | agt | 1152 |
| Val | Ile | Ser | Glu | Ser | Pro | Leu | Gln | Thr | Ala | Val | Glu | Pro | Gln | Arg | Ser |
| | 370 | | | | | 375 | | | | | 380 | | | | |
| atc | gtg | tat | ctc | gat | gag | cct | gag | aac | gga | tca | agt | tgt | cag | acg | ctt | 1200 |
| Ile | Val | Tyr | Leu | Asp | Glu | Pro | Glu | Asn | Gly | Ser | Ser | Cys | Gln | Thr | Leu |
| 385 | | | | | 390 | | | | | 395 | | | | | 400 |
| ctg | ctt | ta | | | | | | | | | | | | | | 1208 |
| Leu | Leu | | | | | | | | | | | | | | |

<210> SEQ ID NO 8
<211> LENGTH: 402
<212> TYPE: PRT
<213> ORGANISM: Homo sapiens

<400> SEQUENCE: 8

Met Ser Asn Asp Leu Val Pro Ser Val Ser Ser Ile Leu Asn Glu Thr
1               5                   10                  15

Thr Pro Ser Tyr Gln Ser Thr Cys Lys Ile Lys Asn Asn Pro Met Glu
            20                  25                  30

Met Glu Tyr Phe Arg Pro Phe Phe Ile Ser Met Tyr Cys Ala Val Phe

```
                35                  40                  45
Leu Val Ala Ser Ser Gly Asn Phe Leu Val Tyr Val Val Met Thr
         50                  55                  60
Asn Lys Arg Met Gln Thr Ile Thr Asn Ile Phe Ile Thr Asn Leu Ala
 65                  70                  75                  80
Val Ser Asp Ile Met Val Asn Phe Thr Ser Leu Trp Leu Thr Pro Thr
                 85                  90                  95
Tyr Thr Ser Ile Gly His Trp Ile Phe Gly Gly Leu Cys His Gly
                100                 105                 110
Leu Pro Leu Phe Gln Gly Thr Ser Ile Phe Ile Ser Thr Trp Thr Leu
             115                 120                 125
Thr Ala Ile Ala Ile Asp Arg Tyr Ile Val Ile His Asn Ser Ser
         130                 135                 140
Asn Ile Asn Ile Asn Asp Arg Met Ser Met Arg Ser Cys Leu Ser Phe
145                 150                 155                 160
Ile Val Leu Ile Trp Leu Cys Ser Leu Leu Leu Val Thr Pro Tyr Ala
                165                 170                 175
Ile Asn Met Lys Leu Asn Tyr Ile His Glu Pro Cys Asp Phe Leu Ile
             180                 185                 190
Cys Ser Glu Asp Trp Ser Asn Ala Glu Phe Arg Ser Ile Phe Gly Ile
         195                 200                 205
Val Val Met Ile Leu Gln Phe Ile Leu Pro Phe Val Leu Ile Ala Ile
     210                 215                 220
Ser Tyr Ile Lys Ile Trp Leu Phe Leu Asn Ser Arg Gln Ser Met Thr
225                 230                 235                 240
Glu Arg Lys Ser Asp Ile Lys Arg Lys Arg Leu Leu Arg Met Leu
                245                 250                 255
Ile Val Met Val Val Ile Phe Ala Ile Cys Trp Phe Pro Phe Asn Leu
             260                 265                 270
Leu Asn Cys Leu Arg Asp Leu Lys Leu Asp Asn Phe Met Arg Gly Tyr
         275                 280                 285
Phe Ser Phe Val Phe Leu Ser Val His Leu Met Ser Met Thr Ala Thr
     290                 295                 300
Ala Trp Asn Pro Ile Leu Tyr Ala Phe Met Asn Glu Thr Phe Arg Glu
305                 310                 315                 320
Glu Phe Ala Lys Val Val Pro Cys Leu Phe Ala Arg Arg Pro Gly Thr
                325                 330                 335
Gly Pro Ile Arg Val Ile Thr Glu Arg Thr Ala Met Ile Thr Asn Pro
             340                 345                 350
Phe Arg Arg Ala Asn Arg Lys Lys Lys Val Glu Glu Gln Pro Val Thr
         355                 360                 365
Val Ile Ser Glu Ser Pro Leu Gln Thr Ala Val Glu Pro Gln Arg Ser
     370                 375                 380
Ile Val Tyr Leu Asp Glu Pro Glu Asn Gly Ser Ser Cys Gln Thr Leu
385                 390                 395                 400
Leu Leu

<210> SEQ ID NO 9
<211> LENGTH: 1220
<212> TYPE: DNA
<213> ORGANISM: Homo sapiens
<220> FEATURE:
<221> NAME/KEY: CDS
<222> LOCATION: (1)..(1218)
<220> FEATURE:
```

<223> OTHER INFORMATION: Clone identifier: CEGPCR12u

<400> SEQUENCE: 9

```
atg tcg aat gat ctc gtg cct tca gtg tct tct ata cta aat gaa aca        48
Met Ser Asn Asp Leu Val Pro Ser Val Ser Ser Ile Leu Asn Glu Thr
 1               5                  10                  15 aca cct tca tat caa agt aca tgt aaa atc aaa aac aac ccc atg gaa        96
Thr Pro Ser Tyr Gln Ser Thr Cys Lys Ile Lys Asn Asn Pro Met Glu
             20                  25                  30 atg gaa tat ttc cgc cca ttc ttt att tct atg tat tgt gct gtt ttt       144
Met Glu Tyr Phe Arg Pro Phe Phe Ile Ser Met Tyr Cys Ala Val Phe
         35                  40                  45 ttg gtt gct agt tcc ggt aat ttt ttg gtg gtg tac gtt gtg atg acg       192
Leu Val Ala Ser Ser Gly Asn Phe Leu Val Val Tyr Val Val Met Thr
     50                  55                  60 aac aag cga atg cag acg atc acc aac att ttt att aca aat ctc gca       240
Asn Lys Arg Met Gln Thr Ile Thr Asn Ile Phe Ile Thr Asn Leu Ala
 65                  70                  75                  80 gtt tct gat ata atg gtt aac ttt aca tcg ttg tgg ctt aca cca aca       288
Val Ser Asp Ile Met Val Asn Phe Thr Ser Leu Trp Leu Thr Pro Thr
             85                  90                  95 tac acc tca ata gga cat tgg ata ttc gga ggt gga ttg tgt cat ggt       336
Tyr Thr Ser Ile Gly His Trp Ile Phe Gly Gly Gly Leu Cys His Gly
        100                 105                 110 tta ccc ctg ttc caa ggt aca agt atc ttc atc agt acg tgg aca ctt       384
Leu Pro Leu Phe Gln Gly Thr Ser Ile Phe Ile Ser Thr Trp Thr Leu
    115                 120                 125 acg gct ata gcc ata gat cga tac ata gtg atc gtg cac aac tca tca       432
Thr Ala Ile Ala Ile Asp Arg Tyr Ile Val Ile Val His Asn Ser Ser
130                 135                 140 aat atc aat ata aat gat aga atg tcc atg aga tct tgc ctt tcg ttc       480
Asn Ile Asn Ile Asn Asp Arg Met Ser Met Arg Ser Cys Leu Ser Phe
145                 150                 155                 160 att gtc ctc att tgg cta tgc tca ttg ctt ctg gtc act ccg tat gcc       528
Ile Val Leu Ile Trp Leu Cys Ser Leu Leu Leu Val Thr Pro Tyr Ala
            165                 170                 175 atc aac atg aag ctc aac tac att cat gaa cca tgt gat ttt ctg ata       576
Ile Asn Met Lys Leu Asn Tyr Ile His Glu Pro Cys Asp Phe Leu Ile
        180                 185                 190 tgt agt gag gac tgg agc aat gcc gaa ttt cga tct att ttt gga att       624
Cys Ser Glu Asp Trp Ser Asn Ala Glu Phe Arg Ser Ile Phe Gly Ile
    195                 200                 205 gtg gtg atg att ctt caa ttc att ttg cca ttt gta ctc att gcc att       672
Val Val Met Ile Leu Gln Phe Ile Leu Pro Phe Val Leu Ile Ala Ile
210                 215                 220 agt tac ata aaa ata tgg ttg ttc cta aat agc cgt caa agt atg acc       720
Ser Tyr Ile Lys Ile Trp Leu Phe Leu Asn Ser Arg Gln Ser Met Thr
225                 230                 235                 240 gag aga aaa tcc gat atc aag cgc aaa aag cgt tta cta cgg atg ttg       768
Glu Arg Lys Ser Asp Ile Lys Arg Lys Lys Arg Leu Leu Arg Met Leu
            245                 250                 255 att gtc atg gtg gtc atc ttc gca att tgc tgg ttc cca ttc aac ctc       816
Ile Val Met Val Val Ile Phe Ala Ile Cys Trp Phe Pro Phe Asn Leu
        260                 265                 270 tta aac tgt ctc cga gat ctc aag ttg gat aat ttc atg cgt ggc tac       864
Leu Asn Cys Leu Arg Asp Leu Lys Leu Asp Asn Phe Met Arg Gly Tyr
    275                 280                 285 ttc agt ttt gtt ttc ctt tcc gtg cat ttg atg agt atg aca gct acc       912
Phe Ser Phe Val Phe Leu Ser Val His Leu Met Ser Met Thr Ala Thr
290                 295                 300
```

-continued

```
gcc tgg aat cca atc ctc tac gca ttc atg aat gag acc ttc cgt gag    960
Ala Trp Asn Pro Ile Leu Tyr Ala Phe Met Asn Glu Thr Phe Arg Glu
305                 310                 315                 320 gag ttc gca aaa gtt gtt ccc tgc ttg ttt gcg cgt cgt cct gga act   1008
Glu Phe Ala Lys Val Val Pro Cys Leu Phe Ala Arg Arg Pro Gly Thr
                325                 330                 335 ggt cca att cgc gtc atc act gaa cgc acc gct atg ata act aac ccg   1056
Gly Pro Ile Arg Val Ile Thr Glu Arg Thr Ala Met Ile Thr Asn Pro
            340                 345                 350 ttt cga cgt gca aac cga aaa aaa aaa gtg gag gaa cag cct gtt acg   1104
Phe Arg Arg Ala Asn Arg Lys Lys Lys Val Glu Glu Gln Pro Val Thr
        355                 360                 365 gtg att tct gaa aca gat tca gag agt cca ctt caa act gca gtg gag   1152
Val Ile Ser Glu Thr Asp Ser Glu Ser Pro Leu Gln Thr Ala Val Glu
    370                 375                 380 ccg cag cgc agt atc gtg tat ctc gat gag cct gag aac gga tca agt   1200
Pro Gln Arg Ser Ile Val Tyr Leu Asp Glu Pro Glu Asn Gly Ser Ser
385                 390                 395                 400 tgt cag acg ctt ctg ctt ta                                        1220
Cys Gln Thr Leu Leu Leu
            405
```

<210> SEQ ID NO 10
<211> LENGTH: 406
<212> TYPE: PRT
<213> ORGANISM: Homo sapiens

<400> SEQUENCE: 10

```
Met Ser Asn Asp Leu Val Pro Ser Val Ser Ile Leu Asn Glu Thr
  1               5                  10                  15

Thr Pro Ser Tyr Gln Ser Thr Cys Lys Ile Lys Asn Asn Pro Met Glu
                 20                  25                  30

Met Glu Tyr Phe Arg Pro Phe Ile Ser Met Tyr Cys Ala Val Phe
             35                  40                  45

Leu Val Ala Ser Ser Gly Asn Phe Leu Val Val Tyr Val Val Met Thr
 50                  55                  60

Asn Lys Arg Met Gln Thr Ile Thr Asn Ile Phe Ile Thr Asn Leu Ala
 65                  70                  75                  80

Val Ser Asp Ile Met Val Asn Phe Thr Ser Leu Trp Leu Thr Pro Thr
                 85                  90                  95

Tyr Thr Ser Ile Gly His Trp Ile Phe Gly Gly Leu Cys His Gly
                100                 105                 110

Leu Pro Leu Phe Gln Gly Thr Ser Ile Phe Ile Ser Thr Trp Thr Leu
            115                 120                 125

Thr Ala Ile Ala Ile Asp Arg Tyr Ile Val Ile Val His Asn Ser Ser
130                 135                 140

Asn Ile Asn Ile Asn Asp Arg Met Ser Met Arg Ser Cys Leu Ser Phe
145                 150                 155                 160

Ile Val Leu Ile Trp Leu Cys Ser Leu Leu Val Thr Pro Tyr Ala
                165                 170                 175

Ile Asn Met Lys Leu Asn Tyr Ile His Glu Pro Cys Asp Phe Leu Ile
            180                 185                 190

Cys Ser Glu Asp Trp Ser Asn Ala Glu Phe Arg Ser Ile Phe Gly Ile
        195                 200                 205

Val Val Met Ile Leu Gln Phe Ile Leu Pro Phe Val Leu Ile Ala Ile
    210                 215                 220
```

```
Ser Tyr Ile Lys Ile Trp Leu Phe Leu Asn Ser Arg Gln Ser Met Thr
225                 230                 235                 240

Glu Arg Lys Ser Asp Ile Lys Arg Lys Arg Leu Leu Arg Met Leu
            245                 250                 255

Ile Val Met Val Val Ile Phe Ala Ile Cys Trp Phe Pro Phe Asn Leu
                260                 265                 270

Leu Asn Cys Leu Arg Asp Leu Lys Leu Asp Asn Phe Met Arg Gly Tyr
            275                 280                 285

Phe Ser Phe Val Phe Leu Ser Val His Leu Met Ser Met Thr Ala Thr
    290                 295                 300

Ala Trp Asn Pro Ile Leu Tyr Ala Phe Met Asn Glu Thr Phe Arg Glu
305                 310                 315                 320

Glu Phe Ala Lys Val Pro Cys Leu Phe Ala Arg Arg Pro Gly Thr
                325                 330                 335

Gly Pro Ile Arg Val Ile Thr Glu Arg Thr Ala Met Ile Thr Asn Pro
                340                 345                 350

Phe Arg Arg Ala Asn Arg Lys Lys Lys Val Glu Glu Gln Pro Val Thr
                355                 360                 365

Val Ile Ser Glu Thr Asp Ser Glu Ser Pro Leu Gln Thr Ala Val Glu
370                 375                 380

Pro Gln Arg Ser Ile Val Tyr Leu Asp Glu Pro Glu Asn Gly Ser Ser
385                 390                 395                 400

Cys Gln Thr Leu Leu Leu
                405

<210> SEQ ID NO 11
<211> LENGTH: 1318
<212> TYPE: DNA
<213> ORGANISM: Homo sapiens
<220> FEATURE:
<221> NAME/KEY: CDS
<222> LOCATION: (1)..(1143)
<220> FEATURE:
<223> OTHER INFORMATION: Clone identifier: CEGPCR12v

<400> SEQUENCE: 11 atg tcg aat gat ctc gtg cct tca gtg tct tct ata cta aat gaa aca    48
Met Ser Asn Asp Leu Val Pro Ser Val Ser Ser Ile Leu Asn Glu Thr
  1               5                  10                  15 aca cct tca tat caa agt aca tgt aaa atc aaa aac aac ccc atg gaa    96
Thr Pro Ser Tyr Gln Ser Thr Cys Lys Ile Lys Asn Asn Pro Met Glu
             20                  25                  30 atg gaa tat ttc cgc cca ttc ttt att tct atg tat tgt gct gtt ttt   144
Met Glu Tyr Phe Arg Pro Phe Phe Ile Ser Met Tyr Cys Ala Val Phe
         35                  40                  45 ttg gtt gct agt tcc ggt aat ttt ttg gtg gtg tac gtt gtg atg acg   192
Leu Val Ala Ser Ser Gly Asn Phe Leu Val Val Tyr Val Val Met Thr
     50                  55                  60 aac aag cga atg cag acg atc acc aac att ttt att aca aat ctc gca   240
Asn Lys Arg Met Gln Thr Ile Thr Asn Ile Phe Ile Thr Asn Leu Ala
 65                  70                  75                  80 gtt tct gat ata atg gtt aac ttt aca tcg ttg tgg ctt aca cca aca   288
Val Ser Asp Ile Met Val Asn Phe Thr Ser Leu Trp Leu Thr Pro Thr
                 85                  90                  95 tac acc tca ata gga cat tgg ata ttc gga ggt gga ttg tgt cat ggt   336
Tyr Thr Ser Ile Gly His Trp Ile Phe Gly Gly Gly Leu Cys His Gly
            100                 105                 110 tta ccc ctg ttc caa ggt aca agt atc ttc atc agt acg tgg aca ctt   384
Leu Pro Leu Phe Gln Gly Thr Ser Ile Phe Ile Ser Thr Trp Thr Leu
```

-continued

```
            115                 120                     125
acg gct ata gcc ata gat cga tac ata gtg atc gtg cac aac tca tca      432
Thr Ala Ile Ala Ile Asp Arg Tyr Ile Val Ile Val His Asn Ser Ser
    130                 135                 140 aat atc aat ata aat gat aga atg tcc atg aga tct tgc ctt tcg ttc      480
Asn Ile Asn Ile Asn Asp Arg Met Ser Met Arg Ser Cys Leu Ser Phe
145                 150                 155                 160 att gtc ctc att tgg cta tgc tca ttg ctt ctg gtc act ccg tat gcc      528
Ile Val Leu Ile Trp Leu Cys Ser Leu Leu Leu Val Thr Pro Tyr Ala
                165                 170                 175 atc aac atg aag ctc aac tac att cat gaa cca tgt gat ttt ctg ata      576
Ile Asn Met Lys Leu Asn Tyr Ile His Glu Pro Cys Asp Phe Leu Ile
            180                 185                 190 tgt agt gag gac tgg agc aat gcc gaa ttt cga tct att ttt gga att      624
Cys Ser Glu Asp Trp Ser Asn Ala Glu Phe Arg Ser Ile Phe Gly Ile
        195                 200                 205 gtg gtg atg att ctt caa ttc att ttg cca ttt gta ctc att gcc att      672
Val Val Met Ile Leu Gln Phe Ile Leu Pro Phe Val Leu Ile Ala Ile
    210                 215                 220 agt tac ata aaa ata tgg ttg ttc cta aat agc cgt caa agt atg acc      720
Ser Tyr Ile Lys Ile Trp Leu Phe Leu Asn Ser Arg Gln Ser Met Thr
225                 230                 235                 240 gag aga aaa tcc gat atc aag cgc aaa aag cgt tta cta cgg atg ttg      768
Glu Arg Lys Ser Asp Ile Lys Arg Lys Lys Arg Leu Leu Arg Met Leu
                245                 250                 255 att gtc atg gtg gtc atc ttc gca att tgc tgg ttc cca ttc aac ctc      816
Ile Val Met Val Val Ile Phe Ala Ile Cys Trp Phe Pro Phe Asn Leu
            260                 265                 270 tta aac tgt ctc cga gat ctc aag ttg gat aat ttc atg cgt ggc tac      864
Leu Asn Cys Leu Arg Asp Leu Lys Leu Asp Asn Phe Met Arg Gly Tyr
        275                 280                 285 ttc agt ttt gtt ttc ctt tcc gtg cat ttg atg agt atg aca gct acc      912
Phe Ser Phe Val Phe Leu Ser Val His Leu Met Ser Met Thr Ala Thr
    290                 295                 300 gcc tgg aat cca atc ctc tac gca ttc atg aat gag acc ttc cgt gag      960
Ala Trp Asn Pro Ile Leu Tyr Ala Phe Met Asn Glu Thr Phe Arg Glu
305                 310                 315                 320 gag ttc gca aaa gtt gtt ccc tgc ttg ttt gcg cgt cgt cct gga act     1008
Glu Phe Ala Lys Val Val Pro Cys Leu Phe Ala Arg Arg Pro Gly Thr
                325                 330                 335 ggt cca att cgc gtc atc act gaa cgc acc gct atg ata act aac ccg     1056
Gly Pro Ile Arg Val Ile Thr Glu Arg Thr Ala Met Ile Thr Asn Pro
            340                 345                 350 ttt cga cgt gca aac cga aaa aaa aaa gtg gag gaa cag cct gtt acg     1104
Phe Arg Arg Ala Asn Arg Lys Lys Lys Val Glu Glu Gln Pro Val Thr
        355                 360                 365 gtg att tct gaa ctt tta cac ccg aca tcc aac gaa gaa taggaagcca      1153
Val Ile Ser Glu Leu Leu His Pro Thr Ser Asn Glu Glu
    370                 375                 380 ttcattccct gcatgcactc gttgtcagtg aactttcaa caaccagca atctttagaa     1213 acagattcag agagtccact tcaaactgca gtggagccgc agcgcagtat cgtgtatctc    1273
gatgagcctg agaacggatc aagttgtcag acgcttctgc tttaa                   1318
```

<210> SEQ ID NO 12
<211> LENGTH: 381
<212> TYPE: PRT
<213> ORGANISM: Homo sapiens

<400> SEQUENCE: 12

```
Met Ser Asn Asp Leu Val Pro Ser Val Ser Ile Leu Asn Glu Thr
 1               5                  10                  15

Thr Pro Ser Tyr Gln Ser Thr Cys Lys Ile Lys Asn Asn Pro Met Glu
                 20                  25                  30

Met Glu Tyr Phe Arg Pro Phe Phe Ile Ser Met Tyr Cys Ala Val Phe
             35                  40                  45

Leu Val Ala Ser Ser Gly Asn Phe Leu Val Val Tyr Val Val Met Thr
         50                  55                  60

Asn Lys Arg Met Gln Thr Ile Thr Asn Ile Phe Ile Thr Asn Leu Ala
 65                  70                  75                  80

Val Ser Asp Ile Met Val Asn Phe Thr Ser Leu Trp Leu Thr Pro Thr
                 85                  90                  95

Tyr Thr Ser Ile Gly His Trp Ile Phe Gly Gly Leu Cys His Gly
             100                 105                 110

Leu Pro Leu Phe Gln Gly Thr Ser Ile Phe Ile Ser Thr Trp Thr Leu
         115                 120                 125

Thr Ala Ile Ala Ile Asp Arg Tyr Ile Val Ile His Asn Ser Ser
130                 135                 140

Asn Ile Asn Ile Asn Asp Arg Met Ser Met Arg Ser Cys Leu Ser Phe
145                 150                 155                 160

Ile Val Leu Ile Trp Leu Cys Ser Leu Leu Leu Val Thr Pro Tyr Ala
                 165                 170                 175

Ile Asn Met Lys Leu Asn Tyr Ile His Glu Pro Cys Asp Phe Leu Ile
             180                 185                 190

Cys Ser Glu Asp Trp Ser Asn Ala Glu Phe Arg Ser Ile Phe Gly Ile
         195                 200                 205

Val Val Met Ile Leu Gln Phe Ile Leu Pro Phe Val Leu Ile Ala Ile
    210                 215                 220

Ser Tyr Ile Lys Ile Trp Leu Phe Leu Asn Ser Arg Gln Ser Met Thr
225                 230                 235                 240

Glu Arg Lys Ser Asp Ile Lys Arg Lys Arg Leu Leu Arg Met Leu
                 245                 250                 255

Ile Val Met Val Val Ile Phe Ala Ile Cys Trp Phe Pro Phe Asn Leu
             260                 265                 270

Leu Asn Cys Leu Arg Asp Leu Lys Leu Asp Asn Phe Met Arg Gly Tyr
         275                 280                 285

Phe Ser Phe Val Phe Leu Ser Val His Leu Met Ser Met Thr Ala Thr
    290                 295                 300

Ala Trp Asn Pro Ile Leu Tyr Ala Phe Met Asn Glu Thr Phe Arg Glu
305                 310                 315                 320

Glu Phe Ala Lys Val Val Pro Cys Leu Phe Ala Arg Arg Pro Gly Thr
                 325                 330                 335

Gly Pro Ile Arg Val Ile Thr Glu Arg Thr Ala Met Ile Thr Asn Pro
             340                 345                 350

Phe Arg Arg Ala Asn Arg Lys Lys Val Glu Glu Gln Pro Val Thr
         355                 360                 365

Val Ile Ser Glu Leu Leu His Pro Thr Ser Asn Glu Glu
    370                 375                 380

<210> SEQ ID NO 13
<211> LENGTH: 1163
<212> TYPE: DNA
<213> ORGANISM: Homo sapiens
<220> FEATURE:
```

```
<221> NAME/KEY: CDS
<222> LOCATION: (1)..(1161)
<220> FEATURE:
<223> OTHER INFORMATION: Clone identifier: CEGPCR13

<400> SEQUENCE: 13
```

| | | | | | | | | | | | | | | | | |
|---|---|---|---|---|---|---|---|---|---|---|---|---|---|---|---|---|
| atg | atc | aac | gaa | aca | gaa | gag | aca | tgt | gat | cga | tat | ata | gac | aag | cat | 48 |
| Met | Ile | Asn | Glu | Thr | Glu | Glu | Thr | Cys | Asp | Arg | Tyr | Ile | Asp | Lys | His | |
| 1 | | | | 5 | | | | | 10 | | | | | 15 | | |
| cca | gat | atg | aca | aat | gaa | cca | aca | gtc | ctt | gtc | aca | ttc | tcc | ctg | ctt | 96 |
| Pro | Asp | Met | Thr | Asn | Glu | Pro | Thr | Val | Leu | Val | Thr | Phe | Ser | Leu | Leu | |
| | | | 20 | | | | | 25 | | | | | 30 | | | |
| tat | ctt | cat | att | ttt | ctt | ctt | gga | atc | cta | gga | aat | tcg | gct | gtt | cta | 144 |
| Tyr | Leu | His | Ile | Phe | Leu | Leu | Gly | Ile | Leu | Gly | Asn | Ser | Ala | Val | Leu | |
| | | 35 | | | | | 40 | | | | | 45 | | | | |
| tat | ctt | aca | atg | aaa | cat | cgt | caa | tta | caa | act | gtt | caa | aat | ata | ttt | 192 |
| Tyr | Leu | Thr | Met | Lys | His | Arg | Gln | Leu | Gln | Thr | Val | Gln | Asn | Ile | Phe | |
| | 50 | | | | | 55 | | | | | 60 | | | | | |
| att | ttg | aac | tta | tgc | gca | tcg | aat | gtt | tta | atg | tgc | ttg | acg | agt | ctt | 240 |
| Ile | Leu | Asn | Leu | Cys | Ala | Ser | Asn | Val | Leu | Met | Cys | Leu | Thr | Ser | Leu | |
| 65 | | | | 70 | | | | | 75 | | | | | 80 | | |
| cca | atc | aca | ttt | atc | aca | aat | gtc | tac | aaa | caa | tgg | ttc | ttc | tca | tcg | 288 |
| Pro | Ile | Thr | Phe | Ile | Thr | Asn | Val | Tyr | Lys | Gln | Trp | Phe | Phe | Ser | Ser | |
| | | | 85 | | | | | 90 | | | | | 95 | | | |
| cct | gtt | tgt | aaa | ctt | att | cca | ttg | gtt | cag | gga | gct | tca | atc | ttt | gtc | 336 |
| Pro | Val | Cys | Lys | Leu | Ile | Pro | Leu | Val | Gln | Gly | Ala | Ser | Ile | Phe | Val | |
| | | | 100 | | | | | 105 | | | | | 110 | | | |
| tcc | act | ttc | tcc | ctt | tcc | gcc | att | gca | ctt | gac | cga | tac | aac | ctc | gtg | 384 |
| Ser | Thr | Phe | Ser | Leu | Ser | Ala | Ile | Ala | Leu | Asp | Arg | Tyr | Asn | Leu | Val | |
| | | 115 | | | | | 120 | | | | | 125 | | | | |
| gtt | cgt | cct | cat | aaa | caa | aaa | ctc | agt | tca | cga | agt | gca | atg | atg | att | 432 |
| Val | Arg | Pro | His | Lys | Gln | Lys | Leu | Ser | Ser | Arg | Ser | Ala | Met | Met | Ile | |
| | 130 | | | | | 135 | | | | | 140 | | | | | |
| gct | ctt | ctc | att | tgg | gtt | att | agt | gta | gtt | gtt | tgt | atg | cca | tat | gga | 480 |
| Ala | Leu | Leu | Ile | Trp | Val | Ile | Ser | Val | Val | Val | Cys | Met | Pro | Tyr | Gly | |
| 145 | | | | 150 | | | | | 155 | | | | | 160 | | |
| tgg | tac | atg | gat | gtg | gag | aag | ctc | aat | gga | tta | tgt | gga | gag | tac | tgt | 528 |
| Trp | Tyr | Met | Asp | Val | Glu | Lys | Leu | Asn | Gly | Leu | Cys | Gly | Glu | Tyr | Cys | |
| | | | 165 | | | | | 170 | | | | | 175 | | | |
| tct | gag | cac | tgg | cca | tta | gca | gaa | gta | cga | aag | gga | tat | act | ttt | ttg | 576 |
| Ser | Glu | His | Trp | Pro | Leu | Ala | Glu | Val | Arg | Lys | Gly | Tyr | Thr | Phe | Leu | |
| | | | 180 | | | | | 185 | | | | | 190 | | | |
| gtg | tta | atc | act | caa | ttt | ttg | ttt | cct | ttt | gct | acg | atg | gct | ttt | tgc | 624 |
| Val | Leu | Ile | Thr | Gln | Phe | Leu | Phe | Pro | Phe | Ala | Thr | Met | Ala | Phe | Cys | |
| | | 195 | | | | | 200 | | | | | 205 | | | | |
| tat | tat | aat | att | ttt | tca | aga | ctc | aga | caa | cga | gtg | gaa | acg | aaa | ctg | 672 |
| Tyr | Tyr | Asn | Ile | Phe | Ser | Arg | Leu | Arg | Gln | Arg | Val | Glu | Thr | Lys | Leu | |
| | 210 | | | | | 215 | | | | | 220 | | | | | |
| aag | aaa | tta | tca | gaa | aga | tct | caa | ctt | ttg | gag | aat | agt | aca | aca | tgt | 720 |
| Lys | Lys | Leu | Ser | Glu | Arg | Ser | Gln | Leu | Leu | Glu | Asn | Ser | Thr | Thr | Cys | |
| 225 | | | | 230 | | | | | 235 | | | | | 240 | | |
| gga | acc | act | aac | cac | att | gtt | agc | att | aac | gcg | gaa | gca | gtt | caa | aat | 768 |
| Gly | Thr | Thr | Asn | His | Ile | Val | Ser | Ile | Asn | Ala | Glu | Ala | Val | Gln | Asn | |
| | | | | 245 | | | | | 250 | | | | | 255 | | |
| ggt | ctg | gaa | aac | aaa | caa | aga | tta | gct | gtt | ctt | gct | caa | caa | aga | agg | 816 |
| Gly | Leu | Glu | Asn | Lys | Gln | Arg | Leu | Ala | Val | Leu | Ala | Gln | Gln | Arg | Arg | |
| | | | 260 | | | | | 265 | | | | | 270 | | | |
| aca | act | act | att | tta | tcg | tgc | atg | gtt | ctt | ctt | ttt | gca | ttt | aca | tgg | 864 |
| Thr | Thr | Thr | Ile | Leu | Ser | Cys | Met | Val | Leu | Leu | Phe | Ala | Phe | Thr | Trp | |
| | | | 275 | | | | | 280 | | | | | 285 | | | |

```
ctt cca cat aat gtt gtc act ttg atg ata gaa tac gat gga ttc ttt      912
Leu Pro His Asn Val Val Thr Leu Met Ile Glu Tyr Asp Gly Phe Phe
    290                 295                 300 ttt cat tct gat gag aca tcg gca acc agt acc gat cat aca tat att      960
Phe His Ser Asp Glu Thr Ser Ala Thr Ser Thr Asp His Thr Tyr Ile
305                 310                 315                 320 gtt tca atg act gct cat tta ata tcc atg tta aca aat gta acc aac     1008
Val Ser Met Thr Ala His Leu Ile Ser Met Leu Thr Asn Val Thr Asn
                325                 330                 335 cca ttt ctg tat gct tgg ctt aac cca atg ttc aaa gaa atg ctt att     1056
Pro Phe Leu Tyr Ala Trp Leu Asn Pro Met Phe Lys Glu Met Leu Ile
        340                 345                 350 aaa act ctc aga ggt gga agt aaa tcc ccg aaa cca gct gac atc aag     1104
Lys Thr Leu Arg Gly Gly Ser Lys Ser Pro Lys Pro Ala Asp Ile Lys
355                 360                 365 caa act tca ttc att cga atg ccg aat agt ggt gcg cca agt caa tct     1152
Gln Thr Ser Phe Ile Arg Met Pro Asn Ser Gly Ala Pro Ser Gln Ser
    370                 375                 380 tcc tac ctg tg                                                      1163
Ser Tyr Leu
385

<210> SEQ ID NO 14
<211> LENGTH: 387
<212> TYPE: PRT
<213> ORGANISM: Homo sapiens

<400> SEQUENCE: 14

Met Ile Asn Glu Thr Glu Thr Cys Asp Arg Tyr Ile Asp Lys His
 1               5                  10                  15

Pro Asp Met Thr Asn Glu Pro Thr Val Leu Val Thr Phe Ser Leu Leu
                20                  25                  30

Tyr Leu His Ile Phe Leu Leu Gly Ile Leu Gly Asn Ser Ala Val Leu
            35                  40                  45

Tyr Leu Thr Met Lys His Arg Gln Leu Gln Thr Val Gln Asn Ile Phe
        50                  55                  60

Ile Leu Asn Leu Cys Ala Ser Asn Val Leu Met Cys Leu Thr Ser Leu
65                  70                  75                  80

Pro Ile Thr Phe Ile Thr Asn Val Tyr Lys Gln Trp Phe Phe Ser Ser
                85                  90                  95

Pro Val Cys Lys Leu Ile Pro Leu Val Gln Gly Ala Ser Ile Phe Val
            100                 105                 110

Ser Thr Phe Ser Leu Ser Ala Ile Ala Leu Asp Arg Tyr Asn Leu Val
        115                 120                 125

Val Arg Pro His Lys Gln Lys Leu Ser Ser Arg Ser Ala Met Met Ile
130                 135                 140

Ala Leu Leu Ile Trp Val Ile Ser Val Val Cys Met Pro Tyr Gly
145                 150                 155                 160

Trp Tyr Met Asp Val Glu Lys Leu Asn Gly Leu Cys Gly Glu Tyr Cys
                165                 170                 175

Ser Glu His Trp Pro Leu Ala Glu Val Arg Lys Gly Tyr Thr Phe Leu
            180                 185                 190

Val Leu Ile Thr Gln Phe Leu Pro Phe Ala Thr Met Ala Phe Cys
        195                 200                 205

Tyr Tyr Asn Ile Phe Ser Arg Leu Arg Gln Arg Val Glu Thr Lys Leu
    210                 215                 220

Lys Lys Leu Ser Glu Arg Ser Gln Leu Leu Glu Asn Ser Thr Thr Cys
```

-continued

```
               225                 230                 235                 240
Gly Thr Thr Asn His Ile Val Ser Ile Asn Ala Glu Ala Val Gln Asn
                245                 250                 255
Gly Leu Glu Asn Lys Gln Arg Leu Ala Val Leu Ala Gln Gln Arg Arg
            260                 265                 270
Thr Thr Thr Ile Leu Ser Cys Met Val Leu Phe Ala Phe Thr Trp
        275                 280                 285
Leu Pro His Asn Val Val Thr Leu Met Ile Glu Tyr Asp Gly Phe Phe
    290                 295                 300
Phe His Ser Asp Glu Thr Ser Ala Thr Ser Thr Asp His Thr Tyr Ile
305                 310                 315                 320
Val Ser Met Thr Ala His Leu Ile Ser Met Leu Thr Asn Val Thr Asn
                325                 330                 335
Pro Phe Leu Tyr Ala Trp Leu Asn Pro Met Phe Lys Glu Met Leu Ile
            340                 345                 350
Lys Thr Leu Arg Gly Gly Ser Lys Ser Pro Lys Pro Ala Asp Ile Lys
        355                 360                 365
Gln Thr Ser Phe Ile Arg Met Pro Asn Ser Gly Ala Pro Ser Gln Ser
    370                 375                 380

Ser Tyr Leu
385
```

<210> SEQ ID NO 15
<211> LENGTH: 1352
<212> TYPE: DNA
<213> ORGANISM: Homo sapiens
<220> FEATURE:
<221> NAME/KEY: CDS
<222> LOCATION: (1)..(1350)
<220> FEATURE:
<223> OTHER INFORMATION: Clone identifier: CEGPCR14

<400> SEQUENCE: 15

```
atg ggt gat gct gaa tct cat cat tgt ata gat gtg aac gcc att ctt        48
Met Gly Asp Ala Glu Ser His His Cys Ile Asp Val Asn Ala Ile Leu
  1               5                  10                  15 cag cag ttc aat gat tgg aca gtc ctc ttt gaa gtt cgg ctt gga tat        96
Gln Gln Phe Asn Asp Trp Thr Val Leu Phe Glu Val Arg Leu Gly Tyr
             20                  25                  30 tca gta cta tac ttt ctc ata tta ata atc gga ttg gtt gga aat ggg       144
Ser Val Leu Tyr Phe Leu Ile Leu Ile Ile Gly Leu Val Gly Asn Gly
         35                  40                  45 cta ttg atc act tca att tta atg cga aag aaa ctt tcc gtg gca aac       192
Leu Leu Ile Thr Ser Ile Leu Met Arg Lys Lys Leu Ser Val Ala Asn
     50                  55                  60 ata ttc ttg ata aac ctg gca gtt tct gat ttg ctt ctt tgc atc acg       240
Ile Phe Leu Ile Asn Leu Ala Val Ser Asp Leu Leu Leu Cys Ile Thr
 65                  70                  75                  80 gcg gtg ccg atc act cca gta ttg gcg ttt atg aag cga tgg ata ttt       288
Ala Val Pro Ile Thr Pro Val Leu Ala Phe Met Lys Arg Trp Ile Phe
                 85                  90                  95 gga ata att atg tgt aaa ttg gtt cca act tgt cag gcg ttt tcg gtg       336
Gly Ile Ile Met Cys Lys Leu Val Pro Thr Cys Gln Ala Phe Ser Val
            100                 105                 110 ctc att tct tca tgg tct ttg tgt tac atc gca att gat aga tat cga       384
Leu Ile Ser Ser Trp Ser Leu Cys Tyr Ile Ala Ile Asp Arg Tyr Arg
        115                 120                 125 agt att gtg acg cca ctc cgg gaa cca tgg tct gat agg cat gca agg       432
Ser Ile Val Thr Pro Leu Arg Glu Pro Trp Ser Asp Arg His Ala Arg
```

-continued

```
            130                 135                 140
tgg ctt ctg atg ttc aca tgg gtg gtc gcc ttc ctt gct agt tat cct      480
Trp Leu Leu Met Phe Thr Trp Val Val Ala Phe Leu Ala Ser Tyr Pro
145                 150                 155                 160 cta tat tac tca cag aac ttg aaa aca atg gtt att gaa aat gtg aca      528
Leu Tyr Tyr Ser Gln Asn Leu Lys Thr Met Val Ile Glu Asn Val Thr
                165                 170                 175 tta tgt gga gat ttt tgc ggc gag ttc aat tgg cag tcg gat gaa ata      576
Leu Cys Gly Asp Phe Cys Gly Glu Phe Asn Trp Gln Ser Asp Glu Ile
                180                 185                 190 tcc aag ttg aca tat act acg agt tta ttg att att cag ctg att att      624
Ser Lys Leu Thr Tyr Thr Thr Ser Leu Leu Ile Ile Gln Leu Ile Ile
            195                 200                 205 cca gca att atc atg tct ttt tgt tat tta atg att cta caa aag gta      672
Pro Ala Ile Ile Met Ser Phe Cys Tyr Leu Met Ile Leu Gln Lys Val
    210                 215                 220 caa acc gac tgg ctt gtc gac gag gga tcc atg ttg act gcc gca caa      720
Gln Thr Asp Trp Leu Val Asp Glu Gly Ser Met Leu Thr Ala Ala Gln
225                 230                 235                 240 cag gct caa aca gca gtt cga aag cga cga gtg atg tac gtg ttg att      768
Gln Ala Gln Thr Ala Val Arg Lys Arg Arg Val Met Tyr Val Leu Ile
                245                 250                 255 cta atg gtt att gtt ttt atg gct tgc tgg ttc ccg ttg tcc gcc gtg      816
Leu Met Val Ile Val Phe Met Ala Cys Trp Phe Pro Leu Ser Ala Val
                260                 265                 270 aat ttg ttc aga gat ctc gga atg cga ttc gag ttc tgt caa act gtt      864
Asn Leu Phe Arg Asp Leu Gly Met Arg Phe Glu Phe Cys Gln Thr Val
            275                 280                 285 tac aag gtt tta atg atg gac caa atg tat ttc aag ttg ctc aat gtg      912
Tyr Lys Val Leu Met Met Asp Gln Met Tyr Phe Lys Leu Leu Asn Val
    290                 295                 300 cac gtc atc gcg atg act tcg atc gta tgg aat ccg gtg ctc tat ttc      960
His Val Ile Ala Met Thr Ser Ile Val Trp Asn Pro Val Leu Tyr Phe
305                 310                 315                 320 tgg atg agc aag cgt cat cga cga gcc ctg aaa gac gac atg acg tgg     1008
Trp Met Ser Lys Arg His Arg Arg Ala Leu Lys Asp Asp Met Thr Trp
                325                 330                 335 ctc acc aat gct cgc cgt cat aca aac gtc ggc gtt ctg tct cgc ttc     1056
Leu Thr Asn Ala Arg Arg His Thr Asn Val Gly Val Leu Ser Arg Phe
                340                 345                 350 aca cct tct cca tca gtt tca gtg gtt tac aga cga act ctg gag cga     1104
Thr Pro Ser Pro Ser Val Ser Val Val Tyr Arg Arg Thr Leu Glu Arg
            355                 360                 365 cat cta ggt gtc aat cat ttc cgc cgt ggc aca ctt gcg gac ccg aca     1152
His Leu Gly Val Asn His Phe Arg Arg Gly Thr Leu Ala Asp Pro Thr
    370                 375                 380 tgc act tca cgt gaa cga agt ctt ccg cga gaa ctt caa tca aat tgt     1200
Cys Thr Ser Arg Glu Arg Ser Leu Pro Arg Glu Leu Gln Ser Asn Cys
385                 390                 395                 400 ttc ctt ctt gtt ccg ctt atg cca tta tgt caa tct gtg acg agg aag     1248
Phe Leu Leu Val Pro Leu Met Pro Leu Cys Gln Ser Val Thr Arg Lys
                405                 410                 415 aat agt cat cta gca atc aat cga gac ggg atc gtc att cca caa gcc     1296
Asn Ser His Leu Ala Ile Asn Arg Asp Gly Ile Val Ile Pro Gln Ala
                420                 425                 430 aat ggc tca agt cgt cgg ccg agc agc gtg aat acc aat tca act cga     1344
Asn Gly Ser Ser Arg Arg Pro Ser Ser Val Asn Thr Asn Ser Thr Arg
            435                 440                 445 gac tgg tg                                                           1352
```

Asp Trp
    450

<210> SEQ ID NO 16
<211> LENGTH: 450
<212> TYPE: PRT
<213> ORGANISM: Homo sapiens

<400> SEQUENCE: 16

Met Gly Asp Ala Glu Ser His His Cys Ile Asp Val Asn Ala Ile Leu
 1               5                  10                  15

Gln Gln Phe Asn Asp Trp Thr Val Leu Phe Glu Val Arg Leu Gly Tyr
                20                  25                  30

Ser Val Leu Tyr Phe Leu Ile Leu Ile Ile Gly Leu Val Gly Asn Gly
            35                  40                  45

Leu Leu Ile Thr Ser Ile Leu Met Arg Lys Lys Leu Ser Val Ala Asn
        50                  55                  60

Ile Phe Leu Ile Asn Leu Ala Val Ser Asp Leu Leu Leu Cys Ile Thr
 65                  70                  75                  80

Ala Val Pro Ile Thr Pro Val Leu Ala Phe Met Lys Arg Trp Ile Phe
                85                  90                  95

Gly Ile Ile Met Cys Lys Leu Val Pro Thr Cys Gln Ala Phe Ser Val
                100                 105                 110

Leu Ile Ser Ser Trp Ser Leu Cys Tyr Ile Ala Ile Asp Arg Tyr Arg
            115                 120                 125

Ser Ile Val Thr Pro Leu Arg Glu Pro Trp Ser Asp Arg His Ala Arg
        130                 135                 140

Trp Leu Leu Met Phe Thr Trp Val Val Ala Phe Leu Ala Ser Tyr Pro
145                 150                 155                 160

Leu Tyr Tyr Ser Gln Asn Leu Lys Thr Met Val Ile Glu Asn Val Thr
                165                 170                 175

Leu Cys Gly Asp Phe Cys Gly Glu Phe Asn Trp Gln Ser Asp Glu Ile
            180                 185                 190

Ser Lys Leu Thr Tyr Thr Thr Ser Leu Leu Ile Ile Gln Leu Ile Ile
        195                 200                 205

Pro Ala Ile Ile Met Ser Phe Cys Tyr Leu Met Ile Leu Gln Lys Val
    210                 215                 220

Gln Thr Asp Trp Leu Val Asp Glu Gly Ser Met Leu Thr Ala Ala Gln
225                 230                 235                 240

Gln Ala Gln Thr Ala Val Arg Lys Arg Arg Val Met Tyr Val Leu Ile
                245                 250                 255

Leu Met Val Ile Val Phe Met Ala Cys Trp Phe Pro Leu Ser Ala Val
                260                 265                 270

Asn Leu Phe Arg Asp Leu Gly Met Arg Phe Glu Phe Cys Gln Thr Val
            275                 280                 285

Tyr Lys Val Leu Met Met Asp Gln Met Tyr Phe Lys Leu Leu Asn Val
        290                 295                 300

His Val Ile Ala Met Thr Ser Ile Val Trp Asn Pro Val Leu Tyr Phe
305                 310                 315                 320

Trp Met Ser Lys Arg His Arg Ala Leu Lys Asp Asp Met Thr Trp
                325                 330                 335

Leu Thr Asn Ala Arg His Thr Asn Val Gly Val Leu Ser Arg Phe
            340                 345                 350

Thr Pro Ser Pro Ser Val Ser Val Val Tyr Arg Arg Thr Leu Glu Arg
        355                 360                 365

-continued

```
His Leu Gly Val Asn His Phe Arg Arg Gly Thr Leu Ala Asp Pro Thr
    370                 375                 380
Cys Thr Ser Arg Glu Arg Ser Leu Pro Arg Glu Leu Gln Ser Asn Cys
385                 390                 395                 400
Phe Leu Leu Val Pro Leu Met Pro Leu Cys Gln Ser Val Thr Arg Lys
                405                 410                 415
Asn Ser His Leu Ala Ile Asn Arg Asp Gly Ile Val Ile Pro Gln Ala
            420                 425                 430
Asn Gly Ser Ser Arg Arg Pro Ser Val Asn Thr Asn Ser Thr Arg
        435                 440                 445
Asp Trp
    450

<210> SEQ ID NO 17
<211> LENGTH: 1652
<212> TYPE: DNA
<213> ORGANISM: Homo sapiens
<220> FEATURE:
<221> NAME/KEY: CDS
<222> LOCATION: (1)..(1650)
<220> FEATURE:
<223> OTHER INFORMATION: Clone identifier: CEGPCR18a

<400> SEQUENCE: 17 atg acc gac gag gag ttg ttc gag atc gct ctt ccc ggc ttc tta tat      48
Met Thr Asp Glu Glu Leu Phe Glu Ile Ala Leu Pro Gly Phe Leu Tyr
  1               5                  10                  15 ctc act gtt ttt cta gtt gga act att gga aac tct atg gta ata ttt     96
Leu Thr Val Phe Leu Val Gly Thr Ile Gly Asn Ser Met Val Ile Phe
             20                  25                  30 gtt gta aac cga ttc aaa cga atg cgc aac gta acg aac atc ttt ctc    144
Val Val Asn Arg Phe Lys Arg Met Arg Asn Val Thr Asn Ile Phe Leu
         35                  40                  45 gcc tcg ctc agc acc gcc gac ttg tgc ctt atc tgg ttt tgt gtg cct    192
Ala Ser Leu Ser Thr Ala Asp Leu Cys Leu Ile Trp Phe Cys Val Pro
     50                  55                  60 ata atg ttc atg aag tat atg tcg cat acg tgg tcg atg ggc agg ttt    240
Ile Met Phe Met Lys Tyr Met Ser His Thr Trp Ser Met Gly Arg Phe
 65                  70                  75                  80 gcg tgc tat tct gtg cac tac att caa cag ttt aca tgc ttc tgc tcg    288
Ala Cys Tyr Ser Val His Tyr Ile Gln Gln Phe Thr Cys Phe Cys Ser
                 85                  90                  95 gtg ctc acg atg act atg att agt ttt gag agg ttt ctt gca ata gca    336
Val Leu Thr Met Thr Met Ile Ser Phe Glu Arg Phe Leu Ala Ile Ala
            100                 105                 110 tat cct atg cga aat atc tgg ttt tca tcc ata gga cga gct aaa aaa    384
Tyr Pro Met Arg Asn Ile Trp Phe Ser Ser Ile Gly Arg Ala Lys Lys
        115                 120                 125 gta atc cta ctc atc tgg atg tca tcc gcg gta ctg gcc gtc cca acc    432
Val Ile Leu Leu Ile Trp Met Ser Ser Ala Val Leu Ala Val Pro Thr
    130                 135                 140 gct gtt cgg atg gat tat gag acc aat ctt tca ttg tcc ggg cag agg    480
Ala Val Arg Met Asp Tyr Glu Thr Asn Leu Ser Leu Ser Gly Gln Arg
145                 150                 155                 160 gtg cat tgg tgt cga aga cgg ttt ccc gcg caa ttt tta gga tat cct    528
Val His Trp Cys Arg Arg Arg Phe Pro Ala Gln Phe Leu Gly Tyr Pro
                165                 170                 175 agg aca tcg ttg aat aaa gca tat gcc atg tat cag ttg ttg cta ctt    576
Arg Thr Ser Leu Asn Lys Ala Tyr Ala Met Tyr Gln Leu Leu Leu Leu
            180                 185                 190
```

```
atc ata ttc ccg gtg ctc aca atg tcc ata tgt tat gct cgt gta tct    624
Ile Ile Phe Pro Val Leu Thr Met Ser Ile Cys Tyr Ala Arg Val Ser
        195                 200                 205 gca ata gtg tac aag tcg tcg aaa gat cgt gta ata ctt tcc caa gct    672
Ala Ile Val Tyr Lys Ser Ser Lys Asp Arg Val Ile Leu Ser Gln Ala
        210                 215                 220 atg gtc gca ttt tca aag gcc gcc act gac gcc gtt acc ttc tcc ggc    720
Met Val Ala Phe Ser Lys Ala Ala Thr Asp Ala Val Thr Phe Ser Gly
225                 230                 235                 240 tac tct gca atc ccc atg att aca act tcc cgg aac ttg aaa acc gcc    768
Tyr Ser Ala Ile Pro Met Ile Thr Thr Ser Arg Asn Leu Lys Thr Ala
                245                 250                 255 aac acg acc atc aag tcc tac agt aat cac aga aat aat cgc gtg gca    816
Asn Thr Thr Ile Lys Ser Tyr Ser Asn His Arg Asn Asn Arg Val Ala
            260                 265                 270 gag gcg aat aag aaa cag ata gtt caa atg tta atc tcc atc gtc tgc    864
Glu Ala Asn Lys Lys Gln Ile Val Gln Met Leu Ile Ser Ile Val Cys
        275                 280                 285 atg tac acg gtt tgc tgg ctc cca acg atc gtc gac gag ctt ctg acg    912
Met Tyr Thr Val Cys Trp Leu Pro Thr Ile Val Asp Glu Leu Leu Thr
290                 295                 300 tcc ttc ggg tac att tgt cga aca tca aat acg cag aca ttg aag cat    960
Ser Phe Gly Tyr Ile Cys Arg Thr Ser Asn Thr Gln Thr Leu Lys His
305                 310                 315                 320 atg cgg atg gga ttt aat gcg ctg acc tat tgc caa tca tgc att aat   1008
Met Arg Met Gly Phe Asn Ala Leu Thr Tyr Cys Gln Ser Cys Ile Asn
                325                 330                 335 cct atc ctg tat gcc ttc att tct cag aat ttc cgg tcc acg ttc aag   1056
Pro Ile Leu Tyr Ala Phe Ile Ser Gln Asn Phe Arg Ser Thr Phe Lys
            340                 345                 350 acc gcc tat tcg aga atg aaa agt cgt ctt cag ggc gtg gaa gaa atg   1104
Thr Ala Tyr Ser Arg Met Lys Ser Arg Leu Gln Gly Val Glu Glu Met
        355                 360                 365 cgc tct cgt atg gga tcg tgc tct tcg gcg agc atg atg tcg acc cgc   1152
Arg Ser Arg Met Gly Ser Cys Ser Ser Ala Ser Met Met Ser Thr Arg
370                 375                 380 aac cag cac cga atc tac ggg tcc agc ttc aac aca ctc aca gtg ccc   1200
Asn Gln His Arg Ile Tyr Gly Ser Ser Phe Asn Thr Leu Thr Val Pro
385                 390                 395                 400 ggt cgc tcc atg atc act ccg aac atg tca cgc gac gtc tca cag ttg   1248
Gly Arg Ser Met Ile Thr Pro Asn Met Ser Arg Asp Val Ser Gln Leu
                405                 410                 415 tca ttg tgc agg ccg acg tcg caa atg tcg ttc tgc cga ccg aag agt   1296
Ser Leu Cys Arg Pro Thr Ser Gln Met Ser Phe Cys Arg Pro Lys Ser
            420                 425                 430 cca atg gcc gga gac tct ccg tcg act ttc atg aga cat cgt cct aga   1344
Pro Met Ala Gly Asp Ser Pro Ser Thr Phe Met Arg His Arg Pro Arg
        435                 440                 445 tcg cca acc gac gtg tcc cat gat tcc gga aga cca cgt agc ccc acg   1392
Ser Pro Thr Asp Val Ser His Asp Ser Gly Arg Pro Arg Ser Pro Thr
450                 455                 460 gat ctt tcg cag tcg aca aag cct tcg cga cga tcc tct ata aga       1440
Asp Leu Ser Gln Ser Thr Lys Pro Ser Arg Arg Ser Ser Ile Arg
465                 470                 475                 480 ccc cgt agc cca aca tcg aca tct caa atg tct acc ata gtc cga tcg   1488
Pro Arg Ser Pro Thr Ser Thr Ser Gln Met Ser Thr Ile Val Arg Ser
                485                 490                 495 aga agt cct aca ggc gca tcg gac acc tct tca ttg ttc cca tca aga   1536
Arg Ser Pro Thr Gly Ala Ser Asp Thr Ser Ser Leu Phe Pro Ser Arg
```

-continued

```
              500               505               510
aca aga agt cca act ctc caa tca aac aca tct ggt caa tcc atg gaa     1584
Thr Arg Ser Pro Thr Leu Gln Ser Asn Thr Ser Gly Gln Ser Met Glu
            515               520               525 cga acc acg gac cga ctg agt gtc cgt gac gct gtc cga cca aaa aca     1632
Arg Thr Thr Asp Arg Leu Ser Val Arg Asp Ala Val Arg Pro Lys Thr
530               535               540 ccg cca gca gtg gtt gtc ta                                          1652
Pro Pro Ala Val Val Val
545               550
```

<210> SEQ ID NO 18
<211> LENGTH: 550
<212> TYPE: PRT
<213> ORGANISM: Homo sapiens

<400> SEQUENCE: 18

```
Met Thr Asp Glu Glu Leu Phe Glu Ile Ala Leu Pro Gly Phe Leu Tyr
 1               5                  10                  15

Leu Thr Val Phe Leu Val Gly Thr Ile Gly Asn Ser Met Val Ile Phe
            20                  25                  30

Val Val Asn Arg Phe Lys Arg Met Arg Asn Val Thr Asn Ile Phe Leu
        35                  40                  45

Ala Ser Leu Ser Thr Ala Asp Leu Cys Leu Ile Trp Phe Cys Val Pro
    50                  55                  60

Ile Met Phe Met Lys Tyr Met Ser His Thr Trp Ser Met Gly Arg Phe
65                  70                  75                  80

Ala Cys Tyr Ser Val His Tyr Ile Gln Gln Phe Thr Cys Phe Cys Ser
                85                  90                  95

Val Leu Thr Met Thr Met Ile Ser Phe Glu Arg Phe Leu Ala Ile Ala
            100                 105                 110

Tyr Pro Met Arg Asn Ile Trp Phe Ser Ser Ile Gly Arg Ala Lys Lys
        115                 120                 125

Val Ile Leu Leu Ile Trp Met Ser Ser Ala Val Leu Ala Val Pro Thr
    130                 135                 140

Ala Val Arg Met Asp Tyr Glu Thr Asn Leu Ser Leu Ser Gly Gln Arg
145                 150                 155                 160

Val His Trp Cys Arg Arg Phe Pro Ala Gln Phe Leu Gly Tyr Pro
                165                 170                 175

Arg Thr Ser Leu Asn Lys Ala Tyr Ala Met Tyr Gln Leu Leu Leu Leu
            180                 185                 190

Ile Ile Phe Pro Val Leu Thr Met Ser Ile Cys Tyr Ala Arg Val Ser
        195                 200                 205

Ala Ile Val Tyr Lys Ser Ser Lys Asp Arg Val Ile Leu Ser Gln Ala
    210                 215                 220

Met Val Ala Phe Ser Lys Ala Ala Thr Asp Ala Val Thr Phe Ser Gly
225                 230                 235                 240

Tyr Ser Ala Ile Pro Met Ile Thr Thr Ser Arg Asn Leu Lys Thr Ala
                245                 250                 255

Asn Thr Thr Ile Lys Ser Tyr Ser Asn His Arg Asn Arg Val Ala
            260                 265                 270

Glu Ala Asn Lys Lys Gln Ile Val Gln Met Leu Ile Ser Ile Val Cys
        275                 280                 285

Met Tyr Thr Val Cys Trp Leu Pro Thr Ile Val Asp Glu Leu Leu Thr
    290                 295                 300
```

```
Ser Phe Gly Tyr Ile Cys Arg Thr Ser Asn Thr Gln Thr Leu Lys His
305                 310                 315                 320

Met Arg Met Gly Phe Asn Ala Leu Thr Tyr Cys Gln Ser Cys Ile Asn
            325                 330                 335

Pro Ile Leu Tyr Ala Phe Ile Ser Gln Asn Phe Arg Ser Thr Phe Lys
                340                 345                 350

Thr Ala Tyr Ser Arg Met Lys Ser Arg Leu Gln Gly Val Glu Glu Met
            355                 360                 365

Arg Ser Arg Met Gly Ser Cys Ser Ser Ala Ser Met Met Ser Thr Arg
        370                 375                 380

Asn Gln His Arg Ile Tyr Gly Ser Ser Phe Asn Thr Leu Thr Val Pro
385                 390                 395                 400

Gly Arg Ser Met Ile Thr Pro Asn Met Ser Arg Asp Val Ser Gln Leu
                405                 410                 415

Ser Leu Cys Arg Pro Thr Ser Gln Met Ser Phe Cys Arg Pro Lys Ser
            420                 425                 430

Pro Met Ala Gly Asp Ser Pro Ser Thr Phe Met Arg His Arg Pro Arg
        435                 440                 445

Ser Pro Thr Asp Val Ser His Asp Ser Gly Arg Pro Arg Ser Pro Thr
450                 455                 460

Asp Leu Ser Gln Ser Thr Lys Pro Ser Arg Arg Ser Ser Ser Ile Arg
465                 470                 475                 480

Pro Arg Ser Pro Thr Ser Thr Ser Gln Met Ser Thr Ile Val Arg Ser
                485                 490                 495

Arg Ser Pro Thr Gly Ala Ser Asp Thr Ser Ser Leu Phe Pro Ser Arg
            500                 505                 510

Thr Arg Ser Pro Thr Leu Gln Ser Asn Thr Ser Gly Gln Ser Met Glu
        515                 520                 525

Arg Thr Thr Asp Arg Leu Ser Val Arg Asp Ala Val Arg Pro Lys Thr
            530                 535                 540

Pro Pro Ala Val Val Val
545                 550

<210> SEQ ID NO 19
<211> LENGTH: 0
<212> TYPE: DNA
<213> ORGANISM: synthetic

<400> SEQUENCE: 19

000

<210> SEQ ID NO 20
<211> LENGTH: 0
<212> TYPE: PRT
<213> ORGANISM: synthetic

<400> SEQUENCE: 20

000

<210> SEQ ID NO 21
<211> LENGTH: 1130
<212> TYPE: DNA
<213> ORGANISM: Homo sapiens
<220> FEATURE:
<221> NAME/KEY: CDS
<222> LOCATION: (1)..(1128)
<220> FEATURE:
<223> OTHER INFORMATION: Clone identifier: CEGPCR4
```

```
<400> SEQUENCE: 21 atg aat ggc tcc gat tgt ctg aat ctc aac tca gaa tta tgg ttg tat        48
Met Asn Gly Ser Asp Cys Leu Asn Leu Asn Ser Glu Leu Trp Leu Tyr
 1               5                  10                  15 cga gaa gat ttg tca tca agg tgg tac ata atg tta gtg ttt gca ttt        96
Arg Glu Asp Leu Ser Ser Arg Trp Tyr Ile Met Leu Val Phe Ala Phe
                20                  25                  30 ctc tac ctg ata atc att gcc gcc gga ata att gga aac tca tgt gtg       144
Leu Tyr Leu Ile Ile Ile Ala Ala Gly Ile Ile Gly Asn Ser Cys Val
            35                  40                  45 att ttg gca atc aca agg aac aaa tca ctt caa act gtt ccg aat ctg       192
Ile Leu Ala Ile Thr Arg Asn Lys Ser Leu Gln Thr Val Pro Asn Leu
    50                  55                  60 ttt att ctt tct tta tca tgt tct gat att gtg gta tgc tgc aca tct       240
Phe Ile Leu Ser Leu Ser Cys Ser Asp Ile Val Val Cys Cys Thr Ser
65                  70                  75                  80 gca aca atc act ccg att act gca ttc aag aaa gaa tgg atc ttt gga       288
Ala Thr Ile Thr Pro Ile Thr Ala Phe Lys Lys Glu Trp Ile Phe Gly
                85                  90                  95 gag gct tta tgc cga att gca cca ttc att gct ggt atc agc ctt tgt       336
Glu Ala Leu Cys Arg Ile Ala Pro Phe Ile Ala Gly Ile Ser Leu Cys
            100                 105                 110 ttc tca act ttc aca ttg act gca atc tcc atc gac aga tac atc ctg       384
Phe Ser Thr Phe Thr Leu Thr Ala Ile Ser Ile Asp Arg Tyr Ile Leu
        115                 120                 125 att cga ttt ccg atg agg aaa cct att acg cat tat caa gcg gtt gga       432
Ile Arg Phe Pro Met Arg Lys Pro Ile Thr His Tyr Gln Ala Val Gly
    130                 135                 140 gtg att gct att att tgc gct ttt gct gca acc atc aca tcc cca ata       480
Val Ile Ala Ile Ile Cys Ala Phe Ala Ala Thr Ile Thr Ser Pro Ile
145                 150                 155                 160 atg ttc aag caa aag ctg gga gag ttt gag aat ttt tgt ggg cag tac       528
Met Phe Lys Gln Lys Leu Gly Glu Phe Glu Asn Phe Cys Gly Gln Tyr
                165                 170                 175 tgc acg gaa aac tgg gga gcc aat gaa agc cag aga aaa att tat ggt       576
Cys Thr Glu Asn Trp Gly Ala Asn Glu Ser Gln Arg Lys Ile Tyr Gly
            180                 185                 190 gca gct ctg atg ttt ctt cag ctc gtc att ccg ctt acc atc atc atc       624
Ala Ala Leu Met Phe Leu Gln Leu Val Ile Pro Leu Thr Ile Ile Ile
        195                 200                 205 ata tcc tac act gcg att tct ttg aag atc gga caa agc atg att ctc       672
Ile Ser Tyr Thr Ala Ile Ser Leu Lys Ile Gly Gln Ser Met Ile Leu
    210                 215                 220 aaa ggg gcg aaa aag caa aaa aca gac aat tgg gaa atg gaa tta agt       720
Lys Gly Ala Lys Lys Gln Lys Thr Asp Asn Trp Glu Met Glu Leu Ser
225                 230                 235                 240 gat caa caa aga atc gct gtg aag aga aga caa aga act aat aga atg       768
Asp Gln Gln Arg Ile Ala Val Lys Arg Arg Gln Arg Thr Asn Arg Met
                245                 250                 255 ctt att ggt atg gta gtc gca ttc gct tgc agc tgg att tgg tca gtg       816
Leu Ile Gly Met Val Val Ala Phe Ala Cys Ser Trp Ile Trp Ser Val
            260                 265                 270 acg ttc aac att ctg agg gac tat gaa tat ttg cca gag ctc atc aaa       864
Thr Phe Asn Ile Leu Arg Asp Tyr Glu Tyr Leu Pro Glu Leu Ile Lys
        275                 280                 285 act caa gaa tat atc ttt gga att gca aca cat tgc att gca atg acc       912
Thr Gln Glu Tyr Ile Phe Gly Ile Ala Thr His Cys Ile Ala Met Thr
    290                 295                 300 tca acg gta tgg aac ccg tta ctc tac gca gtg ctc aac ctc caa ctg       960
```

```
Ser Thr Val Trp Asn Pro Leu Leu Tyr Ala Val Leu Asn Leu Gln Leu
305                 310                 315                 320 cgt gca gca ttc att gac ctg atg cct cac tgg ctt cgt cgt cat tta      1008
Arg Ala Ala Phe Ile Asp Leu Met Pro His Trp Leu Arg Arg His Leu
                    325                 330                 335 aac ctg gaa gga gac aac agc tct cca ttg ctc aac cat ccg acg atg      1056
Asn Leu Glu Gly Asp Asn Ser Ser Pro Leu Leu Asn His Pro Thr Met
                340                 345                 350 aca att aca aac aaa ccg tca aag caa cat aca tta ata cca gca atg      1104
Thr Ile Thr Asn Lys Pro Ser Lys Gln His Thr Leu Ile Pro Ala Met
            355                 360                 365 gac aac cat acg tgt caa caa gtt ta                                   1130
Asp Asn His Thr Cys Gln Gln Val
    370                 375

<210> SEQ ID NO 22
<211> LENGTH: 376
<212> TYPE: PRT
<213> ORGANISM: Homo sapiens

<400> SEQUENCE: 22

Met Asn Gly Ser Asp Cys Leu Asn Leu Asn Ser Glu Leu Trp Leu Tyr
1               5                   10                  15

Arg Glu Asp Leu Ser Ser Arg Trp Tyr Ile Met Leu Val Phe Ala Phe
                20                  25                  30

Leu Tyr Leu Ile Ile Ile Ala Ala Gly Ile Ile Gly Asn Ser Cys Val
            35                  40                  45

Ile Leu Ala Ile Thr Arg Asn Lys Ser Leu Gln Thr Val Pro Asn Leu
        50                  55                  60

Phe Ile Leu Ser Leu Ser Cys Ser Asp Ile Val Val Cys Cys Thr Ser
65                  70                  75                  80

Ala Thr Ile Thr Pro Ile Thr Ala Phe Lys Lys Glu Trp Ile Phe Gly
                85                  90                  95

Glu Ala Leu Cys Arg Ile Ala Pro Phe Ile Ala Gly Ile Ser Leu Cys
            100                 105                 110

Phe Ser Thr Phe Thr Leu Thr Ala Ile Ser Ile Asp Arg Tyr Ile Leu
        115                 120                 125

Ile Arg Phe Pro Met Arg Lys Pro Ile Thr His Tyr Gln Ala Val Gly
130                 135                 140

Val Ile Ala Ile Ile Cys Ala Phe Ala Ala Thr Ile Thr Ser Pro Ile
145                 150                 155                 160

Met Phe Lys Gln Lys Leu Gly Glu Phe Glu Asn Phe Cys Gly Gln Tyr
                165                 170                 175

Cys Thr Glu Asn Trp Gly Ala Asn Glu Ser Gln Arg Lys Ile Tyr Gly
            180                 185                 190

Ala Ala Leu Met Phe Leu Gln Leu Val Ile Pro Leu Thr Ile Ile Ile
        195                 200                 205

Ile Ser Tyr Thr Ala Ile Ser Leu Lys Ile Gly Gln Ser Met Ile Leu
    210                 215                 220

Lys Gly Ala Lys Lys Gln Lys Thr Asp Asn Trp Glu Met Glu Leu Ser
225                 230                 235                 240

Asp Gln Gln Arg Ile Ala Val Lys Arg Arg Gln Arg Thr Asn Arg Met
                245                 250                 255

Leu Ile Gly Met Val Val Ala Phe Ala Cys Ser Trp Ile Trp Ser Val
            260                 265                 270

Thr Phe Asn Ile Leu Arg Asp Tyr Glu Tyr Leu Pro Glu Leu Ile Lys
```

```
                    275                 280                 285
Thr Gln Glu Tyr Ile Phe Gly Ile Ala Thr His Cys Ile Ala Met Thr
    290                 295                 300

Ser Thr Val Trp Asn Pro Leu Leu Tyr Ala Val Leu Asn Leu Gln Leu
305                 310                 315                 320

Arg Ala Ala Phe Ile Asp Leu Met Pro His Trp Leu Arg Arg His Leu
                325                 330                 335

Asn Leu Glu Gly Asp Asn Ser Ser Pro Leu Leu Asn His Pro Thr Met
            340                 345                 350

Thr Ile Thr Asn Lys Pro Ser Lys Gln His Thr Leu Ile Pro Ala Met
            355                 360                 365

Asp Asn His Thr Cys Gln Gln Val
        370                 375

<210> SEQ ID NO 23
<211> LENGTH: 1125
<212> TYPE: DNA
<213> ORGANISM: Homo sapiens
<220> FEATURE:
<221> NAME/KEY: CDS
<222> LOCATION: (1)..(1122)
<220> FEATURE:
<223> OTHER INFORMATION: Clone identifier: CEGPCR6

<400> SEQUENCE: 23 atg att att ttt tat ctt tac gta gca act caa gta ttt gtg gca att      48
Met Ile Ile Phe Tyr Leu Tyr Val Ala Thr Gln Val Phe Val Ala Ile
  1               5                  10                  15 gca ttt gtc ctt ctg atg gca act gca ata att gga aac tct gtc gtg      96
Ala Phe Val Leu Leu Met Ala Thr Ala Ile Ile Gly Asn Ser Val Val
             20                  25                  30 atg tgg ata att tat caa cac aaa gta atg cac tac ggc ttc aac tat     144
Met Trp Ile Ile Tyr Gln His Lys Val Met His Tyr Gly Phe Asn Tyr
         35                  40                  45 ttt ctt ttc aat atg gca ttc gct gat ctt ttg att gct ctc ttc aat     192
Phe Leu Phe Asn Met Ala Phe Ala Asp Leu Leu Ile Ala Leu Phe Asn
     50                  55                  60 gtt ggt act tca tgg acc tat aat tta tac tat gac tgg tgg tat ggt     240
Val Gly Thr Ser Trp Thr Tyr Asn Leu Tyr Tyr Asp Trp Trp Tyr Gly
 65                  70                  75                  80 gat cta tgt aca ctt act tcc ttc ttc ggt att gca cca act acc gta     288
Asp Leu Cys Thr Leu Thr Ser Phe Phe Gly Ile Ala Pro Thr Thr Val
                 85                  90                  95 tcc gtg tgc tca atg atg gct ctc agc tgg gat aga tgt caa gca gtc     336
Ser Val Cys Ser Met Met Ala Leu Ser Trp Asp Arg Cys Gln Ala Val
            100                 105                 110 gtg aat cct cta caa aaa cgt cca cta tct cga aaa aga tcc gtc att     384
Val Asn Pro Leu Gln Lys Arg Pro Leu Ser Arg Lys Arg Ser Val Ile
        115                 120                 125 gct att ctc atc att tgg gtt gtt tca acg gtt act gca ctt ccg ttt     432
Ala Ile Leu Ile Ile Trp Val Val Ser Thr Val Thr Ala Leu Pro Phe
    130                 135                 140 gca att gct gca tct gtc aac tct ctc tac aca tat gac gtg gtt aca     480
Ala Ile Ala Ala Ser Val Asn Ser Leu Tyr Thr Tyr Asp Val Val Thr
145                 150                 155                 160 tca act gtt tca aaa gct cac gtt tgt tca gca cca gtt aat act ttc     528
Ser Thr Val Ser Lys Ala His Val Cys Ser Ala Pro Val Asn Thr Phe
                165                 170                 175 ttt gaa aaa gtg ctc ttt ggg att caa tat gct cta cct ata atc att     576
Phe Glu Lys Val Leu Phe Gly Ile Gln Tyr Ala Leu Pro Ile Ile Ile
```

```
                180                    185                    190
ttg gga tca acg ttc aca cgg att gcc gtt gca ttt cga gca aca aat      624
Leu Gly Ser Thr Phe Thr Arg Ile Ala Val Ala Phe Arg Ala Thr Asn
        195                    200                    205 gaa gcc act gac agt agt ctg aag aac aat cac aca cgc gca aag agc      672
Glu Ala Thr Asp Ser Ser Leu Lys Asn Asn His Thr Arg Ala Lys Ser
    210                    215                    220 aag gca gta aaa atg ctc ttc cta atg gtc gtt gca ttc gtt gtc tgc      720
Lys Ala Val Lys Met Leu Phe Leu Met Val Val Ala Phe Val Val Cys
225                    230                    235                    240 tgg ctt cca tac cac att tat cac gca ttc gct ctt gaa gaa ttc ttc      768
Trp Leu Pro Tyr His Ile Tyr His Ala Phe Ala Leu Glu Glu Phe Phe
                245                    250                    255 gat gca gct cgt gga aaa tat gcg tat ttg ttg att tac tgg att gca      816
Asp Ala Ala Arg Gly Lys Tyr Ala Tyr Leu Leu Ile Tyr Trp Ile Ala
            260                    265                    270 atg tct agt tgt gca tac aat cca att att tat tgt ttt gcc aac gaa      864
Met Ser Ser Cys Ala Tyr Asn Pro Ile Ile Tyr Cys Phe Ala Asn Glu
        275                    280                    285 aga ttc cgc att ggc ttc cgg tac gtc ttc cga tgg att cca gtg att      912
Arg Phe Arg Ile Gly Phe Arg Tyr Val Phe Arg Trp Ile Pro Val Ile
    290                    295                    300 gac tgc aaa aag gaa caa tat gaa tat tca caa tta ttc ccg gat aaa      960
Asp Cys Lys Lys Glu Gln Tyr Glu Tyr Ser Gln Leu Phe Pro Asp Lys
305                    310                    315                    320 atg aga agt atg gct att tct ttg caa aaa gga aga gtg aac tct tcc     1008
Met Arg Ser Met Ala Ile Ser Leu Gln Lys Gly Arg Val Asn Ser Ser
                325                    330                    335 tgt ttg gat aaa aaa gtc aaa gag aat tct tct caa gat ttg gtt tgt     1056
Cys Leu Asp Lys Lys Val Lys Glu Asn Ser Ser Gln Asp Leu Val Cys
            340                    345                    350 gtg atg cat tcc gag aaa aat acg aag aaa tat tca aaa gta cat ctt     1104
Val Met His Ser Glu Lys Asn Thr Lys Lys Tyr Ser Lys Val His Leu
        355                    360                    365 ctg agt tgc cat gaa cgg tga                                         1125
Leu Ser Cys His Glu Arg
    370

<210> SEQ ID NO 24
<211> LENGTH: 374
<212> TYPE: PRT
<213> ORGANISM: Homo sapiens

<400> SEQUENCE: 24

Met Ile Ile Phe Tyr Leu Tyr Val Ala Thr Gln Val Phe Val Ala Ile
  1               5                  10                  15

Ala Phe Val Leu Leu Met Ala Thr Ala Ile Ile Gly Asn Ser Val Val
                 20                  25                  30

Met Trp Ile Ile Tyr Gln His Lys Val Met His Tyr Gly Phe Asn Tyr
             35                  40                  45

Phe Leu Phe Asn Met Ala Phe Ala Asp Leu Leu Ile Ala Leu Phe Asn
         50                  55                  60

Val Gly Thr Ser Trp Thr Tyr Asn Leu Tyr Tyr Asp Trp Trp Tyr Gly
 65                  70                  75                  80

Asp Leu Cys Thr Leu Thr Ser Phe Phe Gly Ile Ala Pro Thr Thr Val
                 85                  90                  95

Ser Val Cys Ser Met Met Ala Leu Ser Trp Asp Arg Cys Gln Ala Val
            100                 105                 110
```

-continued

```
Val Asn Pro Leu Gln Lys Arg Pro Leu Ser Arg Lys Arg Ser Val Ile
        115                 120                 125
Ala Ile Leu Ile Ile Trp Val Val Ser Thr Val Thr Ala Leu Pro Phe
130                 135                 140
Ala Ile Ala Ala Ser Val Asn Ser Leu Tyr Thr Tyr Asp Val Val Thr
145                 150                 155                 160
Ser Thr Val Ser Lys Ala His Val Cys Ser Ala Pro Val Asn Thr Phe
                165                 170                 175
Phe Glu Lys Val Leu Phe Gly Ile Gln Tyr Ala Leu Pro Ile Ile Ile
                180                 185                 190
Leu Gly Ser Thr Phe Thr Arg Ile Ala Val Ala Phe Arg Ala Thr Asn
                195                 200                 205
Glu Ala Thr Asp Ser Ser Leu Lys Asn Asn His Thr Arg Ala Lys Ser
        210                 215                 220
Lys Ala Val Lys Met Leu Phe Leu Met Val Val Ala Phe Val Val Cys
225                 230                 235                 240
Trp Leu Pro Tyr His Ile Tyr His Ala Phe Ala Leu Glu Glu Phe Phe
                245                 250                 255
Asp Ala Ala Arg Gly Lys Tyr Ala Tyr Leu Leu Ile Tyr Trp Ile Ala
                260                 265                 270
Met Ser Ser Cys Ala Tyr Asn Pro Ile Ile Tyr Cys Phe Ala Asn Glu
        275                 280                 285
Arg Phe Arg Ile Gly Phe Arg Tyr Val Phe Arg Trp Ile Pro Val Ile
        290                 295                 300
Asp Cys Lys Lys Glu Gln Tyr Glu Tyr Ser Gln Leu Phe Pro Asp Lys
305                 310                 315                 320
Met Arg Ser Met Ala Ile Ser Leu Gln Lys Gly Arg Val Asn Ser Ser
                325                 330                 335
Cys Leu Asp Lys Lys Val Lys Glu Asn Ser Ser Gln Asp Leu Val Cys
                340                 345                 350
Val Met His Ser Glu Lys Asn Thr Lys Lys Tyr Ser Lys Val His Leu
                355                 360                 365
Leu Ser Cys His Glu Arg
        370
```

<210> SEQ ID NO 25
<211> LENGTH: 1374
<212> TYPE: DNA
<213> ORGANISM: Homo sapiens
<220> FEATURE:
<221> NAME/KEY: CDS
<222> LOCATION: (1)..(1371)
<220> FEATURE:
<223> OTHER INFORMATION: Clone identifier: CEGPCR7

<400> SEQUENCE: 25

```
atg gaa gtt gaa aat ttt acc gac tgt caa gta tat tgg aaa gtg tat       48
Met Glu Val Glu Asn Phe Thr Asp Cys Gln Val Tyr Trp Lys Val Tyr
 1               5                  10                  15 cca gat cct tct caa agt ata tat gcg ata gtg cca ttt ctg acc gtg       96
Pro Asp Pro Ser Gln Ser Ile Tyr Ala Ile Val Pro Phe Leu Thr Val
            20                  25                  30 tac ctt ttt ctc ttt ttt ctt gga ctc ttt gga aat gtg acc ttg att      144
Tyr Leu Phe Leu Phe Phe Leu Gly Leu Phe Gly Asn Val Thr Leu Ile
        35                  40                  45 tac gta act tgc agc cat aaa gct tta ctg agc gtt caa aac ata ttc      192
Tyr Val Thr Cys Ser His Lys Ala Leu Leu Ser Val Gln Asn Ile Phe
    50                  55                  60
```

-continued

```
att ctg aac ctg gcg gcg agc gat tgc atg atg tgc ata tta tcg ctt      240
Ile Leu Asn Leu Ala Ala Ser Asp Cys Met Met Cys Ile Leu Ser Leu
 65              70                  75                  80 cca atc act cca atc aca aat gtg tac aaa aac tgg tac ttt gga aat      288
Pro Ile Thr Pro Ile Thr Asn Val Tyr Lys Asn Trp Tyr Phe Gly Asn
                 85                  90                  95 cta ctc tgc cat ttg ata cca tgc att caa ggt atc agc att ttc gta      336
Leu Leu Cys His Leu Ile Pro Cys Ile Gln Gly Ile Ser Ile Phe Val
            100                 105                 110 tgc aca ttc agt ctc ggt gcg att gct ttg gat cgg tat atc ctt gta      384
Cys Thr Phe Ser Leu Gly Ala Ile Ala Leu Asp Arg Tyr Ile Leu Val
        115                 120                 125 gta aga cca cat tct aca cca cta tcc caa aga gga gca ttt ctt act      432
Val Arg Pro His Ser Thr Pro Leu Ser Gln Arg Gly Ala Phe Leu Thr
    130                 135                 140 act gtt cta ttg tgg atc ctc tct ttt gtt gta act cta ccc tat gcg      480
Thr Val Leu Leu Trp Ile Leu Ser Phe Val Val Thr Leu Pro Tyr Ala
145                 150                 155                 160 ttc aat atg caa atg att gaa tac aca gaa gag aga ata tgc ggc tac      528
Phe Asn Met Gln Met Ile Glu Tyr Thr Glu Glu Arg Ile Cys Gly Tyr
                165                 170                 175 ttt tgc act gaa aag tgg gaa tct gcc aag tct aga aga gcc tac aca      576
Phe Cys Thr Glu Lys Trp Glu Ser Ala Lys Ser Arg Arg Ala Tyr Thr
            180                 185                 190 atg atc gtg atg ctc gcc caa ttc gtg gtc cca ttc gct gtc atg gcc      624
Met Ile Val Met Leu Ala Gln Phe Val Val Pro Phe Ala Val Met Ala
        195                 200                 205 ttc tgc tat gca aat att gtt tcg gtg ctc agc aag cgt gct cag aca      672
Phe Cys Tyr Ala Asn Ile Val Ser Val Leu Ser Lys Arg Ala Gln Thr
    210                 215                 220 aag ata cgc aaa atg gtg gag aga aca agc gcg ttg gag agc tct tgc      720
Lys Ile Arg Lys Met Val Glu Arg Thr Ser Ala Leu Glu Ser Ser Cys
225                 230                 235                 240 gca ttc ccg tcg cat ggt ctt gaa cag tat gaa aat gag ttg aac gaa      768
Ala Phe Pro Ser His Gly Leu Glu Gln Tyr Glu Asn Glu Leu Asn Glu
                245                 250                 255 ttt cta gac aaa cag gaa aag gag aaa caa cga gtt gta ctt cag aac      816
Phe Leu Asp Lys Gln Glu Lys Glu Lys Gln Arg Val Val Leu Gln Asn
            260                 265                 270 aga aga aca acg tca atc cta gtt acc atg gtt gtc tgg ttt ggg ata      864
Arg Arg Thr Thr Ser Ile Leu Val Thr Met Val Val Trp Phe Gly Ile
        275                 280                 285 act tgg ctg cca cat aac gtc att tct ttg att att gaa tat gat gac      912
Thr Trp Leu Pro His Asn Val Ile Ser Leu Ile Ile Glu Tyr Asp Asp
    290                 295                 300 aca caa tcg ttt ttc cga ctt tat ggc aga gat gat tac gat atc agt      960
Thr Gln Ser Phe Phe Arg Leu Tyr Gly Arg Asp Asp Tyr Asp Ile Ser
305                 310                 315                 320 tat tta ctg aac ctt ttc act cac agt att gcc atg tcg aac aat gtt     1008
Tyr Leu Leu Asn Leu Phe Thr His Ser Ile Ala Met Ser Asn Asn Val
                325                 330                 335 tta aac ccg gta ctc tat gcg tgg ctg aac cca agt ttc cgt caa ctg     1056
Leu Asn Pro Val Leu Tyr Ala Trp Leu Asn Pro Ser Phe Arg Gln Leu
            340                 345                 350 gtc ata aag aca tat ttt gga gac cgg cgt aaa agt gac aga ata atc     1104
Val Ile Lys Thr Tyr Phe Gly Asp Arg Arg Lys Ser Asp Arg Ile Ile
        355                 360                 365 aat caa aca tca gtt tac aaa aca aag atc gtg cat gat acg aag cac     1152
Asn Gln Thr Ser Val Tyr Lys Thr Lys Ile Val His Asp Thr Lys His
```

```
                        370                 375                 380
ttg aat gga aga gcc aaa att ggc ggt ggt ggt agc cac gag gcg ttg       1200
Leu Asn Gly Arg Ala Lys Ile Gly Gly Gly Gly Ser His Glu Ala Leu
385                 390                 395                 400 aag gag agg gag ctg aac tcg tgt tcg gaa aat tta agc tat cat gtg       1248
Lys Glu Arg Glu Leu Asn Ser Cys Ser Glu Asn Leu Ser Tyr His Val
                405                 410                 415 aac ggt cat acg agg act cct aca ccg gaa gtt cag ttg aat gaa gtt       1296
Asn Gly His Thr Arg Thr Pro Thr Pro Glu Val Gln Leu Asn Glu Val
            420                 425                 430 tca agt cct gaa ata agt aaa ctt gtt gct gag ccg gaa gaa ttg atc       1344
Ser Ser Pro Glu Ile Ser Lys Leu Val Ala Glu Pro Glu Glu Leu Ile
        435                 440                 445 gag ttc agc gtc aac gac acg cta gtc tga                               1374
Glu Phe Ser Val Asn Asp Thr Leu Val
    450                 455
```

<210> SEQ ID NO 26
<211> LENGTH: 457
<212> TYPE: PRT
<213> ORGANISM: Homo sapiens

<400> SEQUENCE: 26

```
Met Glu Val Glu Asn Phe Thr Asp Cys Gln Val Tyr Trp Lys Val Tyr
 1               5                  10                  15

Pro Asp Pro Ser Gln Ser Ile Tyr Ala Ile Val Pro Phe Leu Thr Val
                20                  25                  30

Tyr Leu Phe Leu Phe Phe Leu Gly Leu Phe Gly Asn Val Thr Leu Ile
            35                  40                  45

Tyr Val Thr Cys Ser His Lys Ala Leu Leu Ser Val Gln Asn Ile Phe
        50                  55                  60

Ile Leu Asn Leu Ala Ala Ser Asp Cys Met Met Cys Ile Leu Ser Leu
65                  70                  75                  80

Pro Ile Thr Pro Ile Thr Asn Val Tyr Lys Asn Trp Tyr Phe Gly Asn
                85                  90                  95

Leu Leu Cys His Leu Ile Pro Cys Ile Gln Gly Ile Ser Ile Phe Val
            100                 105                 110

Cys Thr Phe Ser Leu Gly Ala Ile Ala Leu Asp Arg Tyr Ile Leu Val
        115                 120                 125

Val Arg Pro His Ser Thr Pro Leu Ser Gln Arg Gly Ala Phe Leu Thr
    130                 135                 140

Thr Val Leu Leu Trp Ile Leu Ser Phe Val Val Thr Leu Pro Tyr Ala
145                 150                 155                 160

Phe Asn Met Gln Met Ile Glu Tyr Thr Glu Arg Ile Cys Gly Tyr
                165                 170                 175

Phe Cys Thr Glu Lys Trp Glu Ser Ala Lys Ser Arg Arg Ala Tyr Thr
            180                 185                 190

Met Ile Val Met Leu Ala Gln Phe Val Pro Phe Ala Val Met Ala
        195                 200                 205

Phe Cys Tyr Ala Asn Ile Val Ser Val Leu Ser Lys Arg Ala Gln Thr
    210                 215                 220

Lys Ile Arg Lys Met Val Glu Arg Thr Ser Ala Leu Glu Ser Ser Cys
225                 230                 235                 240

Ala Phe Pro Ser His Gly Leu Glu Gln Tyr Glu Asn Glu Leu Asn Glu
                245                 250                 255

Phe Leu Asp Lys Gln Glu Lys Glu Lys Gln Arg Val Val Leu Gln Asn
```

```
                    260                 265                 270
Arg Arg Thr Thr Ser Ile Leu Val Thr Met Val Val Trp Phe Gly Ile
            275                 280                 285

Thr Trp Leu Pro His Asn Val Ile Ser Leu Ile Ile Glu Tyr Asp Asp
    290                 295                 300

Thr Gln Ser Phe Phe Arg Leu Tyr Gly Arg Asp Asp Tyr Asp Ile Ser
305                 310                 315                 320

Tyr Leu Leu Asn Leu Phe Thr His Ser Ile Ala Met Ser Asn Asn Val
                325                 330                 335

Leu Asn Pro Val Leu Tyr Ala Trp Leu Asn Pro Ser Phe Arg Gln Leu
            340                 345                 350

Val Ile Lys Thr Tyr Phe Gly Asp Arg Arg Lys Ser Asp Arg Ile Ile
            355                 360                 365

Asn Gln Thr Ser Val Tyr Lys Thr Lys Ile Val His Asp Thr Lys His
        370                 375                 380

Leu Asn Gly Arg Ala Lys Ile Gly Gly Gly Ser His Glu Ala Leu
385                 390                 395                 400

Lys Glu Arg Glu Leu Asn Ser Cys Ser Glu Asn Leu Ser Tyr His Val
                405                 410                 415

Asn Gly His Thr Arg Thr Pro Thr Pro Glu Val Gln Leu Asn Glu Val
            420                 425                 430

Ser Ser Pro Glu Ile Ser Lys Leu Val Ala Glu Pro Glu Glu Leu Ile
        435                 440                 445

Glu Phe Ser Val Asn Asp Thr Leu Val
    450                 455
```

<210> SEQ ID NO 27
<211> LENGTH: 1146
<212> TYPE: DNA
<213> ORGANISM: Homo sapiens
<220> FEATURE:
<221> NAME/KEY: CDS
<222> LOCATION: (1)..(1143)
<220> FEATURE:
<223> OTHER INFORMATION: Clone identifier: CEGPCR8

<400> SEQUENCE: 27

```
atg aat acg tca ttt gta gag cca tta tat gca gat gtt gaa caa ctt        48
Met Asn Thr Ser Phe Val Glu Pro Leu Tyr Ala Asp Val Glu Gln Leu
  1               5                  10                  15 gaa cca gtc cct cta ctt aga cat tca tat caa cta act gtt ctt tat        96
Glu Pro Val Pro Leu Leu Arg His Ser Tyr Gln Leu Thr Val Leu Tyr
             20                  25                  30 aca gtt gca tat gga gct gta ttc ttc act ggt gta ctt gga aac acg       144
Thr Val Ala Tyr Gly Ala Val Phe Phe Thr Gly Val Leu Gly Asn Thr
         35                  40                  45 ttt gtt gtc tta gcg gtt tgg gct cat aag aat tta aat ata acc acg       192
Phe Val Val Leu Ala Val Trp Ala His Lys Asn Leu Asn Ile Thr Thr
     50                  55                  60 gat tat cta att ttg tct ctt gca ctt gct gat ctg ttt att tta tgg       240
Asp Tyr Leu Ile Leu Ser Leu Ala Leu Ala Asp Leu Phe Ile Leu Trp
 65                  70                  75                  80 att tgt ctg cca act acg ttg att aat agc att ttc aca gaa tgg ctt       288
Ile Cys Leu Pro Thr Thr Leu Ile Asn Ser Ile Phe Thr Glu Trp Leu
                 85                  90                  95 tgg ggt caa ttt ttc tgc cga ttg tcc aca tgg gct aac gca tct acg       336
Trp Gly Gln Phe Phe Cys Arg Leu Ser Thr Trp Ala Asn Ala Ser Thr
            100                 105                 110
```

| | | | | | | | | | | | | | | | |
|---|---|---|---|---|---|---|---|---|---|---|---|---|---|---|---|
| tca | ttt | gca | tca | gtt | tac | acc | ttg | gtt | gca | gtg | acg | gct | gat | cgt | tat | 384
| Ser | Phe | Ala | Ser | Val | Tyr | Thr | Leu | Val | Ala | Val | Thr | Ala | Asp | Arg | Tyr |
| | 115 | | | | 120 | | | | | 125 | | | | | |

```
tca ttt gca tca gtt tac acc ttg gtt gca gtg acg gct gat cgt tat     384
Ser Phe Ala Ser Val Tyr Thr Leu Val Ala Val Thr Ala Asp Arg Tyr
    115                 120                 125 cta gct att tgc cat acg ttg aaa tac aac act agc tgg gat cga gaa     432
Leu Ala Ile Cys His Thr Leu Lys Tyr Asn Thr Ser Trp Asp Arg Glu
130                 135                 140 tat aca aaa tat gtt ata ttt gct gtt tgg cta gta gct gca ata ttc     480
Tyr Thr Lys Tyr Val Ile Phe Ala Val Trp Leu Val Ala Ala Ile Phe
145                 150                 155                 160 gga ata cct aat tgg tat aac tat gat ttg ata gta tgg caa gaa ggc     528
Gly Ile Pro Asn Trp Tyr Asn Tyr Asp Leu Ile Val Trp Gln Glu Gly
                165                 170                 175 agt tat ggt tac cga tta tgt acg tca caa acg gat caa aaa tta tat     576
Ser Tyr Gly Tyr Arg Leu Cys Thr Ser Gln Thr Asp Gln Lys Leu Tyr
            180                 185                 190 ttt tta ttt gtt aac tta ttg ctg gct ttc ata gtt cca ttt ggt ttg     624
Phe Leu Phe Val Asn Leu Leu Leu Ala Phe Ile Val Pro Phe Gly Leu
        195                 200                 205 att tcg ggt cta tac acg aga ata ttt atc act gta tca aca cat aga     672
Ile Ser Gly Leu Tyr Thr Arg Ile Phe Ile Thr Val Ser Thr His Arg
    210                 215                 220 agt ctg gca gtt gat gca aga gcc cga gaa gat cga gta aaa cta cga     720
Ser Leu Ala Val Asp Ala Arg Ala Arg Glu Asp Arg Val Lys Leu Arg
225                 230                 235                 240 gtt gcc aca atg atg tta aca gta ata att gta ttt gct tgt tgc tgg     768
Val Ala Thr Met Met Leu Thr Val Ile Ile Val Phe Ala Cys Cys Trp
                245                 250                 255 tta cct ctc tat tgc atc ttc aca tat ttt ttc ttc ttt gct gat cag     816
Leu Pro Leu Tyr Cys Ile Phe Thr Tyr Phe Phe Phe Phe Ala Asp Gln
            260                 265                 270 cga tcg gat ctt ttt caa att act tca atg ttg att cgg cca ata ttc     864
Arg Ser Asp Leu Phe Gln Ile Thr Ser Met Leu Ile Arg Pro Ile Phe
        275                 280                 285 caa tgg atg tca tta cta tcg agt tct tta aat cca ata att tat att     912
Gln Trp Met Ser Leu Leu Ser Ser Ser Leu Asn Pro Ile Ile Tyr Ile
    290                 295                 300 gca tac agt cac aag tac aga aga gct ttc aaa agt ata tta ctg atg     960
Ala Tyr Ser His Lys Tyr Arg Arg Ala Phe Lys Ser Ile Leu Leu Met
305                 310                 315                 320 cca tgt aag aca aga tac gaa aga gtc cga agc aca ata ctc cgt cgt    1008
Pro Cys Lys Thr Arg Tyr Glu Arg Val Arg Ser Thr Ile Leu Arg Arg
                325                 330                 335 cac tct cgt ggc ttc aaa tca act gca aca att tca atg tct aat ttt    1056
His Ser Arg Gly Phe Lys Ser Thr Ala Thr Ile Ser Met Ser Asn Phe
            340                 345                 350 gga act gaa cca aca aat tta ggt gga gca tct agt tta ctt att gaa    1104
Gly Thr Glu Pro Thr Asn Leu Gly Gly Ala Ser Ser Leu Leu Ile Glu
        355                 360                 365 cta gat gga aaa cag gtg gaa aga tct act tct gat tgt taa            1146
Leu Asp Gly Lys Gln Val Glu Arg Ser Thr Ser Asp Cys
    370                 375                 380
```

<210> SEQ ID NO 28
<211> LENGTH: 381
<212> TYPE: PRT
<213> ORGANISM: Homo sapiens

<400> SEQUENCE: 28

```
Met Asn Thr Ser Phe Val Glu Pro Leu Tyr Ala Asp Val Glu Gln Leu
 1               5                  10                  15
```

```
Glu Pro Val Pro Leu Leu Arg His Ser Tyr Gln Leu Thr Val Leu Tyr
         20                  25                  30

Thr Val Ala Tyr Gly Ala Val Phe Phe Thr Gly Val Leu Gly Asn Thr
             35                  40                  45

Phe Val Val Leu Ala Val Trp Ala His Lys Asn Leu Asn Ile Thr Thr
         50                  55                  60

Asp Tyr Leu Ile Leu Ser Leu Ala Leu Ala Asp Leu Phe Ile Leu Trp
 65                  70                  75                  80

Ile Cys Leu Pro Thr Thr Leu Ile Asn Ser Ile Phe Thr Glu Trp Leu
                 85                  90                  95

Trp Gly Gln Phe Phe Cys Arg Leu Ser Thr Trp Ala Asn Ala Ser Thr
            100                 105                 110

Ser Phe Ala Ser Val Tyr Thr Leu Val Ala Val Thr Ala Asp Arg Tyr
        115                 120                 125

Leu Ala Ile Cys His Thr Leu Lys Tyr Asn Thr Ser Trp Asp Arg Glu
    130                 135                 140

Tyr Thr Lys Tyr Val Ile Phe Ala Val Trp Leu Val Ala Ala Ile Phe
145                 150                 155                 160

Gly Ile Pro Asn Trp Tyr Asn Tyr Asp Leu Ile Val Trp Gln Glu Gly
                165                 170                 175

Ser Tyr Gly Tyr Arg Leu Cys Thr Ser Gln Thr Asp Gln Lys Leu Tyr
            180                 185                 190

Phe Leu Phe Val Asn Leu Leu Leu Ala Phe Ile Val Pro Phe Gly Leu
        195                 200                 205

Ile Ser Gly Leu Tyr Thr Arg Ile Phe Ile Thr Val Ser Thr His Arg
    210                 215                 220

Ser Leu Ala Val Asp Ala Arg Ala Arg Glu Asp Arg Val Lys Leu Arg
225                 230                 235                 240

Val Ala Thr Met Met Leu Thr Val Ile Ile Val Phe Ala Cys Cys Trp
                245                 250                 255

Leu Pro Leu Tyr Cys Ile Phe Thr Tyr Phe Phe Phe Ala Asp Gln
        260                 265                 270

Arg Ser Asp Leu Phe Gln Ile Thr Ser Met Leu Ile Arg Pro Ile Phe
    275                 280                 285

Gln Trp Met Ser Leu Leu Ser Ser Leu Asn Pro Ile Ile Tyr Ile
290                 295                 300

Ala Tyr Ser His Lys Tyr Arg Ala Phe Lys Ser Ile Leu Leu Met
305                 310                 315                 320

Pro Cys Lys Thr Arg Tyr Glu Arg Val Arg Ser Thr Ile Leu Arg Arg
                325                 330                 335

His Ser Arg Gly Phe Lys Ser Thr Ala Thr Ile Ser Met Ser Asn Phe
            340                 345                 350

Gly Thr Glu Pro Thr Asn Leu Gly Gly Ala Ser Ser Leu Leu Ile Glu
        355                 360                 365

Leu Asp Gly Lys Gln Val Glu Arg Ser Thr Ser Asp Cys
    370                 375                 380

<210> SEQ ID NO 29
<211> LENGTH: 1473
<212> TYPE: DNA
<213> ORGANISM: Homo sapiens
<220> FEATURE:
<221> NAME/KEY: CDS
<222> LOCATION: (1)..(1470)
<220> FEATURE:
<223> OTHER INFORMATION: Clone identifier: CEGPCR9
```

-continued

```
<400> SEQUENCE: 29 atg gaa gtg aaa gat ata gat aac tac tgt gat cgt gga atc agt ccg      48
Met Glu Val Lys Asp Ile Asp Asn Tyr Cys Asp Arg Gly Ile Ser Pro
 1               5                  10                  15 aat gca tcc aat tat ctc acg tac cca ttt gac ggg ctc tgt cta cag      96
Asn Ala Ser Asn Tyr Leu Thr Tyr Pro Phe Asp Gly Leu Cys Leu Gln
                 20                  25                  30 aaa ttt ttt tat caa ctc caa act tct ttg cga agg ttc act cct tac     144
Lys Phe Phe Tyr Gln Leu Gln Thr Ser Leu Arg Arg Phe Thr Pro Tyr
             35                  40                  45 gaa gaa atc att tac aca aca gtt tac atc att atc tct gta gca gct     192
Glu Glu Ile Ile Tyr Thr Thr Val Tyr Ile Ile Ile Ser Val Ala Ala
         50                  55                  60 gtt att gga aat gga ttg gtg ata atg gct gta gta cgg aaa aag aca     240
Val Ile Gly Asn Gly Leu Val Ile Met Ala Val Val Arg Lys Lys Thr
 65                  70                  75                  80 atg aga aca aac aga aat gtt ttg att tta aat ctc gcg ctt tca aac     288
Met Arg Thr Asn Arg Asn Val Leu Ile Leu Asn Leu Ala Leu Ser Asn
                 85                  90                  95 ttg ata ctc gcc atc acc aac atc cca ttt cta tgg ctt ccg tca att     336
Leu Ile Leu Ala Ile Thr Asn Ile Pro Phe Leu Trp Leu Pro Ser Ile
                100                 105                 110 gat ttc gaa ttt ccg tac tct cga ttt ttc tgc aaa ttt gcc aat gtg     384
Asp Phe Glu Phe Pro Tyr Ser Arg Phe Phe Cys Lys Phe Ala Asn Val
            115                 120                 125 ctt ccg ggt agt aat atc tac tgc tca act tta acc atc tcg gtg atg     432
Leu Pro Gly Ser Asn Ile Tyr Cys Ser Thr Leu Thr Ile Ser Val Met
        130                 135                 140 gca att gat aga tat tat tcg gtg aag aaa ttg aaa att gca tca aat     480
Ala Ile Asp Arg Tyr Tyr Ser Val Lys Lys Leu Lys Ile Ala Ser Asn
145                 150                 155                 160 cgt aaa caa tgt ttc cat gct gtt ttg gtt tca ttg gct att tgg att     528
Arg Lys Gln Cys Phe His Ala Val Leu Val Ser Leu Ala Ile Trp Ile
                165                 170                 175 gtg tca ttc atc ctc tcg tta cct ctg ctc ttg tac tat gaa acc tca     576
Val Ser Phe Ile Leu Ser Leu Pro Leu Leu Leu Tyr Tyr Glu Thr Ser
                180                 185                 190 atg ctc tac gtc atg aga gaa att cga gtt gtt gat caa agc ggt cag     624
Met Leu Tyr Val Met Arg Glu Ile Arg Val Val Asp Gln Ser Gly Gln
            195                 200                 205 gaa gtc atc cga agc tac gga tgg aga cag tgc cgt cta gtt tct gcc     672
Glu Val Ile Arg Ser Tyr Gly Trp Arg Gln Cys Arg Leu Val Ser Ala
        210                 215                 220 gga cga tta ccg gac atc acc caa agc atc cag ttg ctc atg tct att     720
Gly Arg Leu Pro Asp Ile Thr Gln Ser Ile Gln Leu Leu Met Ser Ile
225                 230                 235                 240 ctt caa gtc gct ttc cta tac atc gtt cca ctc ttt gtt ctt tca atc     768
Leu Gln Val Ala Phe Leu Tyr Ile Val Pro Leu Phe Val Leu Ser Ile
                245                 250                 255 ttc aac gtg aaa ctc acc cgg ttt tta aaa aca aat gcc aac aaa atg     816
Phe Asn Val Lys Leu Thr Arg Phe Leu Lys Thr Asn Ala Asn Lys Met
                260                 265                 270 agc aaa act cgt gct ccg cca aaa cga ttt gac aga tcc gat agc cac     864
Ser Lys Thr Arg Ala Pro Pro Lys Arg Phe Asp Arg Ser Asp Ser His
            275                 280                 285 cat aat tcg ttg aaa aat aac aac aac cac acg tct tct cta cgt tcg     912
His Asn Ser Leu Lys Asn Asn Asn Asn His Thr Ser Ser Leu Arg Ser
        290                 295                 300
```

```
cca tca atg ccc tca atc aga agt tcg ata acg gag aga aac aag acg       960
Pro Ser Met Pro Ser Ile Arg Ser Ser Ile Thr Glu Arg Asn Lys Thr
305                 310                 315                 320 aat cag aga aca aac aga act act tcg tta ctg att gca atg gcc gga      1008
Asn Gln Arg Thr Asn Arg Thr Thr Ser Leu Leu Ile Ala Met Ala Gly
                325                 330                 335 agc tat gcg gct ctt tgg ttt cca ttc act ctc atc act ttt ttg ata     1056
Ser Tyr Ala Ala Leu Trp Phe Pro Phe Thr Leu Ile Thr Phe Leu Ile
            340                 345                 350 gac ttc gag ttg atc atc aat caa gac tac gtg aac ttg gta gaa cga     1104
Asp Phe Glu Leu Ile Ile Asn Gln Asp Tyr Val Asn Leu Val Glu Arg
        355                 360                 365 att gac caa acc tgc aaa atg gta tcc atg ctg tcc att tgt gtg aac     1152
Ile Asp Gln Thr Cys Lys Met Val Ser Met Leu Ser Ile Cys Val Asn
    370                 375                 380 cca ttt ctc tac gga ttc cta aat acc aat ttt cga cac gaa ttt tcc     1200
Pro Phe Leu Tyr Gly Phe Leu Asn Thr Asn Phe Arg His Glu Phe Ser
385                 390                 395                 400 gac atc tac tac cga tac att cgc tgt gaa aca aag agt cag cca gcc     1248
Asp Ile Tyr Tyr Arg Tyr Ile Arg Cys Glu Thr Lys Ser Gln Pro Ala
                405                 410                 415 ggc cga ttc cat cat gat gta tca tca atc gct cac cat aga caa gac     1296
Gly Arg Phe His His Asp Val Ser Ser Ile Ala His His Arg Gln Asp
            420                 425                 430 tct gtt tac aat gat gag gca aca ctt ttg act aca ggg cgt cag agt     1344
Ser Val Tyr Asn Asp Glu Ala Thr Leu Leu Thr Thr Gly Arg Gln Ser
        435                 440                 445 aat ggt aaa gat ggg agc tcg tct cca ata gga ttc cgc tct agc gtc     1392
Asn Gly Lys Asp Gly Ser Ser Ser Pro Ile Gly Phe Arg Ser Ser Val
    450                 455                 460 cgt gtt tgc tcg ggt caa aca aaa atg att gga gat cgc att gta ttg     1440
Arg Val Cys Ser Gly Gln Thr Lys Met Ile Gly Asp Arg Ile Val Leu
465                 470                 475                 480 gac gat gat atc gag aaa gat agt ttt gtc taa                         1473
Asp Asp Asp Ile Glu Lys Asp Ser Phe Val
                485                 490

<210> SEQ ID NO 30
<211> LENGTH: 490
<212> TYPE: PRT
<213> ORGANISM: Homo sapiens

<400> SEQUENCE: 30

Met Glu Val Lys Asp Ile Asp Asn Tyr Cys Asp Arg Gly Ile Ser Pro
1               5                   10                  15

Asn Ala Ser Asn Tyr Leu Thr Tyr Pro Phe Asp Gly Leu Cys Leu Gln
            20                  25                  30

Lys Phe Phe Tyr Gln Leu Gln Thr Ser Leu Arg Arg Phe Thr Pro Tyr
        35                  40                  45

Glu Glu Ile Ile Tyr Thr Thr Val Tyr Ile Ile Ser Val Ala Ala
    50                  55                  60

Val Ile Gly Asn Gly Leu Val Ile Met Ala Val Arg Lys Lys Thr
65                  70                  75                  80

Met Arg Thr Asn Arg Asn Val Leu Ile Leu Asn Leu Ala Leu Ser Asn
                85                  90                  95

Leu Ile Leu Ala Ile Thr Asn Ile Pro Phe Leu Trp Leu Pro Ser Ile
            100                 105                 110

Asp Phe Glu Phe Pro Tyr Ser Arg Phe Phe Cys Lys Phe Ala Asn Val
        115                 120                 125
```

```
Leu Pro Gly Ser Asn Ile Tyr Cys Ser Thr Leu Thr Ile Ser Val Met
    130                 135                 140

Ala Ile Asp Arg Tyr Tyr Ser Val Lys Leu Lys Ile Ala Ser Asn
145                 150                 155                 160

Arg Lys Gln Cys Phe His Ala Val Leu Val Ser Leu Ala Ile Trp Ile
                165                 170                 175

Val Ser Phe Ile Leu Ser Leu Pro Leu Leu Tyr Tyr Glu Thr Ser
                180                 185                 190

Met Leu Tyr Val Met Arg Glu Ile Arg Val Val Asp Gln Ser Gly Gln
        195                 200                 205

Glu Val Ile Arg Ser Tyr Gly Trp Arg Gln Cys Arg Leu Val Ser Ala
    210                 215                 220

Gly Arg Leu Pro Asp Ile Thr Gln Ser Ile Gln Leu Leu Met Ser Ile
225                 230                 235                 240

Leu Gln Val Ala Phe Leu Tyr Ile Val Pro Leu Phe Val Leu Ser Ile
                245                 250                 255

Phe Asn Val Lys Leu Thr Arg Phe Leu Lys Thr Asn Ala Asn Lys Met
                260                 265                 270

Ser Lys Thr Arg Ala Pro Pro Lys Arg Phe Asp Arg Ser Asp Ser His
        275                 280                 285

His Asn Ser Leu Lys Asn Asn Asn His Thr Ser Ser Leu Arg Ser
    290                 295                 300

Pro Ser Met Pro Ser Ile Arg Ser Ser Ile Thr Glu Arg Asn Lys Thr
305                 310                 315                 320

Asn Gln Arg Thr Asn Arg Thr Thr Ser Leu Leu Ile Ala Met Ala Gly
                325                 330                 335

Ser Tyr Ala Ala Leu Trp Phe Pro Phe Thr Leu Ile Thr Phe Leu Ile
                340                 345                 350

Asp Phe Glu Leu Ile Ile Asn Gln Asp Tyr Val Asn Leu Val Glu Arg
        355                 360                 365

Ile Asp Gln Thr Cys Lys Met Val Ser Met Leu Ser Ile Cys Val Asn
    370                 375                 380

Pro Phe Leu Tyr Gly Phe Leu Asn Thr Asn Phe Arg His Glu Phe Ser
385                 390                 395                 400

Asp Ile Tyr Tyr Arg Tyr Ile Arg Cys Glu Thr Lys Ser Gln Pro Ala
                405                 410                 415

Gly Arg Phe His His Asp Val Ser Ser Ile Ala His His Arg Gln Asp
                420                 425                 430

Ser Val Tyr Asn Asp Glu Ala Thr Leu Leu Thr Thr Gly Arg Gln Ser
        435                 440                 445

Asn Gly Lys Asp Gly Ser Ser Ser Pro Ile Gly Phe Arg Ser Ser Val
    450                 455                 460

Arg Val Cys Ser Gly Gln Thr Lys Met Ile Gly Asp Arg Ile Val Leu
465                 470                 475                 480

Asp Asp Asp Ile Glu Lys Asp Ser Phe Val
                485                 490

<210> SEQ ID NO 31
<211> LENGTH: 1130
<212> TYPE: DNA
<213> ORGANISM: Homo sapiens
<220> FEATURE:
<223> OTHER INFORMATION: CeGPCR11 (F35G8.1)
<220> FEATURE:
<221> NAME/KEY: CDS
```

<222> LOCATION: (1)..(1128)

<400> SEQUENCE: 31

| | | | | | | | | | | | | | | | | |
|---|---|---|---|---|---|---|---|---|---|---|---|---|---|---|---|---|
| atg | aat | atc | gac | tcg | aat | tta | aca | gat | ttt | caa | tgc | gag | tac | ccg | gcg | 48 |
| Met | Asn | Ile | Asp | Ser | Asn | Leu | Thr | Asp | Phe | Gln | Cys | Glu | Tyr | Pro | Ala | |
| 1 | | | | 5 | | | | | 10 | | | | | 15 | | |
| att | gac | ata | gga | att | cat | atg | aaa | acc | ttg | tta | gca | gtc | ggg | tat | ggt | 96 |
| Ile | Asp | Ile | Gly | Ile | His | Met | Lys | Thr | Leu | Leu | Ala | Val | Gly | Tyr | Gly | |
| | | | 20 | | | | | 25 | | | | | 30 | | | |
| ttg | gtg | gga | gcc | ctg | agc | tta | gtt | gga | aat | ctt | gct | gta | ttg | ctc | att | 144 |
| Leu | Val | Gly | Ala | Leu | Ser | Leu | Val | Gly | Asn | Leu | Ala | Val | Leu | Leu | Ile | |
| | | 35 | | | | | 40 | | | | | 45 | | | | |
| gtg | ata | tgc | agg | aga | gaa | atg | caa | aca | gtc | acc | aac | att | ttt | ata | agt | 192 |
| Val | Ile | Cys | Arg | Arg | Glu | Met | Gln | Thr | Val | Thr | Asn | Ile | Phe | Ile | Ser | |
| 50 | | | | | 55 | | | | | 60 | | | | | | |
| agc | gtc | tcc | gcg | gct | gac | ttg | gta | ata | aca | agt | ttc | tcc | tta | tgg | gcg | 240 |
| Ser | Val | Ser | Ala | Ala | Asp | Leu | Val | Ile | Thr | Ser | Phe | Ser | Leu | Trp | Ala | |
| 65 | | | | 70 | | | | | 75 | | | | | 80 | | |
| acc | cca | tta | gcc | tat | tat | caa | cgg | gta | tgg | cat | ttc | gga | aag | tat | atg | 288 |
| Thr | Pro | Leu | Ala | Tyr | Tyr | Gln | Arg | Val | Trp | His | Phe | Gly | Lys | Tyr | Met | |
| | | | | 85 | | | | | 90 | | | | | 95 | | |
| tgc | tat | atg | gtt | tcc | atc | ata | caa | ggc | tta | tcc | ctc | atg | tgg | gta | cca | 336 |
| Cys | Tyr | Met | Val | Ser | Ile | Ile | Gln | Gly | Leu | Ser | Leu | Met | Trp | Val | Pro | |
| | | | 100 | | | | | 105 | | | | | 110 | | | |
| ctg | acc | cta | gca | gca | gtt | gca | tta | gat | cgc | tac | tct | cta | gtt | gct | tct | 384 |
| Leu | Thr | Leu | Ala | Ala | Val | Ala | Leu | Asp | Arg | Tyr | Ser | Leu | Val | Ala | Ser | |
| | | 115 | | | | | 120 | | | | | 125 | | | | |
| ccg | ttc | cgt | cag | cca | atg | tct | aaa | aag | act | tgc | ttg | ctg | atc | atc | gct | 432 |
| Pro | Phe | Arg | Gln | Pro | Met | Ser | Lys | Lys | Thr | Cys | Leu | Leu | Ile | Ile | Ala | |
| 130 | | | | | 135 | | | | | 140 | | | | | | |
| gga | atc | tgg | atg | gga | ggg | ttt | gca | gtt | ttg | tcg | cca | atg | att | cgg | atg | 480 |
| Gly | Ile | Trp | Met | Gly | Gly | Phe | Ala | Val | Leu | Ser | Pro | Met | Ile | Arg | Met | |
| 145 | | | | 150 | | | | | 155 | | | | | 160 | | |
| gta | gat | ttt | gtt | gac | agc | tat | gga | cca | tgc | cat | ttt | tgc | ctg | gaa | tcc | 528 |
| Val | Asp | Phe | Val | Asp | Ser | Tyr | Gly | Pro | Cys | His | Phe | Cys | Leu | Glu | Ser | |
| | | | | 165 | | | | | 170 | | | | | 175 | | |
| tgg | gac | cac | gac | aaa | caa | cac | tac | cga | ctt | ttc | tac | gga | ctc | tcg | gtg | 576 |
| Trp | Asp | His | Asp | Lys | Gln | His | Tyr | Arg | Leu | Phe | Tyr | Gly | Leu | Ser | Val | |
| | | | 180 | | | | | 185 | | | | | 190 | | | |
| ctc | gtg | atc | cgc | tcc | gca | att | cca | ctt | gtt | ctc | att | tcc | ctg | tgc | cac | 624 |
| Leu | Val | Ile | Arg | Ser | Ala | Ile | Pro | Leu | Val | Leu | Ile | Ser | Leu | Cys | His | |
| | | 195 | | | | | 200 | | | | | 205 | | | | |
| tgg | aga | atc | gca | gtt | att | ttg | aac | acg | cag | acg | gag | aaa | ttc | caa | aca | 672 |
| Trp | Arg | Ile | Ala | Val | Ile | Leu | Asn | Thr | Gln | Thr | Glu | Lys | Phe | Gln | Thr | |
| 210 | | | | | 215 | | | | | 220 | | | | | | |
| tta | cgt | agt | gcc | agc | aca | gtc | acc | caa | tcg | act | gac | atc | cgc | cgt | aaa | 720 |
| Leu | Arg | Ser | Ala | Ser | Thr | Val | Thr | Gln | Ser | Thr | Asp | Ile | Arg | Arg | Lys | |
| 225 | | | | 230 | | | | | 235 | | | | | 240 | | |
| caa | cgt | ctt | cag | act | ctc | tta | ttg | gca | atg | gtg | gtc | ata | ttt | gcc | gtg | 768 |
| Gln | Arg | Leu | Gln | Thr | Leu | Leu | Leu | Ala | Met | Val | Val | Ile | Phe | Ala | Val | |
| | | | | 245 | | | | | 250 | | | | | 255 | | |
| tcc | agt | ctc | cca | ctg | gac | ctt | tca | aat | gtt | ctt | caa | gat | ttg | atc | gta | 816 |
| Ser | Ser | Leu | Pro | Leu | Asp | Leu | Ser | Asn | Val | Leu | Gln | Asp | Leu | Ile | Val | |
| | | | 260 | | | | | 265 | | | | | 270 | | | |
| gtg | tac | cag | gtt | cga | cct | gtc | ccc | gac | aac | gtt | cgc | cat | ttt | atc | ttc | 864 |
| Val | Tyr | Gln | Val | Arg | Pro | Val | Pro | Asp | Asn | Val | Arg | His | Phe | Ile | Phe | |
| | | 275 | | | | | 280 | | | | | 285 | | | | |
| ttc | ttt | tgc | cat | tgg | acc | gca | atg | gca | gga | aca | ctt | ctc | aac | ccg | tta | 912 |
| Phe | Phe | Cys | His | Trp | Thr | Ala | Met | Ala | Gly | Thr | Leu | Leu | Asn | Pro | Leu | |
| | | | 290 | | | | | 295 | | | | | 300 | | | |

```
gtc tac gcg tac tac aac gaa aac ttc cgg cgt cag att caa aca tgc      960
Val Tyr Ala Tyr Tyr Asn Glu Asn Phe Arg Arg Gln Ile Gln Thr Cys
305                 310                 315                 320 ttt gga gaa atg cgt gga cag gga gag ttc aag cgg ggg cta tac tct     1008
Phe Gly Glu Met Arg Gly Gln Gly Glu Phe Lys Arg Gly Leu Tyr Ser
                325                 330                 335 att gtc tcc ggc aga tac tcc tac cga gca gac gac gag gaa aat cat     1056
Ile Val Ser Gly Arg Tyr Ser Tyr Arg Ala Asp Asp Glu Glu Asn His
            340                 345                 350 cac aga caa aac aca cgt atc gaa ctg gct aac aat caa act ggt gat     1104
His Arg Gln Asn Thr Arg Ile Glu Leu Ala Asn Asn Gln Thr Gly Asp
        355                 360                 365 atc gaa gtt ctc aga acg gat ctt ta                                  1130
Ile Glu Val Leu Arg Thr Asp Leu
    370                 375

<210> SEQ ID NO 32
<211> LENGTH: 376
<212> TYPE: PRT
<213> ORGANISM: Homo sapiens

<400> SEQUENCE: 32

Met Asn Ile Asp Ser Asn Leu Thr Asp Phe Gln Cys Glu Tyr Pro Ala
1               5                   10                  15

Ile Asp Ile Gly Ile His Met Lys Thr Leu Leu Ala Val Gly Tyr Gly
                20                  25                  30

Leu Val Gly Ala Leu Ser Leu Val Gly Asn Leu Ala Val Leu Leu Ile
            35                  40                  45

Val Ile Cys Arg Arg Glu Met Gln Thr Val Thr Asn Ile Phe Ile Ser
        50                  55                  60

Ser Val Ser Ala Ala Asp Leu Val Ile Thr Ser Phe Ser Leu Trp Ala
65                  70                  75                  80

Thr Pro Leu Ala Tyr Tyr Gln Arg Val Trp His Phe Gly Lys Tyr Met
                85                  90                  95

Cys Tyr Met Val Ser Ile Ile Gln Gly Leu Ser Leu Met Trp Val Pro
                100                 105                 110

Leu Thr Leu Ala Ala Val Ala Leu Asp Arg Tyr Ser Leu Val Ala Ser
            115                 120                 125

Pro Phe Arg Gln Pro Met Ser Lys Lys Thr Cys Leu Leu Ile Ile Ala
130                 135                 140

Gly Ile Trp Met Gly Gly Phe Ala Val Leu Ser Pro Met Ile Arg Met
145                 150                 155                 160

Val Asp Phe Val Asp Ser Tyr Gly Pro Cys His Phe Cys Leu Glu Ser
                165                 170                 175

Trp Asp His Asp Lys Gln His Tyr Arg Leu Phe Tyr Gly Leu Ser Val
            180                 185                 190

Leu Val Ile Arg Ser Ala Ile Pro Leu Val Leu Ile Ser Leu Cys His
        195                 200                 205

Trp Arg Ile Ala Val Ile Leu Asn Thr Gln Thr Glu Lys Phe Gln Thr
    210                 215                 220

Leu Arg Ser Ala Ser Thr Val Thr Gln Ser Thr Asp Ile Arg Arg Lys
225                 230                 235                 240

Gln Arg Leu Gln Thr Leu Leu Leu Ala Met Val Val Ile Phe Ala Val
                245                 250                 255

Ser Ser Leu Pro Leu Asp Leu Ser Asn Val Leu Gln Asp Leu Ile Val
                260                 265                 270
```

```
            Val Tyr Gln Val Arg Pro Val Pro Asp Asn Val Arg His Phe Ile Phe
                275                 280                 285

Phe Phe Cys His Trp Thr Ala Met Ala Gly Thr Leu Leu Asn Pro Leu
                290                 295                 300

Val Tyr Ala Tyr Tyr Asn Glu Asn Phe Arg Arg Gln Ile Gln Thr Cys
            305                 310                 315                 320

Phe Gly Glu Met Arg Gly Gln Gly Glu Phe Lys Arg Gly Leu Tyr Ser
                            325                 330                 335

Ile Val Ser Gly Arg Tyr Ser Tyr Arg Ala Asp Asp Glu Glu Asn His
                            340                 345                 350

His Arg Gln Asn Thr Arg Ile Glu Leu Ala Asn Asn Gln Thr Gly Asp
                        355                 360                 365

Ile Glu Val Leu Arg Thr Asp Leu
                370                 375

<210> SEQ ID NO 33
<211> LENGTH: 1176
<212> TYPE: DNA
<213> ORGANISM: Homo sapiens
<220> FEATURE:
<221> NAME/KEY: CDS
<222> LOCATION: (1)..(1173)
<220> FEATURE:
<223> OTHER INFORMATION: Clone identifier: CEGPCR15

<400> SEQUENCE: 33 atg aca acg tgt ccc cta cca ccc agt tta gac gaa atg gat ctg cga        48
Met Thr Thr Cys Pro Leu Pro Pro Ser Leu Asp Glu Met Asp Leu Arg
  1               5                  10                  15 tta gct gcc gat aaa gtt cta aac ggt tca ctg atc aac tgt aca ttc        96
Leu Ala Ala Asp Lys Val Leu Asn Gly Ser Leu Ile Asn Cys Thr Phe
                20                  25                  30 caa tcg ttt tac gat caa atg tat caa aca cac gga gta tac ttc ata       144
Gln Ser Phe Tyr Asp Gln Met Tyr Gln Thr His Gly Val Tyr Phe Ile
            35                  40                  45 ttt gaa cca act ccg ttc gtt cat cca att gtt tca cag att ttc tat       192
Phe Glu Pro Thr Pro Phe Val His Pro Ile Val Ser Gln Ile Phe Tyr
        50                  55                  60 gga atc ctg ttc aca cta aca ata ttt ctg gcg tta atg ggc aat ttt       240
Gly Ile Leu Phe Thr Leu Thr Ile Phe Leu Ala Leu Met Gly Asn Phe
 65                  70                  75                  80 aca gtg atg tgg ata atc ctg tac cac cgt caa atg cga agc gtc aca       288
Thr Val Met Trp Ile Ile Leu Tyr His Arg Gln Met Arg Ser Val Thr
                85                  90                  95 aat tac tat ctg ttc aac ttg gca gtg gcg gat gcc tcg att tca gtg       336
Asn Tyr Tyr Leu Phe Asn Leu Ala Val Ala Asp Ala Ser Ile Ser Val
            100                 105                 110 ttc aac acg gga ttc tca tgg tct tat aat tat tat tat gtt tgg aaa       384
Phe Asn Thr Gly Phe Ser Trp Ser Tyr Asn Tyr Tyr Tyr Val Trp Lys
        115                 120                 125 ttc gga agc ttt tac tgt cga ata aac aat ttg atg gga ata act ccg       432
Phe Gly Ser Phe Tyr Cys Arg Ile Asn Asn Leu Met Gly Ile Thr Pro
    130                 135                 140 att tgt gca agt gta ttc aca atg att gtc atg agc att gaa aga tat       480
Ile Cys Ala Ser Val Phe Thr Met Ile Val Met Ser Ile Glu Arg Tyr
145                 150                 155                 160 tat gcc ata atc cat cca ttg aaa aag cgt cca gga cga cga tca act       528
Tyr Ala Ile Ile His Pro Leu Lys Lys Arg Pro Gly Arg Arg Ser Thr
                165                 170                 175
```

```
gtt acc atc atc ata atg att tgg ttc atg gca ttt ttg ttc ggg gtt    576
Val Thr Ile Ile Ile Met Ile Trp Phe Met Ala Phe Leu Phe Gly Val
        180                 185                 190 cca gca ttt ctt gcg tca aag gtt gat gtc tat tac ttc tac gat ggt    624
Pro Ala Phe Leu Ala Ser Lys Val Asp Val Tyr Tyr Phe Tyr Asp Gly
        195                 200                 205 tac aca tta tac gag aat cca ctg tgc ctt gca gac aat tat ccc ggt    672
Tyr Thr Leu Tyr Glu Asn Pro Leu Cys Leu Ala Asp Asn Tyr Pro Gly
210                 215                 220 gga aat gaa tca cta ctt gga cag gta tac aac aac gga cta ata act    720
Gly Asn Glu Ser Leu Leu Gly Gln Val Tyr Asn Asn Gly Leu Ile Thr
225                 230                 235                 240 gtt caa tac att ctt cca cta tgc att tta tca gct gct tat tat cga    768
Val Gln Tyr Ile Leu Pro Leu Cys Ile Leu Ser Ala Ala Tyr Tyr Arg
        245                 250                 255 gtt ggt gtt gag ctg aga aag gat aaa acc gtc ggt gac gtg aga cat    816
Val Gly Val Glu Leu Arg Lys Asp Lys Thr Val Gly Asp Val Arg His
        260                 265                 270 gca aaa tca gtg gcc gca aag aag aag gcg tca atc atg ttg gca gtg    864
Ala Lys Ser Val Ala Ala Lys Lys Lys Ala Ser Ile Met Leu Ala Val
        275                 280                 285 gtt gtg ttc att ttc atg att gtc tgg ttc cca tac aat gcc tac tat    912
Val Val Phe Ile Phe Met Ile Val Trp Phe Pro Tyr Asn Ala Tyr Tyr
        290                 295                 300 ctc aca ttg cat tta gtt gag cca att ggg aat aaa atg ttg agt ctg    960
Leu Thr Leu His Leu Val Glu Pro Ile Gly Asn Lys Met Leu Ser Leu
305                 310                 315                 320 tac att tat atc aac atc tat tgg ttg gga atg tcg tca act gtc ttc   1008
Tyr Ile Tyr Ile Asn Ile Tyr Trp Leu Gly Met Ser Ser Thr Val Phe
        325                 330                 335 aat cct gtc atc tat tat ttt atg aac aaa cga ttc cgt gtc gga ttc   1056
Asn Pro Val Ile Tyr Tyr Phe Met Asn Lys Arg Phe Arg Val Gly Phe
        340                 345                 350 cat cac gca ttc cgt tgg ctt cca ttc gtt cgt tcc gat aaa gat gaa   1104
His His Ala Phe Arg Trp Leu Pro Phe Val Arg Ser Asp Lys Asp Glu
        355                 360                 365 tat caa aca att ctt tca cag aca cgt cca tct ctg atg cca ccc aca   1152
Tyr Gln Thr Ile Leu Ser Gln Thr Arg Pro Ser Leu Met Pro Pro Thr
370                 375                 380 acg atg gcg cat acg gat ttc tga                                    1176
Thr Met Ala His Thr Asp Phe
385                 390

<210> SEQ ID NO 34
<211> LENGTH: 391
<212> TYPE: PRT
<213> ORGANISM: Homo sapiens

<400> SEQUENCE: 34

Met Thr Thr Cys Pro Leu Pro Ser Leu Asp Glu Met Asp Leu Arg
 1               5                  10                  15

Leu Ala Ala Asp Lys Val Leu Asn Gly Ser Leu Ile Asn Cys Thr Phe
                20                  25                  30

Gln Ser Phe Tyr Asp Gln Met Tyr Gln Thr His Gly Val Tyr Phe Ile
            35                  40                  45

Phe Glu Pro Thr Pro Phe Val His Pro Ile Val Ser Gln Ile Phe Tyr
        50                  55                  60

Gly Ile Leu Phe Thr Leu Thr Ile Phe Leu Ala Leu Met Gly Asn Phe
65                  70                  75                  80
```

```
Thr Val Met Trp Ile Ile Leu Tyr His Arg Gln Met Arg Ser Val Thr
                    85                  90                  95

Asn Tyr Tyr Leu Phe Asn Leu Ala Val Ala Asp Ala Ser Ile Ser Val
                100                 105                 110

Phe Asn Thr Gly Phe Ser Trp Ser Tyr Asn Tyr Tyr Val Trp Lys
            115                 120                 125

Phe Gly Ser Phe Tyr Cys Arg Ile Asn Asn Leu Met Gly Ile Thr Pro
            130                 135                 140

Ile Cys Ala Ser Val Phe Thr Met Ile Val Met Ser Ile Glu Arg Tyr
145                 150                 155                 160

Tyr Ala Ile Ile His Pro Leu Lys Lys Arg Pro Gly Arg Arg Ser Thr
                165                 170                 175

Val Thr Ile Ile Ile Met Ile Trp Phe Met Ala Phe Leu Phe Gly Val
                180                 185                 190

Pro Ala Phe Leu Ala Ser Lys Val Asp Val Tyr Phe Tyr Asp Gly
            195                 200                 205

Tyr Thr Leu Tyr Glu Asn Pro Leu Cys Leu Ala Asp Asn Tyr Pro Gly
    210                 215                 220

Gly Asn Glu Ser Leu Leu Gly Gln Val Tyr Asn Asn Gly Leu Ile Thr
225                 230                 235                 240

Val Gln Tyr Ile Leu Pro Leu Cys Ile Leu Ser Ala Ala Tyr Tyr Arg
                245                 250                 255

Val Gly Val Glu Leu Arg Lys Asp Lys Thr Val Gly Asp Val Arg His
                260                 265                 270

Ala Lys Ser Val Ala Ala Lys Lys Lys Ala Ser Ile Met Leu Ala Val
            275                 280                 285

Val Val Phe Ile Phe Met Ile Val Trp Phe Pro Tyr Asn Ala Tyr Tyr
290                 295                 300

Leu Thr Leu His Leu Val Glu Pro Ile Gly Asn Lys Met Leu Ser Leu
305                 310                 315                 320

Tyr Ile Tyr Ile Asn Ile Tyr Trp Leu Gly Met Ser Ser Thr Val Phe
                325                 330                 335

Asn Pro Val Ile Tyr Tyr Phe Met Asn Lys Arg Phe Arg Val Gly Phe
                340                 345                 350

His His Ala Phe Arg Trp Leu Pro Phe Val Arg Ser Asp Lys Asp Glu
            355                 360                 365

Tyr Gln Thr Ile Leu Ser Gln Thr Arg Pro Ser Leu Met Pro Pro Thr
    370                 375                 380

Thr Met Ala His Thr Asp Phe
385                 390

<210> SEQ ID NO 35
<211> LENGTH: 1098
<212> TYPE: DNA
<213> ORGANISM: Homo sapiens
<220> FEATURE:
<221> NAME/KEY: CDS
<222> LOCATION: (1)..(1095)
<220> FEATURE:
<223> OTHER INFORMATION: Clone identifier: CEGPCR16

<400> SEQUENCE: 35 atg agt tct tcg aat cac tgc atc gac atc cgt gca tac ttg tgg cag      48
Met Ser Ser Ser Asn His Cys Ile Asp Ile Arg Ala Tyr Leu Trp Gln
  1               5                  10                  15 aca aag cat gac ctg acg ctc cac ccg att ccc atc gcg att ctt gca      96
Thr Lys His Asp Leu Thr Leu His Pro Ile Pro Ile Ala Ile Leu Ala
```

```
                    20                  25                  30
acc atc tac act ata att gtc gta gtt ggc gta acc ggc aat ttg tta    144
Thr Ile Tyr Thr Ile Ile Val Val Val Gly Val Thr Gly Asn Leu Leu
            35                  40                  45 gta gtg atg tcg gtg atg agg ttc aaa gtt ctt caa tca gtc agg aac    192
Val Val Met Ser Val Met Arg Phe Lys Val Leu Gln Ser Val Arg Asn
 50                  55                  60 atg ttc atc gta tct ttg tca gtt tct gac att ttt gtg gcg att gtt    240
Met Phe Ile Val Ser Leu Ser Val Ser Asp Ile Phe Val Ala Ile Val
 65                  70                  75                  80 agt ggt tca gta acg ccg ata acc gca ttc tct aaa gtt tgg tta ttt    288
Ser Gly Ser Val Thr Pro Ile Thr Ala Phe Ser Lys Val Trp Leu Phe
            85                  90                  95 ggt gga cca ttg tgt cat tta cta cct ttg tta cag ggt acc gcg ttg    336
Gly Gly Pro Leu Cys His Leu Leu Pro Leu Leu Gln Gly Thr Ala Leu
            100                 105                 110 agt ttt tcc acg tta acg ctc acc gca att gca att gac aga tat att    384
Ser Phe Ser Thr Leu Thr Leu Thr Ala Ile Ala Ile Asp Arg Tyr Ile
        115                 120                 125 ctc atc tgt cat ccg acg aaa gaa ccg ata cgc aaa gat caa gca ttg    432
Leu Ile Cys His Pro Thr Lys Glu Pro Ile Arg Lys Asp Gln Ala Leu
    130                 135                 140 aaa atg ata agt ttc aac agc gcc atc tca gtt ggg ctt tcg gta cca    480
Lys Met Ile Ser Phe Asn Ser Ala Ile Ser Val Gly Leu Ser Val Pro
145                 150                 155                 160 tta ttc atg aaa cag gaa ctt atg caa ttc cga aac tat tgc gga gaa    528
Leu Phe Met Lys Gln Glu Leu Met Gln Phe Arg Asn Tyr Cys Gly Glu
            165                 170                 175 tat tgc tca gaa aac tgg gga cca gat gct tat ttg aga agc gtt tat    576
Tyr Cys Ser Glu Asn Trp Gly Pro Asp Ala Tyr Leu Arg Ser Val Tyr
            180                 185                 190 gga aca gtg gtg ttc att att caa ttc gtg ttt cca ttg atc acc atc    624
Gly Thr Val Val Phe Ile Ile Gln Phe Val Phe Pro Leu Ile Thr Ile
        195                 200                 205 aca ttt tgc tat gca tct att tct atc aaa cta cga cgt ggt gtc ttt    672
Thr Phe Cys Tyr Ala Ser Ile Ser Ile Lys Leu Arg Arg Gly Val Phe
    210                 215                 220 gtg aga gga agc caa aaa gag ctg atg tct gag gca cgt cgt caa ttg    720
Val Arg Gly Ser Gln Lys Glu Leu Met Ser Glu Ala Arg Arg Gln Leu
225                 230                 235                 240 acg caa cgt cga ctt cgc aca aat cgg atg ctt att atc atg aca gtc    768
Thr Gln Arg Arg Leu Arg Thr Asn Arg Met Leu Ile Ile Met Thr Val
            245                 250                 255 aca ttc gct ctc tca tgg ctg cca tct gtt ggc ttc aac ttt ctc cgg    816
Thr Phe Ala Leu Ser Trp Leu Pro Ser Val Gly Phe Asn Phe Leu Arg
            260                 265                 270 gat tac tca gcg ctt ccc ggc att att gat tca caa gat tac cta ttc    864
Asp Tyr Ser Ala Leu Pro Gly Ile Ile Asp Ser Gln Asp Tyr Leu Phe
        275                 280                 285 gga att att ttc cat tgc att tca atg aca tcg gtg att gtg aat ccc    912
Gly Ile Ile Phe His Cys Ile Ser Met Thr Ser Val Ile Val Asn Pro
    290                 295                 300 ttc ctt tac ggt tac tgt aat gaa cac ttt cgt gct gca ttt gcg gct    960
Phe Leu Tyr Gly Tyr Cys Asn Glu His Phe Arg Ala Ala Phe Ala Ala
305                 310                 315                 320 ctt ctt gac acg gtg aag gca gct tgt gga atg aga cga gtg agt ccg   1008
Leu Leu Asp Thr Val Lys Ala Ala Cys Gly Met Arg Arg Val Ser Pro
            325                 330                 335 ggc aat cca gcg tgc tcc cag cta ctc agt act cac ttt gaa agc acc   1056
```

```
Gly Asn Pro Ala Cys Ser Gln Leu Leu Ser Thr His Phe Glu Ser Thr
            340                 345                 350 aca aga cga tcc gtg act acc acg att cca agt tca att taa              1098
Thr Arg Arg Ser Val Thr Thr Thr Ile Pro Ser Ser Ile
            355                 360                 365

<210> SEQ ID NO 36
<211> LENGTH: 365
<212> TYPE: PRT
<213> ORGANISM: Homo sapiens

<400> SEQUENCE: 36

Met Ser Ser Ser Asn His Cys Ile Asp Ile Arg Ala Tyr Leu Trp Gln
  1               5                  10                  15

Thr Lys His Asp Leu Thr Leu His Pro Ile Pro Ile Ala Ile Leu Ala
             20                  25                  30

Thr Ile Tyr Thr Ile Ile Val Val Gly Val Thr Gly Asn Leu Leu
         35                  40                  45

Val Val Met Ser Val Met Arg Phe Lys Val Leu Gln Ser Val Arg Asn
 50                  55                  60

Met Phe Ile Val Ser Leu Ser Val Ser Asp Ile Phe Val Ala Ile Val
 65                  70                  75                  80

Ser Gly Ser Val Thr Pro Ile Thr Ala Phe Ser Lys Val Trp Leu Phe
                 85                  90                  95

Gly Gly Pro Leu Cys His Leu Leu Pro Leu Leu Gln Gly Thr Ala Leu
            100                 105                 110

Ser Phe Ser Thr Leu Thr Leu Thr Ala Ile Ala Ile Asp Arg Tyr Ile
            115                 120                 125

Leu Ile Cys His Pro Thr Lys Glu Pro Ile Arg Lys Asp Gln Ala Leu
        130                 135                 140

Lys Met Ile Ser Phe Asn Ser Ala Ile Ser Val Gly Leu Ser Val Pro
145                 150                 155                 160

Leu Phe Met Lys Gln Glu Leu Met Gln Phe Arg Asn Tyr Cys Gly Glu
                165                 170                 175

Tyr Cys Ser Glu Asn Trp Gly Pro Asp Ala Tyr Leu Arg Ser Val Tyr
            180                 185                 190

Gly Thr Val Val Phe Ile Ile Gln Phe Val Phe Pro Leu Ile Thr Ile
            195                 200                 205

Thr Phe Cys Tyr Ala Ser Ile Ser Ile Lys Leu Arg Arg Gly Val Phe
        210                 215                 220

Val Arg Gly Ser Gln Lys Glu Leu Met Ser Glu Ala Arg Arg Gln Leu
225                 230                 235                 240

Thr Gln Arg Arg Leu Arg Thr Asn Arg Met Leu Ile Ile Met Thr Val
                245                 250                 255

Thr Phe Ala Leu Ser Trp Leu Pro Ser Val Gly Phe Asn Phe Leu Arg
            260                 265                 270

Asp Tyr Ser Ala Leu Pro Gly Ile Ile Asp Ser Gln Asp Tyr Leu Phe
            275                 280                 285

Gly Ile Ile Phe His Cys Ile Ser Met Thr Ser Val Ile Val Asn Pro
        290                 295                 300

Phe Leu Tyr Gly Tyr Cys Asn Glu His Phe Arg Ala Ala Phe Ala Ala
305                 310                 315                 320

Leu Leu Asp Thr Val Lys Ala Ala Cys Gly Met Arg Arg Val Ser Pro
                325                 330                 335

Gly Asn Pro Ala Cys Ser Gln Leu Leu Ser Thr His Phe Glu Ser Thr
```

-continued

```
                340              345             350
       Thr Arg Arg Ser Val Thr Thr Thr Ile Pro Ser Ser Ile
                    355             360             365
```

<210> SEQ ID NO 37
<211> LENGTH: 1176
<212> TYPE: DNA
<213> ORGANISM: Homo sapiens
<220> FEATURE:
<221> NAME/KEY: CDS
<222> LOCATION: (1)..(1173)
<220> FEATURE:
<223> OTHER INFORMATION: Clone identifier: CEGPCR17

<400> SEQUENCE: 37

```
atg caa ccg cca aac tct acg gga caa tgg aca gaa att cac tgc gat        48
Met Gln Pro Pro Asn Ser Thr Gly Gln Trp Thr Glu Ile His Cys Asp
  1               5                  10                  15 tgg ttt gca gaa atg caa aat tat cag aac agt ctc tac aaa ata aat       96
Trp Phe Ala Glu Met Gln Asn Tyr Gln Asn Ser Leu Tyr Lys Ile Asn
                 20                  25                  30 ttt gat gga tcc cca ata gtg cca atg tat ggg ttg gtg tgc tca ttc      144
Phe Asp Gly Ser Pro Ile Val Pro Met Tyr Gly Leu Val Cys Ser Phe
             35                  40                  45 gga gct ctt gcc aac ttt atc gtt ctc ctc gca ttt gtc aga act gca      192
Gly Ala Leu Ala Asn Phe Ile Val Leu Leu Ala Phe Val Arg Thr Ala
         50                  55                  60 aat ctt cga aac ttg aga aac agt ttc att gtg aat ttg gca ttt tcc      240
Asn Leu Arg Asn Leu Arg Asn Ser Phe Ile Val Asn Leu Ala Phe Ser
 65                  70                  75                  80 gat ttg att ctg tgt gtg gtc aca gcg cca gtc act ctc tat acg agt      288
Asp Leu Ile Leu Cys Val Val Thr Ala Pro Val Thr Leu Tyr Thr Ser
                 85                  90                  95 tta aat tta ttt tgg cca ttc gga gat tgg tcg tgc aag ttt ctc gct      336
Leu Asn Leu Phe Trp Pro Phe Gly Asp Trp Ser Cys Lys Phe Leu Ala
                100                 105                 110 ggt gtt caa gca gtg aac aca ttt gtt tca tca ctt act ctt gca ttc      384
Gly Val Gln Ala Val Asn Thr Phe Val Ser Ser Leu Thr Leu Ala Phe
            115                 120                 125 att gca atg gat cgt gtt ctt cta aca ctt tgt cca gtt cga tgg aga      432
Ile Ala Met Asp Arg Val Leu Leu Thr Leu Cys Pro Val Arg Trp Arg
        130                 135                 140 tta gca gca act gca cca ctt tta tgc tat ggt gtc gta tgg atc att      480
Leu Ala Ala Thr Ala Pro Leu Leu Cys Tyr Gly Val Val Trp Ile Ile
145                 150                 155                 160 tcg atc ata gtt gct ctt cca tat gca ttg gca gta agc tca aag ttg      528
Ser Ile Ile Val Ala Leu Pro Tyr Ala Leu Ala Val Ser Ser Lys Leu
                165                 170                 175 gct cca ttt gat cca tgg agt gat aga gca act ccc aaa atg cta acc      576
Ala Pro Phe Asp Pro Trp Ser Asp Arg Ala Thr Pro Lys Met Leu Thr
            180                 185                 190 tat tgc aac cgt caa gtg cca gaa ata tgt gca gag atg caa gaa gcc      624
Tyr Cys Asn Arg Gln Val Pro Glu Ile Cys Ala Glu Met Gln Glu Ala
        195                 200                 205 tgg gat aat gca att gtc tca aaa acc acg tac aca ttt gta gta ctt      672
Trp Asp Asn Ala Ile Val Ser Lys Thr Thr Tyr Thr Phe Val Val Leu
    210                 215                 220 ggt att caa tat att cta cca ctt gct gcc ttg gca tat gca tat ttc      720
Gly Ile Gln Tyr Ile Leu Pro Leu Ala Ala Leu Ala Tyr Ala Tyr Phe
225                 230                 235                 240 caa atc ggg tca aca att caa aaa cga tca aaa gta tca cgt aca gtg      768
```

-continued

```
Gln Ile Gly Ser Thr Ile Gln Lys Arg Ser Lys Val Ser Arg Thr Val
                245                 250                 255 gat aca aca aga aga atg caa atg caa aat aga aat cga aga gct ctt      816
Asp Thr Thr Arg Arg Met Gln Met Gln Asn Arg Asn Arg Arg Ala Leu
            260                 265                 270 ttg ttg ctc ttt ttg tta gta ctc aca tat gcc gtg tgt tgg gct cca      864
Leu Leu Leu Phe Leu Leu Val Leu Thr Tyr Ala Val Cys Trp Ala Pro
        275                 280                 285 atg aat att tat cat gtt ttg aat ggt ctc gag att att aac tat tca      912
Met Asn Ile Tyr His Val Leu Asn Gly Leu Glu Ile Ile Asn Tyr Ser
    290                 295                 300 caa aat atg tac atc ttc tgt cat ttg gtc gga atc tct tca acg tgt      960
Gln Asn Met Tyr Ile Phe Cys His Leu Val Gly Ile Ser Ser Thr Cys
305                 310                 315                 320 gtt aat cca ata gta tat gca ctg gtc aat gaa tca ttt aga aat gct     1008
Val Asn Pro Ile Val Tyr Ala Leu Val Asn Glu Ser Phe Arg Asn Ala
                325                 330                 335 tta caa tca atg att ctt caa ttc cgc ccg tgt tac gtc aca act acc     1056
Leu Gln Ser Met Ile Leu Gln Phe Arg Pro Cys Tyr Val Thr Thr Thr
            340                 345                 350 ggt aca gca gcc acc aac gtg tat gca tat tct gcg act tcg aag gcg     1104
Gly Thr Ala Ala Thr Asn Val Tyr Ala Tyr Ser Ala Thr Ser Lys Ala
        355                 360                 365 gaa aat gtc act ttg atg cgt gat cct ttc tca aca act cct cgt cca     1152
Glu Asn Val Thr Leu Met Arg Asp Pro Phe Ser Thr Thr Pro Arg Pro
    370                 375                 380 aat gaa cgc cca gac agt gtt tga                                     1176
Asn Glu Arg Pro Asp Ser Val
385                 390
```

<210> SEQ ID NO 38
<211> LENGTH: 391
<212> TYPE: PRT
<213> ORGANISM: Homo sapiens

<400> SEQUENCE: 38

```
Met Gln Pro Pro Asn Ser Thr Gly Gln Trp Thr Glu Ile His Cys Asp
  1               5                  10                  15

Trp Phe Ala Glu Met Gln Asn Tyr Gln Asn Ser Leu Tyr Lys Ile Asn
                 20                  25                  30

Phe Asp Gly Ser Pro Ile Val Pro Met Tyr Gly Leu Val Cys Ser Phe
             35                  40                  45

Gly Ala Leu Ala Asn Phe Ile Val Leu Ala Phe Val Arg Thr Ala
         50                  55                  60

Asn Leu Arg Asn Leu Arg Asn Ser Phe Ile Val Asn Leu Ala Phe Ser
 65                  70                  75                  80

Asp Leu Ile Leu Cys Val Val Thr Ala Pro Val Thr Leu Tyr Thr Ser
                 85                  90                  95

Leu Asn Leu Phe Trp Pro Phe Gly Asp Trp Ser Cys Lys Phe Leu Ala
            100                 105                 110

Gly Val Gln Ala Val Asn Thr Phe Val Ser Ser Leu Thr Leu Ala Phe
        115                 120                 125

Ile Ala Met Asp Arg Val Leu Leu Thr Leu Cys Pro Val Arg Trp Arg
    130                 135                 140

Leu Ala Ala Thr Ala Pro Leu Leu Cys Tyr Gly Val Val Trp Ile Ile
145                 150                 155                 160

Ser Ile Ile Val Ala Leu Pro Tyr Ala Leu Ala Val Ser Ser Lys Leu
                165                 170                 175
```

```
Ala Pro Phe Asp Pro Trp Ser Asp Arg Ala Thr Pro Lys Met Leu Thr
            180                 185                 190

Tyr Cys Asn Arg Gln Val Pro Glu Ile Cys Ala Glu Met Gln Glu Ala
            195                 200                 205

Trp Asp Asn Ala Ile Val Ser Lys Thr Thr Tyr Thr Phe Val Val Leu
            210                 215                 220

Gly Ile Gln Tyr Ile Leu Pro Leu Ala Ala Leu Ala Tyr Ala Tyr Phe
225                 230                 235                 240

Gln Ile Gly Ser Thr Ile Gln Lys Arg Ser Lys Val Ser Arg Thr Val
                245                 250                 255

Asp Thr Thr Arg Arg Met Gln Met Gln Asn Arg Asn Arg Arg Ala Leu
            260                 265                 270

Leu Leu Leu Phe Leu Leu Val Leu Thr Tyr Ala Val Cys Trp Ala Pro
            275                 280                 285

Met Asn Ile Tyr His Val Leu Asn Gly Leu Glu Ile Ile Asn Tyr Ser
            290                 295                 300

Gln Asn Met Tyr Ile Phe Cys His Leu Val Gly Ile Ser Ser Thr Cys
305                 310                 315                 320

Val Asn Pro Ile Val Tyr Ala Leu Val Asn Glu Ser Phe Arg Asn Ala
                325                 330                 335

Leu Gln Ser Met Ile Leu Gln Phe Arg Pro Cys Tyr Val Thr Thr Thr
            340                 345                 350

Gly Thr Ala Ala Thr Asn Val Tyr Ala Tyr Ser Ala Thr Ser Lys Ala
            355                 360                 365

Glu Asn Val Thr Leu Met Arg Asp Pro Phe Ser Thr Thr Pro Arg Pro
            370                 375                 380

Asn Glu Arg Pro Asp Ser Val
385                 390

<210> SEQ ID NO 39
<211> LENGTH: 1500
<212> TYPE: DNA
<213> ORGANISM: Homo sapiens
<220> FEATURE:
<221> NAME/KEY: CDS
<222> LOCATION: (1)..(1497)
<220> FEATURE:
<223> OTHER INFORMATION: Clone identifier: CEGPCR19

<400> SEQUENCE: 39 atg gag att att ctt tgt ttt ttg aac tac ctg gca cat ttt aaa gcg     48
Met Glu Ile Ile Leu Cys Phe Leu Asn Tyr Leu Ala His Phe Lys Ala
  1               5                  10                  15 ggt ttc gag att gat tta ttt aac ttc att aac ata aca att tat aag    96
Gly Phe Glu Ile Asp Leu Phe Asn Phe Ile Asn Ile Thr Ile Tyr Lys
                 20                  25                  30 aaa ttt cct ttt ttt ttt cat cga ctg aaa ttt gat aga aaa ttg gat   144
Lys Phe Pro Phe Phe Phe His Arg Leu Lys Phe Asp Arg Lys Leu Asp
             35                  40                  45 ttt atg att aat ttc cag aac acg ctt ttc gat ttt ccc att tta gaa   192
Phe Met Ile Asn Phe Gln Asn Thr Leu Phe Asp Phe Pro Ile Leu Glu
         50                  55                  60 aaa aac att ttt cga ttt tcg aat tta aaa aat tta aaa act cta aaa   240
Lys Asn Ile Phe Arg Phe Ser Asn Leu Lys Asn Leu Lys Thr Leu Lys
 65                  70                  75                  80 ttt tca acg ata ttt tta ttt tat gga ttt tat gca tgt aat ttt ctt   288
Phe Ser Thr Ile Phe Leu Phe Tyr Gly Phe Tyr Ala Cys Asn Phe Leu
                 85                  90                  95
```

-continued

```
caa aac aac ctt cga tgc atg gtt agt tcg gcg gcc acc att tcg acc      336
Gln Asn Asn Leu Arg Cys Met Val Ser Ser Ala Ala Thr Ile Ser Thr
            100                 105                 110 att tca acc aca acg act ccc tcc acc atc agc aac gtt atc aca agt      384
Ile Ser Thr Thr Thr Thr Pro Ser Thr Ile Ser Asn Val Ile Thr Ser
        115                 120                 125 cat tcg aac aat ggc tcg tgc att cag atc gct gag gcg att gcg gca      432
His Ser Asn Asn Gly Ser Cys Ile Gln Ile Ala Glu Ala Ile Ala Ala
    130                 135                 140 caa ggc atc gat gat att act gta gac ttt tac atc cga tca atc ttc      480
Gln Gly Ile Asp Asp Ile Thr Val Asp Phe Tyr Ile Arg Ser Ile Phe
145                 150                 155                 160 aca ttc ctc tac ggg ttc ctg ttt gta tta ggc att ttt gga aac ggc      528
Thr Phe Leu Tyr Gly Phe Leu Phe Val Leu Gly Ile Phe Gly Asn Gly
                165                 170                 175 ggc gta cta tgg gcg gtg gcg aga aac aag cgg ctc caa tcg gct cgc      576
Gly Val Leu Trp Ala Val Ala Arg Asn Lys Arg Leu Gln Ser Ala Arg
            180                 185                 190 aac gta ttt ctg ctc aac ttg atc ttc acc gat ttg ata ttg gtg ttc      624
Asn Val Phe Leu Leu Asn Leu Ile Phe Thr Asp Leu Ile Leu Val Phe
        195                 200                 205 aca gcg att cca gtc aca cca tgg tac gcg atg acc aaa gac tgg gca      672
Thr Ala Ile Pro Val Thr Pro Trp Tyr Ala Met Thr Lys Asp Trp Ala
    210                 215                 220 ttc ggg tca gtg atg tgc cat tta gtt cct ttg tca aat tcg tgt tcg      720
Phe Gly Ser Val Met Cys His Leu Val Pro Leu Ser Asn Ser Cys Ser
225                 230                 235                 240 gtg ttt gtg acg agt tgg agc ctc act gca atc tcc tta gat aaa ttt      768
Val Phe Val Thr Ser Trp Ser Leu Thr Ala Ile Ser Leu Asp Lys Phe
                245                 250                 255 ctg cat atc aac gat ccc acc aaa caa cca gtt tct att cgt caa gcg      816
Leu His Ile Asn Asp Pro Thr Lys Gln Pro Val Ser Ile Arg Gln Ala
            260                 265                 270 ttg gca ata aca ttt ctt atc tgg ata gtc tca aca ctg ata aat cta      864
Leu Ala Ile Thr Phe Leu Ile Trp Ile Val Ser Thr Leu Ile Asn Leu
        275                 280                 285 ccg tat ctt atg tct ttc gag cac gtc gat gga agc ttt tac gtt cag      912
Pro Tyr Leu Met Ser Phe Glu His Val Asp Gly Ser Phe Tyr Val Gln
    290                 295                 300 ccc gga gaa act cca tac tgc ggg cac ttt tgc gac gag gcg aat tgg      960
Pro Gly Glu Thr Pro Tyr Cys Gly His Phe Cys Asp Glu Ala Asn Trp
305                 310                 315                 320 cag agc gaa aat agt cga aag att tac gga act acg gtt atg ttg tta     1008
Gln Ser Glu Asn Ser Arg Lys Ile Tyr Gly Thr Thr Val Met Leu Leu
                325                 330                 335 cag ttc gtc gtg ccg atg gca gtg atc acg tat tgc tac ttc aaa atc     1056
Gln Phe Val Val Pro Met Ala Val Ile Thr Tyr Cys Tyr Phe Lys Ile
            340                 345                 350 ttg caa aaa gtg tca aaa gac atg atc atc caa aat gct caa ttc tgt     1104
Leu Gln Lys Val Ser Lys Asp Met Ile Ile Gln Asn Ala Gln Phe Cys
        355                 360                 365 caa tca ctg aca caa aag cag aga agt gat gcg acg tca cga aag aag     1152
Gln Ser Leu Thr Gln Lys Gln Arg Ser Asp Ala Thr Ser Arg Lys Lys
    370                 375                 380 aaa gtg aat tat att cta att gca atg gtt gtc aca ttt atc ggg tgt     1200
Lys Val Asn Tyr Ile Leu Ile Ala Met Val Val Thr Phe Ile Gly Cys
385                 390                 395                 400 tgg ttg cct tta aca tta ctc aat ttg gtc aaa gat ttt aaa aaa gag     1248
Trp Leu Pro Leu Thr Leu Leu Asn Leu Val Lys Asp Phe Lys Lys Glu
```

```
ccc gaa tgg cta aaa cgt cag ccg ttc ttc tgg gca ata aat gct cac      1296
Pro Glu Trp Leu Lys Arg Gln Pro Phe Phe Trp Ala Ile Asn Ala His
        420                 425                 430 gtc ata gcc atg tcc tta gtc gtc tgg aac cct ctg cta ttc ttt tgg      1344
Val Ile Ala Met Ser Leu Val Val Trp Asn Pro Leu Leu Phe Phe Trp
            435                 440                 445 ctg aca cga aaa caa aaa cgt tcc gga ctg tca aaa ata ctc aac tca      1392
Leu Thr Arg Lys Gln Lys Arg Ser Gly Leu Ser Lys Ile Leu Asn Ser
450                 455                 460 aca gag ggt tcg aaa aaa gca ggt ggt tct gga ttg cga ggg atc cag      1440
Thr Glu Gly Ser Lys Lys Ala Gly Gly Ser Gly Leu Arg Gly Ile Gln
465                 470                 475                 480 cta cac gac ctc ctc ccg acc tct act cat tcg gac aga tgt gca ggc      1488
Leu His Asp Leu Leu Pro Thr Ser Thr His Ser Asp Arg Cys Ala Gly
                485                 490                 495 aac tct ttc taa                                                      1500
Asn Ser Phe <210> SEQ ID NO 40
<211> LENGTH: 499
<212> TYPE: PRT
<213> ORGANISM: Homo sapiens

<400> SEQUENCE: 40

Met Glu Ile Ile Leu Cys Phe Leu Asn Tyr Leu Ala His Phe Lys Ala
1               5                   10                  15

Gly Phe Glu Ile Asp Leu Phe Asn Phe Ile Asn Ile Thr Ile Tyr Lys
            20                  25                  30

Lys Phe Pro Phe Phe His Arg Leu Lys Phe Asp Arg Lys Leu Asp
        35                  40                  45

Phe Met Ile Asn Phe Gln Asn Thr Leu Phe Asp Phe Pro Ile Leu Glu
    50                  55                  60

Lys Asn Ile Phe Arg Phe Ser Asn Leu Lys Asn Leu Lys Thr Leu Lys
65                  70                  75                  80

Phe Ser Thr Ile Phe Leu Phe Tyr Gly Phe Tyr Ala Cys Asn Phe Leu
                85                  90                  95

Gln Asn Asn Leu Arg Cys Met Val Ser Ala Ala Thr Ile Ser Thr
            100                 105                 110

Ile Ser Thr Thr Thr Thr Pro Ser Thr Ile Ser Asn Val Ile Thr Ser
        115                 120                 125

His Ser Asn Asn Gly Ser Cys Ile Gln Ile Ala Glu Ala Ile Ala Ala
    130                 135                 140

Gln Gly Ile Asp Asp Ile Thr Val Asp Phe Tyr Ile Arg Ser Ile Phe
145                 150                 155                 160

Thr Phe Leu Tyr Gly Phe Leu Phe Val Leu Gly Ile Phe Gly Asn Gly
                165                 170                 175

Gly Val Leu Trp Ala Val Ala Arg Asn Lys Arg Leu Gln Ser Ala Arg
            180                 185                 190

Asn Val Phe Leu Leu Asn Leu Ile Phe Thr Asp Leu Ile Leu Val Phe
        195                 200                 205

Thr Ala Ile Pro Val Thr Pro Trp Tyr Ala Met Thr Lys Asp Trp Ala
    210                 215                 220

Phe Gly Ser Val Met Cys His Leu Val Pro Leu Ser Asn Ser Cys Ser
225                 230                 235                 240

Val Phe Val Thr Ser Trp Ser Leu Thr Ala Ile Ser Leu Asp Lys Phe
```

```
                        245                 250                         255
Leu His Ile Asn Asp Pro Thr Lys Gln Pro Val Ser Ile Arg Gln Ala
                260                 265                 270

Leu Ala Ile Thr Phe Leu Ile Trp Ile Val Ser Thr Leu Ile Asn Leu
            275                 280                 285

Pro Tyr Leu Met Ser Phe Glu His Val Asp Gly Ser Phe Tyr Val Gln
        290                 295                 300

Pro Gly Glu Thr Pro Tyr Cys Gly His Phe Cys Asp Glu Ala Asn Trp
305                 310                 315                 320

Gln Ser Glu Asn Ser Arg Lys Ile Tyr Gly Thr Thr Val Met Leu Leu
                325                 330                 335

Gln Phe Val Val Pro Met Ala Val Ile Thr Tyr Cys Tyr Phe Lys Ile
            340                 345                 350

Leu Gln Lys Val Ser Lys Asp Met Ile Ile Gln Asn Ala Gln Phe Cys
        355                 360                 365

Gln Ser Leu Thr Gln Lys Gln Arg Ser Asp Ala Thr Ser Arg Lys Lys
370                 375                 380

Lys Val Asn Tyr Ile Leu Ile Ala Met Val Val Thr Phe Ile Gly Cys
385                 390                 395                 400

Trp Leu Pro Leu Thr Leu Leu Asn Leu Val Lys Asp Phe Lys Lys Glu
                405                 410                 415

Pro Glu Trp Leu Lys Arg Gln Pro Phe Phe Trp Ala Ile Asn Ala His
                420                 425                 430

Val Ile Ala Met Ser Leu Val Val Trp Asn Pro Leu Leu Phe Phe Trp
            435                 440                 445

Leu Thr Arg Lys Gln Lys Arg Ser Gly Leu Ser Lys Ile Leu Asn Ser
        450                 455                 460

Thr Glu Gly Ser Lys Lys Ala Gly Gly Ser Gly Leu Arg Gly Ile Gln
465                 470                 475                 480

Leu His Asp Leu Leu Pro Thr Ser Thr His Ser Asp Arg Cys Ala Gly
                485                 490                 495

Asn Ser Phe

<210> SEQ ID NO 41
<211> LENGTH: 1335
<212> TYPE: DNA
<213> ORGANISM: Homo sapiens
<220> FEATURE:
<221> NAME/KEY: CDS
<222> LOCATION: (1)..(1332)
<220> FEATURE:
<223> OTHER INFORMATION: Clone identifier: CEGPCR20

<400> SEQUENCE: 41 atg tcg ttg gga aat gtc atc att gcc tct tca gta aat aca cgt tca      48
Met Ser Leu Gly Asn Val Ile Ile Ala Ser Ser Val Asn Thr Arg Ser
 1               5                  10                  15 ccc ata gat tcc cac ttg ttt aga aaa att ttg tgt ttt aga att tat      96
Pro Ile Asp Ser His Leu Phe Arg Lys Ile Leu Cys Phe Arg Ile Tyr
            20                  25                  30 gac gac act atc agt ttt gag aga aaa att gga ata atc att cca aca     144
Asp Asp Thr Ile Ser Phe Glu Arg Lys Ile Gly Ile Ile Ile Pro Thr
        35                  40                  45 att ttt gcc gtt atc att ttg gtc gga ctt gtt ggt aat gct ctg gtg     192
Ile Phe Ala Val Ile Ile Leu Val Gly Leu Val Gly Asn Ala Leu Val
    50                  55                  60 gtg att gtt gct ttt gga cga caa atg aga aat tca acc aac act ctt     240
```

```
Val Ile Val Ala Phe Gly Arg Gln Met Arg Asn Ser Thr Asn Thr Leu
 65                  70                  75                  80 att att gga ctt gcc ata tct gac ttg atg ttc ctt ttg ctt tgc gtt       288
Ile Ile Gly Leu Ala Ile Ser Asp Leu Met Phe Leu Leu Leu Cys Val
                     85                  90                  95 cct ttc aca gct gtg gat tac gca gct ccg aca tgg atc ttt ccc gag       336
Pro Phe Thr Ala Val Asp Tyr Ala Ala Pro Thr Trp Ile Phe Pro Glu
            100                 105                 110 tgg aca tgc tct atg atc aat ttc ttc cag cat acg tct gca tac tgt       384
Trp Thr Cys Ser Met Ile Asn Phe Phe Gln His Thr Ser Ala Tyr Cys
        115                 120                 125 agt gtt tgg aca ttg acc ctt atg gcc ctc gat aga tat cta gca gtt       432
Ser Val Trp Thr Leu Thr Leu Met Ala Leu Asp Arg Tyr Leu Ala Val
    130                 135                 140 gta tat cca gtt gaa tca atg acg tta cga aca cca agg aac act gtg       480
Val Tyr Pro Val Glu Ser Met Thr Leu Arg Thr Pro Arg Asn Thr Val
145                 150                 155                 160 att gcg tta tgc ttc att tac atc att atc att gct tct cag att cct       528
Ile Ala Leu Cys Phe Ile Tyr Ile Ile Ile Ala Ser Gln Ile Pro
                    165                 170                 175 gtg gga cga atg cac ggg att tat gtg tat gac ttt att atg gaa aaa       576
Val Gly Arg Met His Gly Ile Tyr Val Tyr Asp Phe Ile Met Glu Lys
                180                 185                 190 cgg tca acg tgc gca att ctg aca att gcc act gca gag gct act ccg       624
Arg Ser Thr Cys Ala Ile Leu Thr Ile Ala Thr Ala Glu Ala Thr Pro
            195                 200                 205 acg atg gct cga aca tat ttt atg aca ttc aat gtg ttt ggt tac gtg       672
Thr Met Ala Arg Thr Tyr Phe Met Thr Phe Asn Val Phe Gly Tyr Val
        210                 215                 220 ctt cca ctg ggc att tct gtt gtc ctg tat ggt ctt atg ttg aga aaa       720
Leu Pro Leu Gly Ile Ser Val Val Leu Tyr Gly Leu Met Leu Arg Lys
225                 230                 235                 240 ctt tgg gac atg cca agg ccg ggt aac tct caa tct gtt ggt ggt aga       768
Leu Trp Asp Met Pro Arg Pro Gly Asn Ser Gln Ser Val Gly Gly Arg
                    245                 250                 255 aat ctt aca aat cgt gat agt ggt tca agt att cgt cgg agg ccg gaa       816
Asn Leu Thr Asn Arg Asp Ser Gly Ser Ser Ile Arg Arg Arg Pro Glu
                260                 265                 270 gca act gct gcc aaa aga aaa gtt acc cgc ctt gta ctg tgt gtt ttg       864
Ala Thr Ala Ala Lys Arg Lys Val Thr Arg Leu Val Leu Cys Val Leu
            275                 280                 285 atc acc tgg gca ctt tgc tgg ctt cca cta aac gtg tgc ttt ttc atg       912
Ile Thr Trp Ala Leu Cys Trp Leu Pro Leu Asn Val Cys Phe Phe Met
        290                 295                 300 tct ggt ctc gcc tac ccg gaa cca ctt gtt ata tct cat ggt gtc atc       960
Ser Gly Leu Ala Tyr Pro Glu Pro Leu Val Ile Ser His Gly Val Ile
305                 310                 315                 320 atg gta att gtt cag att gct agt caa gtt ctt gcc tac acc aat tcg      1008
Met Val Ile Val Gln Ile Ala Ser Gln Val Leu Ala Tyr Thr Asn Ser
                    325                 330                 335 tgt ctt aat cca att cta tac gct ttg atg tcg cag agt ttc cgg gaa      1056
Cys Leu Asn Pro Ile Leu Tyr Ala Leu Met Ser Gln Ser Phe Arg Glu
                340                 345                 350 gga ttc att cga gtc atg aaa atg cta ata aat aag cta tcg cgt gga      1104
Gly Phe Ile Arg Val Met Lys Met Leu Ile Asn Lys Leu Ser Arg Gly
            355                 360                 365 agg ttc tgc act aat tac cga cga agt gct ctt cgg aca gag ctc aca      1152
Arg Phe Cys Thr Asn Tyr Arg Arg Ser Ala Leu Arg Thr Glu Leu Thr
        370                 375                 380
```

| | | | | | | | | | | | | |
|---|---|---|---|---|---|---|---|---|---|---|---|---|
| cac | tat | aac | caa | act | cca | gca | cat | cca | gca | aac | act | gtg gtt caa gtg | 1200 |
| His | Tyr | Asn | Gln | Thr | Pro | Ala | His | Pro | Ala | Asn | Thr | Val Val Gln Val |
| 385 | | | | 390 | | | | 395 | | | | 400 |

```
cac tat aac caa act cca gca cat cca gca aac act gtg gtt caa gtg    1200
His Tyr Asn Gln Thr Pro Ala His Pro Ala Asn Thr Val Val Gln Val
385             390             395             400 tca aac gga gaa cga tcc tcg ctt ctg aaa gat aac tcg agc tct gcg    1248
Ser Asn Gly Glu Arg Ser Ser Leu Leu Lys Asp Asn Ser Ser Ser Ala
            405             410             415 acg tct gta caa cca ctt cgg acg tca att caa gcg aag aaa aca aag    1296
Thr Ser Val Gln Pro Leu Arg Thr Ser Ile Gln Ala Lys Lys Thr Lys
        420             425             430 aat gtc tgt gat acg atg ctc ttt gtg tgt ttc ttc taa                1335
Asn Val Cys Asp Thr Met Leu Phe Val Cys Phe Phe
        435             440

<210> SEQ ID NO 42
<211> LENGTH: 444
<212> TYPE: PRT
<213> ORGANISM: Homo sapiens

<400> SEQUENCE: 42

Met Ser Leu Gly Asn Val Ile Ile Ala Ser Ser Val Asn Thr Arg Ser
 1               5                  10                  15

Pro Ile Asp Ser His Leu Phe Arg Lys Ile Leu Cys Phe Arg Ile Tyr
            20                  25                  30

Asp Asp Thr Ile Ser Phe Glu Arg Lys Ile Gly Ile Ile Ile Pro Thr
        35                  40                  45

Ile Phe Ala Val Ile Leu Val Gly Leu Val Gly Asn Ala Leu Val
    50                  55                  60

Val Ile Val Ala Phe Gly Arg Gln Met Arg Asn Ser Thr Asn Thr Leu
65                  70                  75                  80

Ile Ile Gly Leu Ala Ile Ser Asp Leu Met Phe Leu Leu Leu Cys Val
                85                  90                  95

Pro Phe Thr Ala Val Asp Tyr Ala Ala Pro Thr Trp Ile Phe Pro Glu
            100                 105                 110

Trp Thr Cys Ser Met Ile Asn Phe Phe Gln His Thr Ser Ala Tyr Cys
        115                 120                 125

Ser Val Trp Thr Leu Thr Leu Met Ala Leu Asp Arg Tyr Leu Ala Val
130                 135                 140

Val Tyr Pro Val Glu Ser Met Thr Leu Arg Thr Pro Arg Asn Thr Val
145                 150                 155                 160

Ile Ala Leu Cys Phe Ile Tyr Ile Ile Ile Ala Ser Gln Ile Pro
                165                 170                 175

Val Gly Arg Met His Gly Ile Tyr Val Tyr Asp Phe Ile Met Glu Lys
            180                 185                 190

Arg Ser Thr Cys Ala Ile Leu Thr Ile Ala Thr Ala Glu Ala Thr Pro
        195                 200                 205

Thr Met Ala Arg Thr Tyr Phe Met Thr Phe Asn Val Phe Gly Tyr Val
    210                 215                 220

Leu Pro Leu Gly Ile Ser Val Val Leu Tyr Gly Leu Met Leu Arg Lys
225                 230                 235                 240

Leu Trp Asp Met Pro Arg Pro Gly Asn Ser Gln Ser Val Gly Arg
                245                 250                 255

Asn Leu Thr Asn Arg Asp Ser Gly Ser Ser Ile Arg Arg Pro Glu
            260                 265                 270

Ala Thr Ala Ala Lys Arg Lys Val Thr Arg Leu Val Leu Cys Val Leu
        275                 280                 285

Ile Thr Trp Ala Leu Cys Trp Leu Pro Leu Asn Val Cys Phe Phe Met
```

```
                        290                 295                 300
Ser Gly Leu Ala Tyr Pro Glu Pro Leu Val Ile Ser His Gly Val Ile
305                 310                 315                 320

Met Val Ile Val Gln Ile Ala Ser Gln Val Leu Ala Tyr Thr Asn Ser
                    325                 330                 335

Cys Leu Asn Pro Ile Leu Tyr Ala Leu Met Ser Gln Ser Phe Arg Glu
                340                 345                 350

Gly Phe Ile Arg Val Met Lys Met Leu Ile Asn Lys Leu Ser Arg Gly
                355                 360                 365

Arg Phe Cys Thr Asn Tyr Arg Arg Ser Ala Leu Arg Thr Glu Leu Thr
        370                 375                 380

His Tyr Asn Gln Thr Pro Ala His Pro Ala Asn Thr Val Val Gln Val
385                 390                 395                 400

Ser Asn Gly Glu Arg Ser Ser Leu Leu Lys Asp Asn Ser Ser Ser Ala
                405                 410                 415

Thr Ser Val Gln Pro Leu Arg Thr Ser Ile Gln Ala Lys Lys Thr Lys
                420                 425                 430

Asn Val Cys Asp Thr Met Leu Phe Val Cys Phe Phe
                435                 440

<210> SEQ ID NO 43
<211> LENGTH: 1131
<212> TYPE: DNA
<213> ORGANISM: Homo sapiens
<220> FEATURE:
<221> NAME/KEY: CDS
<222> LOCATION: (1)..(1128)
<220> FEATURE:
<223> OTHER INFORMATION: Clone identifier: CEGPCR3

<400> SEQUENCE: 43 atg gag ggt ggt cga aac tgt gta atg aca gta caa cag tgg caa cct     48
Met Glu Gly Gly Arg Asn Cys Val Met Thr Val Gln Gln Trp Gln Pro
 1               5                  10                  15 gaa tac aat gat atg aac cag ata aga gca ata ttc tcg tta ctg tac     96
Glu Tyr Asn Asp Met Asn Gln Ile Arg Ala Ile Phe Ser Leu Leu Tyr
                20                  25                  30 ctt ctt gtt tgg gtt gga gct att gtt ggc aac act cta gta ctt tat    144
Leu Leu Val Trp Val Gly Ala Ile Val Gly Asn Thr Leu Val Leu Tyr
            35                  40                  45 gta ctc act ttt aat cag gta tca ctg tca gtt agg acg gta ttt gtt    192
Val Leu Thr Phe Asn Gln Val Ser Leu Ser Val Arg Thr Val Phe Val
        50                  55                  60 gga tgt cta gct ggt tca gac ctt cta atg tgc ctt ttc tcg ttg cca    240
Gly Cys Leu Ala Gly Ser Asp Leu Leu Met Cys Leu Phe Ser Leu Pro
65                  70                  75                  80 att acc gcg att tct ata ttt tca aga gtt tgg gta ttt cct gct ata    288
Ile Thr Ala Ile Ser Ile Phe Ser Arg Val Trp Val Phe Pro Ala Ile
                85                  90                  95 ttt tgc aag ttg atc gga gtt ttc cag ggc ggt acg att ttt gtc tca    336
Phe Cys Lys Leu Ile Gly Val Phe Gln Gly Gly Thr Ile Phe Val Ser
                100                 105                 110 tca ttc aca tta aca gtt att gct ctg gac aga tgt gta cta att cta    384
Ser Phe Thr Leu Thr Val Ile Ala Leu Asp Arg Cys Val Leu Ile Leu
            115                 120                 125 cgt cca aat cag gag ata gta aat ttc ccg aga gct gtc ttc att gtt    432
Arg Pro Asn Gln Glu Ile Val Asn Phe Pro Arg Ala Val Phe Ile Val
        130                 135                 140 ttc tgc att tgg ctt ctc gga tac tct cta gca ctt cct gta ggc atc    480
```

-continued

```
Phe Cys Ile Trp Leu Leu Gly Tyr Ser Leu Ala Leu Pro Val Gly Ile
145                 150                 155                 160 tac agc gac att gca gta tac gac gaa att tgc ggc aca ttc tgt gaa      528
Tyr Ser Asp Ile Ala Val Tyr Asp Glu Ile Cys Gly Thr Phe Cys Glu
                165                 170                 175 gag aat tgg cct gat ttc aat ccg gat act gga aga tcg gga att cga      576
Glu Asn Trp Pro Asp Phe Asn Pro Asp Thr Gly Arg Ser Gly Ile Arg
            180                 185                 190 aga gct tat gga ctt tct gtg ttg gta ctt caa ttt ggt att cct gca      624
Arg Ala Tyr Gly Leu Ser Val Leu Val Leu Gln Phe Gly Ile Pro Ala
        195                 200                 205 ttg ata agt tca att tgt tac tgg atg att agt cga gtg atg tca gat      672
Leu Ile Ser Ser Ile Cys Tyr Trp Met Ile Ser Arg Val Met Ser Asp
    210                 215                 220 caa tta gca aga aga aga ggg cac aat att cga ccg gaa tct gaa aca      720
Gln Leu Ala Arg Arg Arg Gly His Asn Ile Arg Pro Glu Ser Glu Thr
225                 230                 235                 240 aag ctg gtg aat cga aag aca aga gct aat cga atg atg atc gta atg      768
Lys Leu Val Asn Arg Lys Thr Arg Ala Asn Arg Met Met Ile Val Met
                245                 250                 255 gtt gtt gga ttc gtt ctc gcg tgg atg cca ttc aat gca gtc aat ctc      816
Val Val Gly Phe Val Leu Ala Trp Met Pro Phe Asn Ala Val Asn Leu
            260                 265                 270 tac cgt gac cta ttt gga att tct aaa tgg tat tct aca gtc ttt gcg      864
Tyr Arg Asp Leu Phe Gly Ile Ser Lys Trp Tyr Ser Thr Val Phe Ala
        275                 280                 285 ctt tgc cac gta tgc gca atg tgc tcc gct gtg ctc aac cca atc atc      912
Leu Cys His Val Cys Ala Met Cys Ser Ala Val Leu Asn Pro Ile Ile
    290                 295                 300 tat tcc tgg ttc aat cct caa ttc cga caa agt atc acc act ttg ttc      960
Tyr Ser Trp Phe Asn Pro Gln Phe Arg Gln Ser Ile Thr Thr Leu Phe
305                 310                 315                 320 aag ggt act gat gaa gct aga ttg atc aag aag aaa cca caa tct acc     1008
Lys Gly Thr Asp Glu Ala Arg Leu Ile Lys Lys Lys Pro Gln Ser Thr
                325                 330                 335 agt aaa atg gtt tcg tat ccg act aat ttc tcc gag atc cga aaa gaa     1056
Ser Lys Met Val Ser Tyr Pro Thr Asn Phe Ser Glu Ile Arg Lys Glu
            340                 345                 350 aca gaa att gca tcg aca aag aca aaa atc aca att gct gaa aac gac     1104
Thr Glu Ile Ala Ser Thr Lys Thr Lys Ile Thr Ile Ala Glu Asn Asp
        355                 360                 365 tat cga gct gga gat caa ctt tta taa                                 1131
Tyr Arg Ala Gly Asp Gln Leu Leu
    370                 375
```

<210> SEQ ID NO 44
<211> LENGTH: 376
<212> TYPE: PRT
<213> ORGANISM: Homo sapiens

<400> SEQUENCE: 44

```
Met Glu Gly Gly Arg Asn Cys Val Met Thr Val Gln Gln Trp Gln Pro
1               5                   10                  15

Glu Tyr Asn Asp Met Asn Gln Ile Arg Ala Ile Phe Ser Leu Leu Tyr
                20                  25                  30

Leu Leu Val Trp Val Gly Ala Ile Val Gly Asn Thr Leu Val Leu Tyr
            35                  40                  45

Val Leu Thr Phe Asn Gln Val Ser Leu Ser Val Arg Thr Val Phe Val
        50                  55                  60
```

```
Gly Cys Leu Ala Gly Ser Asp Leu Leu Met Cys Leu Phe Ser Leu Pro
 65                  70                  75                  80

Ile Thr Ala Ile Ser Ile Phe Ser Arg Val Trp Val Phe Pro Ala Ile
                 85                  90                  95

Phe Cys Lys Leu Ile Gly Val Phe Gln Gly Gly Thr Ile Phe Val Ser
            100                 105                 110

Ser Phe Thr Leu Thr Val Ile Ala Leu Asp Arg Cys Val Leu Ile Leu
        115                 120                 125

Arg Pro Asn Gln Glu Ile Val Asn Phe Pro Arg Ala Val Phe Ile Val
130                 135                 140

Phe Cys Ile Trp Leu Leu Gly Tyr Ser Leu Ala Leu Pro Val Gly Ile
145                 150                 155                 160

Tyr Ser Asp Ile Ala Val Tyr Asp Glu Ile Cys Gly Thr Phe Cys Glu
                165                 170                 175

Glu Asn Trp Pro Asp Phe Asn Pro Asp Thr Gly Arg Ser Gly Ile Arg
            180                 185                 190

Arg Ala Tyr Gly Leu Ser Val Leu Val Leu Gln Phe Gly Ile Pro Ala
        195                 200                 205

Leu Ile Ser Ser Ile Cys Tyr Trp Met Ile Ser Arg Val Met Ser Asp
210                 215                 220

Gln Leu Ala Arg Arg Gly His Asn Ile Arg Pro Glu Ser Glu Thr
225                 230                 235                 240

Lys Leu Val Asn Arg Lys Thr Arg Ala Asn Arg Met Met Ile Val Met
                245                 250                 255

Val Val Gly Phe Val Leu Ala Trp Met Pro Phe Asn Ala Val Asn Leu
            260                 265                 270

Tyr Arg Asp Leu Phe Gly Ile Ser Lys Trp Tyr Ser Thr Val Phe Ala
        275                 280                 285

Leu Cys His Val Cys Ala Met Cys Ser Ala Val Leu Asn Pro Ile Ile
290                 295                 300

Tyr Ser Trp Phe Asn Pro Gln Phe Arg Gln Ser Ile Thr Thr Leu Phe
305                 310                 315                 320

Lys Gly Thr Asp Glu Ala Arg Leu Ile Lys Lys Pro Gln Ser Thr
                325                 330                 335

Ser Lys Met Val Ser Tyr Pro Thr Asn Phe Ser Glu Ile Arg Lys Glu
            340                 345                 350

Thr Glu Ile Ala Ser Thr Lys Thr Lys Ile Thr Ile Ala Glu Asn Asp
        355                 360                 365

Tyr Arg Ala Gly Asp Gln Leu Leu
370                 375

<210> SEQ ID NO 45
<211> LENGTH: 1209
<212> TYPE: DNA
<213> ORGANISM: Homo sapiens
<220> FEATURE:
<221> NAME/KEY: CDS
<222> LOCATION: (1)..(1209)
<220> FEATURE:
<223> OTHER INFORMATION: Clone identifier: CEGPCR5

<400> SEQUENCE: 45 atg gga tcg gtg aat gaa tca tgt gac aat tat gta gaa att ttc aac        48
Met Gly Ser Val Asn Glu Ser Cys Asp Asn Tyr Val Glu Ile Phe Asn
 1               5                  10                  15 aaa atc aac tac ttt ttt cga gat gat cag gtt atc aat ggg act gag       96
Lys Ile Asn Tyr Phe Phe Arg Asp Asp Gln Val Ile Asn Gly Thr Glu
```

-continued

```
                  20                      25                      30
tat tca cca aaa gag ttc gga tat ttc atc aca ttc gca tac atg ctg    144
Tyr Ser Pro Lys Glu Phe Gly Tyr Phe Ile Thr Phe Ala Tyr Met Leu
             35                      40                      45 atc att ttg ttt gga gca ata ggc aac ttt ttg aca atc atc gta gtc    192
Ile Ile Leu Phe Gly Ala Ile Gly Asn Phe Leu Thr Ile Ile Val Val
     50                      55                      60 ata ctc aac cca gca atg cgg aca aca agg aac ttt ttc att tta aac    240
Ile Leu Asn Pro Ala Met Arg Thr Thr Arg Asn Phe Phe Ile Leu Asn
65                      70                      75                      80 ttg gcg ctg tcg gac ttt ttt gtt tgt att gtg aca gcg ccg acc aca    288
Leu Ala Leu Ser Asp Phe Phe Val Cys Ile Val Thr Ala Pro Thr Thr
                     85                      90                      95 tta tac acg gtt ctc tac atg ttc tgg cca ttt agc agg aca tta tgc    336
Leu Tyr Thr Val Leu Tyr Met Phe Trp Pro Phe Ser Arg Thr Leu Cys
             100                     105                     110 aaa att gcg ggt tcg ctg caa ggc ttt aac ata ttt tta tcc aca ttc    384
Lys Ile Ala Gly Ser Leu Gln Gly Phe Asn Ile Phe Leu Ser Thr Phe
     115                     120                     125 tcg ata gcc tca att gct gtt gat aga tac gtg ctc att atc ttc cca    432
Ser Ile Ala Ser Ile Ala Val Asp Arg Tyr Val Leu Ile Ile Phe Pro
130                     135                     140 acg aag cga gaa cga caa caa aat ctg tcg ttc tgc ttt ttt atc atg    480
Thr Lys Arg Glu Arg Gln Gln Asn Leu Ser Phe Cys Phe Phe Ile Met
145                     150                     155                     160 atc tgg gtg att tcc cta atc ctt gcg gtt cca ctt ctg cag gct tct    528
Ile Trp Val Ile Ser Leu Ile Leu Ala Val Pro Leu Leu Gln Ala Ser
                     165                     170                     175 gat ttg aca ccg gtt ttc gtt gag cca tcg tgc gat ttg gct ctt tac    576
Asp Leu Thr Pro Val Phe Val Glu Pro Ser Cys Asp Leu Ala Leu Tyr
             180                     185                     190 att tgc cat gag caa aat gag ata tgg gaa aag atg atc ata tca aaa    624
Ile Cys His Glu Gln Asn Glu Ile Trp Glu Lys Met Ile Ile Ser Lys
     195                     200                     205 ggc acc tac acg ttg gca gtt ctt atc acc caa tac gca ttt ccc ctg    672
Gly Thr Tyr Thr Leu Ala Val Leu Ile Thr Gln Tyr Ala Phe Pro Leu
210                     215                     220 ttt tca cta gtc ttc gcc tac tcc cgg ata gca cat cgg atg aag ctg    720
Phe Ser Leu Val Phe Ala Tyr Ser Arg Ile Ala His Arg Met Lys Leu
225                     230                     235                     240 aga ttt gca aac cga aat cag aat gtg aca aca aat acc aat acg agt    768
Arg Phe Ala Asn Arg Asn Gln Asn Val Thr Thr Asn Thr Asn Thr Ser
                     245                     250                     255 cag agg aga cga tcc gtc gtg gaa cgt caa cga cgc acc cac ctc ctt    816
Gln Arg Arg Arg Ser Val Val Glu Arg Gln Arg Arg Thr His Leu Leu
             260                     265                     270 ctt gta tgc gtt gta gct gta ttc gcc gtc gcc tgg ctg cca ctc aac    864
Leu Val Cys Val Val Ala Val Phe Ala Val Ala Trp Leu Pro Leu Asn
     275                     280                     285 gtt ttt cat atc ttc aac aca ttc gag ctg gtc aac agt ttt tcc gtt    912
Val Phe His Ile Phe Asn Thr Phe Glu Leu Val Asn Ser Phe Ser Val
290                     295                     300 aca acg ttc agc atc tgt cac tgc ttg gca atg tgc tcg gcg tgc ttg    960
Thr Thr Phe Ser Ile Cys His Cys Leu Ala Met Cys Ser Ala Cys Leu
305                     310                     315                     320 aat ccg ctg atc tat gca ttt ttc aat cat aac ttc cgg atc gaa ttt   1008
Asn Pro Leu Ile Tyr Ala Phe Phe Asn His Asn Phe Arg Ile Glu Phe
                     325                     330                     335 atg cat ctt ttc gat aga gtt ggg ttg aga tcc ctt cga gtc gtg ata   1056
```

```
Met His Leu Phe Asp Arg Val Gly Leu Arg Ser Leu Arg Val Val Ile
            340                 345                 350 ttt gga gag caa gag tcg ctc aag aaa agt atg cgc act gaa ttc aga    1104
Phe Gly Glu Gln Glu Ser Leu Lys Lys Ser Met Arg Thr Glu Phe Arg
            355                 360                 365 agc cgt gga ggc tgt aag acg gta act act gca gag cca gca acc ttc    1152
Ser Arg Gly Gly Cys Lys Thr Val Thr Thr Ala Glu Pro Ala Thr Phe
    370                 375                 380 cag aga atg aat gaa agt atg att ctg agt gcg atg gag caa gat gag    1200
Gln Arg Met Asn Glu Ser Met Ile Leu Ser Ala Met Glu Gln Asp Glu
385                 390                 395                 400 cag ctg tga                                                         1209
Gln Leu
```

<210> SEQ ID NO 46
<211> LENGTH: 402
<212> TYPE: PRT
<213> ORGANISM: Homo sapiens

<400> SEQUENCE: 46

```
Met Gly Ser Val Asn Glu Ser Cys Asp Asn Tyr Val Glu Ile Phe Asn
  1               5                  10                  15

Lys Ile Asn Tyr Phe Phe Arg Asp Asp Gln Val Ile Asn Gly Thr Glu
                 20                  25                  30

Tyr Ser Pro Lys Glu Phe Gly Tyr Phe Ile Thr Phe Ala Tyr Met Leu
             35                  40                  45

Ile Ile Leu Phe Gly Ala Ile Gly Asn Phe Leu Thr Ile Val Val
         50                  55                  60

Ile Leu Asn Pro Ala Met Arg Thr Thr Arg Asn Phe Phe Ile Leu Asn
 65                  70                  75                  80

Leu Ala Leu Ser Asp Phe Phe Val Cys Ile Val Thr Ala Pro Thr Thr
                 85                  90                  95

Leu Tyr Thr Val Leu Tyr Met Phe Trp Pro Phe Ser Arg Thr Leu Cys
                100                 105                 110

Lys Ile Ala Gly Ser Leu Gln Gly Phe Asn Ile Phe Leu Ser Thr Phe
            115                 120                 125

Ser Ile Ala Ser Ile Ala Val Asp Arg Tyr Val Leu Ile Ile Phe Pro
        130                 135                 140

Thr Lys Arg Glu Arg Gln Gln Asn Leu Ser Phe Cys Phe Phe Ile Met
145                 150                 155                 160

Ile Trp Val Ile Ser Leu Ile Leu Ala Val Pro Leu Leu Gln Ala Ser
                165                 170                 175

Asp Leu Thr Pro Val Phe Val Glu Pro Ser Cys Asp Leu Ala Leu Tyr
            180                 185                 190

Ile Cys His Glu Gln Asn Glu Ile Trp Glu Lys Met Ile Ile Ser Lys
        195                 200                 205

Gly Thr Tyr Thr Leu Ala Val Leu Ile Thr Gln Tyr Ala Phe Pro Leu
    210                 215                 220

Phe Ser Leu Val Phe Ala Tyr Ser Arg Ile Ala His Arg Met Lys Leu
225                 230                 235                 240

Arg Phe Ala Asn Arg Asn Gln Asn Val Thr Thr Asn Thr Asn Thr Ser
                245                 250                 255

Gln Arg Arg Arg Ser Val Val Glu Arg Gln Arg Thr His Leu Leu
            260                 265                 270

Leu Val Cys Val Val Ala Val Phe Ala Val Ala Trp Leu Pro Leu Asn
        275                 280                 285
```

```
Val Phe His Ile Phe Asn Thr Phe Glu Leu Val Asn Ser Phe Ser Val
    290                 295                 300

Thr Thr Phe Ser Ile Cys His Cys Leu Ala Met Cys Ser Ala Cys Leu
305                 310                 315                 320

Asn Pro Leu Ile Tyr Ala Phe Phe Asn His Asn Phe Arg Ile Glu Phe
                325                 330                 335

Met His Leu Phe Asp Arg Val Gly Leu Arg Ser Leu Arg Val Val Ile
            340                 345                 350

Phe Gly Glu Gln Glu Ser Leu Lys Lys Ser Met Arg Thr Glu Phe Arg
        355                 360                 365

Ser Arg Gly Gly Cys Lys Thr Val Thr Thr Ala Glu Pro Ala Thr Phe
    370                 375                 380

Gln Arg Met Asn Glu Ser Met Ile Leu Ser Ala Met Glu Gln Asp Glu
385                 390                 395                 400

Gln Leu

<210> SEQ ID NO 47
<211> LENGTH: 31
<212> TYPE: DNA
<213> ORGANISM: Homo sapiens
<220> FEATURE:
<223> OTHER INFORMATION: Description of Artificial Sequence: PCR primer
<220> FEATURE:
<223> OTHER INFORMATION: AC7.1_F

<400> SEQUENCE: 47
gccgccatgc tgtatgcaat tatagccttc a                              31

<210> SEQ ID NO 48
<211> LENGTH: 31
<212> TYPE: DNA
<213> ORGANISM: Homo sapiens
<220> FEATURE:
<223> OTHER INFORMATION: Description of Artificial Sequence: PCR primer
<220> FEATURE:
<223> OTHER INFORMATION: AC7.1_R

<400> SEQUENCE: 48
tctagatcag ggagaaagat tatttgtaga a                              31

<210> SEQ ID NO 49
<211> LENGTH: 31
<212> TYPE: DNA
<213> ORGANISM: Homo sapiens
<220> FEATURE:
<223> OTHER INFORMATION: Description of Artificial Sequence: PCR primer
<220> FEATURE:
<223> OTHER INFORMATION: C09B7.1_F

<400> SEQUENCE: 49
gccgccatgg cccgtgcagt caacatatct c                              31

<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: C09B7.1_R

<400> SEQUENCE: 50
tctagattat gaataggtga aagtgttgaa t                              31
```

<210> SEQ ID NO 51
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: C10C6.2_F

<400> SEQUENCE: 51
gccgccatgg agggtggtcg aaactgtgta a                            31

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: C10C6.2_R

<400> SEQUENCE: 52
tctagattat aaaagttgat ctccagctcg a                            31

<210> SEQ ID NO 53
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: C16D6.2_F

<400> SEQUENCE: 53
gccgccatga atggctccga ttgtctgaat c                            31

<210> SEQ ID NO 54
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: C16D6.2_R

<400> SEQUENCE: 54
tctagatcac gtgcatagtg tcgtcgaacg g                            31

<210> SEQ ID NO 55
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: C25G6.5_F

<400> SEQUENCE: 55
gccgccatgg gatcggtgaa tgaatcatgt g                            31

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:

<223> OTHER INFORMATION: C25G6.5_R

<400> SEQUENCE: 56
tctagatcaa ctcagtaccc cttcaactat a                               31

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: C38C10.1_F

<400> SEQUENCE: 57
gccgccatga ttattttta tctttacgta g                               31

<210> SEQ ID NO 58
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: C38C10.1_R

<400> SEQUENCE: 58
tctagatcac cgttcatggc aactcagaag a                               31

<210> SEQ ID NO 59
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: C39E6.6_F

<400> SEQUENCE: 59
gccgccatgg aagttgaaaa ttttaccgac t                               31

<210> SEQ ID NO 60
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: C39E6.6_R

<400> SEQUENCE: 60
ctcgagtcag actagcgtgt cgttgacgct g                               31

<210> SEQ ID NO 61
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: C50F7.1_F

<400> SEQUENCE: 61
gccgccatga atacgtcatt tgtagagcca t                               31

<210> SEQ ID NO 62
<211> LENGTH: 31

```
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: C50F7.1_R

<400> SEQUENCE: 62
tctagattaa caatcagaag tagatctttc c                             31

<210> SEQ ID NO 63
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: C56G3.1_F

<400> SEQUENCE: 63
gccgccatgg aagtgaaaga tatagataac t                             31

<210> SEQ ID NO 64
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: C56G3.1_R

<400> SEQUENCE: 64
tctagattag acaaaactat ctttctcgat a                             31

<210> SEQ ID NO 65
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: F01E11.5_F

<400> SEQUENCE: 65
gccgccatgt gcttcgcaga aaaaggagaa g                             31

<210> SEQ ID NO 66
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: F01E11.5_R

<400> SEQUENCE: 66
tctagattag acacgagaag ttgagctggg t                             31

<210> SEQ ID NO 67
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: F35G8.1_F

<400> SEQUENCE: 67
```
gccgccatgg gactccaagg gcgtgcaatt a          31

<210> SEQ ID NO 68
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: F35G8.1_R

<400> SEQUENCE: 68
tctagattaa agatccgttc tgagaacttc g          31

<210> SEQ ID NO 69
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: F41E7.3_F

<400> SEQUENCE: 69
gccgccatgg aaatggaata tttccgccca t          31

<210> SEQ ID NO 70
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: F41E7.3_R

<400> SEQUENCE: 70
tctagattaa agcagaagcg tctgacaact t          31

<210> SEQ ID NO 71
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: T05A1.1_F

<400> SEQUENCE: 71
gccgccatga tcaacgaaac agaagagaca t          31

<210> SEQ ID NO 72
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: T05A1.1_R

<400> SEQUENCE: 72
ctcgagtcat tggcaaacaa aataagtata a          31

<210> SEQ ID NO 73
<211> LENGTH: 31
<212> TYPE: DNA
<213> ORGANISM: Artificial Sequence
<220> FEATURE:
<223> OTHER INFORMATION: Description of Artificial Sequence: PCR primer

<220> FEATURE:
<223> OTHER INFORMATION: ZC412.1_F

<400> SEQUENCE: 73
gccgccatgg gtgatgctga atctcatcat t                              31

<210> SEQ ID NO 74
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: ZC412.1_R

<400> SEQUENCE: 74
tctagattat tgtttcgttt cgaaacagac a                              31

<210> SEQ ID NO 75
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: C49A9.7_F

<400> SEQUENCE: 75
gccgccatga caacgtgtcc cctaccaccc a                              31

<210> SEQ ID NO 76
<211> LENGTH: 31
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: C49A9.7_R

<400> SEQUENCE: 76
tctagatcag aaatccgtat gcgccatcgt t                              31

<210> SEQ ID NO 77
<211> LENGTH: 12
<212> TYPE: PRT
<213> ORGANISM: Caenorhabditis elegans/flp 3
<220> FEATURE:
<221> NAME/KEY: MOD_RES
<222> LOCATION: (12)
<223> OTHER INFORMATION: AMIDATION

<400> SEQUENCE: 77

Ala Ser Glu Asp Ala Leu Phe Gly Thr Met Arg Phe
 1               5                  10

<210> SEQ ID NO 78
<211> LENGTH: 8
<212> TYPE: PRT
<213> ORGANISM: Caenorhabditis elegans/flp 4
<220> FEATURE:
<221> NAME/KEY: MOD_RES
<222> LOCATION: (8)
<223> OTHER INFORMATION: AMIDATION

<400> SEQUENCE: 78

Ala Ser Pro Ser Phe Ile Arg Phe
 1               5

```
<210> SEQ ID NO 79
<211> LENGTH: 8
<212> TYPE: PRT
<213> ORGANISM: A. suum
<220> FEATURE:
<223> OTHER INFORMATION: AF3
<220> FEATURE:
<221> NAME/KEY: MOD_RES
<222> LOCATION: (8)
<223> OTHER INFORMATION: AMIDATION

<400> SEQUENCE: 79

Ala Val Pro Gly Val Leu Arg Phe
 1               5

<210> SEQ ID NO 80
<211> LENGTH: 8
<212> TYPE: PRT
<213> ORGANISM: Caenorhabditis elegans/flp 18
<220> FEATURE:
<221> NAME/KEY: MOD_RES
<222> LOCATION: (8)
<223> OTHER INFORMATION: AMIDATION

<400> SEQUENCE: 80

Asp Val Pro Gly Val Leu Arg Phe
 1               5

<210> SEQ ID NO 81
<211> LENGTH: 11
<212> TYPE: PRT
<213> ORGANISM: Caenorhabditis elegans/flp 3
<220> FEATURE:
<221> NAME/KEY: MOD_RES
<222> LOCATION: (11)
<223> OTHER INFORMATION: AMIDATION

<400> SEQUENCE: 81

Glu Ala Glu Glu Pro Leu Gly Thr Met Arg Phe
 1               5                  10

<210> SEQ ID NO 82
<211> LENGTH: 12
<212> TYPE: PRT
<213> ORGANISM: Caenorhabditis elegans/flp 3
<220> FEATURE:
<221> NAME/KEY: MOD_RES
<222> LOCATION: (12)
<223> OTHER INFORMATION: AMIDATION

<400> SEQUENCE: 82

Glu Asp Gly Asn Ala Pro Phe Gly Thr Met Arg Phe
 1               5                  10

<210> SEQ ID NO 83
<211> LENGTH: 14
<212> TYPE: PRT
<213> ORGANISM: Caenorhabditis elegans/flp 14
<220> FEATURE:
<221> NAME/KEY: MOD_RES
<222> LOCATION: (14)
<223> OTHER INFORMATION: AMIDATION

<400> SEQUENCE: 83

Glu Ile Val Phe His Gln Ile Ser Pro Ile Phe Phe Arg Phe
 1               5                  10

<210> SEQ ID NO 84
```

```
<211> LENGTH: 9
<212> TYPE: PRT
<213> ORGANISM: A. suum
<220> FEATURE:
<223> OTHER INFORMATION: AF4
<220> FEATURE:
<221> NAME/KEY: MOD_RES
<222> LOCATION: (9)
<223> OTHER INFORMATION: AMIDATION

<400> SEQUENCE: 84

Gly Asp Val Pro Gly Val Leu Arg Phe
  1               5

<210> SEQ ID NO 85
<211> LENGTH: 9
<212> TYPE: PRT
<213> ORGANISM: Caenorhabditis elegans/flp15
<220> FEATURE:
<221> NAME/KEY: MOD_RES
<222> LOCATION: (9)
<223> OTHER INFORMATION: AMIDATION

<400> SEQUENCE: 85

Gly Gly Pro Gln Gly Pro Leu Arg Phe
  1               5

<210> SEQ ID NO 86
<211> LENGTH: 9
<212> TYPE: PRT
<213> ORGANISM: A. suum/C.elegans (flp 21)
<220> FEATURE:
<223> OTHER INFORMATION: AF9
<220> FEATURE:
<221> NAME/KEY: MOD_RES
<222> LOCATION: (9)
<223> OTHER INFORMATION: AMIDATION

<400> SEQUENCE: 86

Gly Leu Gly Pro Arg Pro Leu Arg Phe
  1               5

<210> SEQ ID NO 87
<211> LENGTH: 8
<212> TYPE: PRT
<213> ORGANISM: A. suum
<220> FEATURE:
<223> OTHER INFORMATION: AF20
<220> FEATURE:
<221> NAME/KEY: MOD_RES
<222> LOCATION: (8)
<223> OTHER INFORMATION: AMIDATION

<400> SEQUENCE: 87

Gly Met Pro Gly Val Leu Arg Phe
  1               5

<210> SEQ ID NO 88
<211> LENGTH: 7
<212> TYPE: PRT
<213> ORGANISM: Manduca
<220> FEATURE:
<221> NAME/KEY: MOD_RES
<222> LOCATION: (7)
<223> OTHER INFORMATION: AMIDATION

<400> SEQUENCE: 88

Gly Asn Ser Phe Leu Arg Phe
  1               5
```

```
<210> SEQ ID NO 89
<211> LENGTH: 8
<212> TYPE: PRT
<213> ORGANISM: Caenorhabditis elegans/flp 15
<220> FEATURE:
<221> NAME/KEY: MOD_RES
<222> LOCATION: (8)
<223> OTHER INFORMATION: AMIDATION

<400> SEQUENCE: 89

Gly Pro Ser Gly Pro Leu Arg Phe
  1               5

<210> SEQ ID NO 90
<211> LENGTH: 5
<212> TYPE: PRT
<213> ORGANISM: Artificial Sequence
<220> FEATURE:
<221> NAME/KEY: SITE
<222> LOCATION: (3)
<223> OTHER INFORMATION: Xaa=Norleucine
<220> FEATURE:
<221> NAME/KEY: MOD_RES
<222> LOCATION: (5)
<223> OTHER INFORMATION: AMIDATION
<220> FEATURE:
<223> OTHER INFORMATION: Description of Artificial Sequence: Synthetic

<400> SEQUENCE: 90

Ile Leu Xaa Arg Phe
  1               5

<210> SEQ ID NO 91
<211> LENGTH: 7
<212> TYPE: PRT
<213> ORGANISM: Caenorhabditis elegans/flp 1
<220> FEATURE:
<221> NAME/KEY: MOD_RES
<222> LOCATION: (7)
<223> OTHER INFORMATION: AMIDATION

<400> SEQUENCE: 91

Lys Pro Asn Phe Leu Arg Phe
  1               5

<210> SEQ ID NO 92
<211> LENGTH: 9
<212> TYPE: PRT
<213> ORGANISM: Caenorhabditis elegans/flp 18
<220> FEATURE:
<221> NAME/KEY: MOD_RES
<222> LOCATION: (9)
<223> OTHER INFORMATION: AMIDATION

<400> SEQUENCE: 92

Lys Ser Val Pro Gly Val Leu Arg Phe
  1               5

<210> SEQ ID NO 93
<211> LENGTH: 10
<212> TYPE: PRT
<213> ORGANISM: Caenorhabditis elegans/flp11
<220> FEATURE:
<221> NAME/KEY: MOD_RES
<222> LOCATION: (10)
<223> OTHER INFORMATION: AMIDATION

<400> SEQUENCE: 93

Asn Gly Ala Pro Gln Pro Phe Val Arg Phe
```

<210> SEQ ID NO 94
<211> LENGTH: 10
<212> TYPE: PRT
<213> ORGANISM: Locust
<220> FEATURE:
<223> OTHER INFORMATION: SchistoFLRFa
<220> FEATURE:
<221> NAME/KEY: MOD_RES
<222> LOCATION: (10)
<223> OTHER INFORMATION: AMIDATION

<400> SEQUENCE: 94

Pro Asp Val Asp His Val Phe Leu Arg Phe
 1               5                  10

<210> SEQ ID NO 95
<211> LENGTH: 11
<212> TYPE: PRT
<213> ORGANISM: Locust
<220> FEATURE:
<223> OTHER INFORMATION: leucomyosuppressin
<220> FEATURE:
<221> NAME/KEY: MOD_RES
<222> LOCATION: (11)
<223> OTHER INFORMATION: AMIDATION
<220> FEATURE:
<221> NAME/KEY: SITE
<222> LOCATION: (1)
<223> OTHER INFORMATION: Xaa= pyro

<400> SEQUENCE: 95

Xaa Glu Asp Val Asp His Val Phe Leu Arg Phe
 1               5                  10

<210> SEQ ID NO 96
<211> LENGTH: 13
<212> TYPE: PRT
<213> ORGANISM: Caenorhabditis elegans/flp3
<220> FEATURE:
<221> NAME/KEY: MOD_RES
<222> LOCATION: (13)
<223> OTHER INFORMATION: AMIDATION

<400> SEQUENCE: 96

Ser Ala Asp Asp Ser Ala Pro Phe Gly Thr Met Arg Phe
 1               5                  10

<210> SEQ ID NO 97
<211> LENGTH: 10
<212> TYPE: PRT
<213> ORGANISM: Caenorhabditis elegans/flp 3
<220> FEATURE:
<221> NAME/KEY: MOD_RES
<222> LOCATION: (10)
<223> OTHER INFORMATION: AMIDATION

<400> SEQUENCE: 97

Ser Ala Glu Pro Phe Gly Thr Met Arg Phe
 1               5                  10

<210> SEQ ID NO 98
<211> LENGTH: 9
<212> TYPE: PRT
<213> ORGANISM: Caenorhabditis elegans/flp 18
<220> FEATURE:
<221> NAME/KEY: MOD_RES
<222> LOCATION: (9)
<223> OTHER INFORMATION: AMIDATION

```
<400> SEQUENCE: 98

Ser Glu Val Pro Gly Val Leu Arg Phe
  1               5

<210> SEQ ID NO 99
<211> LENGTH: 8
<212> TYPE: PRT
<213> ORGANISM: Caenorhabditis elegans/flp 3
<220> FEATURE:
<221> NAME/KEY: MOD_RES
<222> LOCATION: (8)
<223> OTHER INFORMATION: AMIDATION

<400> SEQUENCE: 99

Ser Pro Leu Gly Thr Met Arg Phe
  1               5

<210> SEQ ID NO 100
<211> LENGTH: 8
<212> TYPE: PRT
<213> ORGANISM: Caenorhabditis elegans/flp 18
<220> FEATURE:
<221> NAME/KEY: MOD_RES
<222> LOCATION: (8)
<223> OTHER INFORMATION: AMIDATION

<400> SEQUENCE: 100

Ser Val Pro Gly Val Leu Arg Phe
  1               5

<210> SEQ ID NO 101
<211> LENGTH: 10
<212> TYPE: PRT
<213> ORGANISM: Drosophila
<220> FEATURE:
<221> NAME/KEY: MOD_RES
<222> LOCATION: (10)
<223> OTHER INFORMATION: AMIDATION

<400> SEQUENCE: 101

Thr Asp Val Asp His Val Phe Leu Arg Phe
  1               5                  10

<210> SEQ ID NO 102
<211> LENGTH: 8
<212> TYPE: PRT
<213> ORGANISM: lobster
<220> FEATURE:
<223> OTHER INFORMATION: Lobster peptide II
<220> FEATURE:
<221> NAME/KEY: MOD_RES
<222> LOCATION: (8)
<223> OTHER INFORMATION: AMIDATION

<400> SEQUENCE: 102

Thr Asn Arg Asn Phe Leu Arg Phe
  1               5

<210> SEQ ID NO 103
<211> LENGTH: 11
<212> TYPE: PRT
<213> ORGANISM: locust
<220> FEATURE:
<221> NAME/KEY: SITE
<222> LOCATION: (1)
<223> OTHER INFORMATION: Xaa=IodoY
<220> FEATURE:
<221> NAME/KEY: MOD_RES
```

<222> LOCATION: (11)
<223> OTHER INFORMATION: AMIDATION

<400> SEQUENCE: 103

Xaa Pro Asp Val Asp His Val Phe Leu Arg Phe
 1               5                  10

<210> SEQ ID NO 104
<211> LENGTH: 1193
<212> TYPE: DNA
<213> ORGANISM: Homo sapiens
<220> FEATURE:
<221> NAME/KEY: CDS
<222> LOCATION: (1)..(1191)
<220> FEATURE:
<223> OTHER INFORMATION: Clone identifier: CEGPCR19.2

<400> SEQUENCE: 104

| | |
|---|---|
| atg gtt agt tcg gcg gcc acc att tcg acc att tca acc aca acg act<br>Met Val Ser Ser Ala Ala Thr Ile Ser Thr Ile Ser Thr Thr Thr Thr<br> 1               5                  10                  15 | 48 |
| ccc tcc acc atc agc aac gtt atc aca agt cat tcg aac aat ggc tcg<br>Pro Ser Thr Ile Ser Asn Val Ile Thr Ser His Ser Asn Asn Gly Ser<br>                 20                  25                  30 | 96 |
| tgc att cag atc gct gag gcg att gcg gca caa ggc atc gat gat att<br>Cys Ile Gln Ile Ala Glu Ala Ile Ala Ala Gln Gly Ile Asp Asp Ile<br>             35                  40                  45 | 144 |
| act gta gac ttt tac atc cga tca atc ttc aca ttc ctc tac ggg ttc<br>Thr Val Asp Phe Tyr Ile Arg Ser Ile Phe Thr Phe Leu Tyr Gly Phe<br>         50                  55                  60 | 192 |
| ctg ttt gta tta ggc att ttt gga aac ggc ggc gta cta tgg gcg gtg<br>Leu Phe Val Leu Gly Ile Phe Gly Asn Gly Gly Val Leu Trp Ala Val<br>     65                  70                  75                  80 | 240 |
| gcg aga aac aag cgg ctc caa tcg gct cgc aac gta ttt ctg ctc aac<br>Ala Arg Asn Lys Arg Leu Gln Ser Ala Arg Asn Val Phe Leu Leu Asn<br>                 85                  90                  95 | 288 |
| ttg atc ttc acc gat ttg ata ttg gtg ttc aca gcg att cca gtc aca<br>Leu Ile Phe Thr Asp Leu Ile Leu Val Phe Thr Ala Ile Pro Val Thr<br>             100                 105                 110 | 336 |
| cca tgg tac gcg atg acc aaa gac tgg gca ttc ggg tca gtg atg tgc<br>Pro Trp Tyr Ala Met Thr Lys Asp Trp Ala Phe Gly Ser Val Met Cys<br>         115                 120                 125 | 384 |
| cat tta gtt cct ttg tca aat tcg tgt tcg gtg ttt gtg acg agt tgg<br>His Leu Val Pro Leu Ser Asn Ser Cys Ser Val Phe Val Thr Ser Trp<br>     130                 135                 140 | 432 |
| agc ctc act gca atc tcc tta gat aaa ttt ctg cat atc aac gat ccc<br>Ser Leu Thr Ala Ile Ser Leu Asp Lys Phe Leu His Ile Asn Asp Pro<br>145                 150                 155                 160 | 480 |
| acc aaa caa cca gtt tct att cgt caa gcg ttg gca ata aca ttt ctt<br>Thr Lys Gln Pro Val Ser Ile Arg Gln Ala Leu Ala Ile Thr Phe Leu<br>                 165                 170                 175 | 528 |
| atc tgg ata gtc tca aca ctg ata aat cta ccg tat ctt atg tct ttc<br>Ile Trp Ile Val Ser Thr Leu Ile Asn Leu Pro Tyr Leu Met Ser Phe<br>             180                 185                 190 | 576 |
| gag cac gtc gat gga agc ttt tac gtt cag ccc gga gaa act cca tac<br>Glu His Val Asp Gly Ser Phe Tyr Val Gln Pro Gly Glu Thr Pro Tyr<br>         195                 200                 205 | 624 |
| tgc ggg cac ttt tgc gac gag gcg aat tgg cag agc gaa aat agt cga<br>Cys Gly His Phe Cys Asp Glu Ala Asn Trp Gln Ser Glu Asn Ser Arg<br>     210                 215                 220 | 672 |
| aag att tac gga act acg gtt atg ttg tta cag ttc gtc gtg ccg atg<br>Lys Ile Tyr Gly Thr Thr Val Met Leu Leu Gln Phe Val Val Pro Met | 720 |

```
                225                 230                 235                 240
gca gtg atc acg tat tgc tac ttc aaa atc ttg caa aaa gtg tca aaa       768
Ala Val Ile Thr Tyr Cys Tyr Phe Lys Ile Leu Gln Lys Val Ser Lys
            245                 250                 255 gac atg atc atc caa aat gct caa ttc tgt caa tca ctg aca caa aag       816
Asp Met Ile Ile Gln Asn Ala Gln Phe Cys Gln Ser Leu Thr Gln Lys
        260                 265                 270 cag aga agt gat gcg acg tca cga aag aag aaa gtg aat tat att cta       864
Gln Arg Ser Asp Ala Thr Ser Arg Lys Lys Lys Val Asn Tyr Ile Leu
        275                 280                 285 att gca atg gtt gtc aca ttt atc ggg tgt tgg ttg cct tta aca tta       912
Ile Ala Met Val Val Thr Phe Ile Gly Cys Trp Leu Pro Leu Thr Leu
        290                 295                 300 ctc aat ttg gtc aaa gat ttt aaa aaa gag ccc gaa tgg cta aaa cgt       960
Leu Asn Leu Val Lys Asp Phe Lys Lys Glu Pro Glu Trp Leu Lys Arg
305                 310                 315                 320 cag ccg ttc ttc tgg gca ata aat gct cac gtc ata gcc atg tcc tta      1008
Gln Pro Phe Phe Trp Ala Ile Asn Ala His Val Ile Ala Met Ser Leu
            325                 330                 335 gtc gtc tgg aac cct ctg cta ttc ttt tgg ctg aca cga aaa caa aaa      1056
Val Val Trp Asn Pro Leu Leu Phe Phe Trp Leu Thr Arg Lys Gln Lys
            340                 345                 350 cgt tcc gga ctg tca aaa ata ctc aac tca aca gag ggt tcg aaa aaa      1104
Arg Ser Gly Leu Ser Lys Ile Leu Asn Ser Thr Glu Gly Ser Lys Lys
        355                 360                 365 gca ggt ggt tct gga ttg cga ggg atc cag cta cac gac ctc ctc ccg      1152
Ala Gly Gly Ser Gly Leu Arg Gly Ile Gln Leu His Asp Leu Leu Pro
        370                 375                 380 acc tct act cat tcg gac aga tgt gca ggc aac tct ttc ta              1193
Thr Ser Thr His Ser Asp Arg Cys Ala Gly Asn Ser Phe
385                 390                 395

<210> SEQ ID NO 105
<211> LENGTH: 397
<212> TYPE: PRT
<213> ORGANISM: Homo sapiens

<400> SEQUENCE: 105

Met Val Ser Ser Ala Ala Thr Ile Ser Thr Ile Ser Thr Thr Thr Thr
 1               5                  10                  15

Pro Ser Thr Ile Ser Asn Val Ile Thr Ser His Ser Asn Asn Gly Ser
             20                  25                  30

Cys Ile Gln Ile Ala Glu Ala Ile Ala Ala Gln Gly Ile Asp Asp Ile
         35                  40                  45

Thr Val Asp Phe Tyr Ile Arg Ser Ile Phe Thr Phe Leu Tyr Gly Phe
     50                  55                  60

Leu Phe Val Leu Gly Ile Phe Gly Asn Gly Gly Val Leu Trp Ala Val
 65                  70                  75                  80

Ala Arg Asn Lys Arg Leu Gln Ser Ala Arg Asn Val Phe Leu Leu Asn
                 85                  90                  95

Leu Ile Phe Thr Asp Leu Ile Leu Val Phe Thr Ala Ile Pro Val Thr
            100                 105                 110

Pro Trp Tyr Ala Met Thr Lys Asp Trp Ala Phe Gly Ser Val Met Cys
        115                 120                 125

His Leu Val Pro Leu Ser Asn Ser Cys Ser Val Phe Val Thr Ser Trp
    130                 135                 140

Ser Leu Thr Ala Ile Ser Leu Asp Lys Phe Leu His Ile Asn Asp Pro
145                 150                 155                 160
```

```
Thr Lys Gln Pro Val Ser Ile Arg Gln Ala Leu Ala Ile Thr Phe Leu
                165                 170                 175
Ile Trp Ile Val Ser Thr Leu Ile Asn Leu Pro Tyr Leu Met Ser Phe
            180                 185                 190
Glu His Val Asp Gly Ser Phe Tyr Val Gln Pro Gly Glu Thr Pro Tyr
            195                 200                 205
Cys Gly His Phe Cys Asp Glu Ala Asn Trp Gln Ser Glu Asn Ser Arg
            210                 215                 220
Lys Ile Tyr Gly Thr Thr Val Met Leu Leu Gln Phe Val Val Pro Met
225                 230                 235                 240
Ala Val Ile Thr Tyr Cys Tyr Phe Lys Ile Leu Gln Lys Val Ser Lys
                245                 250                 255
Asp Met Ile Ile Gln Asn Ala Gln Phe Cys Gln Ser Leu Thr Gln Lys
                260                 265                 270
Gln Arg Ser Asp Ala Thr Ser Arg Lys Lys Lys Val Asn Tyr Ile Leu
                275                 280                 285
Ile Ala Met Val Val Thr Phe Ile Gly Cys Trp Leu Pro Leu Thr Leu
                290                 295                 300
Leu Asn Leu Val Lys Asp Phe Lys Lys Glu Pro Glu Trp Leu Lys Arg
305                 310                 315                 320
Gln Pro Phe Phe Trp Ala Ile Asn Ala His Val Ile Ala Met Ser Leu
                325                 330                 335
Val Val Trp Asn Pro Leu Leu Phe Phe Trp Leu Thr Arg Lys Gln Lys
                340                 345                 350
Arg Ser Gly Leu Ser Lys Ile Leu Asn Ser Thr Glu Gly Ser Lys Lys
                355                 360                 365
Ala Gly Gly Ser Gly Leu Arg Gly Ile Gln Leu His Asp Leu Leu Pro
                370                 375                 380
Thr Ser Thr His Ser Asp Arg Cys Ala Gly Asn Ser Phe
385                 390                 395

<210> SEQ ID NO 106
<211> LENGTH: 1301
<212> TYPE: DNA
<213> ORGANISM: Homo sapiens
<220> FEATURE:
<221> NAME/KEY: CDS
<222> LOCATION: (1)..(1299)
<220> FEATURE:
<223> OTHER INFORMATION: Clone identifier: CEGPCR19.1

<400> SEQUENCE: 106 atg gtt agt tcg gcg gcc acc att tcg acc att tca acc aca acg act      48
Met Val Ser Ser Ala Ala Thr Ile Ser Thr Ile Ser Thr Thr Thr Thr
  1               5                  10                  15 ccc tcc acc atc agc aac gtt atc aca agt cat tcg aac aat ggc tcg      96
Pro Ser Thr Ile Ser Asn Val Ile Thr Ser His Ser Asn Asn Gly Ser
             20                  25                  30 tgc att cag atc gct gag gcg att gcg gca caa ggc atc gat gat att     144
Cys Ile Gln Ile Ala Glu Ala Ile Ala Ala Gln Gly Ile Asp Asp Ile
         35                  40                  45 act gta gac ttt tac atc cga tca atc ttc aca ttc ctc tac ggg ttc     192
Thr Val Asp Phe Tyr Ile Arg Ser Ile Phe Thr Phe Leu Tyr Gly Phe
     50                  55                  60 ctg ttt gta tta ggc att ttt gga aac ggc ggc gta cta tgg gcg gtg     240
Leu Phe Val Leu Gly Ile Phe Gly Asn Gly Gly Val Leu Trp Ala Val
 65                  70                  75                  80
```

-continued

| | | |
|---|---|---|
| gcg aga aac aag cgg ctc caa tcg gct cgc aac gta ttt ctc aac<br>Ala Arg Asn Lys Arg Leu Gln Ser Ala Arg Asn Val Phe Leu Leu Asn<br>               85                      90                     95 | 288 |
| ttg atc ttc acc gat ttg ata ttg gtg ttc aca gcg att cca gtc aca<br>Leu Ile Phe Thr Asp Leu Ile Leu Val Phe Thr Ala Ile Pro Val Thr<br>          100                   105                   110 | 336 |
| cca tgg tac gcg atg acc aaa gac tgg gca ttc ggg tca gtg atg tgc<br>Pro Trp Tyr Ala Met Thr Lys Asp Trp Ala Phe Gly Ser Val Met Cys<br>          115                   120                   125 | 384 |
| cat tta gtt cct ttg tca aat tcg tgt tcg gtg ttt gtg acg agt tgg<br>His Leu Val Pro Leu Ser Asn Ser Cys Ser Val Phe Val Thr Ser Trp<br>130                     135                   140 | 432 |
| agc ctc act gca atc tcc tta gat aaa ttt ctg cat atc aac gat ccc<br>Ser Leu Thr Ala Ile Ser Leu Asp Lys Phe Leu His Ile Asn Asp Pro<br>145                     150                   155                   160 | 480 |
| acc aaa caa cca gtt tct att cgt caa gcg ttg gca ata aca ttt ctt<br>Thr Lys Gln Pro Val Ser Ile Arg Gln Ala Leu Ala Ile Thr Phe Leu<br>                  165                   170                   175 | 528 |
| atc tgg ata gtc tca aca ctg ata aat cta ccg tat ctt atg tct ttc<br>Ile Trp Ile Val Ser Thr Leu Ile Asn Leu Pro Tyr Leu Met Ser Phe<br>               180                   185                   190 | 576 |
| gag cac gtc gat gga agc ttt tac gtt cag ccc gga gaa act cca tac<br>Glu His Val Asp Gly Ser Phe Tyr Val Gln Pro Gly Glu Thr Pro Tyr<br>          195                   200                   205 | 624 |
| tgc ggg cac ttt tgc gac gag gcg aat tgg cag agc gaa aat agt cga<br>Cys Gly His Phe Cys Asp Glu Ala Asn Trp Gln Ser Glu Asn Ser Arg<br>          210                   215                   220 | 672 |
| aag att tac gga act acg gtt atg ttg tta cag ttc gtc gtg ccg atg<br>Lys Ile Tyr Gly Thr Thr Val Met Leu Leu Gln Phe Val Val Pro Met<br>225                     230                   235                   240 | 720 |
| gca gtg atc acg tat tgc tac ttc aaa atc ttg caa aaa gtg tca aaa<br>Ala Val Ile Thr Tyr Cys Tyr Phe Lys Ile Leu Gln Lys Val Ser Lys<br>                  245                   250                   255 | 768 |
| gac atg atc atc caa aat gct caa ttc tgt caa tca ctg aca caa aag<br>Asp Met Ile Ile Gln Asn Ala Gln Phe Cys Gln Ser Leu Thr Gln Lys<br>               260                   265                   270 | 816 |
| cag aga agt gat gcg acg tca cga aag aag aaa gtg aat tat att cta<br>Gln Arg Ser Asp Ala Thr Ser Arg Lys Lys Lys Val Asn Tyr Ile Leu<br>          275                   280                   285 | 864 |
| att gca atg gtt gtc aca ttt atc ggg tgt tgg ttg cct tta aca tta<br>Ile Ala Met Val Val Thr Phe Ile Gly Cys Trp Leu Pro Leu Thr Leu<br>290                     295                   300 | 912 |
| ctc aat ttg gtc aaa gat ttt aaa aaa gag ccc gaa tgg cta aaa cgt<br>Leu Asn Leu Val Lys Asp Phe Lys Lys Glu Pro Glu Trp Leu Lys Arg<br>305                     310                   315                   320 | 960 |
| cag ccg ttc ttc tgg gca ata aat gct cac gtc ata gcc atg tcc tta<br>Gln Pro Phe Phe Trp Ala Ile Asn Ala His Val Ile Ala Met Ser Leu<br>               325                   330                   335 | 1008 |
| gtc gtc tgg aac cct ctg cta ttc ttt tgg ctg aca cga aaa caa aaa<br>Val Val Trp Asn Pro Leu Leu Phe Phe Trp Leu Thr Arg Lys Gln Lys<br>          340                   345                   350 | 1056 |
| cgt tcc gga ctg tca aaa ata ctc aac tca aca gag att gtg tcc tcg<br>Arg Ser Gly Leu Ser Lys Ile Leu Asn Ser Thr Glu Ile Val Ser Ser<br>               355                   360                   365 | 1104 |
| ttt gcc agt aga gtg agt aac tcg att cgg cgg tca acg ttt cgg aga<br>Phe Ala Ser Arg Val Ser Asn Ser Ile Arg Arg Ser Thr Phe Arg Arg<br>370                     375                   380 | 1152 |
| aac aat att gac agg gtt cga aaa aag cag gtg gtt ctg gat tgc gag<br>Asn Asn Ile Asp Arg Val Arg Lys Lys Gln Val Val Leu Asp Cys Glu<br>385                     390                   395                   400 | 1200 |

-continued

```
gga tcc agc tac acg acc tcc tcc cga cct cta ctc att cgg aca gat     1248
Gly Ser Ser Tyr Thr Thr Ser Ser Arg Pro Leu Leu Ile Arg Thr Asp
                405                 410                 415 gtg cag gca act ctt tct aat ggc tcg acg agt act acc cgc gag atg     1296
Val Gln Ala Thr Leu Ser Asn Gly Ser Thr Ser Thr Thr Arg Glu Met
                420                 425                 430 ctg ta                                                              1301
Leu
```

<210> SEQ ID NO 107
<211> LENGTH: 433
<212> TYPE: PRT
<213> ORGANISM: Homo sapiens

<400> SEQUENCE: 107

```
Met Val Ser Ser Ala Ala Thr Ile Ser Thr Ile Ser Thr Thr Thr Thr
  1               5                  10                  15

Pro Ser Thr Ile Ser Asn Val Ile Thr Ser His Ser Asn Asn Gly Ser
                 20                  25                  30

Cys Ile Gln Ile Ala Glu Ala Ile Ala Ala Gln Gly Ile Asp Asp Ile
             35                  40                  45

Thr Val Asp Phe Tyr Ile Arg Ser Ile Phe Thr Phe Leu Tyr Gly Phe
         50                  55                  60

Leu Phe Val Leu Gly Ile Phe Gly Asn Gly Gly Val Leu Trp Ala Val
 65                  70                  75                  80

Ala Arg Asn Lys Arg Leu Gln Ser Ala Arg Asn Val Phe Leu Leu Asn
                 85                  90                  95

Leu Ile Phe Thr Asp Leu Ile Leu Val Phe Thr Ala Ile Pro Val Thr
                100                 105                 110

Pro Trp Tyr Ala Met Thr Lys Asp Trp Ala Phe Gly Ser Val Met Cys
            115                 120                 125

His Leu Val Pro Leu Ser Asn Ser Cys Ser Val Phe Val Thr Ser Trp
        130                 135                 140

Ser Leu Thr Ala Ile Ser Leu Asp Lys Phe His Ile Asn Asp Pro
145                 150                 155                 160

Thr Lys Gln Pro Val Ser Ile Arg Gln Ala Leu Ala Ile Thr Phe Leu
                165                 170                 175

Ile Trp Ile Val Ser Thr Leu Ile Asn Leu Pro Tyr Leu Met Ser Phe
            180                 185                 190

Glu His Val Asp Gly Ser Phe Tyr Val Gln Pro Gly Glu Thr Pro Tyr
        195                 200                 205

Cys Gly His Phe Cys Asp Glu Ala Asn Trp Gln Ser Glu Asn Ser Arg
    210                 215                 220

Lys Ile Tyr Gly Thr Thr Val Met Leu Leu Gln Phe Val Val Pro Met
225                 230                 235                 240

Ala Val Ile Thr Tyr Cys Tyr Phe Lys Ile Leu Gln Lys Val Ser Lys
                245                 250                 255

Asp Met Ile Ile Gln Asn Ala Gln Phe Cys Gln Ser Leu Thr Gln Lys
            260                 265                 270

Gln Arg Ser Asp Ala Thr Ser Arg Lys Lys Val Asn Tyr Ile Leu
        275                 280                 285

Ile Ala Met Val Val Thr Phe Ile Gly Cys Trp Leu Pro Leu Thr Leu
    290                 295                 300

Leu Asn Leu Val Lys Asp Phe Lys Lys Glu Pro Glu Trp Leu Lys Arg
305                 310                 315                 320
```

```
Gln Pro Phe Phe Trp Ala Ile Asn Ala His Val Ile Ala Met Ser Leu
                325                 330                 335

Val Val Trp Asn Pro Leu Leu Phe Phe Trp Leu Thr Arg Lys Gln Lys
            340                 345                 350

Arg Ser Gly Leu Ser Lys Ile Leu Asn Ser Thr Glu Ile Val Ser Ser
        355                 360                 365

Phe Ala Ser Arg Val Ser Asn Ser Ile Arg Arg Ser Thr Phe Arg Arg
    370                 375                 380

Asn Asn Ile Asp Arg Val Arg Lys Lys Gln Val Val Leu Asp Cys Glu
385                 390                 395                 400

Gly Ser Ser Tyr Thr Thr Ser Ser Arg Pro Leu Leu Ile Arg Thr Asp
            405                 410                 415

Val Gln Ala Thr Leu Ser Asn Gly Ser Thr Ser Thr Thr Arg Glu Met
                420                 425                 430

Leu

<210> SEQ ID NO 108
<211> LENGTH: 1277
<212> TYPE: DNA
<213> ORGANISM: Homo sapiens
<220> FEATURE:
<223> OTHER INFORMATION: Clone identifier: CEGPCR21 (F02E8.2)
<220> FEATURE:
<221> NAME/KEY: CDS
<222> LOCATION: (1)..(1275)

<400> SEQUENCE: 108 atg aca cat gac aat gaa tat caa tct gca ctt gta ttc gat aga att      48
Met Thr His Asp Asn Glu Tyr Gln Ser Ala Leu Val Phe Asp Arg Ile
 1               5                  10                  15 aga cga tta atc tta aac aac tcg aat acc cca ata acg aca aaa gag      96
Arg Arg Leu Ile Leu Asn Asn Ser Asn Thr Pro Ile Thr Thr Lys Glu
             20                  25                  30 ctt ata aag cat tgc ttt cat cca gat gtt cag ttt ctt gct cac atg     144
Leu Ile Lys His Cys Phe His Pro Asp Val Gln Phe Leu Ala His Met
         35                  40                  45 acc ctg aaa tcg ttg gat cat ccc ggt gaa cag ttt aat aat tca tca     192
Thr Leu Lys Ser Leu Asp His Pro Gly Glu Gln Phe Asn Asn Ser Ser
     50                  55                  60 aat caa ctt tta tta gat cgc gct ttt cta aac cca ata ctc aca ctc     240
Asn Gln Leu Leu Leu Asp Arg Ala Phe Leu Asn Pro Ile Leu Thr Leu
 65                  70                  75                  80 att ttt gtt ttt gtc ggg ctt gtg ggt ctc att ggc aat ttg ctc aca     288
Ile Phe Val Phe Val Gly Leu Val Gly Leu Ile Gly Asn Leu Leu Thr
                 85                  90                  95 gtt att gtg att ttc aag aca aat tcc ctg cac tcg cac aca aac tat     336
Val Ile Val Ile Phe Lys Thr Asn Ser Leu His Ser His Thr Asn Tyr
            100                 105                 110 ttc ttg gca aat ctt gct acc ggc gac ttc tgt ctc atc gtt gtt gga     384
Phe Leu Ala Asn Leu Ala Thr Gly Asp Phe Cys Leu Ile Val Val Gly
        115                 120                 125 gtt tcg ttt gac ttg gtg aat atc tgg aac gat gag gaa ccg ctg gac     432
Val Ser Phe Asp Leu Val Asn Ile Trp Asn Asp Glu Glu Pro Leu Asp
    130                 135                 140 att ttt gga tat tgc tct ctt aca agc act ttt ata tct ctg ttc aca     480
Ile Phe Gly Tyr Cys Ser Leu Thr Ser Thr Phe Ile Ser Leu Phe Thr
145                 150                 155                 160 ttt gct tca att ctc aca att gtt ctt ttg acg gca gaa aga ttt aca     528
Phe Ala Ser Ile Leu Thr Ile Val Leu Leu Thr Ala Glu Arg Phe Thr
```

```
                      165                 170                 175
gcg att tgt tat cct ttt tcc cat aga aca att ttc gac gag aag cgt      576
Ala Ile Cys Tyr Pro Phe Ser His Arg Thr Ile Phe Asp Glu Lys Arg
            180                 185                 190 gtt aaa agg ttt ata ctg ctt att tgg ttc gta gca ctt ctt cca tca      624
Val Lys Arg Phe Ile Leu Leu Ile Trp Phe Val Ala Leu Leu Pro Ser
        195                 200                 205 att ttc att ggc tct atg ttc aaa cga gtg tct caa gac ttt tgt ggc      672
Ile Phe Ile Gly Ser Met Phe Lys Arg Val Ser Gln Asp Phe Cys Gly
    210                 215                 220 ttc aat cgc caa atg act tat atc ggt cga tgt gat ttg gtg aca tct      720
Phe Asn Arg Gln Met Thr Tyr Ile Gly Arg Cys Asp Leu Val Thr Ser
225                 230                 235                 240 cca gat agt ttc ttc cgg tac cca ttt gaa tca gca ata acc atc act      768
Pro Asp Ser Phe Phe Arg Tyr Pro Phe Glu Ser Ala Ile Thr Ile Thr
                245                 250                 255 ttt gta ctt ccc ttg ttc ttc att att tat tgt tac ttc cgg att cta      816
Phe Val Leu Pro Leu Phe Phe Ile Ile Tyr Cys Tyr Phe Arg Ile Leu
            260                 265                 270 gtc aca ttg aac gag atg tcc aat tcg act cat gtg cac act cca gtc      864
Val Thr Leu Asn Glu Met Ser Asn Ser Thr His Val His Thr Pro Val
        275                 280                 285 gga act gct cgt agt gat agt gga gct ttt cct ttt ccc cat aca tct      912
Gly Thr Ala Arg Ser Asp Ser Gly Ala Phe Pro Phe Pro His Thr Ser
    290                 295                 300 aat aac tct aac act caa agt ttc ccg cta aca gtc cat act aaa aat      960
Asn Asn Ser Asn Thr Gln Ser Phe Pro Leu Thr Val His Thr Lys Asn
305                 310                 315                 320 gtc caa ccg ccg cga agt caa caa gcc cag aaa atg gtc att aag atg     1008
Val Gln Pro Pro Arg Ser Gln Gln Ala Gln Lys Met Val Ile Lys Met
                325                 330                 335 ctt gtt act gta acc gct gta ttt ttt gtc tgc tat ctt cca tat cac     1056
Leu Val Thr Val Thr Ala Val Phe Phe Val Cys Tyr Leu Pro Tyr His
            340                 345                 350 gct caa cgt ctc atc gtc aaa tac aac agc aag gat tgt tcc aac tca     1104
Ala Gln Arg Leu Ile Val Lys Tyr Asn Ser Lys Asp Cys Ser Asn Ser
        355                 360                 365 gac ttc tgc aag ctt ctc tac cca ata gca gga atc ctc caa tac atc     1152
Asp Phe Cys Lys Leu Leu Tyr Pro Ile Ala Gly Ile Leu Gln Tyr Ile
    370                 375                 380 tcc gct tct ttg aat cca att ttc tac aac ctc atg tct gta cga ttt     1200
Ser Ala Ser Leu Asn Pro Ile Phe Tyr Asn Leu Met Ser Val Arg Phe
385                 390                 395                 400 cgc aac gga ttc aag aag ctc atc aaa gac gtc tgg gca cat cga gcc     1248
Arg Asn Gly Phe Lys Lys Leu Ile Lys Asp Val Trp Ala His Arg Ala
                405                 410                 415 cgt agt tac agc aat cta gct cgt gtc ta                              1277
Arg Ser Tyr Ser Asn Leu Ala Arg Val
            420                 425

<210> SEQ ID NO 109
<211> LENGTH: 425
<212> TYPE: PRT
<213> ORGANISM: Homo sapiens

<400> SEQUENCE: 109

Met Thr His Asp Asn Glu Tyr Gln Ser Ala Leu Val Phe Asp Arg Ile
  1               5                  10                  15

Arg Arg Leu Ile Leu Asn Asn Ser Asn Thr Pro Ile Thr Thr Lys Glu
             20                  25                  30
```

```
Leu Ile Lys His Cys Phe His Pro Asp Val Gln Phe Leu Ala His Met
        35                  40                  45

Thr Leu Lys Ser Leu Asp His Pro Gly Glu Gln Phe Asn Asn Ser Ser
    50                  55                  60

Asn Gln Leu Leu Leu Asp Arg Ala Phe Leu Asn Pro Ile Leu Thr Leu
65                  70                  75                  80

Ile Phe Val Phe Val Gly Leu Val Gly Leu Ile Gly Asn Leu Leu Thr
                85                  90                  95

Val Ile Val Ile Phe Lys Thr Asn Ser Leu His Ser His Thr Asn Tyr
            100                 105                 110

Phe Leu Ala Asn Leu Ala Thr Gly Asp Phe Cys Leu Ile Val Val Gly
            115                 120                 125

Val Ser Phe Asp Leu Val Asn Ile Trp Asn Asp Glu Glu Pro Leu Asp
        130                 135                 140

Ile Phe Gly Tyr Cys Ser Leu Thr Ser Thr Phe Ile Ser Leu Phe Thr
145                 150                 155                 160

Phe Ala Ser Ile Leu Thr Ile Val Leu Leu Thr Ala Glu Arg Phe Thr
                165                 170                 175

Ala Ile Cys Tyr Pro Phe Ser His Arg Thr Ile Phe Asp Glu Lys Arg
            180                 185                 190

Val Lys Arg Phe Ile Leu Leu Ile Trp Phe Val Ala Leu Leu Pro Ser
        195                 200                 205

Ile Phe Ile Gly Ser Met Phe Lys Arg Val Ser Gln Asp Phe Cys Gly
    210                 215                 220

Phe Asn Arg Gln Met Thr Tyr Ile Gly Arg Cys Asp Leu Val Thr Ser
225                 230                 235                 240

Pro Asp Ser Phe Phe Arg Tyr Pro Phe Glu Ser Ala Ile Thr Ile Thr
                245                 250                 255

Phe Val Leu Pro Leu Phe Phe Ile Ile Tyr Cys Tyr Phe Arg Ile Leu
            260                 265                 270

Val Thr Leu Asn Glu Met Ser Asn Ser Thr His Val His Thr Pro Val
        275                 280                 285

Gly Thr Ala Arg Ser Asp Ser Gly Ala Phe Pro Phe Pro His Thr Ser
    290                 295                 300

Asn Asn Ser Asn Thr Gln Ser Phe Pro Leu Thr Val His Thr Lys Asn
305                 310                 315                 320

Val Gln Pro Pro Arg Ser Gln Gln Ala Gln Lys Met Val Ile Lys Met
                325                 330                 335

Leu Val Thr Val Thr Ala Val Phe Phe Val Cys Tyr Leu Pro Tyr His
            340                 345                 350

Ala Gln Arg Leu Ile Val Lys Tyr Asn Ser Lys Asp Cys Ser Asn Ser
        355                 360                 365

Asp Phe Cys Lys Leu Leu Tyr Pro Ile Ala Gly Ile Leu Gln Tyr Ile
    370                 375                 380

Ser Ala Ser Leu Asn Pro Ile Phe Tyr Asn Leu Met Ser Val Arg Phe
385                 390                 395                 400

Arg Asn Gly Phe Lys Lys Leu Ile Lys Asp Val Trp Ala His Arg Ala
                405                 410                 415

Arg Ser Tyr Ser Asn Leu Ala Arg Val
            420                 425

<210> SEQ ID NO 110
<211> LENGTH: 1310
```

```
<212> TYPE: DNA
<213> ORGANISM: Homo sapiens
<220> FEATURE:
<223> OTHER INFORMATION: Clone identifier: CeGPCR22 (C06G4.5)
<220> FEATURE:
<221> NAME/KEY: CDS
<222> LOCATION: (1)..(1308)

<400> SEQUENCE: 110
```

| | | | | | | | | | | | | | | | | |
|---|---|---|---|---|---|---|---|---|---|---|---|---|---|---|---|---|
| atg | tct | aca | aat | ttg | gtg | gac | tat | gtc | gat | gat | tcg | tat | ttg | aat | caa | 48 |
| Met | Ser | Thr | Asn | Leu | Val | Asp | Tyr | Val | Asp | Asp | Ser | Tyr | Leu | Asn | Gln | |
| 1 | | | | 5 | | | | | 10 | | | | | 15 | | |
| tca | atg | aat | tca | gaa | aat | gga | ttg | gat | tca | gtc | aca | cag | att | atg | tat | 96 |
| Ser | Met | Asn | Ser | Glu | Asn | Gly | Leu | Asp | Ser | Val | Thr | Gln | Ile | Met | Tyr | |
| | | | 20 | | | | | 25 | | | | | 30 | | | |
| gat | atg | aaa | aag | tac | aat | ata | gtg | aat | gat | gtt | cta | cct | cct | ccc | aat | 144 |
| Asp | Met | Lys | Lys | Tyr | Asn | Ile | Val | Asn | Asp | Val | Leu | Pro | Pro | Pro | Asn | |
| | | 35 | | | | | 40 | | | | | 45 | | | | |
| cac | gaa | gat | cta | cat | gtt | gta | ata | atg | gca | gtt | tca | tac | ctt | ctt | tta | 192 |
| His | Glu | Asp | Leu | His | Val | Val | Ile | Met | Ala | Val | Ser | Tyr | Leu | Leu | Leu | |
| | 50 | | | | | 55 | | | | | 60 | | | | | |
| ttt | tta | tta | ggt | act | tgt | gga | aat | gtg | gca | gtg | tta | act | aca | ata | tac | 240 |
| Phe | Leu | Leu | Gly | Thr | Cys | Gly | Asn | Val | Ala | Val | Leu | Thr | Thr | Ile | Tyr | |
| 65 | | | | | 70 | | | | | 75 | | | | | 80 | |
| cat | gtt | att | cga | tcg | tct | cga | gcc | acg | ttg | gat | aac | aca | tta | ata | tat | 288 |
| His | Val | Ile | Arg | Ser | Ser | Arg | Ala | Thr | Leu | Asp | Asn | Thr | Leu | Ile | Tyr | |
| | | | | 85 | | | | | 90 | | | | | 95 | | |
| gtc | att | gtg | ctt | tct | tgt | gtc | gac | ttc | gga | gtt | tgt | ttg | tca | ctt | cca | 336 |
| Val | Ile | Val | Leu | Ser | Cys | Val | Asp | Phe | Gly | Val | Cys | Leu | Ser | Leu | Pro | |
| | | | 100 | | | | | 105 | | | | | 110 | | | |
| att | acg | gtt | att | gat | cag | att | ctc | ggt | ttc | tgg | atg | ttt | ggc | aaa | ata | 384 |
| Ile | Thr | Val | Ile | Asp | Gln | Ile | Leu | Gly | Phe | Trp | Met | Phe | Gly | Lys | Ile | |
| | | 115 | | | | | 120 | | | | | 125 | | | | |
| cca | tgt | aaa | ctt | cat | gca | gta | ttc | gag | aat | ttc | ggt | aaa | atc | ctg | agt | 432 |
| Pro | Cys | Lys | Leu | His | Ala | Val | Phe | Glu | Asn | Phe | Gly | Lys | Ile | Leu | Ser | |
| | 130 | | | | | 135 | | | | | 140 | | | | | |
| gct | ctc | att | ctg | acg | gca | atg | agt | ttt | gat | cgg | tac | gcc | gga | gtt | tgc | 480 |
| Ala | Leu | Ile | Leu | Thr | Ala | Met | Ser | Phe | Asp | Arg | Tyr | Ala | Gly | Val | Cys | |
| 145 | | | | | 150 | | | | | 155 | | | | | 160 | |
| cat | cca | cag | cga | aaa | cgg | ttg | aga | tca | agg | aat | ttt | gca | att | act | ata | 528 |
| His | Pro | Gln | Arg | Lys | Arg | Leu | Arg | Ser | Arg | Asn | Phe | Ala | Ile | Thr | Ile | |
| | | | | 165 | | | | | 170 | | | | | 175 | | |
| ctt | tta | gtt | ctt | gcc | gta | tat | gca | ttc | atc | aca | ctc | tgc | ccg | tta | tta | 576 |
| Leu | Leu | Val | Leu | Ala | Val | Tyr | Ala | Phe | Ile | Thr | Leu | Cys | Pro | Leu | Leu | |
| | | | 180 | | | | | 185 | | | | | 190 | | | |
| tgg | tct | ttt | act | gca | cgg | gaa | att | ata | ctt | tat | gcg | aag | gaa | aca | gca | 624 |
| Trp | Ser | Phe | Thr | Ala | Arg | Glu | Ile | Ile | Leu | Tyr | Ala | Lys | Glu | Thr | Ala | |
| | | 195 | | | | | 200 | | | | | 205 | | | | |
| ccc | gga | atg | ctg | aca | aga | atg | aaa | att | gag | aaa | tgc | aca | gtg | gat | atc | 672 |
| Pro | Gly | Met | Leu | Thr | Arg | Met | Lys | Ile | Glu | Lys | Cys | Thr | Val | Asp | Ile | |
| | 210 | | | | | 215 | | | | | 220 | | | | | |
| gac | tca | caa | atg | ttc | aca | gct | ttc | acg | att | tat | cag | ttc | att | ctc | tgt | 720 |
| Asp | Ser | Gln | Met | Phe | Thr | Ala | Phe | Thr | Ile | Tyr | Gln | Phe | Ile | Leu | Cys | |
| 225 | | | | | 230 | | | | | 235 | | | | | 240 | |
| tat | tgt | act | cca | ttg | gtt | ctc | atc | gcc | ttt | ttc | tat | acg | aaa | ctt | ctc | 768 |
| Tyr | Cys | Thr | Pro | Leu | Val | Leu | Ile | Ala | Phe | Phe | Tyr | Thr | Lys | Leu | Leu | |
| | | | 245 | | | | | 250 | | | | | 255 | | | |
| agc | aaa | ctc | cgt | gaa | cac | aca | agg | acg | ttt | aag | agc | tct | caa | atc | cca | 816 |
| Ser | Lys | Leu | Arg | Glu | His | Thr | Arg | Thr | Phe | Lys | Ser | Ser | Gln | Ile | Pro | |
| | | 260 | | | | | 265 | | | | | 270 | | | | |
| ttt | ttg | cac | att | tcg | ttg | tac | act | cta | gca | gtt | gca | tgt | ttc | tat | ttt | 864 |

```
                Phe Leu His Ile Ser Leu Tyr Thr Leu Ala Val Ala Cys Phe Tyr Phe
                        275                 280                 285 tta tgc tgg acc cca ttc tgg atg gct aca tta ttc gca gtt tat ctc        912
Leu Cys Trp Thr Pro Phe Trp Met Ala Thr Leu Phe Ala Val Tyr Leu
        290                 295                 300 gaa aac tca gca aat tcg agt agt gtt cca cca gtt ttt gta tat att        960
Glu Asn Ser Ala Asn Ser Ser Ser Val Pro Pro Val Phe Val Tyr Ile
305                 310                 315                 320 atg tat ttt att cat gct cta ccg ttc acc aac tct gcc att aat tgg       1008
Met Tyr Phe Ile His Ala Leu Pro Phe Thr Asn Ser Ala Ile Asn Trp
                325                 330                 335 att tta tac ggt gca cta aat ggc caa ctt caa caa aga tat cga tca       1056
Ile Leu Tyr Gly Ala Leu Asn Gly Gln Leu Gln Gln Arg Tyr Arg Ser
        340                 345                 350 aat cgt tca aat tct aca aaa aag acg aca aca aca gct tca aca           1104
Asn Arg Ser Asn Ser Thr Lys Lys Thr Thr Thr Thr Ala Ser Thr
        355                 360                 365 gct tta ttg gaa aag aaa atc aca aat ttg aat act aac tct aat tat       1152
Ala Leu Leu Glu Lys Lys Ile Thr Asn Leu Asn Thr Asn Ser Asn Tyr
370                 375                 380 cag gta aat ggc tca atg aac tca ata gcc act gca gct cca aca aaa       1200
Gln Val Asn Gly Ser Met Asn Ser Ile Ala Thr Ala Ala Pro Thr Lys
385                 390                 395                 400 acg att gga aat aat gaa gta ctt gtt gcc acg tca aca att gat gat       1248
Thr Ile Gly Asn Asn Glu Val Leu Val Ala Thr Ser Thr Ile Asp Asp
                405                 410                 415 gat gtt gca act gat gtt gta gat gtt cga ctt ttg agt aat cat aat       1296
Asp Val Ala Thr Asp Val Val Asp Val Arg Leu Leu Ser Asn His Asn
                420                 425                 430 cca act ttt ctt tg                                                    1310
Pro Thr Phe Leu
        435

<210> SEQ ID NO 111
<211> LENGTH: 436
<212> TYPE: PRT
<213> ORGANISM: Homo sapiens

<400> SEQUENCE: 111

Met Ser Thr Asn Leu Val Asp Tyr Val Asp Ser Tyr Leu Asn Gln
1               5                   10                  15

Ser Met Asn Ser Glu Asn Gly Leu Asp Ser Val Thr Gln Ile Met Tyr
                20                  25                  30

Asp Met Lys Lys Tyr Asn Ile Val Asn Asp Val Leu Pro Pro Asn
            35                  40                  45

His Glu Asp Leu His Val Val Ile Met Ala Val Ser Tyr Leu Leu Leu
        50                  55                  60

Phe Leu Leu Gly Thr Cys Gly Asn Val Ala Val Leu Thr Thr Ile Tyr
65                  70                  75                  80

His Val Ile Arg Ser Ser Arg Ala Thr Leu Asp Asn Thr Leu Ile Tyr
                85                  90                  95

Val Ile Val Leu Ser Cys Val Asp Phe Gly Val Cys Leu Ser Leu Pro
            100                 105                 110

Ile Thr Val Ile Asp Gln Ile Leu Gly Phe Trp Met Phe Gly Lys Ile
        115                 120                 125

Pro Cys Lys Leu His Ala Val Phe Glu Asn Phe Gly Lys Ile Leu Ser
    130                 135                 140

Ala Leu Ile Leu Thr Ala Met Ser Phe Asp Arg Tyr Ala Gly Val Cys
```

```
                 145                 150                 155                 160
His Pro Gln Arg Lys Arg Leu Arg Ser Arg Asn Phe Ala Ile Thr Ile
                165                 170                 175

Leu Leu Val Leu Ala Val Tyr Ala Phe Ile Thr Leu Cys Pro Leu Leu
            180                 185                 190

Trp Ser Phe Thr Ala Arg Glu Ile Ile Leu Tyr Ala Lys Glu Thr Ala
        195                 200                 205

Pro Gly Met Leu Thr Arg Met Lys Ile Glu Lys Cys Thr Val Asp Ile
    210                 215                 220

Asp Ser Gln Met Phe Thr Ala Phe Thr Ile Tyr Gln Phe Ile Leu Cys
225                 230                 235                 240

Tyr Cys Thr Pro Leu Val Leu Ile Ala Phe Phe Tyr Thr Lys Leu Leu
                245                 250                 255

Ser Lys Leu Arg Glu His Thr Arg Thr Phe Lys Ser Ser Gln Ile Pro
            260                 265                 270

Phe Leu His Ile Ser Leu Tyr Thr Leu Ala Val Ala Cys Phe Tyr Phe
        275                 280                 285

Leu Cys Trp Thr Pro Phe Trp Met Ala Thr Leu Phe Ala Val Tyr Leu
    290                 295                 300

Glu Asn Ser Ala Asn Ser Ser Val Pro Pro Val Phe Val Tyr Ile
305                 310                 315                 320

Met Tyr Phe Ile His Ala Leu Pro Phe Thr Asn Ser Ala Ile Asn Trp
                325                 330                 335

Ile Leu Tyr Gly Ala Leu Asn Gly Gln Leu Gln Arg Tyr Arg Ser
            340                 345                 350

Asn Arg Ser Asn Ser Thr Lys Lys Thr Thr Thr Thr Ala Ser Thr
        355                 360                 365

Ala Leu Leu Glu Lys Lys Ile Thr Asn Leu Asn Thr Asn Ser Asn Tyr
    370                 375                 380

Gln Val Asn Gly Ser Met Asn Ser Ile Ala Thr Ala Ala Pro Thr Lys
385                 390                 395                 400

Thr Ile Gly Asn Asn Glu Val Leu Val Ala Thr Ser Thr Ile Asp Asp
                405                 410                 415

Asp Val Ala Thr Asp Val Val Asp Val Arg Leu Leu Ser Asn His Asn
            420                 425                 430

Pro Thr Phe Leu
        435

<210> SEQ ID NO 112
<211> LENGTH: 1130
<212> TYPE: DNA
<213> ORGANISM: Homo sapiens
<220> FEATURE:
<223> OTHER INFORMATION: Clone identifier: CEGPCR23 (T02E9.1)
<220> FEATURE:
<221> NAME/KEY: CDS
<222> LOCATION: (1)..(1128)

<400> SEQUENCE: 112 atg aat atc aca aat tca agc atc ggg tac cca cct cca cca ctg gta      48
Met Asn Ile Thr Asn Ser Ser Ile Gly Tyr Pro Pro Pro Pro Leu Val
 1               5                  10                  15 ggt gca tca ttt gca aaa aca gct ata cca tat tca ata tgt ttt gtt      96
Gly Ala Ser Phe Ala Lys Thr Ala Ile Pro Tyr Ser Ile Cys Phe Val
            20                  25                  30 ttt gga act ctc ggc aac acg gcc gtt ctc tcc tac gtt ttc ttc att     144
Phe Gly Thr Leu Gly Asn Thr Ala Val Leu Ser Tyr Val Phe Phe Ile
```

```
            35                   40                   45
aca cga tcc cta aaa tca tct gta act gca ctt ggg aac aca ttt att     192
Thr Arg Ser Leu Lys Ser Ser Val Thr Ala Leu Gly Asn Thr Phe Ile
         50                  55                  60 tac atc gtt gca tta tgc gca gtc gat ctt ctt gtc acc gtt tcg att     240
Tyr Ile Val Ala Leu Cys Ala Val Asp Leu Leu Val Thr Val Ser Ile
 65                  70                  75                  80 cca ttc tcc cta tcg tac atg att ctc aac aac tgg gta ttc gga gag     288
Pro Phe Ser Leu Ser Tyr Met Ile Leu Asn Asn Trp Val Phe Gly Glu
                 85                  90                  95 ctg gtg tgc aag atc cac ttt atg ctt gag ctt tct aat aag atg tgc     336
Leu Val Cys Lys Ile His Phe Met Leu Glu Leu Ser Asn Lys Met Cys
                100                 105                 110 tcc aca ttc att cta acc gca ctg gca ttt gat cgt tac atg gca ata     384
Ser Thr Phe Ile Leu Thr Ala Leu Ala Phe Asp Arg Tyr Met Ala Ile
            115                 120                 125 tgt cat ccg gaa ata aaa cga atc cat gag atg cgt cac acg att tat     432
Cys His Pro Glu Ile Lys Arg Ile His Glu Met Arg His Thr Ile Tyr
    130                 135                 140 atc acg aca att ctt gca aca ttg tca ctt ttt ctc ata tct cca gtc     480
Ile Thr Thr Ile Leu Ala Thr Leu Ser Leu Phe Leu Ile Ser Pro Val
145                 150                 155                 160 gtt ttg tct gcc aga gtg acg agt ttc aaa agt gga caa tat ttt gtg     528
Val Leu Ser Ala Arg Val Thr Ser Phe Lys Ser Gly Gln Tyr Phe Val
                165                 170                 175 agc gca aag aat gaa cgg cac gaa gtt atc cga caa atg tgt att gac     576
Ser Ala Lys Asn Glu Arg His Glu Val Ile Arg Gln Met Cys Ile Asp
            180                 185                 190 gga atg gca tta gag tgg aag gtt tgg gtg tct gca ttt ctg atc ttc     624
Gly Met Ala Leu Glu Trp Lys Val Trp Val Ser Ala Phe Leu Ile Phe
    195                 200                 205 ttt gca ttc tta ctt cca tgc act ctt cta acc tac ttt tac gcg aag     672
Phe Ala Phe Leu Leu Pro Cys Thr Leu Leu Thr Tyr Phe Tyr Ala Lys
210                 215                 220 atc gtc ctt cgt ctg agg aga caa aga aga aca atg ctc caa tct cga     720
Ile Val Leu Arg Leu Arg Arg Gln Arg Arg Thr Met Leu Gln Ser Arg
                225                 230                 235                 240 att ccc ctc cgc cgc att aca ata tac aca atg gca gcc acg ttc ttc     768
Ile Pro Leu Arg Arg Ile Thr Ile Tyr Thr Met Ala Ala Thr Phe Phe
            245                 250                 255 tat ctt tcg tgt cat att cca ttt tgg ctc cca cag atc tac aac att     816
Tyr Leu Ser Cys His Ile Pro Phe Trp Leu Pro Gln Ile Tyr Asn Ile
    260                 265                 270 ttc tcg aca gtt ctt ggg cac aaa atg aat cca aaa gtc atg aca ttc     864
Phe Ser Thr Val Leu Gly His Lys Met Asn Pro Lys Val Met Thr Phe
275                 280                 285 acc tat tat tca cat ctt ctt ccg ttc ata tcg gcg gca ttt aac tgg     912
Thr Tyr Tyr Ser His Leu Leu Pro Phe Ile Ser Ala Ala Phe Asn Trp
                290                 295                 300 ata ttc tat gct cga ctt aat agt caa ttc aaa aaa gga ttg gtt cta     960
Ile Phe Tyr Ala Arg Leu Asn Ser Gln Phe Lys Lys Gly Leu Val Leu
305                 310                 315                 320 gtt acg gaa aga atg atc aga aag cga aca aaa tcg atg cat gag aaa     1008
Val Thr Glu Arg Met Ile Arg Lys Arg Thr Lys Ser Met His Glu Lys
                325                 330                 335 gga tac agt gag gca gct gtt gag ctt acg agc aag ttc gat gat gtc     1056
Gly Tyr Ser Glu Ala Ala Val Glu Leu Thr Ser Lys Phe Asp Asp Val
            340                 345                 350 cca ttg atg tgt cca cac tgt gaa gct caa ctt tct att cgt tca agt     1104
```

```
Pro Leu Met Cys Pro His Cys Glu Ala Gln Leu Ser Ile Arg Ser Ser
            355                 360                 365 agt aat gga aag aag aat tca aga ta                                        1130
Ser Asn Gly Lys Lys Asn Ser Arg
    370                 375

<210> SEQ ID NO 113
<211> LENGTH: 376
<212> TYPE: PRT
<213> ORGANISM: Homo sapiens

<400> SEQUENCE: 113

Met Asn Ile Thr Asn Ser Ser Ile Gly Tyr Pro Pro Pro Leu Val
 1               5                  10                  15

Gly Ala Ser Phe Ala Lys Thr Ala Ile Pro Tyr Ser Ile Cys Phe Val
                20                  25                  30

Phe Gly Thr Leu Gly Asn Thr Ala Val Leu Ser Tyr Val Phe Phe Ile
            35                  40                  45

Thr Arg Ser Leu Lys Ser Ser Val Thr Ala Leu Gly Asn Thr Phe Ile
    50                  55                  60

Tyr Ile Val Ala Leu Cys Ala Val Asp Leu Leu Val Thr Val Ser Ile
65                  70                  75                  80

Pro Phe Ser Leu Ser Tyr Met Ile Leu Asn Asn Trp Val Phe Gly Glu
                85                  90                  95

Leu Val Cys Lys Ile His Phe Met Leu Glu Leu Ser Asn Lys Met Cys
            100                 105                 110

Ser Thr Phe Ile Leu Thr Ala Leu Ala Phe Asp Arg Tyr Met Ala Ile
            115                 120                 125

Cys His Pro Glu Ile Lys Arg Ile His Glu Met Arg His Thr Ile Tyr
    130                 135                 140

Ile Thr Thr Ile Leu Ala Thr Leu Ser Leu Phe Leu Ile Ser Pro Val
145                 150                 155                 160

Val Leu Ser Ala Arg Val Thr Ser Phe Lys Ser Gly Gln Tyr Phe Val
                165                 170                 175

Ser Ala Lys Asn Glu Arg His Glu Val Ile Arg Gln Met Cys Ile Asp
            180                 185                 190

Gly Met Ala Leu Glu Trp Lys Val Trp Val Ser Ala Phe Leu Ile Phe
    195                 200                 205

Phe Ala Phe Leu Leu Pro Cys Thr Leu Leu Thr Tyr Phe Tyr Ala Lys
210                 215                 220

Ile Val Leu Arg Leu Arg Arg Gln Arg Arg Thr Met Leu Gln Ser Arg
225                 230                 235                 240

Ile Pro Leu Arg Arg Ile Thr Ile Tyr Thr Met Ala Ala Thr Phe Phe
                245                 250                 255

Tyr Leu Ser Cys His Ile Pro Phe Trp Leu Pro Gln Ile Tyr Asn Ile
            260                 265                 270

Phe Ser Thr Val Leu Gly His Lys Met Asn Pro Lys Val Met Thr Phe
        275                 280                 285

Thr Tyr Tyr Ser His Leu Leu Pro Phe Ile Ser Ala Ala Phe Asn Trp
    290                 295                 300

Ile Phe Tyr Ala Arg Leu Asn Ser Gln Phe Lys Lys Gly Leu Val Leu
305                 310                 315                 320

Val Thr Glu Arg Met Ile Arg Lys Arg Thr Lys Ser Met His Glu Lys
                325                 330                 335

Gly Tyr Ser Glu Ala Ala Val Glu Leu Thr Ser Lys Phe Asp Asp Val
```

```
                    340                 345                 350
Pro Leu Met Cys Pro His Cys Glu Ala Gln Leu Ser Ile Arg Ser Ser
                355                 360                 365

Ser Asn Gly Lys Lys Asn Ser Arg
        370                 375

<210> SEQ ID NO 114
<211> LENGTH: 1284
<212> TYPE: DNA
<213> ORGANISM: Homo sapiens
<220> FEATURE:
<223> OTHER INFORMATION: Clone identifier: CEGPCR24a (Y59H11AL.a-01)
<220> FEATURE:
<221> NAME/KEY: CDS
<222> LOCATION: (1)..(1281)

<400> SEQUENCE: 114 atg gac gaa gga ggg ggt att gga agc agt ttg ctc tcc aga atc acg      48
Met Asp Glu Gly Gly Gly Ile Gly Ser Ser Leu Leu Ser Arg Ile Thr
  1               5                  10                  15 acg aca gcc tct gaa att atg atg cga aac gaa ccg acg aca act gaa     96
Thr Thr Ala Ser Glu Ile Met Met Arg Asn Glu Pro Thr Thr Thr Glu
             20                  25                  30 aat cca gct gtt caa gaa atg aat cat att tat cat ttg aca cca agt    144
Asn Pro Ala Val Gln Glu Met Asn His Ile Tyr His Leu Thr Pro Ser
         35                  40                  45 atg aag atg tta tgt att ctt ttc tat agt ata ctt tgc gta tgc tgt    192
Met Lys Met Leu Cys Ile Leu Phe Tyr Ser Ile Leu Cys Val Cys Cys
     50                  55                  60 gtc tat gga aat gtg ctc gtt att ctg gtt att gtt tat ttt aaa cga    240
Val Tyr Gly Asn Val Leu Val Ile Leu Val Ile Val Tyr Phe Lys Arg
 65                  70                  75                  80 ctt cga acg gcg act aat att ttg ata ttg aac ttg gca gtt gct gat    288
Leu Arg Thr Ala Thr Asn Ile Leu Ile Leu Asn Leu Ala Val Ala Asp
                 85                  90                  95 ctt ctc ata tca gta ttc tgc att ccg ttc agc tat tgg caa gta ttg    336
Leu Leu Ile Ser Val Phe Cys Ile Pro Phe Ser Tyr Trp Gln Val Leu
            100                 105                 110 att tat gat gat caa cgt tgg ctc ttc ggc tca atg atg tgc tct tta    384
Ile Tyr Asp Asp Gln Arg Trp Leu Phe Gly Ser Met Met Cys Ser Leu
        115                 120                 125 tta gca ttc ctt caa gca atg gct gta ttt tta tca gct tgg aca ctt    432
Leu Ala Phe Leu Gln Ala Met Ala Val Phe Leu Ser Ala Trp Thr Leu
    130                 135                 140 gtc gtt atc agt ttt gat cgg tgg atg gct ata atg ttc ctt tta act    480
Val Val Ile Ser Phe Asp Arg Trp Met Ala Ile Met Phe Leu Leu Thr
145                 150                 155                 160 cca aat att cga att aca aga cga aga gct ctt tat ctg gta gct gcc    528
Pro Asn Ile Arg Ile Thr Arg Arg Arg Ala Leu Tyr Leu Val Ala Ala
                165                 170                 175 acg tgg ata ttc agt atc cta atg gcg ttg ccg tta ctc ttc aca acg    576
Thr Trp Ile Phe Ser Ile Leu Met Ala Leu Pro Leu Leu Phe Thr Thr
            180                 185                 190 aga ttt ttc gaa gac caa gac ggt tta ccg aat tgt gga gaa aat tgg    624
Arg Phe Phe Glu Asp Gln Asp Gly Leu Pro Asn Cys Gly Glu Asn Trp
        195                 200                 205 acg tat ttt gga gat tct gga gaa caa gtg aga aaa gtg tat tct tca    672
Thr Tyr Phe Gly Asp Ser Gly Glu Gln Val Arg Lys Val Tyr Ser Ser
    210                 215                 220 atg gtc tta att cta caa tat gtt gta cct caa gca gtt tta ata ata    720
Met Val Leu Ile Leu Gln Tyr Val Val Pro Gln Ala Val Leu Ile Ile
```

-continued

```
                    225                 230                 235                 240
act tac aca cat att gga att aaa atg tgg aat agt cga gta cca gga     768
Thr Tyr Thr His Ile Gly Ile Lys Met Trp Asn Ser Arg Val Pro Gly
                245                 250                 255 atg cag aat gga gca aca aag aaa atg atc gtt gat cga cat gaa agt     816
Met Gln Asn Gly Ala Thr Lys Lys Met Ile Val Asp Arg His Glu Ser
            260                 265                 270 gtc aaa aag ctg gtc cca atg gtg att ctc att tcg gca ctc ttc gca     864
Val Lys Lys Leu Val Pro Met Val Ile Leu Ile Ser Ala Leu Phe Ala
        275                 280                 285 ctt tgt tgg ctt cct tta ctt ata ctg atc aac gtc att cca gaa ttc     912
Leu Cys Trp Leu Pro Leu Leu Ile Leu Ile Asn Val Ile Pro Glu Phe
    290                 295                 300 tat cca gat atc aac agt tgg gga tat att ctg tat ttg tgg tgg ttt     960
Tyr Pro Asp Ile Asn Ser Trp Gly Tyr Ile Leu Tyr Leu Trp Trp Phe
305                 310                 315                 320 gct cat gga ctt gcc atg tct cat tca atg gtc aac cca att atc tat    1008
Ala His Gly Leu Ala Met Ser His Ser Met Val Asn Pro Ile Ile Tyr
                325                 330                 335 ttc att cga aat gcc cgt ttc cgt gaa gga ttc tgt ttc ttc tct tca    1056
Phe Ile Arg Asn Ala Arg Phe Arg Glu Gly Phe Cys Phe Phe Ser Ser
            340                 345                 350 aaa ctt ctt cca tgt ata tca ttt aaa gaa ctt cgt ctt tta act gat    1104
Lys Leu Leu Pro Cys Ile Ser Phe Lys Glu Leu Arg Leu Leu Thr Asp
        355                 360                 365 aat act agc aga aga cat cgc tta cga gat att cac gaa gtg gag tcc    1152
Asn Thr Ser Arg Arg His Arg Leu Arg Asp Ile His Glu Val Glu Ser
    370                 375                 380 ttg aca ggc aaa cat gtc gtt cgg cac gtt tct tcg aag ccc gac cac    1200
Leu Thr Gly Lys His Val Val Arg His Val Ser Ser Lys Pro Asp His
385                 390                 395                 400 tcg tcg tcg tcc gaa aca act ctg cca att ctc tcg cgt agc ttt tcc    1248
Ser Ser Ser Ser Glu Thr Thr Leu Pro Ile Leu Ser Arg Ser Phe Ser
                405                 410                 415 cgt atc att aag aaa att gat cta cca tgt act tga                    1284
Arg Ile Ile Lys Lys Ile Asp Leu Pro Cys Thr
            420                 425
```

<210> SEQ ID NO 115
<211> LENGTH: 427
<212> TYPE: PRT
<213> ORGANISM: Homo sapiens

<400> SEQUENCE: 115

```
Met Asp Glu Gly Gly Gly Ile Gly Ser Ser Leu Leu Ser Arg Ile Thr
 1               5                  10                  15

Thr Thr Ala Ser Glu Ile Met Met Arg Asn Glu Pro Thr Thr Thr Glu
            20                  25                  30

Asn Pro Ala Val Gln Glu Met Asn His Ile Tyr His Leu Thr Pro Ser
        35                  40                  45

Met Lys Met Leu Cys Ile Leu Phe Tyr Ser Ile Leu Cys Val Cys Cys
    50                  55                  60

Val Tyr Gly Asn Val Leu Val Ile Leu Val Ile Val Tyr Phe Lys Arg
65                  70                  75                  80

Leu Arg Thr Ala Thr Asn Ile Leu Ile Leu Asn Leu Ala Val Ala Asp
                85                  90                  95

Leu Leu Ile Ser Val Phe Cys Ile Pro Phe Ser Tyr Trp Gln Val Leu
            100                 105                 110
```

-continued

```
Ile Tyr Asp Asp Gln Arg Trp Leu Phe Gly Ser Met Met Cys Ser Leu
            115                 120                 125

Leu Ala Phe Leu Gln Ala Met Ala Val Phe Leu Ser Ala Trp Thr Leu
        130                 135                 140

Val Val Ile Ser Phe Asp Arg Trp Met Ala Ile Met Phe Leu Leu Thr
145                 150                 155                 160

Pro Asn Ile Arg Ile Thr Arg Arg Ala Leu Tyr Leu Val Ala Ala
                165                 170                 175

Thr Trp Ile Phe Ser Ile Leu Met Ala Leu Pro Leu Leu Phe Thr Thr
                180                 185                 190

Arg Phe Phe Glu Asp Gln Asp Gly Leu Pro Asn Cys Gly Glu Asn Trp
                195                 200                 205

Thr Tyr Phe Gly Asp Ser Gly Glu Gln Val Arg Lys Val Tyr Ser Ser
        210                 215                 220

Met Val Leu Ile Leu Gln Tyr Val Val Pro Gln Ala Val Leu Ile Ile
225                 230                 235                 240

Thr Tyr Thr His Ile Gly Ile Lys Met Trp Asn Ser Arg Val Pro Gly
                245                 250                 255

Met Gln Asn Gly Ala Thr Lys Lys Met Ile Val Asp Arg His Glu Ser
                260                 265                 270

Val Lys Lys Leu Val Pro Met Val Ile Leu Ile Ser Ala Leu Phe Ala
        275                 280                 285

Leu Cys Trp Leu Pro Leu Leu Ile Leu Ile Asn Val Ile Pro Glu Phe
    290                 295                 300

Tyr Pro Asp Ile Asn Ser Trp Gly Tyr Ile Leu Tyr Leu Trp Trp Phe
305                 310                 315                 320

Ala His Gly Leu Ala Met Ser His Ser Met Val Asn Pro Ile Ile Tyr
                325                 330                 335

Phe Ile Arg Asn Ala Arg Phe Arg Glu Gly Phe Cys Phe Phe Ser Ser
                340                 345                 350

Lys Leu Leu Pro Cys Ile Ser Phe Lys Glu Leu Arg Leu Leu Thr Asp
        355                 360                 365

Asn Thr Ser Arg Arg His Arg Leu Arg Asp Ile His Glu Val Glu Ser
    370                 375                 380

Leu Thr Gly Lys His Val Val Arg His Val Ser Ser Lys Pro Asp His
385                 390                 395                 400

Ser Ser Ser Ser Glu Thr Thr Leu Pro Ile Leu Ser Arg Ser Phe Ser
                405                 410                 415

Arg Ile Ile Lys Lys Ile Asp Leu Pro Cys Thr
                420                 425
```

<210> SEQ ID NO 116
<211> LENGTH: 1305
<212> TYPE: DNA
<213> ORGANISM: Homo sapiens
<220> FEATURE:
<223> OTHER INFORMATION: Clone identifier: CEGPCR24b (Y59H11A1.a-02)
<220> FEATURE:
<221> NAME/KEY: CDS
<222> LOCATION: (1)..(1302)

<400> SEQUENCE: 116

```
atg gac gaa gga ggg ggt att gga agc agt ttg ctc tcc aga atc acg        48
Met Asp Glu Gly Gly Gly Ile Gly Ser Ser Leu Leu Ser Arg Ile Thr
 1               5                  10                  15 acg aca gcc tct gaa att atg atg cga aac gaa ccg acg aca act gaa        96
Thr Thr Ala Ser Glu Ile Met Met Arg Asn Glu Pro Thr Thr Thr Glu
```

```
                 20                  25                  30
aat cca gct gtt caa gaa atg aat cat att tat cat ttg aca cca agt      144
Asn Pro Ala Val Gln Glu Met Asn His Ile Tyr His Leu Thr Pro Ser
         35                  40                  45 atg aag atg tta tgt att ctt ttc tat agt ata ctt tgc gta tgc tgt      192
Met Lys Met Leu Cys Ile Leu Phe Tyr Ser Ile Leu Cys Val Cys Cys
     50                  55                  60 gtc tat gga aat gtg ctc gtt att ctg gtt att gtt tat ttt aaa cga      240
Val Tyr Gly Asn Val Leu Val Ile Leu Val Ile Val Tyr Phe Lys Arg
 65                  70                  75                  80 ctt cga acg gcg act aat att ttg ata ttg aac ttg gca gtt gct gat      288
Leu Arg Thr Ala Thr Asn Ile Leu Ile Leu Asn Leu Ala Val Ala Asp
                 85                  90                  95 ctt ctc ata tca gta ttc tgc att ccg ttc agc tat tgg caa gta ttg      336
Leu Leu Ile Ser Val Phe Cys Ile Pro Phe Ser Tyr Trp Gln Val Leu
             100                 105                 110 att tat gat gat caa cgt tgg ctc ttc ggc tca atg atg tgc tct tta      384
Ile Tyr Asp Asp Gln Arg Trp Leu Phe Gly Ser Met Met Cys Ser Leu
         115                 120                 125 tta gca ttc ctt caa gca atg gct gta ttt tta tca gct tgg aca ctt      432
Leu Ala Phe Leu Gln Ala Met Ala Val Phe Leu Ser Ala Trp Thr Leu
     130                 135                 140 gtc gtt atc agt ttt gat cgg tgg atg gct ata atg ttc ctt tta act      480
Val Val Ile Ser Phe Asp Arg Trp Met Ala Ile Met Phe Leu Leu Thr
145                 150                 155                 160 cca aat att cga att aca aga cga aga gct ctt tat ctg gta gct gcc      528
Pro Asn Ile Arg Ile Thr Arg Arg Arg Ala Leu Tyr Leu Val Ala Ala
                 165                 170                 175 acg tgg ata ttc agt atc cta atg gcg ttg ccg tta ctc ttc aca acg      576
Thr Trp Ile Phe Ser Ile Leu Met Ala Leu Pro Leu Leu Phe Thr Thr
             180                 185                 190 aga ttt ttc gaa gac caa gac ggt tta ccg aat tgt gga gaa aat tgg      624
Arg Phe Phe Glu Asp Gln Asp Gly Leu Pro Asn Cys Gly Glu Asn Trp
         195                 200                 205 acg tat ttt gga gat tct gga gaa caa gtg aga aaa gtg tat tct tca      672
Thr Tyr Phe Gly Asp Ser Gly Glu Gln Val Arg Lys Val Tyr Ser Ser
     210                 215                 220 atg gtc tta att cta caa tat gtt gta cct caa gca gtt tta ata ata      720
Met Val Leu Ile Leu Gln Tyr Val Val Pro Gln Ala Val Leu Ile Ile
225                 230                 235                 240 act tac aca cat att gga att aaa atg tgg aat agt cga gta cca gga      768
Thr Tyr Thr His Ile Gly Ile Lys Met Trp Asn Ser Arg Val Pro Gly
                 245                 250                 255 atg cag aat gga gca aca aag aaa atg atc gtt gat cga cat gaa agt      816
Met Gln Asn Gly Ala Thr Lys Lys Met Ile Val Asp Arg His Glu Ser
             260                 265                 270 gtc aaa aag ctg gtc cca atg gtg att ctc att tcg gca ctc ttc gca      864
Val Lys Lys Leu Val Pro Met Val Ile Leu Ile Ser Ala Leu Phe Ala
         275                 280                 285 ctt tgt tgg ctt cct tta ctt ata ctg atc aac gtc att cca gaa ttc      912
Leu Cys Trp Leu Pro Leu Leu Ile Leu Ile Asn Val Ile Pro Glu Phe
     290                 295                 300 tat cca gat atc aac agt tgg gga tat att ctg tat ttg tgg tgg ttt      960
Tyr Pro Asp Ile Asn Ser Trp Gly Tyr Ile Leu Tyr Leu Trp Trp Phe
305                 310                 315                 320 gct cat gga ctt gcc atg tct cat tca atg gtc aac cca att atc tat     1008
Ala His Gly Leu Ala Met Ser His Ser Met Val Asn Pro Ile Ile Tyr
                 325                 330                 335 ttc att cga aat gcc cgt ttc cgt gaa gga ttc tgt ttc ttc tct tca     1056
```

```
Phe Ile Arg Asn Ala Arg Phe Arg Glu Gly Phe Cys Phe Phe Ser Ser
                340                 345                 350 aaa ctt ctt cca tgt ata tca ttt aaa gaa ctt cgt ctt tta act gat      1104
Lys Leu Leu Pro Cys Ile Ser Phe Lys Glu Leu Arg Leu Leu Thr Asp
            355                 360                 365 aat act agc aga agt ttt cga aac cgt tca cgg ttt tct ggt gtc ata      1152
Asn Thr Ser Arg Ser Phe Arg Asn Arg Ser Arg Phe Ser Gly Val Ile
        370                 375                 380 aat ccg act tca agc gat gaa aaa cct gct aca tcg ctt acg aga tat      1200
Asn Pro Thr Ser Ser Asp Glu Lys Pro Ala Thr Ser Leu Thr Arg Tyr
385                 390                 395                 400 tca cga agt gga gtc ctt gac agg caa aca tgt cgt tcg gca cgt ttc      1248
Ser Arg Ser Gly Val Leu Asp Arg Gln Thr Cys Arg Ser Ala Arg Phe
                405                 410                 415 ttc gaa gcc cga cca ctc gtc gtc gtc cga aac aac tct gcc aat tct      1296
Phe Glu Ala Arg Pro Leu Val Val Val Arg Asn Asn Ser Ala Asn Ser
            420                 425                 430 ctc gcg tag                                                           1305
Leu Ala
```

<210> SEQ ID NO 117
<211> LENGTH: 434
<212> TYPE: PRT
<213> ORGANISM: Homo sapiens

<400> SEQUENCE: 117

```
Met Asp Glu Gly Gly Gly Ile Gly Ser Ser Leu Leu Ser Arg Ile Thr
1               5                   10                  15

Thr Thr Ala Ser Glu Ile Met Met Arg Asn Glu Pro Thr Thr Thr Glu
            20                  25                  30

Asn Pro Ala Val Gln Glu Met Asn His Ile Tyr His Leu Thr Pro Ser
        35                  40                  45

Met Lys Met Leu Cys Ile Leu Phe Tyr Ser Ile Leu Cys Val Cys Cys
    50                  55                  60

Val Tyr Gly Asn Val Leu Val Ile Leu Val Ile Val Tyr Phe Lys Arg
65                  70                  75                  80

Leu Arg Thr Ala Thr Asn Ile Leu Ile Leu Asn Leu Ala Val Ala Asp
                85                  90                  95

Leu Leu Ile Ser Val Phe Cys Ile Pro Phe Ser Tyr Trp Gln Val Leu
            100                 105                 110

Ile Tyr Asp Asp Gln Arg Trp Leu Phe Gly Ser Met Met Cys Ser Leu
        115                 120                 125

Leu Ala Phe Leu Gln Ala Met Ala Val Phe Leu Ser Ala Trp Thr Leu
    130                 135                 140

Val Val Ile Ser Phe Asp Arg Trp Met Ala Ile Met Phe Leu Leu Thr
145                 150                 155                 160

Pro Asn Ile Arg Ile Thr Arg Arg Arg Ala Leu Tyr Leu Val Ala Ala
                165                 170                 175

Thr Trp Ile Phe Ser Ile Leu Met Ala Leu Pro Leu Leu Phe Thr Thr
            180                 185                 190

Arg Phe Phe Glu Asp Gln Asp Gly Leu Pro Asn Cys Gly Glu Asn Trp
        195                 200                 205

Thr Tyr Phe Gly Asp Ser Gly Glu Gln Val Arg Lys Val Tyr Ser Ser
    210                 215                 220

Met Val Leu Ile Leu Gln Tyr Val Val Pro Gln Ala Val Leu Ile Ile
225                 230                 235                 240
```

```
Thr Tyr Thr His Ile Gly Ile Lys Met Trp Asn Ser Arg Val Pro Gly
                245                 250                 255
Met Gln Asn Gly Ala Thr Lys Lys Met Ile Val Asp Arg His Glu Ser
                260                 265                 270
Val Lys Lys Leu Val Pro Met Val Ile Leu Ile Ser Ala Leu Phe Ala
                275                 280                 285
Leu Cys Trp Leu Pro Leu Leu Ile Leu Ile Asn Val Ile Pro Glu Phe
                290                 295                 300
Tyr Pro Asp Ile Asn Ser Trp Gly Tyr Ile Leu Tyr Leu Trp Trp Phe
305                 310                 315                 320
Ala His Gly Leu Ala Met Ser His Ser Met Val Asn Pro Ile Ile Tyr
                325                 330                 335
Phe Ile Arg Asn Ala Arg Phe Arg Glu Gly Phe Cys Phe Phe Ser Ser
                340                 345                 350
Lys Leu Leu Pro Cys Ile Ser Phe Lys Glu Leu Arg Leu Leu Thr Asp
                355                 360                 365
Asn Thr Ser Arg Ser Phe Arg Asn Arg Ser Arg Phe Ser Gly Val Ile
                370                 375                 380
Asn Pro Thr Ser Ser Asp Glu Lys Pro Ala Thr Ser Leu Thr Arg Tyr
385                 390                 395                 400
Ser Arg Ser Gly Val Leu Asp Arg Gln Thr Cys Arg Ser Ala Arg Phe
                405                 410                 415
Phe Glu Ala Arg Pro Leu Val Val Val Arg Asn Asn Ser Ala Asn Ser
                420                 425                 430
Leu Ala

<210> SEQ ID NO 118
<211> LENGTH: 10
<212> TYPE: PRT
<213> ORGANISM: A. suum/C. elegans (flp21 modified)
<220> FEATURE:
<221> NAME/KEY: SITE
<222> LOCATION: (1)
<223> OTHER INFORMATION: Xaa=IodoY
<220> FEATURE:
<221> NAME/KEY: MOD_RES
<222> LOCATION: (10)
<223> OTHER INFORMATION: AMIDATION
<220> FEATURE:
<223> OTHER INFORMATION: [I]Y AF9

<400> SEQUENCE: 118

Xaa Gly Leu Gly Pro Arg Pro Leu Arg Phe
 1               5                  10

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      analog
<220> FEATURE:
<221> NAME/KEY: SITE
<222> LOCATION: (1)
<223> OTHER INFORMATION: Xaa=IodoY
<220> FEATURE:
<221> NAME/KEY: MOD_RES
<222> LOCATION: (9)
<223> OTHER INFORMATION: AMIDATION

<400> SEQUENCE: 119

Xaa Asp Val Pro Gly Val Leu Arg Phe
```

<210> SEQ ID NO 120
<211> LENGTH: 12
<212> TYPE: PRT
<213> ORGANISM: C. elegans/flp 18
<220> FEATURE:
<221> NAME/KEY: MOD_RES
<222> LOCATION: (12)
<223> OTHER INFORMATION: AMIDATION

<400> SEQUENCE: 120

Asp Phe Asp Gly Ala Met Pro Gly Val Leu Arg Phe
 1               5                  10

<210> SEQ ID NO 121
<211> LENGTH: 8
<212> TYPE: PRT
<213> ORGANISM: C. elegans/flp 18
<220> FEATURE:
<221> NAME/KEY: MOD_RES
<222> LOCATION: (8)
<223> OTHER INFORMATION: AMIDATION

<400> SEQUENCE: 121

Glu Ile Pro Gly Val Leu Arg Phe
 1               5

<210> SEQ ID NO 122
<211> LENGTH: 7
<212> TYPE: PRT
<213> ORGANISM: Drosophila
<220> FEATURE:
<221> NAME/KEY: MOD_RES
<222> LOCATION: (7)
<223> OTHER INFORMATION: AMIDATION

<400> SEQUENCE: 122

Ser Asp Asn Phe Met Arg Phe
 1               5

<210> SEQ ID NO 123
<211> LENGTH: 7
<212> TYPE: PRT
<213> ORGANISM: Drosophila
<220> FEATURE:
<221> NAME/KEY: MOD_RES
<222> LOCATION: (7)
<223> OTHER INFORMATION: AMIDATION

<400> SEQUENCE: 123

Pro Asp Asn Phe Met Arg Phe
 1               5

<210> SEQ ID NO 124
<211> LENGTH: 0
<212> TYPE: PRT
<213> ORGANISM: synthetic

<400> SEQUENCE: 124

000

<210> SEQ ID NO 125
<211> LENGTH: 10
<212> TYPE: PRT
<213> ORGANISM: [Y] AF9 analog
<220> FEATURE:
<221> NAME/KEY: MOD_RES

```
<222> LOCATION: (10)
<223> OTHER INFORMATION: AMIDATION

<400> SEQUENCE: 125

Tyr Gly Leu Gly Pro Arg Pro Leu Arg Phe
 1               5                  10

<210> SEQ ID NO 126
<211> LENGTH: 4
<212> TYPE: PRT
<213> ORGANISM: Leech
<220> FEATURE:
<221> NAME/KEY: MOD_RES
<222> LOCATION: (4)
<223> OTHER INFORMATION: AMIDATION

<400> SEQUENCE: 126

Tyr Leu Arg Phe
 1

<210> SEQ ID NO 127
<211> LENGTH: 8
<212> TYPE: PRT
<213> ORGANISM: Lobster
<220> FEATURE:
<221> NAME/KEY: MOD_RES
<222> LOCATION: (8)
<223> OTHER INFORMATION: AMIDATION

<400> SEQUENCE: 127

Ser Asp Arg Asn Phe Leu Arg Phe
 1               5

<210> SEQ ID NO 128
<211> LENGTH: 4
<212> TYPE: PRT
<213> ORGANISM: Trematoda
<220> FEATURE:
<221> NAME/KEY: MOD_RES
<222> LOCATION: (4)
<223> OTHER INFORMATION: AMIDATION

<400> SEQUENCE: 128

Phe Leu Arg Phe
 1

<210> SEQ ID NO 129
<211> LENGTH: 4
<212> TYPE: PRT
<213> ORGANISM: Mollusca
<220> FEATURE:
<221> NAME/KEY: MOD_RES
<222> LOCATION: (4)
<223> OTHER INFORMATION: AMIDATION

<400> SEQUENCE: 129

Phe Met Arg Phe
 1

<210> SEQ ID NO 130
<211> LENGTH: 0
<212> TYPE: PRT
<213> ORGANISM: synthetic

<400> SEQUENCE: 130

000
```

```
<210> SEQ ID NO 131
<211> LENGTH: 7
<212> TYPE: PRT
<213> ORGANISM: Manduca
<220> FEATURE:
<221> NAME/KEY: MOD_RES
<222> LOCATION: (7)
<223> OTHER INFORMATION: AMIDATION

<400> SEQUENCE: 131

Asp Pro Ser Phe Leu Arg Phe
 1               5

<210> SEQ ID NO 132
<211> LENGTH: 0
<212> TYPE: PRT
<213> ORGANISM: synthetic

<400> SEQUENCE: 132

000

<210> SEQ ID NO 133
<211> LENGTH: 8
<212> TYPE: PRT
<213> ORGANISM: A. suum
<220> FEATURE:
<221> NAME/KEY: MOD_RES
<222> LOCATION: (8)
<223> OTHER INFORMATION: AMIDATION

<400> SEQUENCE: 133

Ala Gly Pro Arg Phe Ile Arg Phe
 1               5

<210> SEQ ID NO 134
<211> LENGTH: 0
<212> TYPE: PRT
<213> ORGANISM: synthetic

<400> SEQUENCE: 134

000

<210> SEQ ID NO 135
<211> LENGTH: 7
<212> TYPE: PRT
<213> ORGANISM: C. elegans (flp 1)
<220> FEATURE:
<221> NAME/KEY: MOD_RES
<222> LOCATION: (7)
<223> OTHER INFORMATION: AMIDATION

<400> SEQUENCE: 135

Lys Pro Asn Phe Leu Arg Tyr
 1               5

<210> SEQ ID NO 136
<211> LENGTH: 10
<212> TYPE: PRT
<213> ORGANISM: L. decemlineata
<220> FEATURE:
<221> NAME/KEY: MOD_RES
<222> LOCATION: (10)
<223> OTHER INFORMATION: AMIDATION

<400> SEQUENCE: 136

Ala Arg Gly Pro Gln Leu Arg Leu Arg Phe
 1               5                   10
```

```
<210> SEQ ID NO 137
<211> LENGTH: 4
<212> TYPE: PRT
<213> ORGANISM: Trematoda
<220> FEATURE:
<221> NAME/KEY: MOD_RES
<222> LOCATION: (4)
<223> OTHER INFORMATION: AMIDATION

<400> SEQUENCE: 137

Tyr Ile Arg Phe
 1

<210> SEQ ID NO 138
<211> LENGTH: 0
<212> TYPE: PRT
<213> ORGANISM: synthetic

<400> SEQUENCE: 138

000

<210> SEQ ID NO 139
<211> LENGTH: 8
<212> TYPE: PRT
<213> ORGANISM: C. elegans (flp 5)
<220> FEATURE:
<221> NAME/KEY: MOD_RES
<222> LOCATION: (8)
<223> OTHER INFORMATION: AMIDATION

<400> SEQUENCE: 139

Ala Gly Ala Lys Phe Ile Arg Phe
 1               5

<210> SEQ ID NO 140
<211> LENGTH: 0
<212> TYPE: PRT
<213> ORGANISM: synthetic

<400> SEQUENCE: 140

000

<210> SEQ ID NO 141
<211> LENGTH: 7
<212> TYPE: PRT
<213> ORGANISM: C. elegans (flp 14)
<220> FEATURE:
<221> NAME/KEY: MOD_RES
<222> LOCATION: (7)
<223> OTHER INFORMATION: AMIDATION

<400> SEQUENCE: 141

Lys His Glu Tyr Leu Arg Phe
 1               5

<210> SEQ ID NO 142
<211> LENGTH: 0
<212> TYPE: PRT
<213> ORGANISM: synthetic

<400> SEQUENCE: 142

000

<210> SEQ ID NO 143
<211> LENGTH: 8
<212> TYPE: PRT
```

```
<213> ORGANISM: C. elegans flp3
<220> FEATURE:
<221> NAME/KEY: MOD_RES
<222> LOCATION: (8)
<223> OTHER INFORMATION: AMIDATION

<400> SEQUENCE: 143

Ser Pro Leu Gly Thr Met Arg Phe
 1               5

<210> SEQ ID NO 144
<211> LENGTH: 0
<212> TYPE: PRT
<213> ORGANISM: synthetic

<400> SEQUENCE: 144

000

<210> SEQ ID NO 145
<211> LENGTH: 0
<212> TYPE: PRT
<213> ORGANISM: synthetic

<400> SEQUENCE: 145

000

<210> SEQ ID NO 146
<211> LENGTH: 0
<212> TYPE: PRT
<213> ORGANISM: synthetic

<400> SEQUENCE: 146

000

<210> SEQ ID NO 147
<211> LENGTH: 0
<212> TYPE: PRT
<213> ORGANISM: synthetic

<400> SEQUENCE: 147

000

<210> SEQ ID NO 148
<211> LENGTH: 0
<212> TYPE: PRT
<213> ORGANISM: synthetic

<400> SEQUENCE: 148

000

<210> SEQ ID NO 149
<211> LENGTH: 0
<212> TYPE: PRT
<213> ORGANISM: synthetic

<400> SEQUENCE: 149

000

<210> SEQ ID NO 150
<211> LENGTH: 11
<212> TYPE: PRT
<213> ORGANISM: A. suum
<220> FEATURE:
<221> NAME/KEY: MOD_RES
<222> LOCATION: (11)
```

```
<223> OTHER INFORMATION: AMIDATION

<400> SEQUENCE: 150

Ala Glu Gly Leu Ser Ser Pro Leu Ile Arg Phe
 1               5                   10

<210> SEQ ID NO 151
<211> LENGTH: 8
<212> TYPE: PRT
<213> ORGANISM: A. suum
<220> FEATURE:
<221> NAME/KEY: MOD_RES
<222> LOCATION: (8)
<223> OTHER INFORMATION: AMIDATION

<400> SEQUENCE: 151

Phe Asp Arg Asp Phe Met His Phe
 1               5

<210> SEQ ID NO 152
<211> LENGTH: 4
<212> TYPE: PRT
<213> ORGANISM: Artificial Sequence
<220> FEATURE:
<221> NAME/KEY: MOD_RES
<222> LOCATION: (4)
<223> OTHER INFORMATION: AMIDATION
<220> FEATURE:
<223> OTHER INFORMATION: Description of Artificial Sequence: synthetic
      analog

<400> SEQUENCE: 152

Val Leu Arg Phe
 1

<210> SEQ ID NO 153
<211> LENGTH: 5
<212> TYPE: PRT
<213> ORGANISM: Artificial Sequence
<220> FEATURE:
<221> NAME/KEY: MOD_RES
<222> LOCATION: (5)
<223> OTHER INFORMATION: AMIDATION
<220> FEATURE:
<223> OTHER INFORMATION: Description of Artificial Sequence: synthetic
      analog

<400> SEQUENCE: 153

Gly Val Leu Arg Phe
 1               5

<210> SEQ ID NO 154
<211> LENGTH: 5
<212> TYPE: PRT
<213> ORGANISM: Artificial Sequence
<220> FEATURE:
<221> NAME/KEY: MOD_RES
<222> LOCATION: (5)
<223> OTHER INFORMATION: AMIDATION
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: synthetic
      analog

<400> SEQUENCE: 154

Gly Val Leu Arg Phe
 1               5
```

<210> SEQ ID NO 155
<211> LENGTH: 6
<212> TYPE: PRT
<213> ORGANISM: Artificial Sequence
<220> FEATURE:
<221> NAME/KEY: MOD_RES
<222> LOCATION: (6)
<223> OTHER INFORMATION: AMIDATION
<220> FEATURE:
<223> OTHER INFORMATION: Description of Artificial Sequence: synthetic
      analog

<400> SEQUENCE: 155

Pro Gly Val Leu Arg Phe
 1               5

<210> SEQ ID NO 156
<211> LENGTH: 7
<212> TYPE: PRT
<213> ORGANISM: Artificial Sequence
<220> FEATURE:
<221> NAME/KEY: MOD_RES
<222> LOCATION: (7)
<223> OTHER INFORMATION: AMIDATION
<220> FEATURE:
<223> OTHER INFORMATION: Description of Artificial Sequence: synthetic
      analog

<400> SEQUENCE: 156

Val Pro Gly Val Leu Arg Phe
 1               5

<210> SEQ ID NO 157
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (7)
<223> OTHER INFORMATION: AMIDATION
<220> FEATURE:
<223> OTHER INFORMATION: Description of Artificial Sequence: synthetic
      analog

<400> SEQUENCE: 157

Val Pro Gly Val Leu Arg Phe
 1               5

<210> SEQ ID NO 158
<211> LENGTH: 9
<212> TYPE: PRT
<213> ORGANISM: Artificial Sequence
<220> FEATURE:
<221> NAME/KEY: MOD_RES
<222> LOCATION: (9)
<223> OTHER INFORMATION: AMIDATION
<220> FEATURE:
<223> OTHER INFORMATION: Description of Artificial Sequence: synthetic
      analog

<400> SEQUENCE: 158

Tyr Asp Val Pro Gly Val Leu Arg Phe
 1               5

<210> SEQ ID NO 159

```
<211> LENGTH: 8
<212> TYPE: PRT
<213> ORGANISM: Artificial Sequence
<220> FEATURE:
<221> NAME/KEY: MOD_RES
<222> LOCATION: (8)
<223> OTHER INFORMATION: AMIDATION
<220> FEATURE:
<223> OTHER INFORMATION: Description of Artificial Sequence: synthetic
      analog

<400> SEQUENCE: 159

Tyr Val Pro Gly Val Leu Arg Phe
 1               5

<210> SEQ ID NO 160
<211> LENGTH: 8
<212> TYPE: PRT
<213> ORGANISM: Artificial Sequence
<220> FEATURE:
<221> NAME/KEY: MOD_RES
<222> LOCATION: (8)
<223> OTHER INFORMATION: AMIDATION
<220> FEATURE:
<221> NAME/KEY: SITE
<222> LOCATION: (1)
<223> OTHER INFORMATION: Xaa=3-Iodo-Y
<220> FEATURE:
<223> OTHER INFORMATION: Description of Artificial Sequence: synthetic
      analog

<400> SEQUENCE: 160

Xaa Val Pro Gly Val Leu Arg Phe
 1               5

<210> SEQ ID NO 161
<211> LENGTH: 7
<212> TYPE: PRT
<213> ORGANISM: Artificial Sequence
<220> FEATURE:
<221> NAME/KEY: MOD_RES
<222> LOCATION: (7)
<223> OTHER INFORMATION: AMIDATION
<220> FEATURE:
<223> OTHER INFORMATION: Description of Artificial Sequence: synthetic
      analog

<400> SEQUENCE: 161

Tyr Pro Gly Val Leu Arg Phe
 1               5

<210> SEQ ID NO 162
<211> LENGTH: 7
<212> TYPE: PRT
<213> ORGANISM: Artificial Sequence
<220> FEATURE:
<221> NAME/KEY: MOD_RES
<222> LOCATION: (7)
<223> OTHER INFORMATION: AMIDATION
<220> FEATURE:
<221> NAME/KEY: SITE
<222> LOCATION: (1)
<223> OTHER INFORMATION: Xaa= 3-Iodo-Y
<220> FEATURE:
<223> OTHER INFORMATION: Description of Artificial Sequence: synthetic
      analog

<400> SEQUENCE: 162

Xaa Pro Gly Val Leu Arg Phe
 1               5
```

```
<210> SEQ ID NO 163
<211> LENGTH: 6
<212> TYPE: PRT
<213> ORGANISM: Artificial Sequence
<220> FEATURE:
<221> NAME/KEY: MOD_RES
<222> LOCATION: (6)
<223> OTHER INFORMATION: AMIDATION
<220> FEATURE:
<223> OTHER INFORMATION: Description of Artificial Sequence: synthetic
      analog

<400> SEQUENCE: 163

Tyr Gly Val Leu Arg Phe
 1               5

<210> SEQ ID NO 164
<211> LENGTH: 6
<212> TYPE: PRT
<213> ORGANISM: Artificial Sequence
<220> FEATURE:
<221> NAME/KEY: SITE
<222> LOCATION: (1)
<223> OTHER INFORMATION: Xaa=3-Iodo-Y
<220> FEATURE:
<221> NAME/KEY: MOD_RES
<222> LOCATION: (6)
<223> OTHER INFORMATION: AMIDATION
<220> FEATURE:
<223> OTHER INFORMATION: Description of Artificial Sequence: synthetic
      analog

<400> SEQUENCE: 164

Xaa Gly Val Leu Arg Phe
 1               5

<210> SEQ ID NO 165
<211> LENGTH: 7
<212> TYPE: PRT
<213> ORGANISM: P. redivivus
<220> FEATURE:
<221> NAME/KEY: MOD_RES
<222> LOCATION: (7)
<223> OTHER INFORMATION: AMIDATION
<220> FEATURE:
<223> OTHER INFORMATION: PF4

<400> SEQUENCE: 165

Lys Pro Asn Phe Ile Arg Phe
 1               5

<210> SEQ ID NO 166
<211> LENGTH: 8
<212> TYPE: PRT
<213> ORGANISM: C. elegans flp1
<220> FEATURE:
<221> NAME/KEY: MOD_RES
<222> LOCATION: (8)
<223> OTHER INFORMATION: AMIDATION

<400> SEQUENCE: 166

Ser Gln Pro Asn Phe Leu Arg Phe
 1               5

<210> SEQ ID NO 167
<211> LENGTH: 8
<212> TYPE: PRT
<213> ORGANISM: H. contortus
<220> FEATURE:
<221> NAME/KEY: MOD_RES
<222> LOCATION: (8)
```

```
<223> OTHER INFORMATION: AMIDATION

<400> SEQUENCE: 167

Leu Gln Pro Asn Phe Leu Arg Phe
 1               5

<210> SEQ ID NO 168
<211> LENGTH: 0
<212> TYPE: PRT
<213> ORGANISM: Artificial Sequence
<220> FEATURE:
<223> OTHER INFORMATION: Description of Artificial Sequence: synthetic
      analog

<400> SEQUENCE: 168

000

<210> SEQ ID NO 169
<211> LENGTH: 0
<212> TYPE: PRT
<213> ORGANISM: Artificial Sequence
<220> FEATURE:
<223> OTHER INFORMATION: Description of Artificial Sequence: synthetic
      analog

<400> SEQUENCE: 169

000

<210> SEQ ID NO 170
<211> LENGTH: 0
<212> TYPE: PRT
<213> ORGANISM: Artificial Sequence
<220> FEATURE:
<223> OTHER INFORMATION: Description of Artificial Sequence: synthetic
      analog

<400> SEQUENCE: 170

000

<210> SEQ ID NO 171
<211> LENGTH: 25
<212> TYPE: DNA
<213> ORGANISM: Artificial Sequence
<220> FEATURE:
<223> OTHER INFORMATION: SCN162
<220> FEATURE:
<223> OTHER INFORMATION: Description of Artificial Sequence: synthetic

<400> SEQUENCE: 171
acgtttaaga gctctcaaat cccat                                          25

<210> SEQ ID NO 172
<211> LENGTH: 25
<212> TYPE: DNA
<213> ORGANISM: Artificial Sequence
<220> FEATURE:
<223> OTHER INFORMATION: SCN160
<220> FEATURE:
<223> OTHER INFORMATION: Description of Artificial Sequence: synthetic

<400> SEQUENCE: 172
ccagagctca tcaaaactca agaat                                          25

<210> SEQ ID NO 173
<211> LENGTH: 31
<212> TYPE: DNA
<213> ORGANISM: Artificial Sequence
```

```
<220> FEATURE:
<223> OTHER INFORMATION: DEL-1850 (CEGPCR12c_F.2)
<220> FEATURE:
<223> OTHER INFORMATION: Description of Artificial Sequence: primer

<400> SEQUENCE: 173
gccgccatgt cgaatgatct cgtgccttca g                               31

<210> SEQ ID NO 174
<211> LENGTH: 25
<212> TYPE: DNA
<213> ORGANISM: Artificial Sequence
<220> FEATURE:
<223> OTHER INFORMATION: SCN189
<220> FEATURE:
<223> OTHER INFORMATION: Description of Artificial Sequence: synthetic

<400> SEQUENCE: 174
ttacaattta aaactaggtg cttct                                      25

<210> SEQ ID NO 175
<211> LENGTH: 31
<212> TYPE: DNA
<213> ORGANISM: Artificial Sequence
<220> FEATURE:
<223> OTHER INFORMATION: SCN199
<220> FEATURE:
<223> OTHER INFORMATION: Description of Artificial Sequence: synthetic

<400> SEQUENCE: 175
gccgccatga cttttcggc caccgattcg a                                31

<210> SEQ ID NO 176
<211> LENGTH: 1233
<212> TYPE: DNA
<213> ORGANISM: C. elegans
<220> FEATURE:
<221> NAME/KEY: CDS
<222> LOCATION: (1)..(1230)
<220> FEATURE:
<223> OTHER INFORMATION: CEGPCR2

<400> SEQUENCE: 176 atg gcc cgt gca gtc aac ata tct cca ttc gct tct tat aca gtc gta    48
Met Ala Arg Ala Val Asn Ile Ser Pro Phe Ala Ser Tyr Thr Val Val
 1               5                  10                  15 cca att acc tcg gca tgg cca ccg gac gac ttg aaa gcc gat cga gtt    96
Pro Ile Thr Ser Ala Trp Pro Pro Asp Asp Leu Lys Ala Asp Arg Val
             20                  25                  30 caa ctt gcc agt ttc acg act gga aaa gct ctg cta gcc att gcc att   144
Gln Leu Ala Ser Phe Thr Thr Gly Lys Ala Leu Leu Ala Ile Ala Ile
         35                  40                  45 ctt gca atg att att atg aca acg gtc ggc aat gcg ctg gtt tgc tta   192
Leu Ala Met Ile Ile Met Thr Thr Val Gly Asn Ala Leu Val Cys Leu
     50                  55                  60 gca gtt tta ctg gta cga aag ttg aaa cat cct caa aat ttt ctt ttg   240
Ala Val Leu Leu Val Arg Lys Leu Lys His Pro Gln Asn Phe Leu Leu
 65                  70                  75                  80 gtc tca ctg gca gtg gcg gac ttt ttc gtg ggg ctc gtt gtg atg cca   288
Val Ser Leu Ala Val Ala Asp Phe Phe Val Gly Leu Val Val Met Pro
                 85                  90                  95 ctt gca ctg att gac ctt ctc ttc gat aaa tgg cca ctt gga agc acc   336
Leu Ala Leu Ile Asp Leu Leu Phe Asp Lys Trp Pro Leu Gly Ser Thr
            100                 105                 110 atg tgt tcg gtg tac aca aca tcc gac cta acg cta tgc act gct tca   384
```

```
Met Cys Ser Val Tyr Thr Thr Ser Asp Leu Thr Leu Cys Thr Ala Ser
            115                 120                 125
att gtg aat ctg tgt gca ata tca gtt gat aga tat ctg gtg att tca      432
Ile Val Asn Leu Cys Ala Ile Ser Val Asp Arg Tyr Leu Val Ile Ser
        130                 135                 140
agt cca ctt cgg tat tct gca aaa cga aca act aaa cgt atc atg atg      480
Ser Pro Leu Arg Tyr Ser Ala Lys Arg Thr Thr Lys Arg Ile Met Met
145                 150                 155                 160
tat att gcc tgt gta tgg atc atc gct gcc att gtg agc att tcg tcg      528
Tyr Ile Ala Cys Val Trp Ile Ile Ala Ala Ile Val Ser Ile Ser Ser
                165                 170                 175
cac att atc gca aat ctt ctg aac gac ggc act tat gtc gat gac acg      576
His Ile Ile Ala Asn Leu Leu Asn Asp Gly Thr Tyr Val Asp Asp Thr
            180                 185                 190
gga act tgt cag gtc atc cct cat ttc atc tat caa agc tat gct aca      624
Gly Thr Cys Gln Val Ile Pro His Phe Ile Tyr Gln Ser Tyr Ala Thr
        195                 200                 205
att atc tca ttc tat gcg cca aca ttt atc atg gtc atc ttg aac atc      672
Ile Ile Ser Phe Tyr Ala Pro Thr Phe Ile Met Val Ile Leu Asn Ile
    210                 215                 220
aaa att tgg cga gca gca aaa cga ttg gca gct caa gac agg ttg atg      720
Lys Ile Trp Arg Ala Ala Lys Arg Leu Ala Ala Gln Asp Arg Leu Met
225                 230                 235                 240
tct cac tgt aac tct gtg gat gcc tcc gaa cgg cca cga aat gga tca      768
Ser His Cys Asn Ser Val Asp Ala Ser Glu Arg Pro Arg Asn Gly Ser
                245                 250                 255
gct gag aca aag gat ttc ctg aat gag aaa gaa aca att gat gtt ccg      816
Ala Glu Thr Lys Asp Phe Leu Asn Glu Lys Glu Thr Ile Asp Val Pro
            260                 265                 270
aaa aaa gag cgg gcc aat tca aca aac tcg agg ctt ttc aag ttg gaa      864
Lys Lys Glu Arg Ala Asn Ser Thr Asn Ser Arg Leu Phe Lys Leu Glu
        275                 280                 285
cgt aaa tat ctt cat cga ccc agt gca ttc ttt tcg gct gca aaa gga      912
Arg Lys Tyr Leu His Arg Pro Ser Ala Phe Phe Ser Ala Ala Lys Gly
    290                 295                 300
cca ttg att cgg cag acg gag aaa agt gaa tgc aaa gcc cgg aaa aca      960
Pro Leu Ile Arg Gln Thr Glu Lys Ser Glu Cys Lys Ala Arg Lys Thr
305                 310                 315                 320
ttg ggg gtc atc atg tca gtg ttc att att tgc tgg ctc cca ttc ttc     1008
Leu Gly Val Ile Met Ser Val Phe Ile Ile Cys Trp Leu Pro Phe Phe
                325                 330                 335
att ctt gcc ata ttc aag tct ttc ggc atg tgg atc ccg gat tgg ttg     1056
Ile Leu Ala Ile Phe Lys Ser Phe Gly Met Trp Ile Pro Asp Trp Leu
            340                 345                 350
gat ctg cta gca ctg tgg tta ggc tac tca aat agc aca tta aat cca     1104
Asp Leu Leu Ala Leu Trp Leu Gly Tyr Ser Asn Ser Thr Leu Asn Pro
        355                 360                 365
ttg atc tac tgc aag tac aac aaa gag ttt cga ata cca ttc cgt gaa     1152
Leu Ile Tyr Cys Lys Tyr Asn Lys Glu Phe Arg Ile Pro Phe Arg Glu
    370                 375                 380
atg ctt gct tgt cgc tgt gct act tta cag act gta atg cga caa caa     1200
Met Leu Ala Cys Arg Cys Ala Thr Leu Gln Thr Val Met Arg Gln Gln
385                 390                 395                 400
agc ttc acc agc cgc tac gga cct cct gtg tga                          1233
Ser Phe Thr Ser Arg Tyr Gly Pro Pro Val
                405                 410

<210> SEQ ID NO 177
<211> LENGTH: 410
<212> TYPE: PRT
```

-continued

<213> ORGANISM: C. elegans

<400> SEQUENCE: 177

```
Met Ala Arg Ala Val Asn Ile Ser Pro Phe Ala Ser Tyr Thr Val Val
  1               5                  10                  15

Pro Ile Thr Ser Ala Trp Pro Pro Asp Asp Leu Lys Ala Asp Arg Val
             20                  25                  30

Gln Leu Ala Ser Phe Thr Thr Gly Lys Ala Leu Leu Ala Ile Ala Ile
         35                  40                  45

Leu Ala Met Ile Ile Met Thr Thr Val Gly Asn Ala Leu Val Cys Leu
     50                  55                  60

Ala Val Leu Leu Val Arg Lys Leu Lys His Pro Gln Asn Phe Leu Leu
 65                  70                  75                  80

Val Ser Leu Ala Val Ala Asp Phe Phe Val Gly Leu Val Val Met Pro
                 85                  90                  95

Leu Ala Leu Ile Asp Leu Leu Phe Asp Lys Trp Pro Leu Gly Ser Thr
                100                 105                 110

Met Cys Ser Val Tyr Thr Thr Ser Asp Leu Thr Leu Cys Thr Ala Ser
            115                 120                 125

Ile Val Asn Leu Cys Ala Ile Ser Val Asp Arg Tyr Leu Val Ile Ser
        130                 135                 140

Ser Pro Leu Arg Tyr Ser Ala Lys Arg Thr Thr Lys Arg Ile Met Met
145                 150                 155                 160

Tyr Ile Ala Cys Val Trp Ile Ala Ala Ile Val Ser Ile Ser Ser
                165                 170                 175

His Ile Ile Ala Asn Leu Leu Asn Asp Gly Thr Tyr Val Asp Asp Thr
            180                 185                 190

Gly Thr Cys Gln Val Ile Pro His Phe Ile Tyr Gln Ser Tyr Ala Thr
        195                 200                 205

Ile Ile Ser Phe Tyr Ala Pro Thr Phe Ile Met Val Ile Leu Asn Ile
    210                 215                 220

Lys Ile Trp Arg Ala Ala Lys Arg Leu Ala Ala Gln Asp Arg Leu Met
225                 230                 235                 240

Ser His Cys Asn Ser Val Asp Ala Ser Glu Arg Pro Arg Asn Gly Ser
                245                 250                 255

Ala Glu Thr Lys Asp Phe Leu Asn Glu Lys Thr Ile Asp Val Pro
            260                 265                 270

Lys Lys Glu Arg Ala Asn Ser Thr Asn Ser Arg Leu Phe Lys Leu Glu
        275                 280                 285

Arg Lys Tyr Leu His Arg Pro Ser Ala Phe Phe Ser Ala Ala Lys Gly
    290                 295                 300

Pro Leu Ile Arg Gln Thr Glu Lys Ser Glu Cys Lys Ala Arg Lys Thr
305                 310                 315                 320

Leu Gly Val Ile Met Ser Val Phe Ile Ile Cys Trp Leu Pro Phe Phe
                325                 330                 335

Ile Leu Ala Ile Phe Lys Ser Phe Gly Met Trp Ile Pro Asp Trp Leu
            340                 345                 350

Asp Leu Leu Ala Leu Trp Leu Gly Tyr Ser Asn Ser Thr Leu Asn Pro
        355                 360                 365

Leu Ile Tyr Cys Lys Tyr Asn Lys Glu Phe Arg Ile Pro Phe Arg Glu
    370                 375                 380

Met Leu Ala Cys Arg Cys Ala Thr Leu Gln Thr Val Met Arg Gln Gln
385                 390                 395                 400
```

```
Ser Phe Thr Ser Arg Tyr Gly Pro Pro Val
            405                 410

<210> SEQ ID NO 178
<211> LENGTH: 1749
<212> TYPE: DNA
<213> ORGANISM: C. elegans
<220> FEATURE:
<223> OTHER INFORMATION: CEGPCR25 (Y39A3B.5)
<220> FEATURE:
<221> NAME/KEY: CDS
<222> LOCATION: (1)..(1746)

<400> SEQUENCE: 178 atg tca acg gta cat cag gag gaa ata tgc cgg ttt cgt ggt aca aca      48
Met Ser Thr Val His Gln Glu Glu Ile Cys Arg Phe Arg Gly Thr Thr
  1               5                  10                  15 gaa aat tac aca atc gcc gtg acg ttt ttc atg att ttt ttg cta tca      96
Glu Asn Tyr Thr Ile Ala Val Thr Phe Phe Met Ile Phe Leu Leu Ser
             20                  25                  30 gtc gtc gga aat tcg gtg gtt ttg ata gtg att att aag caa cgt gca     144
Val Val Gly Asn Ser Val Val Leu Ile Val Ile Ile Lys Gln Arg Ala
         35                  40                  45 atg cga tca ata acc aat ata tat tta atg aat ctg gcg gca tcg gat     192
Met Arg Ser Ile Thr Asn Ile Tyr Leu Met Asn Leu Ala Ala Ser Asp
     50                  55                  60 atg atg tta tca gtg gtt tgt atg ccg ccg aca ctt gtc tcc atg gtt     240
Met Met Leu Ser Val Val Cys Met Pro Pro Thr Leu Val Ser Met Val
 65                  70                  75                  80 atg aat tgt tgg atg ttc ggc aat tat atg tgc aaa att ttg gct tat     288
Met Asn Cys Trp Met Phe Gly Asn Tyr Met Cys Lys Ile Leu Ala Tyr
                 85                  90                  95 ttg caa ccc gta gta gtc act gct tca gcg tac acc cta gca gta atc     336
Leu Gln Pro Val Val Val Thr Ala Ser Ala Tyr Thr Leu Ala Val Ile
            100                 105                 110 gca ttc gag agg tac ttt gca att tgc aag ccg ctt cac tca agg att     384
Ala Phe Glu Arg Tyr Phe Ala Ile Cys Lys Pro Leu His Ser Arg Ile
        115                 120                 125 tgg caa acc aga tcc cac gcc tac gca atg atc aca ctt gtg tgg gtg     432
Trp Gln Thr Arg Ser His Ala Tyr Ala Met Ile Thr Leu Val Trp Val
    130                 135                 140 atc gcc att gcc gcc aat att ctg atg ctt ttt atg tac gaa caa caa     480
Ile Ala Ile Ala Ala Asn Ile Leu Met Leu Phe Met Tyr Glu Gln Gln
145                 150                 155                 160 acg tat agc tcg aat gga tac acg tgt gct cca att cat ccg ccg att     528
Thr Tyr Ser Ser Asn Gly Tyr Thr Cys Ala Pro Ile His Pro Pro Ile
                165                 170                 175 tat cat ttt gct tat cag gaa aat cgg aaa ttt cac tta aaa tcg ata     576
Tyr His Phe Ala Tyr Gln Glu Asn Arg Lys Phe His Leu Lys Ser Ile
            180                 185                 190 ata tat ttt cag gta tac atg acc gtc gtc cta ctt gta atc ccg cta     624
Ile Tyr Phe Gln Val Tyr Met Thr Val Val Leu Leu Val Ile Pro Leu
        195                 200                 205 gtt gtg atg gcg ggt ttg tac ggc aac gtc att acc tcc cta aaa tcc     672
Val Val Met Ala Gly Leu Tyr Gly Asn Val Ile Thr Ser Leu Lys Ser
    210                 215                 220 ggc atc aaa ctg gaa atc gcc tct gtg gat ccg ccg ctc gcc acc gcc     720
Gly Ile Lys Leu Glu Ile Ala Ser Val Asp Pro Pro Leu Ala Thr Ala
225                 230                 235                 240 aca acc aca ggt gct aaa aat tta ggc tcc cac tct gac tcg gct cac     768
Thr Thr Thr Gly Ala Lys Asn Leu Gly Ser His Ser Asp Ser Ala His
                245                 250                 255
```

-continued

```
ctt ttg ttg aac aat gtg ctc gtc ggt agc tcg caa tta gct cgt gcc      816
Leu Leu Leu Asn Asn Val Leu Val Gly Ser Ser Gln Leu Ala Arg Ala
            260                 265                 270 acg tcg tgc atc gcg ttg aac acg ttt tcc tgc aac aac acc act aac      864
Thr Ser Cys Ile Ala Leu Asn Thr Phe Ser Cys Asn Asn Thr Thr Asn
        275                 280                 285 ccc ttc agt acc ctg aca ccg ccg ccg att cag cag aaa aat cga          912
Pro Phe Ser Thr Leu Thr Pro Pro Pro Ile Gln Gln Lys Asn Arg
    290                 295                 300 tcg aag ccg caa ctt ctg cag ctg ccc gga aaa atc gat aat ttc gaa      960
Ser Lys Pro Gln Leu Leu Gln Leu Pro Gly Lys Ile Asp Asn Phe Glu
305                 310                 315                 320 gag ttc cgc ctt cag tgc ctg tcc gac tgt cgt agt gat gga gtg ttg     1008
Glu Phe Arg Leu Gln Cys Leu Ser Asp Cys Arg Ser Asp Gly Val Leu
            325                 330                 335 ttt ccc ccg cca gca att gtt gcg tcg atg acc gac gag caa aag tta    1056
Phe Pro Pro Pro Ala Ile Val Ala Ser Met Thr Asp Glu Gln Lys Leu
            340                 345                 350 tcg ttc tgg aat aag ctg tcg aac aag ctg act ttt agt cag caa gat    1104
Ser Phe Trp Asn Lys Leu Ser Asn Lys Leu Thr Phe Ser Gln Gln Asp
            355                 360                 365 aaa acc gtg caa cac cca aac ttt ggg cat cgc aaa tcc gac aca tca    1152
Lys Thr Val Gln His Pro Asn Phe Gly His Arg Lys Ser Asp Thr Ser
370                 375                 380 att tgc ctc gaa aat cct agt tta agg tct acg cac act cag aaa agt    1200
Ile Cys Leu Glu Asn Pro Ser Leu Arg Ser Thr His Thr Gln Lys Ser
385                 390                 395                 400 gca atg gca aag caa aga gtg att aaa atg ctc att gtt gtc gta att    1248
Ala Met Ala Lys Gln Arg Val Ile Lys Met Leu Ile Val Val Val Ile
                405                 410                 415 atc ttt ttc tgt tgt tgg acg cct tcc tac atc tgg tgg tta ttg        1296
Ile Phe Phe Cys Cys Trp Thr Pro Ser Tyr Ile Trp Trp Leu Leu Leu
            420                 425                 430 atc gcg gga gac tcg ttt caa agc ctc aac tta tct gtc tgg aac agc    1344
Ile Ala Gly Asp Ser Phe Gln Ser Leu Asn Leu Ser Val Trp Asn Ser
            435                 440                 445 gat atc aac aca ttc atc act ctt ctt acc tat att tct tca tgc acc    1392
Asp Ile Asn Thr Phe Ile Thr Leu Leu Thr Tyr Ile Ser Ser Cys Thr
450                 455                 460 aat ccc atc aca tat tgc ttc ctg aac aaa aaa ttt agg aat gcg gtg    1440
Asn Pro Ile Thr Tyr Cys Phe Leu Asn Lys Lys Phe Arg Asn Ala Val
465                 470                 475                 480 tat gca aca ttt ggc agg aag aaa aat atg cga cat cat ttt cag aag    1488
Tyr Ala Thr Phe Gly Arg Lys Lys Asn Met Arg His His Phe Gln Lys
                485                 490                 495 gta tat ttt gat att ttt gaa tta ttg ata ttt ttt aaa atc aat tat    1536
Val Tyr Phe Asp Ile Phe Glu Leu Leu Ile Phe Phe Lys Ile Asn Tyr
                500                 505                 510 caa aaa tca ata aaa tct ccg gtt tca gtt ttt tct aac tat ctg ttt    1584
Gln Lys Ser Ile Lys Ser Pro Val Ser Val Phe Ser Asn Tyr Leu Phe
                515                 520                 525 ttc ggc ttt tcg gcg ccg cta att tct gtt aac ctt agt ttg att ttg    1632
Phe Gly Phe Ser Ala Pro Leu Ile Ser Val Asn Leu Ser Leu Ile Leu
        530                 535                 540 ttc agg tct aca ttc cgg tca acg gcg gaa cta att aca cta aca aag    1680
Phe Arg Ser Thr Phe Arg Ser Thr Ala Glu Leu Ile Thr Leu Thr Lys
545                 550                 555                 560 gag agc cga gac aaa tta tta aca ggt act aac aca cac aaa ttt gta    1728
Glu Ser Arg Asp Lys Leu Leu Thr Gly Thr Asn Thr His Lys Phe Val
```

```
                565                 570                 575
gtg att tcg ctt ttt gtc tag                                           1749
Val Ile Ser Leu Phe Val
            580
```

<210> SEQ ID NO 179
<211> LENGTH: 582
<212> TYPE: PRT
<213> ORGANISM: C. elegans

<400> SEQUENCE: 179

```
Met Ser Thr Val His Gln Glu Glu Ile Cys Arg Phe Arg Gly Thr Thr
  1               5                  10                  15

Glu Asn Tyr Thr Ile Ala Val Thr Phe Phe Met Ile Phe Leu Leu Ser
             20                  25                  30

Val Val Gly Asn Ser Val Val Leu Ile Val Ile Lys Gln Arg Ala
         35                  40                  45

Met Arg Ser Ile Thr Asn Ile Tyr Leu Met Asn Leu Ala Ala Ser Asp
 50                  55                  60

Met Met Leu Ser Val Val Cys Met Pro Pro Thr Leu Val Ser Met Val
 65                  70                  75                  80

Met Asn Cys Trp Met Phe Gly Asn Tyr Met Cys Lys Ile Leu Ala Tyr
                 85                  90                  95

Leu Gln Pro Val Val Val Thr Ala Ser Ala Tyr Thr Leu Ala Val Ile
            100                 105                 110

Ala Phe Glu Arg Tyr Phe Ala Ile Cys Lys Pro Leu His Ser Arg Ile
        115                 120                 125

Trp Gln Thr Arg Ser His Ala Tyr Ala Met Ile Thr Leu Val Trp Val
    130                 135                 140

Ile Ala Ile Ala Ala Asn Ile Leu Met Leu Phe Met Tyr Glu Gln Gln
145                 150                 155                 160

Thr Tyr Ser Ser Asn Gly Tyr Thr Cys Ala Pro Ile His Pro Pro Ile
                165                 170                 175

Tyr His Phe Ala Tyr Gln Glu Asn Arg Lys Phe His Leu Lys Ser Ile
            180                 185                 190

Ile Tyr Phe Gln Val Tyr Met Thr Val Val Leu Leu Val Ile Pro Leu
        195                 200                 205

Val Val Met Ala Gly Leu Tyr Gly Asn Val Ile Thr Ser Leu Lys Ser
    210                 215                 220

Gly Ile Lys Leu Glu Ile Ala Ser Val Asp Pro Leu Ala Thr Ala
225                 230                 235                 240

Thr Thr Thr Gly Ala Lys Asn Leu Gly Ser His Ser Asp Ser Ala His
                245                 250                 255

Leu Leu Leu Asn Asn Val Leu Val Gly Ser Ser Gln Leu Ala Arg Ala
            260                 265                 270

Thr Ser Cys Ile Ala Leu Asn Thr Phe Ser Cys Asn Asn Thr Thr Asn
        275                 280                 285

Pro Phe Ser Thr Leu Thr Pro Pro Pro Ile Gln Gln Lys Asn Arg
    290                 295                 300

Ser Lys Pro Gln Leu Leu Gln Leu Pro Gly Lys Ile Asp Asn Phe Glu
305                 310                 315                 320

Glu Phe Arg Leu Gln Cys Leu Ser Asp Cys Arg Ser Asp Gly Val Leu
                325                 330                 335

Phe Pro Pro Pro Ala Ile Val Ala Ser Met Thr Asp Glu Gln Lys Leu
            340                 345                 350
```

-continued

```
Ser Phe Trp Asn Lys Leu Ser Asn Lys Leu Thr Phe Ser Gln Gln Asp
            355                 360                 365

Lys Thr Val Gln His Pro Asn Phe Gly His Arg Lys Ser Asp Thr Ser
    370                 375                 380

Ile Cys Leu Glu Asn Pro Ser Leu Arg Ser Thr His Thr Gln Lys Ser
385                 390                 395                 400

Ala Met Ala Lys Gln Arg Val Ile Lys Met Leu Ile Val Val Val Ile
                405                 410                 415

Ile Phe Phe Cys Cys Trp Thr Pro Ser Tyr Ile Trp Trp Leu Leu Leu
                420                 425                 430

Ile Ala Gly Asp Ser Phe Gln Ser Leu Asn Leu Ser Val Trp Asn Ser
            435                 440                 445

Asp Ile Asn Thr Phe Ile Thr Leu Leu Thr Tyr Ile Ser Ser Cys Thr
    450                 455                 460

Asn Pro Ile Thr Tyr Cys Phe Leu Asn Lys Lys Phe Arg Asn Ala Val
465                 470                 475                 480

Tyr Ala Thr Phe Gly Arg Lys Lys Asn Met Arg His His Phe Gln Lys
                485                 490                 495

Val Tyr Phe Asp Ile Phe Glu Leu Leu Ile Phe Phe Lys Ile Asn Tyr
            500                 505                 510

Gln Lys Ser Ile Lys Ser Pro Val Ser Val Phe Ser Asn Tyr Leu Phe
            515                 520                 525

Phe Gly Phe Ser Ala Pro Leu Ile Ser Val Asn Leu Ser Leu Ile Leu
            530                 535                 540

Phe Arg Ser Thr Phe Arg Ser Thr Ala Glu Leu Ile Thr Leu Thr Lys
545                 550                 555                 560

Glu Ser Arg Asp Lys Leu Leu Thr Gly Thr Asn Thr His Lys Phe Val
                565                 570                 575

Val Ile Ser Leu Phe Val
            580

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: synthetic

<400> SEQUENCE: 180

Phe Asp Asp Tyr Gly His Leu Arg Pro
1               5
```